(12) United States Patent
Wu et al.

(10) Patent No.: US 7,785,828 B1
(45) Date of Patent: Aug. 31, 2010

(54) PRODUCTION OF ANTIMICROBIAL PROTEINS IN FUSION PROTEINS

(75) Inventors: Gusui Wu, Davis, CA (US); Wessel Lageweg, Bracknell (NL); Maarten H. Stuiver, Bracknell (GB); Lu Liu, Redwood City, CA (US); Wei Wei, Palo Alto, CA (US); Michael A. Dojka, Jr., Redwood City, CA (US); Linda K. Dojka, legal representative, Ludington, MI (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 637 days.

(21) Appl. No.: 10/544,414

(22) PCT Filed: Feb. 6, 2004

(86) PCT No.: PCT/US2004/003378
§ 371 (c)(1),
(2), (4) Date: Jul. 12, 2006

(87) PCT Pub. No.: WO2004/072239
PCT Pub. Date: Aug. 26, 2004

Related U.S. Application Data

(60) Provisional application No. 60/445,493, filed on Feb. 6, 2003.

(51) Int. Cl.
*C07K 14/00* (2006.01)
*C07K 14/415* (2006.01)
*C12N 15/62* (2006.01)
*C12N 15/09* (2006.01)

(52) U.S. Cl. .................. 435/69.1; 435/468; 435/69.7; 435/6

(58) Field of Classification Search .................. None
See application file for complete search history.

(56) References Cited

U.S. PATENT DOCUMENTS

| 5,773,696 A | 6/1998 | Liang et al. |
| 6,855,865 B2 * | 2/2005 | Famodu et al. ............... 800/279 |
| 2003/0228654 A1 * | 12/2003 | Imaeda et al. ............... 435/69.1 |

OTHER PUBLICATIONS

Pryor et al. Protein Expression and Purification (1997) 10:309-319.*
LaVallie et al. Current Opinion in Biotechnology (1995) 6:501-506.*
International Search Report mailed on Nov. 1, 2006, for PCT Application No. PCT/US2004/03378, filed on Feb. 6, 2004, 1 page.
Written Opinion of the International Searching Authority mailed on Nov. 1, 2006, for PCT Application No. PCT/US04/03378, filed on Feb. 6, 2004, 6 pages.

* cited by examiner

*Primary Examiner*—Medina A Ibrahim
(74) *Attorney, Agent, or Firm*—Morrison & Foerster LLP

(57) ABSTRACT

The invention relates to a method of producing cysteine containing polypeptides in fusion proteins by recombinantly expressing in a host cell sequences encoding an antifungal polypeptide, a maltose binding protein, and a histidine tag. The method is carried out in the presence of a reducing agent to prevent misfolding of the fusion proteins.

8 Claims, 2 Drawing Sheets

Cleavage sites for Factor Xa and for Genenase

- - -I-E-G-R-Q-K-L-C- - -   [Junction between Factor Xa cleavage site (italic) and N-terminus of NP] [SEQ NO: 17]

- - -H-Y-N-L-C- - -   [Junction between Genenase I cleavage site (italic) and N-terminus of NP] [SEQ NO: 18]

Figure 2. Relative NP expression level versus disease spread for L3-135 (A), L2-12 (B) and DmAMP1 (C).

SEQUENCE LISTING

```
<160> NUMBER OF SEQ ID NOS: 792

<210> SEQ ID NO 1
<211> LENGTH: 50
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 1
<223> OTHER INFORMATION: Xaa = Asn or Glu or Lys
<220> FEATURE:
<221> NAME/KEY: VARIANT
<222> LOCATION: 5
<223> OTHER INFORMATION: Xaa= Lys or Arg
<220> FEATURE:
<221> NAME/KEY: VARIANT
<222> LOCATION: 8
<223> OTHER INFORMATION: Xaa= Lys or Leu
<220> FEATURE:
<221> NAME/KEY: VARIANT
<222> LOCATION: 11
<223> OTHER INFORMATION: Xaa= Ser or Thr
<220> FEATURE:
<221> NAME/KEY: VARIANT
<222> LOCATION: 18
<223> OTHER INFORMATION: Xaa= Gly or Lys
<220> FEATURE:
<221> NAME/KEY: VARIANT
<222> LOCATION: 19
<223> OTHER INFORMATION: Xaa = Hys or Asn
<220> FEATURE:
<221> NAME/KEY: VARIANT
<222> LOCATION: 21
<223> OTHER INFORMATION: Xaa= Asp or Asn
<220> FEATURE:
<221> NAME/KEY: VARIANT
<222> LOCATION: 22
<223> OTHER INFORMATION: Xaa= Asn or Thr
<220> FEATURE:
<221> NAME/KEY: VARIANT
<222> LOCATION: 23
```

```
<223> OTHER INFORMATION: Xaa= Gln or Lys
<220> FEATURE:
<221> NAME/KEY: VARIANT
<222> LOCATION: 25
<223> OTHER INFORMATION: Xaa= Lys or Arg
<220> FEATURE:
<221> NAME/KEY: VARIANT
<222> LOCATION: 26
<223> OTHER INFORMATION: Xaa= Ser or Asn
<220> FEATURE:
<221> NAME/KEY: VARIANT
<222> LOCATION: 29
<223> OTHER INFORMATION: Xaa= Gly or Ser or Ile
<220> FEATURE:
<221> NAME/KEY: VARIANT
<222> LOCATION: 31
<223> OTHER INFORMATION: Xaa= Ala or Lys
<220> FEATURE:
<221> NAME/KEY: VARIANT
<222> LOCATION: 37
<223> OTHER INFORMATION: Xaa= Val or Lys
<220> FEATURE:
<221> NAME/KEY: VARIANT
<222> LOCATION: 39
<223> OTHER INFORMATION: Xaa= Asn or Ser
<220> FEATURE:
<221> NAME/KEY: VARIANT
<222> LOCATION: 42
<223> OTHER INFORMATION: Xaa= His or Trp
<220> FEATURE:
<221> NAME/KEY: VARIANT
<222> LOCATION: 43
<223> OTHER INFORMATION: Xaa= Met or Lys

<400> SEQUENCE: 1

Xaa Leu Cys Glu Xaa Ala Ser Xaa Thr Trp Xaa Gly Asn Cys Gly Asn
 1               5                  10                  15

Thr Xaa Xaa Cys Xaa Xaa Xaa Cys Xaa Xaa Trp Glu Xaa Ala Xaa His
             20                  25                  30

Gly Ala Cys His Xaa Arg Xaa Gly Lys Xaa Xaa Cys Phe Cys Tyr Phe
         35                  40                  45

Asn Cys
   50

<210> SEQ ID NO 2
<211> LENGTH: 51
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 2
<223> OTHER INFORMATION: Xaa = Lys or Gln
<220> FEATURE:
<221> NAME/KEY: VARIANT
<222> LOCATION: 5
<223> OTHER INFORMATION: Xaa= Glu or Gln
<220> FEATURE:
<221> NAME/KEY: VARIANT
<222> LOCATION: 6
<223> OTHER INFORMATION: Xaa= Arg or Lys
<220> FEATURE:
<221> NAME/KEY: VARIANT
<222> LOCATION: 9
<223> OTHER INFORMATION: Xaa= Gly or Arg
<220> FEATURE:
<221> NAME/KEY: VARIANT
<222> LOCATION: 16
<223> OTHER INFORMATION: Xaa= Gly or Met
<220> FEATURE:
<221> NAME/KEY: VARIANT
<222> LOCATION: 18
<223> OTHER INFORMATION: Xaa= Asn or Ser
```

```
<220> FEATURE:
<221> NAME/KEY: VARIANT
<222> LOCATION: 27
<223> OTHER INFORMATION: Xaa= Arg or Asn
<220> FEATURE:
<221> NAME/KEY: VARIANT
<222> LOCATION: 30
<223> OTHER INFORMATION: Xaa= Lys or Arg
<220> FEATURE:
<221> NAME/KEY: VARIANT
<222> LOCATION: 32
<223> OTHER INFORMATION: Xaa = Lys or Arg
<220> FEATURE:
<221> NAME/KEY: VARIANT
<222> LOCATION: 39
<223> OTHER INFORMATION: Xaa= Arg or Val
<220> FEATURE:
<221> NAME/KEY: VARIANT
<222> LOCATION: 49
<223> OTHER INFORMATION: Xaa= Phe or Val

<400> SEQUENCE: 2

Gln Xaa Leu Cys Xaa Xaa Pro Ser Xaa Thr Trp Ser Gly Val Cys Xaa
 1               5                  10                  15

Asn Xaa Asn Ala Cys Lys Asn Gln Cys Ile Xaa Leu Glu Xaa Ala Xaa
            20                  25                  30

His Gly Ser Cys Asn Tyr Xaa Phe Pro Ala His Lys Cys Ile Cys Tyr
        35                  40                  45

Xaa Pro Cys
    50

<210> SEQ ID NO 3
<211> LENGTH: 50
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 1
<223> OTHER INFORMATION: Xaa = Lys or Asn or Gln
<220> FEATURE:
<221> NAME/KEY: VARIANT
<222> LOCATION: 5
<223> OTHER INFORMATION: Xaa = Arg or Lys
<220> FEATURE:
<221> NAME/KEY: VARIANT
<222> LOCATION: 6
<223> OTHER INFORMATION: Xaa = Ala or Pro
<220> FEATURE:
<221> NAME/KEY: VARIANT
<222> LOCATION: 8
<223> OTHER INFORMATION: Xaa = Gln or Lys
<220> FEATURE:
<221> NAME/KEY: VARIANT
<222> LOCATION: 11
<223> OTHER INFORMATION: Xaa = Thr or Ser
<220> FEATURE:
<221> NAME/KEY: VARIANT
<222> LOCATION: 13
<223> OTHER INFORMATION: Xaa = His or Asn
<220> FEATURE:
<221> NAME/KEY: VARIANT
<222> LOCATION: 22
<223> OTHER INFORMATION: Xaa = Lys or Asn
<220> FEATURE:
<221> NAME/KEY: VARIANT
<222> LOCATION: 25
<223> OTHER INFORMATION: Xaa = Lys or Arg
<220> FEATURE:
<221> NAME/KEY: VARIANT
<222> LOCATION: 26
<223> OTHER INFORMATION: Xaa = Asn or Ser
<220> FEATURE:
```

```
<221> NAME/KEY: VARIANT
<222> LOCATION: 29
<223> OTHER INFORMATION: Xaa = Gly or Lys
<220> FEATURE:
<221> NAME/KEY: VARIANT
<222> LOCATION: 31
<223> OTHER INFORMATION: Xaa = Lys or Ala
<220> FEATURE:
<221> NAME/KEY: VARIANT
<222> LOCATION: 37
<223> OTHER INFORMATION: Xaa = Val or Lys
<220> FEATURE:
<221> NAME/KEY: VARIANT
<222> LOCATION: 39
<223> OTHER INFORMATION: Xaa = Asn or Ser
<220> FEATURE:
<221> NAME/KEY: VARIANT
<222> LOCATION: 42
<223> OTHER INFORMATION: Xaa = Trp or His
<220> FEATURE:
<221> NAME/KEY: VARIANT
<222> LOCATION: 49
<223> OTHER INFORMATION: Xaa = Asn or Ser

<400> SEQUENCE: 3

Xaa Leu Cys Glu Xaa Xaa Ser Xaa Thr Trp Xaa Gly Xaa Cys Gly Asn
 1               5                   10                  15

Thr Lys His Cys Asp Xaa Gln Cys Xaa Xaa Trp Glu Xaa Ala Xaa His
                20                  25                  30

Gly Ala Cys His Xaa Arg Xaa Gly Lys Xaa Lys Cys Phe Cys Tyr Phe
            35                  40                  45

Xaa Cys
    50

<210> SEQ ID NO 4
<211> LENGTH: 51
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 2
<223> OTHER INFORMATION: Xaa =Lys or Asn or Gln
<220> FEATURE:
<221> NAME/KEY: VARIANT
<222> LOCATION: 6
<223> OTHER INFORMATION: Xaa = Arg or Lys
<220> FEATURE:
<221> NAME/KEY: VARIANT
<222> LOCATION: 7
<223> OTHER INFORMATION: Xaa = Ala or Pro
<220> FEATURE:
<221> NAME/KEY: VARIANT
<222> LOCATION: 9
<223> OTHER INFORMATION: Xaa = Gln or Lys
<220> FEATURE:
<221> NAME/KEY: VARIANT
<222> LOCATION: 12
<223> OTHER INFORMATION: Xaa = Thr or Ser
<220> FEATURE:
<221> NAME/KEY: VARIANT
<222> LOCATION: 14
<223> OTHER INFORMATION: Xaa = His or Asn
<220> FEATURE:
<221> NAME/KEY: VARIANT
<222> LOCATION: 23
<223> OTHER INFORMATION: Xaa = Lys or Asn
<220> FEATURE:
<221> NAME/KEY: VARIANT
<222> LOCATION: 26
<223> OTHER INFORMATION: Xaa = Asn or Ser
<220> FEATURE:
<221> NAME/KEY: VARIANT
```

```
<222> LOCATION: 27
<223> OTHER INFORMATION: Xaa = Asn or Ser
<220> FEATURE:
<221> NAME/KEY: VARIANT
<222> LOCATION: 30
<223> OTHER INFORMATION: Xaa = Gly or Lys
<220> FEATURE:
<221> NAME/KEY: VARIANT
<222> LOCATION: 32
<223> OTHER INFORMATION: Xaa = Lys or Ala
<220> FEATURE:
<221> NAME/KEY: VARIANT
<222> LOCATION: 38
<223> OTHER INFORMATION: Xaa= Val or Lys
<220> FEATURE:
<221> NAME/KEY: VARIANT
<222> LOCATION: 40
<223> OTHER INFORMATION: Xaa = Asn or Ser
<220> FEATURE:
<221> NAME/KEY: VARIANT
<222> LOCATION: 43
<223> OTHER INFORMATION: Xaa = Trp or His
<220> FEATURE:
<221> NAME/KEY: VARIANT
<222> LOCATION: 50
<223> OTHER INFORMATION: Xaa = Asn or Ser

<400> SEQUENCE: 4

Val Xaa Leu Cys Glu Xaa Xaa Ser Xaa Thr Trp Xaa Gly Xaa Cys Gly
 1               5                  10                  15

Asn Thr Lys His Cys Asp Xaa Gln Cys Xaa Xaa Trp Glu Xaa Ala Xaa
             20                  25                  30

His Gly Ala Cys His Xaa Arg Xaa Gly Lys Xaa Lys Cys Phe Cys Tyr
         35                  40                  45

Phe Xaa Cys
     50

<210> SEQ ID NO 5
<211> LENGTH: 52
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 3
<223> OTHER INFORMATION: Xaa = Lys or Asn or Gln
<220> FEATURE:
<221> NAME/KEY: VARIANT
<222> LOCATION: 7
<223> OTHER INFORMATION: Xaa = Arg or Lys
<220> FEATURE:
<221> NAME/KEY: VARIANT
<222> LOCATION: 8
<223> OTHER INFORMATION: Xaa = Asp or Pro
<220> FEATURE:
<221> NAME/KEY: VARIANT
<222> LOCATION: 10
<223> OTHER INFORMATION: Xaa = Gln or Lys
<220> FEATURE:
<221> NAME/KEY: VARIANT
<222> LOCATION: 13
<223> OTHER INFORMATION: Xaa = Thr or Ser
<220> FEATURE:
<221> NAME/KEY: VARIANT
<222> LOCATION: 15
<223> OTHER INFORMATION: Xaa = His or Asn
<220> FEATURE:
<221> NAME/KEY: VARIANT
<222> LOCATION: 24
<223> OTHER INFORMATION: Xaa = Lys or Asn
<220> FEATURE:
<221> NAME/KEY: VARIANT
<222> LOCATION: 27
```

```
<223> OTHER INFORMATION: Xaa = Lys or Arg
<220> FEATURE:
<221> NAME/KEY: VARIANT
<222> LOCATION: 28
<223> OTHER INFORMATION: Xaa = Asn or Ser
<220> FEATURE:
<221> NAME/KEY: VARIANT
<222> LOCATION: 31
<223> OTHER INFORMATION: Xaa = Gly or Lys
<220> FEATURE:
<221> NAME/KEY: VARIANT
<222> LOCATION: 33
<223> OTHER INFORMATION: Xaa = Lys or Ala
<220> FEATURE:
<221> NAME/KEY: VARIANT
<222> LOCATION: 39
<223> OTHER INFORMATION: Xaa = Val or Lys
<220> FEATURE:
<221> NAME/KEY: VARIANT
<222> LOCATION: 41
<223> OTHER INFORMATION: Xaa = Asn or Ser
<220> FEATURE:
<221> NAME/KEY: VARIANT
<222> LOCATION: 44
<223> OTHER INFORMATION: Xaa = Trp or His
<220> FEATURE:
<221> NAME/KEY: VARIANT
<222> LOCATION: 51
<223> OTHER INFORMATION: Xaa = Asn or Ser

<400> SEQUENCE: 5

Gly Val Xaa Leu Cys Glu Xaa Xaa Ser Xaa Thr Trp Xaa Gly Xaa Cys
 1               5                  10                  15

Gly Asn Thr Lys His Cys Asp Xaa Gln Cys Xaa Xaa Trp Glu Xaa Ala
             20                  25                  30

Xaa His Gly Ala Cys His Xaa Arg Xaa Gly Lys Xaa Lys Cys Phe Cys
         35                  40                  45

Tyr Phe Xaa Cys
     50

<210> SEQ ID NO 6
<211> LENGTH: 53
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 4
<223> OTHER INFORMATION: Xaa = Lys or Asn or Gln
<220> FEATURE:
<221> NAME/KEY: VARIANT
<222> LOCATION: 8
<223> OTHER INFORMATION: Xaa = Arg or Lys
<220> FEATURE:
<221> NAME/KEY: VARIANT
<222> LOCATION: 9
<223> OTHER INFORMATION: Xaa = Ala or Pro
<220> FEATURE:
<221> NAME/KEY: VARIANT
<222> LOCATION: 11
<223> OTHER INFORMATION: Xaa = Gln or Lys
<220> FEATURE:
<221> NAME/KEY: VARIANT
<222> LOCATION: 14
<223> OTHER INFORMATION: Xaa = Thr or Ser
<220> FEATURE:
<221> NAME/KEY: VARIANT
<222> LOCATION: 16
<223> OTHER INFORMATION: Xaa = His or Asn
<220> FEATURE:
<221> NAME/KEY: VARIANT
<222> LOCATION: 25
<223> OTHER INFORMATION: Xaa = Lys or Asn
```

```
<220> FEATURE:
<221> NAME/KEY: VARIANT
<222> LOCATION: 28
<223> OTHER INFORMATION: Xaa = Lys or Arg
<220> FEATURE:
<221> NAME/KEY: VARIANT
<222> LOCATION: 29
<223> OTHER INFORMATION: Xaa = Asn or Ser
<220> FEATURE:
<221> NAME/KEY: VARIANT
<222> LOCATION: 32
<223> OTHER INFORMATION: Xaa = Gly or Lys
<220> FEATURE:
<221> NAME/KEY: VARIANT
<222> LOCATION: 34
<223> OTHER INFORMATION: Xaa = Lys or Ala
<220> FEATURE:
<221> NAME/KEY: VARIANT
<222> LOCATION: 40
<223> OTHER INFORMATION: Xaa = Val or Lys
<220> FEATURE:
<221> NAME/KEY: VARIANT
<222> LOCATION: 42
<223> OTHER INFORMATION: Xaa = Asn or Ser
<220> FEATURE:
<221> NAME/KEY: VARIANT
<222> LOCATION: 45
<223> OTHER INFORMATION: Xaa = Trp or His
<220> FEATURE:
<221> NAME/KEY: VARIANT
<222> LOCATION: 52
<223> OTHER INFORMATION: Xaa = Asn or Ser

<400> SEQUENCE: 6

Asp Gly Val Xaa Leu Cys Glu Xaa Xaa Ser Xaa Thr Trp Xaa Gly Xaa
 1               5                  10                  15

Cys Gly Asn Thr Lys His Cys Asp Xaa Gln Cys Xaa Xaa Trp Glu Xaa
                20                  25                  30

Ala Xaa His Gly Ala Cys His Xaa Arg Xaa Gly Lys Xaa Lys Cys Phe
            35                  40                  45

Cys Tyr Phe Xaa Cys
        50

<210> SEQ ID NO 7
<211> LENGTH: 50
<212> TYPE: PRT
<213> ORGANISM: Artificial Sequence
<220> FEATURE:
<223> OTHER INFORMATION: Defensin like

<400> SEQUENCE: 7

Asn Leu Cys Glu Arg Ala Ser Lys Thr Trp Ser Gly Asn Cys Gly Asn
 1               5                  10                  15

Thr Lys His Cys Asp Asn Gln Cys Lys Ser Trp Glu Gly Ala Lys His
                20                  25                  30

Gly Ala Cys His Val Arg Asn Gly Lys Trp Lys Cys Phe Cys Tyr Phe
            35                  40                  45

Asn Cys
    50

<210> SEQ ID NO 8
<211> LENGTH: 51
<212> TYPE: PRT
<213> ORGANISM: Artificial Sequence
<220> FEATURE:
<223> OTHER INFORMATION: Defensin like

<400> SEQUENCE: 8
```

-continued

```
Gln Lys Leu Cys Gln Arg Pro Ser Arg Thr Trp Ser Gly Val Cys Gly
 1               5                   10                  15

Asn Ser Asn Ala Cys Lys Asn Gln Cys Ile Arg Leu Glu Lys Ala Arg
                20                  25                  30

His Gly Ser Cys Asn Tyr Arg Phe Pro Ala His Lys Cys Ile Cys Tyr
            35                  40                  45

Phe Pro Cys
        50

<210> SEQ ID NO 9
<211> LENGTH: 53
<212> TYPE: PRT
<213> ORGANISM: Artificial Sequence
<220> FEATURE:
<223> OTHER INFORMATION: Defensin like

<400> SEQUENCE: 9

Asp Gly Val Lys Leu Cys Glu Arg Ala Ser Gln Thr Trp Thr Gly His
 1               5                   10                  15

Cys Gly Asn Thr Lys His Cys Asp Lys Gln Cys Lys Asn Trp Glu Gly
                20                  25                  30

Ala Lys His Gly Ala Cys His Val Arg Asn Gly Lys Trp Lys Cys Phe
            35                  40                  45

Cys Tyr Phe Asn Cys
        50

<210> SEQ ID NO 10
<211> LENGTH: 50
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 1
<223> OTHER INFORMATION: Xaa = Asn or Glu
<220> FEATURE:
<221> NAME/KEY: VARIANT
<222> LOCATION: 5
<223> OTHER INFORMATION: Xaa = Lys or Arg
<220> FEATURE:
<221> NAME/KEY: VARIANT
<222> LOCATION: 11
<223> OTHER INFORMATION: Xaa = Thr or Ser
<220> FEATURE:
<221> NAME/KEY: VARIANT
<222> LOCATION: 22
<223> OTHER INFORMATION: Xaa = Thr or Asn
<220> FEATURE:
<221> NAME/KEY: VARIANT
<222> LOCATION: 25
<223> OTHER INFORMATION: Xaa = Lys or Arg
<220> FEATURE:
<221> NAME/KEY: VARIANT
<222> LOCATION: 26
<223> OTHER INFORMATION: Xaa = Asn or Ser
<220> FEATURE:
<221> NAME/KEY: VARIANT
<222> LOCATION: 29
<223> OTHER INFORMATION: Xaa = Gly or Ser
<220> FEATURE:
<221> NAME/KEY: VARIANT
<222> LOCATION: 31
<223> OTHER INFORMATION: Xaa = Ala or Lys
<220> FEATURE:
<221> NAME/KEY: VARIANT
<222> LOCATION: (37)...(37)
<223> OTHER INFORMATION: Xaa = Val or Arg
<220> FEATURE:
<221> NAME/KEY: VARIANT
```

```
<222> LOCATION: 39
<223> OTHER INFORMATION: Xaa = Ser or Asn
<220> FEATURE:
<221> NAME/KEY: VARIANT
<222> LOCATION: 42
<223> OTHER INFORMATION: Xaa = His or Trp

<400> SEQUENCE: 10

Xaa Leu Cys Glu Xaa Ala Ser Lys Thr Trp Xaa Gly Asn Cys Gly Asn
 1               5                  10                  15

Thr Lys His Cys Asp Xaa Gln Cys Xaa Xaa Trp Glu Xaa Ala Xaa His
            20                  25                  30

Gly Ala Cys His Xaa Arg Xaa Gly Lys Xaa Lys Cys Phe Cys Tyr Phe
                35                  40                  45

Asn Cys
    50

<210> SEQ ID NO 11
<211> LENGTH: 53
<212> TYPE: PRT
<213> ORGANISM: Artificial Sequence
<220> FEATURE:
<223> OTHER INFORMATION: Defensin like
<220> FEATURE:
<221> NAME/KEY: VARIANT
<222> LOCATION: 8
<223> OTHER INFORMATION: Xaa = Arg or Lys
<220> FEATURE:
<221> NAME/KEY: VARIANT
<222> LOCATION: 9
<223> OTHER INFORMATION: Xaa = Ala or Pro
<220> FEATURE:
<221> NAME/KEY: VARIANT
<222> LOCATION: 11
<223> OTHER INFORMATION: Xaa = Lys or Gln
<220> FEATURE:
<221> NAME/KEY: VARIANT
<222> LOCATION: 14
<223> OTHER INFORMATION: Xaa = Ser or Thr
<220> FEATURE:
<221> NAME/KEY: VARIANT
<222> LOCATION: 16
<223> OTHER INFORMATION: Xaa = His or Asn
<220> FEATURE:
<221> NAME/KEY: VARIANT
<222> LOCATION: 25
<223> OTHER INFORMATION: Xaa = Lys or Asn or Thr
<220> FEATURE:
<221> NAME/KEY: VARIANT
<222> LOCATION: 28
<223> OTHER INFORMATION: Xaa = Lys or Arg
<220> FEATURE:
<221> NAME/KEY: VARIANT
<222> LOCATION: 29
<223> OTHER INFORMATION: Xaa = Asn or Ser
<220> FEATURE:
<221> NAME/KEY: VARIANT
<222> LOCATION: 32
<223> OTHER INFORMATION: Xaa = Lys or Gly
<220> FEATURE:
<221> NAME/KEY: VARIANT
<222> LOCATION: 34
<223> OTHER INFORMATION: Xaa = Ala or Lys
<220> FEATURE:
<221> NAME/KEY: VARIANT
<222> LOCATION: 40
<223> OTHER INFORMATION: Xaa = Val or Lys
<220> FEATURE:
<221> NAME/KEY: VARIANT
<222> LOCATION: 42
<223> OTHER INFORMATION: Xaa = Asn or Ser

<400> SEQUENCE: 11
```

-continued

```
Asp Gly Val Lys Leu Cys Glu Xaa Xaa Ser Xaa Thr Trp Xaa Gly Xaa
1               5                   10                  15

Cys Gly Asn Thr Lys His Cys Asp Xaa Gln Cys Xaa Xaa Trp Glu Xaa
                20                  25                  30

Ala Xaa His Gly Ala Cys His Xaa Arg Xaa Gly Lys Trp Lys Cys Phe
        35                  40                  45

Cys Tyr Phe Asn Cys
    50
```

<210> SEQ ID NO 12
<211> LENGTH: 6
<212> TYPE: PRT
<213> ORGANISM: Artificial Sequence
<220> FEATURE:
<223> OTHER INFORMATION: Synthetic Construct

<400> SEQUENCE: 12

```
Pro Gly Ala Ala His Tyr
1               5
```

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

```
Ile Glu Asp Gly Arg
1               5
```

<210> SEQ ID NO 14
<211> LENGTH: 6
<212> TYPE: PRT
<213> ORGANISM: Artificial Sequence
<220> FEATURE:
<223> OTHER INFORMATION: Synthetic Construct

<400> SEQUENCE: 14

```
Pro Gly Ala Ala His Tyr
1               5
```

<210> SEQ ID NO 15
<211> LENGTH: 30
<212> TYPE: PRT
<213> ORGANISM: Artificial Sequence
<220> FEATURE:
<223> OTHER INFORMATION: Synthetic Construct

<400> SEQUENCE: 15

```
Met Gly Phe Val Leu Phe Ser Gln Leu Pro Ser Phe Leu Leu Val Ser
1               5                   10                  15

Thr Leu Leu Leu Phe Leu Val Ile Ser His Ser Cys Arg Ala
                20                  25                  30
```

<210> SEQ ID NO 16
<211> LENGTH: 90
<212> TYPE: DNA
<213> ORGANISM: Artificial Sequence
<220> FEATURE:
<223> OTHER INFORMATION: Synthetic Construct

<400> SEQUENCE: 16

```
atgggcttcg tgctgttcag ccagctgccc agcttcctgc tggtgagcac cctgctgctg      60
```
ttcctggtga tcagccacag ctgccgcgcc                                       90

<210> SEQ ID NO 17
<211> LENGTH: 8
<212> TYPE: PRT
<213> ORGANISM: Artificial Sequence
<220> FEATURE:
<223> OTHER INFORMATION: Synthetic Construct

<400> SEQUENCE: 17

Ile Glu Gly Arg Gln Lys Leu Cys
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic Construct

<400> SEQUENCE: 18

His Tyr Asn Leu Cys
1               5

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Ile Glu Asp Gly Arg
1               5

<210> SEQ ID NO 20
<211> LENGTH: 51
<212> TYPE: PRT
<213> ORGANISM: Artificial Sequence
<220> FEATURE:
<223> OTHER INFORMATION: Defensin like

<400> SEQUENCE: 20

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 21
<211> LENGTH: 51
<212> TYPE: PRT
<213> ORGANISM: Artificial Sequence
<220> FEATURE:
<223> OTHER INFORMATION: Defensin like

<400> SEQUENCE: 21

Gln Lys Leu Cys Gln Lys Pro Ser Arg Thr Trp Ser Gly Val Cys Gly
1               5                   10                  15

Asn Asn Asn Ala Cys Lys Asn Gln Cys Ile Arg Leu Glu Lys Ala Arg
            20                  25                  30

```
His Gly Ser Cys Asn Tyr Val Phe Pro Ala His Lys Cys Ile Cys Tyr
        35                  40                  45

Phe Pro Cys
    50

<210> SEQ ID NO 22
<211> LENGTH: 51
<212> TYPE: PRT
<213> ORGANISM: Artificial Sequence
<220> FEATURE:
<223> OTHER INFORMATION: Defensin like

<400> SEQUENCE: 22

Gln Lys Leu Cys Gln Arg Ser Ser Arg Thr Trp Ser Gly Val Cys Gly
1               5                   10                  15

Asn Ser Asn Ala Cys Lys Asn Gln Cys Ile Arg Leu Glu Gly Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 23
<211> LENGTH: 51
<212> TYPE: PRT
<213> ORGANISM: Artificial Sequence
<220> FEATURE:
<223> OTHER INFORMATION: Defensin like

<400> SEQUENCE: 23

Gln Lys Leu Cys Gln Arg Pro Ser Arg Thr Trp Ser Gly Val Cys Gly
1               5                   10                  15

Asn Ser Asn Ala Cys Lys Asn Gln Cys Ile Asn Leu Glu Gly Ala Lys
            20                  25                  30

His Gly Ser Cys Asn Tyr Arg Phe Pro Ala His Lys Cys Ile Cys Tyr
        35                  40                  45

Val Pro Cys
    50

<210> SEQ ID NO 24
<211> LENGTH: 51
<212> TYPE: PRT
<213> ORGANISM: Artificial Sequence
<220> FEATURE:
<223> OTHER INFORMATION: Defensin like

<400> SEQUENCE: 24

Gln Lys Leu Cys Glu Arg Pro Ser Gly Thr Trp Ser Gly Val Cys Gly
1               5                   10                  15

Asn Ser Asn Ala Cys Lys Asn Gln Cys Ile Arg Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 25
<211> LENGTH: 51
<212> TYPE: PRT
<213> ORGANISM: Artificial Sequence
<220> FEATURE:
<223> OTHER INFORMATION: Defensin like
```

```
<400> SEQUENCE: 25

Gln Lys Leu Cys Gln Arg Pro Ser Gly Thr Trp Ser Gly Val Cys Met
1               5                   10                  15

Asn Asn Asn Ala Cys Lys Asn Gln Cys Ile Arg Leu Glu Lys Ala Lys
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 26
<211> LENGTH: 51
<212> TYPE: PRT
<213> ORGANISM: Artificial Sequence
<220> FEATURE:
<223> OTHER INFORMATION: Defensin like

<400> SEQUENCE: 26

Gln Lys Leu Cys Glu Arg Pro Ser Arg Thr Trp Ser Gly Val Cys Gly
1               5                   10                  15

Asn Ser Asn Ala Cys Lys Asn Gln Cys Ile Asn Leu Glu Gly Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 27
<211> LENGTH: 51
<212> TYPE: PRT
<213> ORGANISM: Artificial Sequence
<220> FEATURE:
<223> OTHER INFORMATION: Defensin like

<400> SEQUENCE: 27

Gln Lys Leu Cys Glu Arg Pro Ser Gly Thr Trp Ser Gly Val Cys Gly
1               5                   10                  15

Asn Ser Asn Ala Cys Lys Asn Gln Cys Ile Arg Leu Glu Gly Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 28
<211> LENGTH: 51
<212> TYPE: PRT
<213> ORGANISM: Artificial Sequence
<220> FEATURE:
<223> OTHER INFORMATION: Defensin like

<400> SEQUENCE: 28

Gln Lys Leu Cys Glu Lys Pro Ser Gly Thr Trp Ser Gly Val Cys Gly
1               5                   10                  15

Asn Ser Asn Ala Cys Lys Asn Gln Cys Ile Arg Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
```

-continued

```
                50

<210> SEQ ID NO 29
<211> LENGTH: 51
<212> TYPE: PRT
<213> ORGANISM: Artificial Sequence
<220> FEATURE:
<223> OTHER INFORMATION: Defensin like

<400> SEQUENCE: 29

Gln Lys Leu Cys Gln Arg Pro Ser Gly Thr Trp Ser Gly Val Cys Gly
  1               5                  10                  15

Asn Asn Asn Ala Cys Lys Asn Gln Cys Ile Arg Leu Glu Gly Ala Lys
             20                  25                  30

His Gly Ser Cys Asn Tyr Ile Phe Pro Ala His Lys Cys Ile Cys Tyr
         35                  40                  45

Phe Pro Cys
        50

<210> SEQ ID NO 30
<211> LENGTH: 51
<212> TYPE: PRT
<213> ORGANISM: Artificial Sequence
<220> FEATURE:
<223> OTHER INFORMATION: Defensin like

<400> SEQUENCE: 30

Gln Lys Leu Cys Gln Arg Pro Ser Arg Thr Trp Ser Gly Val Cys Gly
  1               5                  10                  15

Asn Ser Asn Ala Cys Lys Asn Gln Cys Ile Asn Leu Glu Lys Ala Arg
             20                  25                  30

His Gly Ser Cys Asn Tyr Arg Phe Pro Ala His Lys Cys Ile Cys Tyr
         35                  40                  45

Phe Pro Cys
        50

<210> SEQ ID NO 31
<211> LENGTH: 51
<212> TYPE: PRT
<213> ORGANISM: Artificial Sequence
<220> FEATURE:
<223> OTHER INFORMATION: Defensin like

<400> SEQUENCE: 31

Gln Lys Leu Cys Gln Arg Ser Ser Arg Thr Trp Ser Gly Val Cys Gly
  1               5                  10                  15

Asn Asn Asn Ala Cys Lys Asn Gln Cys Ile Arg Leu Glu Gly Ala Arg
             20                  25                  30

His Gly Ser Cys Asn Tyr Arg Phe Pro Ala His Lys Cys Ile Cys Tyr
         35                  40                  45

Phe Pro Cys
        50

<210> SEQ ID NO 32
<211> LENGTH: 51
<212> TYPE: PRT
<213> ORGANISM: Artificial Sequence
<220> FEATURE:
<223> OTHER INFORMATION: Defensin like

<400> SEQUENCE: 32

Gln Lys Leu Cys Gln Arg Pro Ser Gly Thr Trp Ser Gly Val Cys Gly
```

-continued

```
                1               5                  10                 15
Asn Asn Asn Ala Cys Lys Asn Gln Cys Ile Arg Leu Glu Lys Ala Arg
            20                  25                 30

His Gly Ser Cys Asn Tyr Arg Phe Pro Ala His Lys Cys Ile Cys Tyr
            35                  40                 45

Phe Pro Cys
        50

<210> SEQ ID NO 33
<211> LENGTH: 51
<212> TYPE: PRT
<213> ORGANISM: Artificial Sequence
<220> FEATURE:
<223> OTHER INFORMATION: Defensin like

<400> SEQUENCE: 33

Gln Lys Leu Cys Gln Arg Pro Ser Arg Thr Trp Ser Gly Val Cys Met
 1               5                  10                 15

Asn Asn Asn Ala Cys Lys Asn Gln Cys Ile Arg Leu Glu Gly Ala Arg
            20                  25                 30

His Gly Ser Cys Asn Tyr Arg Phe Pro Ala His Lys Cys Ile Cys Tyr
            35                  40                 45

Phe Pro Cys
        50

<210> SEQ ID NO 34
<211> LENGTH: 51
<212> TYPE: PRT
<213> ORGANISM: Artificial Sequence
<220> FEATURE:
<223> OTHER INFORMATION: Defensin like

<400> SEQUENCE: 34

Gln Lys Leu Cys Glu Arg Pro Ser Gly Thr Trp Ser Gly Val Cys Met
 1               5                  10                 15

Asn Ser Asn Ala Cys Lys Asn Gln Cys Ile Arg Leu Glu Gly Ala Arg
            20                  25                 30

His Gly Ser Cys Asn Tyr Val Phe Pro Ala His Lys Cys Ile Cys Tyr
            35                  40                 45

Phe Pro Cys
        50

<210> SEQ ID NO 35
<211> LENGTH: 51
<212> TYPE: PRT
<213> ORGANISM: Artificial Sequence
<220> FEATURE:
<223> OTHER INFORMATION: Defensin like

<400> SEQUENCE: 35

Gln Lys Leu Cys Gln Arg Pro Ser Arg Thr Trp Ser Gly Val Cys Gly
 1               5                  10                 15

Asn Ser Asn Ala Cys Lys Asn Gln Cys Ile Arg Leu Glu Lys Ala Arg
            20                  25                 30

His Gly Ser Cys Asn Tyr Arg Phe Pro Ala His Lys Cys Ile Cys Tyr
            35                  40                 45

Phe Pro Cys
        50

<210> SEQ ID NO 36
```

```
<211> LENGTH: 51
<212> TYPE: PRT
<213> ORGANISM: Artificial Sequence
<220> FEATURE:
<223> OTHER INFORMATION: Defensin like

<400> SEQUENCE: 36

Gln Lys Leu Cys Gln Lys Pro Ser Arg Thr Trp Ser Gly Val Cys Gly
1               5                   10                  15

Asn Ser Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Val Pro Cys
    50

<210> SEQ ID NO 37
<211> LENGTH: 51
<212> TYPE: PRT
<213> ORGANISM: Artificial Sequence
<220> FEATURE:
<223> OTHER INFORMATION: Defensin like

<400> SEQUENCE: 37

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Asn Leu Glu Gly Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 38
<211> LENGTH: 51
<212> TYPE: PRT
<213> ORGANISM: Artificial Sequence
<220> FEATURE:
<223> OTHER INFORMATION: Defensin like

<400> SEQUENCE: 38

Gln Lys Leu Cys Gln Arg Pro Ser Gly Thr Trp Ser Gly Val Cys Met
1               5                   10                  15

Asn Asn Asn Ala Cys Lys Asn Gln Cys Ile Arg Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 39
<211> LENGTH: 51
<212> TYPE: PRT
<213> ORGANISM: Artificial Sequence
<220> FEATURE:
<223> OTHER INFORMATION: Defensin like

<400> SEQUENCE: 39

Gln Lys Leu Cys Gln Arg Pro Ser Arg Thr Trp Ser Gly Val Cys Gly
1               5                   10                  15

Asn Asn Asn Ala Cys Lys Asn Gln Cys Ile Arg Leu Glu Lys Ala Arg
            20                  25                  30
```

His Gly Ser Cys Asn Tyr Arg Phe Pro Ala His Lys Cys Ile Cys Tyr
            35                  40                  45

Val Pro Cys
    50

<210> SEQ ID NO 40
<211> LENGTH: 51
<212> TYPE: PRT
<213> ORGANISM: Artificial Sequence
<220> FEATURE:
<223> OTHER INFORMATION: Defensin like

<400> SEQUENCE: 40

Gln Lys Leu Cys Glu Arg Ser Ser Arg Thr Trp Ser Gly Val Cys Gly
1               5                   10                  15

Asn Ser Asn Ala Cys Lys Asn Gln Cys Ile Arg Leu Glu Gly Ala Arg
            20                  25                  30

His Gly Ser Cys Asn Tyr Val Phe Pro Ala His Lys Cys Ile Cys Tyr
            35                  40                  45

Phe Pro Cys
    50

<210> SEQ ID NO 41
<211> LENGTH: 51
<212> TYPE: PRT
<213> ORGANISM: Artificial Sequence
<220> FEATURE:
<223> OTHER INFORMATION: Defensin like

<400> SEQUENCE: 41

Gln Lys Leu Cys Gln Arg Pro Ser Gly Thr Trp Ser Gly Val Cys Gly
1               5                   10                  15

Asn Ser Asn Ala Cys Lys Asn Gln Cys Ile Arg Leu Glu Gly Ala Arg
            20                  25                  30

His Gly Ser Cys Asn Tyr Arg Phe Pro Ala His Lys Cys Ile Cys Tyr
            35                  40                  45

Phe Pro Cys
    50

<210> SEQ ID NO 42
<211> LENGTH: 51
<212> TYPE: PRT
<213> ORGANISM: Artificial Sequence
<220> FEATURE:
<223> OTHER INFORMATION: Defensin like

<400> SEQUENCE: 42

Gln Lys Leu Cys Gln Arg Pro Ser Arg Thr Trp Ser Gly Val Cys Met
1               5                   10                  15

Asn Ser Asn Ala Cys Lys Asn Gln Cys Ile Arg Leu Glu Lys Ala Arg
            20                  25                  30

His Gly Ser Cys Asn Tyr Arg Phe Pro Ala His Lys Cys Ile Cys Tyr
            35                  40                  45

Phe Pro Cys
    50

<210> SEQ ID NO 43
<211> LENGTH: 51
<212> TYPE: PRT
<213> ORGANISM: Artificial Sequence
<220> FEATURE:

```
<223> OTHER INFORMATION: Defensin like

<400> SEQUENCE: 43

Gln Gln Leu Cys Gln Arg Pro Ser Arg Thr Trp Ser Gly Val Cys Met
1               5                   10                  15

Asn Asn Asn Ala Cys Lys Asn Gln Cys Ile Arg Leu Glu Gly Ala Arg
                20                  25                  30

His Gly Ser Cys Asn Tyr Arg Phe Pro Ala His Lys Cys Ile Cys Tyr
            35                  40                  45

Val Pro Cys
        50

<210> SEQ ID NO 44
<211> LENGTH: 51
<212> TYPE: PRT
<213> ORGANISM: Artificial Sequence
<220> FEATURE:
<223> OTHER INFORMATION: Defensin like

<400> SEQUENCE: 44

Gln Lys Leu Cys Glu Lys Pro Ser Arg Thr Trp Ser Gly Val Cys Gly
1               5                   10                  15

Asn Asn Asn Ala Cys Lys Asn Gln Cys Ile Arg Leu Glu Lys Ala Arg
                20                  25                  30

His Gly Ser Cys Asn Tyr Arg Phe Pro Ala His Lys Cys Ile Cys Tyr
            35                  40                  45

Val Pro Cys
        50

<210> SEQ ID NO 45
<211> LENGTH: 50
<212> TYPE: PRT
<213> ORGANISM: Artificial Sequence
<220> FEATURE:
<223> OTHER INFORMATION: Defensin like

<400> SEQUENCE: 45

Asn Leu Cys Glu Arg Ala Ser Leu Thr Trp Thr Gly Asn Cys Gly Asn
1               5                   10                  15

Thr Lys His Cys Asp Thr Gln Cys Lys Asn Trp Glu Gly Ala Lys His
                20                  25                  30

Gly Ala Cys His Val Arg Asn Gly Lys Trp Lys Cys Phe Cys Tyr Phe
            35                  40                  45

Asn Cys
    50

<210> SEQ ID NO 46
<211> LENGTH: 50
<212> TYPE: PRT
<213> ORGANISM: Artificial Sequence
<220> FEATURE:
<223> OTHER INFORMATION: Defensin like

<400> SEQUENCE: 46

Glu Leu Cys Glu Lys Ala Ser Lys Thr Trp Ser Gly Asn Cys Gly Asn
1               5                   10                  15

Thr Lys His Cys Asp Asn Gln Cys Arg Ser Trp Glu Gly Ala Ala His
                20                  25                  30

Gly Ala Cys His Lys Arg Ser Gly Lys Trp Lys Cys Phe Cys Tyr Phe
            35                  40                  45
```

```
Asn Cys
    50

<210> SEQ ID NO 47
<211> LENGTH: 50
<212> TYPE: PRT
<213> ORGANISM: Artificial Sequence
<220> FEATURE:
<223> OTHER INFORMATION: Defensin like

<400> SEQUENCE: 47

Asn Leu Cys Glu Arg Ala Ser Lys Thr Trp Ser Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 48
<211> LENGTH: 50
<212> TYPE: PRT
<213> ORGANISM: Artificial Sequence
<220> FEATURE:
<223> OTHER INFORMATION: Defensin like

<400> SEQUENCE: 48

Asn Leu Cys Glu Arg Ala Ser Lys Thr Trp Ser Gly Asn Cys Gly Asn
1               5                   10                  15

Thr Lys His Cys Asp Asp Gln Cys Lys Ser Trp Glu Gly Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 49
<211> LENGTH: 50
<212> TYPE: PRT
<213> ORGANISM: Artificial Sequence
<220> FEATURE:
<223> OTHER INFORMATION: Defensin like

<400> SEQUENCE: 49

Asn Leu Cys Glu Lys Ala Ser Lys Thr Trp Thr Gly Asn Cys Gly Asn
1               5                   10                  15

Thr Lys His Cys Asp Asn Gln Cys Lys Ser Trp Glu Gly Ala Ala His
            20                  25                  30

Gly Ala Cys His Val Arg Ser Gly Lys His Met Cys Phe Cys Tyr Phe
        35                  40                  45

Asn Cys
    50

<210> SEQ ID NO 50
<211> LENGTH: 50
<212> TYPE: PRT
<213> ORGANISM: Artificial Sequence
<220> FEATURE:
<223> OTHER INFORMATION: Defensin like

<400> SEQUENCE: 50
```

```
Lys Leu Cys Glu Arg Ala Ser Lys Thr Trp Ser Gly Asn Cys Gly Asn
1               5                   10                  15

Thr Lys His Cys Asp Asp Gln Cys Lys Asn Trp Glu Ser Ala Ala His
            20                  25                  30

Gly Ala Cys His Val Arg Ser Gly Asn His Lys Cys Phe Cys Tyr Phe
            35                  40                  45

Asn Cys
    50

<210> SEQ ID NO 51
<211> LENGTH: 50
<212> TYPE: PRT
<213> ORGANISM: Artificial Sequence
<220> FEATURE:
<223> OTHER INFORMATION: Defensin like

<400> SEQUENCE: 51

Asn Leu Cys Glu Lys Ala Ser Leu Thr Trp Thr Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Ser Gly Lys Trp Lys Cys Phe Cys Tyr Phe
            35                  40                  45

Asn Cys
    50

<210> SEQ ID NO 52
<211> LENGTH: 50
<212> TYPE: PRT
<213> ORGANISM: Artificial Sequence
<220> FEATURE:
<223> OTHER INFORMATION: Defensin like

<400> SEQUENCE: 52

Asn Leu Cys Glu Lys Ala Ser Leu Thr Trp Thr Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Asn Gly Asn His Lys Cys Phe Cys Tyr Phe
            35                  40                  45

Asn Cys
    50

<210> SEQ ID NO 53
<211> LENGTH: 50
<212> TYPE: PRT
<213> ORGANISM: Artificial Sequence
<220> FEATURE:
<223> OTHER INFORMATION: Defensin like

<400> SEQUENCE: 53

Glu Leu Cys Glu Arg Ala Ser Leu Thr Trp Thr Gly Asn Cys Gly Asn
1               5                   10                  15

Thr Lys His Cys Asp Thr Gln Cys Lys Asn Trp Glu Gly Ala Ala His
            20                  25                  30

Gly Ala Cys His Val Cys Ser Gly Lys His Lys Cys Phe Cys Tyr Phe
            35                  40                  45

Asn Cys
    50
```

<210> SEQ ID NO 54
<211> LENGTH: 50
<212> TYPE: PRT
<213> ORGANISM: Artificial Sequence
<220> FEATURE:
<223> OTHER INFORMATION: Defensin like

<400> SEQUENCE: 54

Asn Leu Cys Glu Lys Ala Ser Leu Thr Trp Ser Gly Asn Cys Gly Asn
1               5                   10                  15

Thr Lys His Cys Asp Asn Lys Cys Lys Asn Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 55
<211> LENGTH: 50
<212> TYPE: PRT
<213> ORGANISM: Artificial Sequence
<220> FEATURE:
<223> OTHER INFORMATION: Defensin like

<400> SEQUENCE: 55

Asn Leu Cys Glu Arg Ala Ser Leu Thr Trp Ser Gly Asn Cys Gly Asn
1               5                   10                  15

Thr Lys His Cys Asp Thr Gln Cys Lys Ser Trp Glu Ser Ala Lys His
            20                  25                  30

Gly Ala Cys His Val Arg Ser Gly Lys His Met Cys Phe Cys Tyr Phe
        35                  40                  45

Asn Cys
    50

<210> SEQ ID NO 56
<211> LENGTH: 50
<212> TYPE: PRT
<213> ORGANISM: Artificial Sequence
<220> FEATURE:
<223> OTHER INFORMATION: Defensin like

<400> SEQUENCE: 56

Asn Leu Cys Glu Lys Ala Ser Leu Thr Trp Ser Gly Asn Cys Gly Asn
1               5                   10                  15

Thr Arg His Cys Asp Thr Gln Cys Arg Ser Trp Glu Gly Ala Ala His
            20                  25                  30

Gly Ala Cys His Val Arg Ser Gly Asn His Lys Cys Phe Cys Tyr Phe
        35                  40                  45

Asn Cys
    50

<210> SEQ ID NO 57
<211> LENGTH: 50
<212> TYPE: PRT
<213> ORGANISM: Artificial Sequence
<220> FEATURE:
<223> OTHER INFORMATION: Defensin like

<400> SEQUENCE: 57

Lys Leu Cys Glu Arg Ala Ser Lys Thr Trp Ser Gly Asn Cys Gly Asn
1               5                   10                  15

Thr Lys His Cys Asp Asn Gln Cys Arg Ser Trp Glu Gly Ala Lys His

-continued

```
                    20                  25                  30
Gly Ala Cys His Val Arg Ser Gly Lys Trp Met Cys Phe Cys Tyr Phe
        35                  40                  45

Asn Cys
    50

<210> SEQ ID NO 58
<211> LENGTH: 50
<212> TYPE: PRT
<213> ORGANISM: Artificial Sequence
<220> FEATURE:
<223> OTHER INFORMATION: Defensin like

<400> SEQUENCE: 58

Asn Leu Cys Glu Lys Ala Ser Leu Thr Trp Ser Gly Asn Cys Gly Asn
1               5                   10                  15

Thr Lys His Cys Asp Asp Gln Cys Arg Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 59
<211> LENGTH: 50
<212> TYPE: PRT
<213> ORGANISM: Artificial Sequence
<220> FEATURE:
<223> OTHER INFORMATION: Defensin like

<400> SEQUENCE: 59

Glu Leu Cys Glu Lys Ala Ser Lys Thr Trp Ser Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 60
<211> LENGTH: 50
<212> TYPE: PRT
<213> ORGANISM: Artificial Sequence
<220> FEATURE:
<223> OTHER INFORMATION: Defensin like

<400> SEQUENCE: 60

Glu Leu Cys Glu Lys Ala Ser Lys Thr Trp Ser Gly Asn Cys Gly Asn
1               5                   10                  15

Thr Lys His Cys Asp Thr Lys Cys Lys Asn Trp Glu Gly Ala Lys His
            20                  25                  30

Gly Ala Cys His Lys Arg Asn Gly Lys Trp Met Cys Phe Cys Tyr Phe
        35                  40                  45

Asn Cys
    50

<210> SEQ ID NO 61
<211> LENGTH: 50
<212> TYPE: PRT
<213> ORGANISM: Artificial Sequence
```

```
<220> FEATURE:
<223> OTHER INFORMATION: Defensin like

<400> SEQUENCE: 61

Glu Leu Cys Glu Lys Ala Ser Lys Thr Trp Thr Gly Asn Cys Gly Asn
 1               5                  10                  15

Thr Lys His Cys Asp Thr Gln Cys Lys Asn Trp Glu Ser Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 62
<211> LENGTH: 50
<212> TYPE: PRT
<213> ORGANISM: Artificial Sequence
<220> FEATURE:
<223> OTHER INFORMATION: Defensin like

<400> SEQUENCE: 62

Asn Leu Cys Glu Arg Ala Ser Lys Thr Trp Thr Gly Asn Cys Gly Asn
 1               5                  10                  15

Thr Gly His Cys Asp Asn Lys Cys Lys Ser Trp Glu Gly Ala Lys His
            20                  25                  30

Gly Ala Cys His Val Arg Asn Gly Lys Trp Met Cys Phe Cys Tyr Phe
        35                  40                  45

Asn Cys
    50

<210> SEQ ID NO 63
<211> LENGTH: 50
<212> TYPE: PRT
<213> ORGANISM: Artificial Sequence
<220> FEATURE:
<223> OTHER INFORMATION: Defensin like

<400> SEQUENCE: 63

Asn Leu Cys Glu Lys Ala Ser Lys Thr Trp Ser Gly Asn Cys Gly Asn
 1               5                  10                  15

Thr Lys His Cys Asp Asp Gln Cys Arg Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 64
<211> LENGTH: 50
<212> TYPE: PRT
<213> ORGANISM: Artificial Sequence
<220> FEATURE:
<223> OTHER INFORMATION: Defensin like

<400> SEQUENCE: 64

Asn Leu Cys Glu Arg Ala Ser Lys Thr Trp Ser Gly Asn Cys Gly Asn
 1               5                  10                  15

Thr Lys His Cys Asp Thr Gln Cys Lys Asn Trp Glu Gly Ala Lys His
            20                  25                  30

Gly Ala Cys His Lys Arg Ser Gly Lys Trp Met Cys Phe Cys Tyr Phe
        35                  40                  45
```

Asn Cys
    50

<210> SEQ ID NO 65
<211> LENGTH: 50
<212> TYPE: PRT
<213> ORGANISM: Artificial Sequence
<220> FEATURE:
<223> OTHER INFORMATION: Defensin like

<400> SEQUENCE: 65

Glu Leu Cys Glu Lys Ala Ser Lys Thr Trp Thr Gly Asn Cys Gly Asn
 1               5                  10                  15

Thr Lys His Cys Asp Asn Gln Cys Lys Ser Trp Glu Gly Ala Ala His
            20                  25                  30

Gly Ala Cys His Lys Arg Ser Gly Lys Trp Met Cys Phe Cys Tyr Phe
        35                  40                  45

Asn Cys
    50

<210> SEQ ID NO 66
<211> LENGTH: 50
<212> TYPE: PRT
<213> ORGANISM: Artificial Sequence
<220> FEATURE:
<223> OTHER INFORMATION: Defensin like

<400> SEQUENCE: 66

Glu Leu Cys Glu Lys Ala Ser Lys Thr Trp Ser Gly Asn Cys Gly Asn
 1               5                  10                  15

Thr Lys His Cys Asp Asn Gln Cys Lys Ser Trp Glu Gly Ala Lys His
            20                  25                  30

Gly Ala Cys His Lys Arg Ser Gly Lys His Lys Cys Phe Cys Tyr Phe
        35                  40                  45

Asn Cys
    50

<210> SEQ ID NO 67
<211> LENGTH: 50
<212> TYPE: PRT
<213> ORGANISM: Artificial Sequence
<220> FEATURE:
<223> OTHER INFORMATION: Defensin like

<400> SEQUENCE: 67

Asn Leu Cys Glu Arg Ala Ser Lys Thr Trp Thr Gly Asn Cys Gly Asn
 1               5                  10                  15

Thr Lys His Cys Asp Thr Gln Cys Lys Asn Trp Glu Ser Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 68
<211> LENGTH: 50
<212> TYPE: PRT
<213> ORGANISM: Artificial Sequence
<220> FEATURE:
<223> OTHER INFORMATION: Defensin like

<400> SEQUENCE: 68

```
Asn Leu Cys Glu Arg Ala Ser Lys Thr Trp Ser Gly Asn Cys Gly Asn
1               5                   10                  15

Thr Lys His Cys Asp Thr Gln Cys Arg Asn Trp Glu Ser Ala Ala His
            20                  25                  30

Gly Ala Cys His Lys Arg Asn Gly Lys Trp Lys Cys Phe Cys Tyr Phe
            35                  40                  45

Asn Cys
    50
```

<210> SEQ ID NO 69
<211> LENGTH: 50
<212> TYPE: PRT
<213> ORGANISM: Artificial Sequence
<220> FEATURE:
<223> OTHER INFORMATION: Defensin like

<400> SEQUENCE: 69

```
Asn Leu Cys Glu Arg Ala Ser Lys Thr Trp Thr Gly Asn Cys Gly Asn
1               5                   10                  15

Thr Gly His Cys Asn Asn Gln Cys Arg Ser Trp Glu Gly Ala Lys His
            20                  25                  30

Gly Ala Cys His Val Arg Ser Gly Lys His Lys Cys Phe Cys Tyr Phe
            35                  40                  45

Asn Cys
    50
```

<210> SEQ ID NO 70
<211> LENGTH: 50
<212> TYPE: PRT
<213> ORGANISM: Artificial Sequence
<220> FEATURE:
<223> OTHER INFORMATION: Defensin like

<400> SEQUENCE: 70

```
Asn Leu Cys Glu Arg Ala Ser Lys Thr Trp Ser Gly Asn Cys Gly Asn
1               5                   10                  15

Thr Lys His Cys Asp Thr Gln Cys Arg Lys Trp Glu Gly Ala Lys His
            20                  25                  30

Gly Ala Cys His Lys Arg Asn Gly Lys Trp Met Cys Phe Cys Tyr Phe
            35                  40                  45

Asn Cys
    50
```

<210> SEQ ID NO 71
<211> LENGTH: 50
<212> TYPE: PRT
<213> ORGANISM: Artificial Sequence
<220> FEATURE:
<223> OTHER INFORMATION: Defensin like

<400> SEQUENCE: 71

```
Asn Leu Cys Glu Arg Ala Ser Lys Thr Trp Thr Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Lys Arg Asn Gly Lys Trp Lys Cys Phe Cys Tyr Phe
            35                  40                  45

Asn Cys
    50
```

<210> SEQ ID NO 72
<211> LENGTH: 50
<212> TYPE: PRT
<213> ORGANISM: Artificial Sequence
<220> FEATURE:
<223> OTHER INFORMATION: Defensin like

<400> SEQUENCE: 72

Asn Leu Cys Glu Arg Ala Ser Leu Thr Trp Thr Gly Asn Cys Gly Asn
 1               5                  10                  15

Thr Gly His Cys Asp Thr Lys Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 73
<211> LENGTH: 50
<212> TYPE: PRT
<213> ORGANISM: Artificial Sequence
<220> FEATURE:
<223> OTHER INFORMATION: Defensin like

<400> SEQUENCE: 73

Asn Leu Cys Glu Arg Ala Ser Lys Thr Trp Thr Gly Asn Cys Gly Asn
 1               5                  10                  15

Thr Lys His Cys Asp Thr Lys Cys Arg Ser Trp Glu Ser Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 74
<211> LENGTH: 50
<212> TYPE: PRT
<213> ORGANISM: Artificial Sequence
<220> FEATURE:
<223> OTHER INFORMATION: Defensin like

<400> SEQUENCE: 74

Asn Leu Cys Glu Lys Ala Ser Lys Thr Trp Thr Gly Asn Cys Gly Asn
 1               5                  10                  15

Thr Lys His Cys Asp Thr Gln Cys Lys Ser Trp Glu Gly Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 75
<211> LENGTH: 50
<212> TYPE: PRT
<213> ORGANISM: Artificial Sequence
<220> FEATURE:
<223> OTHER INFORMATION: Defensin like

<400> SEQUENCE: 75

Asn Leu Cys Glu Arg Ala Ser Lys Thr Trp Thr Gly Asn Cys Gly Asn
 1               5                  10                  15

```
Thr Lys His Cys Asp Thr Gln Cys Lys Ser Trp Glu Gly Ala Ala His
            20                  25                  30

Gly Ala Cys His Val Arg Ser Gly Lys His Lys Cys Phe Cys Tyr Phe
        35                  40                  45

Asn Cys
    50

<210> SEQ ID NO 76
<211> LENGTH: 50
<212> TYPE: PRT
<213> ORGANISM: Artificial Sequence
<220> FEATURE:
<223> OTHER INFORMATION: Defensin like

<400> SEQUENCE: 76

Asn Leu Cys Glu Lys Ala Ser Lys Thr Trp Thr Gly Asn Cys Gly Asn
 1               5                  10                  15

Thr Gly His Cys Asp Thr Gln Cys Arg Asn Trp Glu Gly Ala Lys His
            20                  25                  30

Gly Ala Cys His Lys Arg Asn Gly Lys His Lys Cys Phe Cys Tyr Phe
        35                  40                  45

Asn Cys
    50

<210> SEQ ID NO 77
<211> LENGTH: 50
<212> TYPE: PRT
<213> ORGANISM: Artificial Sequence
<220> FEATURE:
<223> OTHER INFORMATION: Defensin like

<400> SEQUENCE: 77

Glu Leu Cys Glu Lys Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Val Arg Ser Gly Lys Trp Lys Cys Phe Cys Tyr Phe
        35                  40                  45

Asn Cys
    50

<210> SEQ ID NO 78
<211> LENGTH: 50
<212> TYPE: PRT
<213> ORGANISM: Artificial Sequence
<220> FEATURE:
<223> OTHER INFORMATION: Defensin like

<400> SEQUENCE: 78

Asn Leu Cys Glu Arg Ala Ser Lys Thr Trp Thr Gly Asn Cys Gly Asn
 1               5                  10                  15

Thr Lys His Cys Asp Thr Gln Cys Lys Ser Trp Glu Ser Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 79
<211> LENGTH: 50
<212> TYPE: PRT
```

<213> ORGANISM: Artificial Sequence
<220> FEATURE:
<223> OTHER INFORMATION: Defensin like

<400> SEQUENCE: 79

Glu Leu Cys Glu Lys Ala Ser Leu Thr Trp Thr Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 80
<211> LENGTH: 50
<212> TYPE: PRT
<213> ORGANISM: Artificial Sequence
<220> FEATURE:
<223> OTHER INFORMATION: Defensin like

<400> SEQUENCE: 80

Asn Leu Cys Glu Lys Ala Ser Lys Thr Trp Thr Gly Asn Cys Gly Asn
1               5                   10                  15

Thr Lys His Cys Asp Asn Gln Cys Arg Asn Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 81
<211> LENGTH: 50
<212> TYPE: PRT
<213> ORGANISM: Artificial Sequence
<220> FEATURE:
<223> OTHER INFORMATION: Defensin like

<400> SEQUENCE: 81

Asn Leu Cys Glu Arg Ala Ser Lys Thr Trp Thr Gly Asn Cys Gly Asn
1               5                   10                  15

Thr Lys His Cys Asp Thr Gln Cys Lys Ile Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 82
<211> LENGTH: 50
<212> TYPE: PRT
<213> ORGANISM: Artificial Sequence
<220> FEATURE:
<223> OTHER INFORMATION: Defensin like

<400> SEQUENCE: 82

Asn Leu Cys Glu Lys Ala Ser Lys Thr Trp Thr Gly Asn Cys Gly Asn
1               5                   10                  15

Thr Lys His Cys Asp Asn Gln Cys Lys Asn Trp Glu Ser Ala Ala His
            20                  25                  30

Gly Ala Cys His Lys Arg Asn Gly Lys Trp Lys Cys Phe Cys Tyr Phe

```
                35                  40                  45
Asn Cys
    50

<210> SEQ ID NO 83
<211> LENGTH: 50
<212> TYPE: PRT
<213> ORGANISM: Artificial Sequence
<220> FEATURE:
<223> OTHER INFORMATION: Defensin like

<400> SEQUENCE: 83

Asn Leu Cys Glu Arg Ala Ser Leu Thr Trp Ser Gly Asn Cys Gly Asn
 1               5                  10                  15

Thr Lys His Cys Asp Asp Gln Cys Lys Ser Trp Glu Ser Ala Lys His
            20                  25                  30

Gly Ala Cys His Lys Arg Asn Gly Lys His Lys Cys Phe Cys Tyr Phe
        35                  40                  45

Asn Cys
    50

<210> SEQ ID NO 84
<211> LENGTH: 50
<212> TYPE: PRT
<213> ORGANISM: Artificial Sequence
<220> FEATURE:
<223> OTHER INFORMATION: Defensin like

<400> SEQUENCE: 84

Asn Leu Cys Glu Arg Ala Ser Lys Thr Trp Ser Gly Asn Cys Gly Asn
 1               5                  10                  15

Thr Lys His Cys Asp Asp Lys Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 85
<211> LENGTH: 50
<212> TYPE: PRT
<213> ORGANISM: Artificial Sequence
<220> FEATURE:
<223> OTHER INFORMATION: Defensin like

<400> SEQUENCE: 85

Glu Leu Cys Glu Arg Ala Ser Lys Thr Trp Thr Gly Asn Cys Gly Asn
 1               5                  10                  15

Thr Lys His Cys Asp Asn Gln Cys Arg Ser Trp Glu Ser Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 86
<211> LENGTH: 50
<212> TYPE: PRT
<213> ORGANISM: Artificial Sequence
<220> FEATURE:
<223> OTHER INFORMATION: Defensin like
```

-continued

<400> SEQUENCE: 86

Asn Leu Cys Glu Arg Ala Ser Lys Thr Trp Thr Gly Asn Cys Gly Asn
1               5                   10                  15

Thr Gly His Cys Asp Thr Gln Cys Lys Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 87
<211> LENGTH: 50
<212> TYPE: PRT
<213> ORGANISM: Artificial Sequence
<220> FEATURE:
<223> OTHER INFORMATION: Defensin like

<400> SEQUENCE: 87

Asn Leu Cys Glu Arg Ala Ser Lys Thr Trp Thr Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Ser Gly Lys His Met Cys Phe Cys Tyr Phe
        35                  40                  45

Asn Cys
    50

<210> SEQ ID NO 88
<211> LENGTH: 50
<212> TYPE: PRT
<213> ORGANISM: Artificial Sequence
<220> FEATURE:
<223> OTHER INFORMATION: Defensin like

<400> SEQUENCE: 88

Asn Leu Cys Glu Lys Ala Ser Lys Thr Trp Thr Gly Asn Cys Gly Asn
1               5                   10                  15

Thr Lys His Cys Asp Asp Gln Cys Lys Asn Trp Glu Gly Ala Lys His
            20                  25                  30

Gly Ala Cys His Lys Arg Asn Gly Lys Trp Met Cys Phe Cys Tyr Phe
        35                  40                  45

Asn Cys
    50

<210> SEQ ID NO 89
<211> LENGTH: 50
<212> TYPE: PRT
<213> ORGANISM: Artificial Sequence
<220> FEATURE:
<223> OTHER INFORMATION: Defensin like

<400> SEQUENCE: 89

Asn Leu Cys Glu Arg Ala Ser Lys Thr Trp Ser Gly Asn Cys Gly Asn
1               5                   10                  15

Thr Lys His Cys Asp Thr Gln Cys Lys Asn Trp Glu Ser Ala Lys His
            20                  25                  30

Gly Ala Cys His Lys Arg Asn Gly Lys His Lys Cys Phe Cys Tyr Phe
        35                  40                  45

Asn Cys
    50

<210> SEQ ID NO 90
<211> LENGTH: 50
<212> TYPE: PRT
<213> ORGANISM: Artificial Sequence
<220> FEATURE:
<223> OTHER INFORMATION: Defensin like

<400> SEQUENCE: 90

Glu Leu Cys Glu Arg Ala Ser Leu Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 91
<211> LENGTH: 50
<212> TYPE: PRT
<213> ORGANISM: Artificial Sequence
<220> FEATURE:
<223> OTHER INFORMATION: Defensin like

<400> SEQUENCE: 91

Lys Leu Cys Glu Arg Ala Ser Leu Thr Trp Ser Gly Asn Cys Gly Asn
1               5                   10                  15

Thr Lys His Cys Asp Thr Lys Cys Lys Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 92
<211> LENGTH: 50
<212> TYPE: PRT
<213> ORGANISM: Artificial Sequence
<220> FEATURE:
<223> OTHER INFORMATION: Defensin like

<400> SEQUENCE: 92

Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Ser Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 93
<211> LENGTH: 50
<212> TYPE: PRT
<213> ORGANISM: Artificial Sequence
<220> FEATURE:
<223> OTHER INFORMATION: Defensin like

<400> SEQUENCE: 93

Asn Leu Trp Glu Lys Ala Ser Leu Thr Trp Thr Gly Asn Cys Gly Asn
1               5                   10                  15

-continued

```
Thr Lys His Cys Asp Asn Gln Cys Lys Asn Trp Glu Ser Ala Ala His
            20                  25                  30

Gly Ala Cys His Lys Arg Ser Gly Lys Trp Met Cys Phe Cys Tyr Phe
        35                  40                  45

Asn Cys
    50

<210> SEQ ID NO 94
<211> LENGTH: 50
<212> TYPE: PRT
<213> ORGANISM: Artificial Sequence
<220> FEATURE:
<223> OTHER INFORMATION: Defensin like

<400> SEQUENCE: 94

Asn Leu Cys Glu Arg Ala Ser Lys Thr Trp Thr Gly Asn Cys Gly Asn
1               5                   10                  15

Thr Gly His Cys Asp Asn Lys Cys Lys Ser Trp Glu Gly Ala Lys His
            20                  25                  30

Gly Ala Cys His Val Arg Ser Gly Lys Trp Met Cys Phe Cys Tyr Phe
        35                  40                  45

Asn Cys
    50

<210> SEQ ID NO 95
<211> LENGTH: 50
<212> TYPE: PRT
<213> ORGANISM: Artificial Sequence
<220> FEATURE:
<223> OTHER INFORMATION: Defensin like

<400> SEQUENCE: 95

Glu Leu Cys Glu Arg Ala Ser Lys Thr Trp Ser Gly Asn Cys Gly Asn
1               5                   10                  15

Thr Lys His Cys Asp Thr Gln Cys Arg Asn Trp Glu Ser Ala Lys His
            20                  25                  30

Gly Ala Cys His Val Arg Ser Gly Lys Trp Lys Cys Phe Cys Tyr Phe
        35                  40                  45

Asn Cys
    50

<210> SEQ ID NO 96
<211> LENGTH: 50
<212> TYPE: PRT
<213> ORGANISM: Artificial Sequence
<220> FEATURE:
<223> OTHER INFORMATION: Defensin like

<400> SEQUENCE: 96

Lys Leu Cys Glu Lys Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Lys Arg Asn Gly Lys Trp Met Cys Phe Cys Tyr Phe
        35                  40                  45

Asn Cys
    50

<210> SEQ ID NO 97
<211> LENGTH: 50
```

```
<212> TYPE: PRT
<213> ORGANISM: Artificial Sequence
<220> FEATURE:
<223> OTHER INFORMATION: Defensin like

<400> SEQUENCE: 97

Asn Leu Cys Glu Lys Ala Ser Lys Thr Trp Thr Gly Asn Cys Gly Asn
1               5                   10                  15

Thr Gly His Cys Asp Asn Lys Cys Lys Ser Trp Glu Gly Ala Lys His
            20                  25                  30

Gly Ala Cys His Ile Arg Ser Gly Lys Trp Lys Cys Phe Cys Tyr Phe
        35                  40                  45

Asn Cys
    50

<210> SEQ ID NO 98
<211> LENGTH: 50
<212> TYPE: PRT
<213> ORGANISM: Artificial Sequence
<220> FEATURE:
<223> OTHER INFORMATION: Defensin like

<400> SEQUENCE: 98

Asn Leu Cys Glu Lys Ala Ser Leu Thr Trp Ser Gly Asn Cys Gly Asn
1               5                   10                  15

Thr Lys His Cys Asp Thr Gln Cys Lys Ser Trp Glu Ser Ala Ala His
            20                  25                  30

Gly Ala Cys His Lys Arg Ser Gly Lys His Lys Cys Phe Cys Tyr Phe
        35                  40                  45

Asn Cys
    50

<210> SEQ ID NO 99
<211> LENGTH: 50
<212> TYPE: PRT
<213> ORGANISM: Artificial Sequence
<220> FEATURE:
<223> OTHER INFORMATION: Defensin like

<400> SEQUENCE: 99

Asn Leu Cys Glu Arg Ala Ser Lys Thr Trp Ser Gly Asn Cys Gly Asn
1               5                   10                  15

Thr Lys His Cys Asp Thr Gln Cys Arg Ser Trp Glu Gly Ala Ala His
            20                  25                  30

Gly Ala Cys His Lys Arg Ser Gly Lys His Met Cys Phe Cys Tyr Phe
        35                  40                  45

Asn Cys
    50

<210> SEQ ID NO 100
<211> LENGTH: 50
<212> TYPE: PRT
<213> ORGANISM: Artificial Sequence
<220> FEATURE:
<223> OTHER INFORMATION: Defensin like

<400> SEQUENCE: 100

Glu Leu Cys Glu Lys Ala Ser Lys Thr Trp Ser Gly Asn Cys Gly Asn
1               5                   10                  15

Thr Lys His Cys Asp Thr Lys Cys Lys Ser Trp Glu Ser Ala Lys His
            20                  25                  30
```

Gly Ala Cys His Lys Arg Ser Gly Asn Trp Lys Cys Phe Cys Tyr Phe
         35                  40                  45

Asn Cys
     50

<210> SEQ ID NO 101
<211> LENGTH: 50
<212> TYPE: PRT
<213> ORGANISM: Artificial Sequence
<220> FEATURE:
<223> OTHER INFORMATION: Defensin like

<400> SEQUENCE: 101

Glu Leu Cys Glu Lys Ala Ser Lys Thr Trp Thr Gly Asn Cys Gly Asn
 1               5                  10                  15

Thr Lys His Cys Asp Thr Gln Cys Lys Ser Trp Glu Gly Ala Ala His
             20                  25                  30

Gly Ala Cys His Lys Arg Asn Gly Lys Trp Met Cys Phe Cys Tyr Phe
         35                  40                  45

Asn Cys
     50

<210> SEQ ID NO 102
<211> LENGTH: 50
<212> TYPE: PRT
<213> ORGANISM: Artificial Sequence
<220> FEATURE:
<223> OTHER INFORMATION: Defensin like

<400> SEQUENCE: 102

Asn Leu Cys Glu Arg Ala Ser Leu Thr Trp Thr Gly Asn Cys Gly Asn
 1               5                  10                  15

Thr Lys His Cys Asp Asn Gln Cys Lys Ser Trp Glu Gly Ala Ala His
             20                  25                  30

Gly Ala Cys His Val Arg Asn Gly Lys His Lys Cys Phe Cys Tyr Phe
         35                  40                  45

Asn Cys
     50

<210> SEQ ID NO 103
<211> LENGTH: 50
<212> TYPE: PRT
<213> ORGANISM: Artificial Sequence
<220> FEATURE:
<223> OTHER INFORMATION: Defensin like

<400> SEQUENCE: 103

Glu Leu Cys Glu Arg Ala Ser Lys Thr Trp Thr Gly Asn Cys Gly Asn
 1               5                  10                  15

Thr Lys His Cys Asp Thr Gln Cys Lys Ser Trp Glu Gly Ala Ala His
             20                  25                  30

Gly Ala Cys His Val Arg Ser Gly Lys His Lys Cys Phe Cys Tyr Phe
         35                  40                  45

Asn Cys
     50

<210> SEQ ID NO 104
<211> LENGTH: 50
<212> TYPE: PRT
<213> ORGANISM: Artificial Sequence
<220> FEATURE:
<223> OTHER INFORMATION: Defensin like

```
<400> SEQUENCE: 104

Glu Leu Cys Glu Lys Ala Ser Leu Thr Trp Ser Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Asn Gly Lys Trp Met Cys Phe Cys Tyr Phe
        35                  40                  45

Asn Cys
    50

<210> SEQ ID NO 105
<211> LENGTH: 50
<212> TYPE: PRT
<213> ORGANISM: Artificial Sequence
<220> FEATURE:
<223> OTHER INFORMATION: Defensin like

<400> SEQUENCE: 105

Asn Leu Cys Glu Arg Ala Ser Leu Thr Trp Thr Gly Asn Cys Gly Asn
1               5                   10                  15

Thr Gly His Cys Asp Thr Gln Cys Lys Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 106
<211> LENGTH: 50
<212> TYPE: PRT
<213> ORGANISM: Artificial Sequence
<220> FEATURE:
<223> OTHER INFORMATION: Defensin like

<400> SEQUENCE: 106

Asn Leu Cys Glu Lys Ala Ser Lys Thr Trp Ser Gly Asn Cys Gly Asn
1               5                   10                  15

Thr Lys His Cys Asp Thr Gln Cys Arg Asn Trp Glu Ser Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 107
<211> LENGTH: 50
<212> TYPE: PRT
<213> ORGANISM: Artificial Sequence
<220> FEATURE:
<223> OTHER INFORMATION: Defensin like

<400> SEQUENCE: 107

Asn Leu Cys Glu Arg Ala Ser Lys Thr Trp Ser Gly Asn Cys Gly Asn
1               5                   10                  15

Thr Lys His Cys Asp Asn Lys Cys Lys Asn Trp Glu Ser Ala Ala His
            20                  25                  30

Gly Ala Cys His Val Arg Asn Gly Lys His Met Cys Phe Cys Tyr Phe
        35                  40                  45

Asn Cys
```

50

<210> SEQ ID NO 108
<211> LENGTH: 50
<212> TYPE: PRT
<213> ORGANISM: Artificial Sequence
<220> FEATURE:
<223> OTHER INFORMATION: Defensin like

<400> SEQUENCE: 108

```
Asn Leu Cys Glu Arg Ala Ser Lys Thr Trp Ser Gly Asn Cys Gly Asn
 1               5                  10                  15

Thr Lys His Cys Asp Asp Gln Cys Arg Ser Trp Glu Gly Ala Lys His
            20                  25                  30

Gly Ala Cys His Lys Arg Ser Gly Lys Trp Met Cys Phe Cys Tyr Phe
        35                  40                  45

Asn Cys
    50
```

<210> SEQ ID NO 109
<211> LENGTH: 50
<212> TYPE: PRT
<213> ORGANISM: Artificial Sequence
<220> FEATURE:
<223> OTHER INFORMATION: Defensin like

<400> SEQUENCE: 109

```
Asn Leu Cys Glu Lys Ala Ser Lys Thr Trp Thr Gly Asn Cys Gly Asn
 1               5                  10                  15

Thr Lys His Cys Asp Thr Gln Cys Arg Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50
```

<210> SEQ ID NO 110
<211> LENGTH: 50
<212> TYPE: PRT
<213> ORGANISM: Artificial Sequence
<220> FEATURE:
<223> OTHER INFORMATION: Defensin like

<400> SEQUENCE: 110

```
Asn Leu Cys Glu Lys Ala Ser Lys Thr Trp Ser Gly Asn Cys Gly Asn
 1               5                  10                  15

Thr Lys His Cys Asp Thr Gln Cys Arg Asn Trp Glu Gly Ala Ala His
            20                  25                  30

Gly Ala Cys His Lys Arg Ser Gly Lys Trp Lys Cys Phe Cys Tyr Phe
        35                  40                  45

Asn Cys
    50
```

<210> SEQ ID NO 111
<211> LENGTH: 50
<212> TYPE: PRT
<213> ORGANISM: Artificial Sequence
<220> FEATURE:
<223> OTHER INFORMATION: Defensin like

<400> SEQUENCE: 111

```
Asn Leu Cys Glu Lys Ala Ser Lys Thr Trp Ser Gly Asn Cys Gly Asn
```

-continued

```
                 1               5                  10                  15
Thr Gly His Cys Asp Thr Gln Cys Lys Asn Trp Glu Gly Ala Lys His
                20                  25                  30

Gly Ala Cys His Val Arg Asn Gly Lys His Lys Cys Phe Cys Tyr Phe
                35                  40                  45

Asn Cys
    50

<210> SEQ ID NO 112
<211> LENGTH: 50
<212> TYPE: PRT
<213> ORGANISM: Artificial Sequence
<220> FEATURE:
<223> OTHER INFORMATION: Defensin like

<400> SEQUENCE: 112

Asn Leu Cys Glu Lys Ala Ser Lys Thr Trp Ser Gly Asn Cys Gly Asn
  1               5                  10                  15

Thr Lys His Cys Asp Thr Gln Cys Lys Ser Trp Glu Gly Ala Lys His
                20                  25                  30

Gly Ala Cys His Val Arg Asn Gly Lys His Lys Cys Phe Cys Tyr Phe
                35                  40                  45

Asn Cys
    50

<210> SEQ ID NO 113
<211> LENGTH: 50
<212> TYPE: PRT
<213> ORGANISM: Artificial Sequence
<220> FEATURE:
<223> OTHER INFORMATION: Defensin like

<400> SEQUENCE: 113

Asn Leu Cys Glu Lys Ala Ser Lys Thr Trp Thr Gly Asn Cys Gly Asn
  1               5                  10                  15

Thr Lys His Cys Asp Asn Gln Cys Arg Ser Trp Glu Gly Ala Ala His
                20                  25                  30

Gly Ala Cys His Lys Arg Asn Gly Lys Trp Lys Cys Phe Cys Tyr Phe
                35                  40                  45

Asn Cys
    50

<210> SEQ ID NO 114
<211> LENGTH: 50
<212> TYPE: PRT
<213> ORGANISM: Artificial Sequence
<220> FEATURE:
<223> OTHER INFORMATION: Defensin like

<400> SEQUENCE: 114

Asn Leu Cys Glu Lys Ala Ser Lys Thr Trp Thr Gly Asn Cys Gly Asn
  1               5                  10                  15

Thr Lys His Cys Asp Asn Gln Cys Lys Ser Trp Glu Gly Ala Lys His
                20                  25                  30

Gly Ala Cys His Lys Arg Ser Gly Lys Trp Lys Cys Phe Cys Tyr Phe
                35                  40                  45

Asn Cys
    50

<210> SEQ ID NO 115
```

```
<211> LENGTH: 50
<212> TYPE: PRT
<213> ORGANISM: Artificial Sequence
<220> FEATURE:
<223> OTHER INFORMATION: Defensin like

<400> SEQUENCE: 115

Asn Leu Cys Glu Arg Ala Ser Lys Thr Trp Ser Gly Asn Cys Gly Asn
1               5                   10                  15

Thr Lys His Cys Asp Thr Lys Cys Arg Ser Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 116
<211> LENGTH: 50
<212> TYPE: PRT
<213> ORGANISM: Artificial Sequence
<220> FEATURE:
<223> OTHER INFORMATION: Defensin like

<400> SEQUENCE: 116

Asn Leu Cys Glu Lys Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 117
<211> LENGTH: 50
<212> TYPE: PRT
<213> ORGANISM: Artificial Sequence
<220> FEATURE:
<223> OTHER INFORMATION: Defensin like

<400> SEQUENCE: 117

Asn Leu Cys Glu Arg Ala Ser Lys Thr Trp Ser Gly Asn Cys Gly Asn
1               5                   10                  15

Thr Lys His Cys Asp Thr Gln Cys Lys Ser Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 118
<211> LENGTH: 50
<212> TYPE: PRT
<213> ORGANISM: Artificial Sequence
<220> FEATURE:
<223> OTHER INFORMATION: Defensin like

<400> SEQUENCE: 118

Asn Leu Cys Glu Arg Ala Ser Lys Thr Trp Ser Gly Asn Cys Gly Asn
1               5                   10                  15

Thr Lys His Cys Asp Asn Gln Cys Lys Ser Trp Glu Gly Ala Ala His
            20                  25                  30
```

```
Gly Ala Cys His Lys Arg Ser Gly Lys His Lys Cys Phe Cys Tyr Phe
        35                  40                  45

Asn Cys
    50

<210> SEQ ID NO 119
<211> LENGTH: 50
<212> TYPE: PRT
<213> ORGANISM: Artificial Sequence
<220> FEATURE:
<223> OTHER INFORMATION: Defensin like

<400> SEQUENCE: 119

Asn Leu Cys Glu Arg Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 120
<211> LENGTH: 50
<212> TYPE: PRT
<213> ORGANISM: Artificial Sequence
<220> FEATURE:
<223> OTHER INFORMATION: Defensin like

<400> SEQUENCE: 120

Asn Leu Cys Glu Lys Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 121
<211> LENGTH: 50
<212> TYPE: PRT
<213> ORGANISM: Artificial Sequence
<220> FEATURE:
<223> OTHER INFORMATION: Defensin like

<400> SEQUENCE: 121

Asn Leu Cys Glu Arg Ala Ser Lys Thr Trp Thr Gly Asn Cys Gly Asn
1               5                   10                  15

Thr Lys His Cys Asp Thr Gln Cys Arg Ser Trp Glu Gly Ala Ala His
            20                  25                  30

Gly Ala Cys His Val Arg Ser Gly Lys His Lys Cys Phe Cys Tyr Phe
        35                  40                  45

Asn Cys
    50

<210> SEQ ID NO 122
<211> LENGTH: 50
<212> TYPE: PRT
<213> ORGANISM: Artificial Sequence
<220> FEATURE:
```

<223> OTHER INFORMATION: Defensin like

<400> SEQUENCE: 122

Asn Leu Cys Glu Arg Ala Ser Lys Thr Trp Thr Gly Asn Cys Gly Asn
1               5                   10                  15

Thr Lys His Cys Asp Asn Gln Cys Lys Ser Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 123
<211> LENGTH: 50
<212> TYPE: PRT
<213> ORGANISM: Artificial Sequence
<220> FEATURE:
<223> OTHER INFORMATION: Defensin like

<400> SEQUENCE: 123

Asn Leu Cys Glu Arg Ala Ser Lys Thr Trp Ser Gly Asn Cys Gly Asn
1               5                   10                  15

Thr Lys His Cys Asp Thr Gln Cys Lys Ser Trp Glu Gly Ala Ala His
            20                  25                  30

Gly Ala Cys His Val Arg Ser Gly Lys His Lys Cys Phe Cys Tyr Phe
        35                  40                  45

Asn Cys
    50

<210> SEQ ID NO 124
<211> LENGTH: 50
<212> TYPE: PRT
<213> ORGANISM: Artificial Sequence
<220> FEATURE:
<223> OTHER INFORMATION: Defensin like

<400> SEQUENCE: 124

Asn Leu Cys Glu Arg Ala Ser Lys Thr Trp Ser Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 125
<211> LENGTH: 50
<212> TYPE: PRT
<213> ORGANISM: Artificial Sequence
<220> FEATURE:
<223> OTHER INFORMATION: Defensin like

<400> SEQUENCE: 125

Asn Leu Cys Glu Arg Ala Ser Lys Thr Trp Thr Gly Asn Cys Gly Asn
1               5                   10                  15

Thr Lys His Cys Asp Thr Gln Cys Arg Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 126
<211> LENGTH: 50
<212> TYPE: PRT
<213> ORGANISM: Artificial Sequence
<220> FEATURE:
<223> OTHER INFORMATION: Defensin like

<400> SEQUENCE: 126

Asn Leu Cys Glu Arg Ala Ser Lys Thr Trp Thr Gly Asn Cys Gly Asn
1               5                   10                  15

Thr Lys His Cys Asp Thr Gln Cys Lys Asn Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 127
<211> LENGTH: 50
<212> TYPE: PRT
<213> ORGANISM: Artificial Sequence
<220> FEATURE:
<223> OTHER INFORMATION: Defensin like

<400> SEQUENCE: 127

Asn Leu Cys Glu Arg Ala Ser Lys Thr Trp Ser Gly Asn Cys Gly Asn
1               5                   10                  15

Thr Gly His Cys Asp Thr Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 128
<211> LENGTH: 50
<212> TYPE: PRT
<213> ORGANISM: Artificial Sequence
<220> FEATURE:
<223> OTHER INFORMATION: Defensin like

<400> SEQUENCE: 128

Asn Leu Cys Glu Arg Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 129
<211> LENGTH: 50
<212> TYPE: PRT
<213> ORGANISM: Artificial Sequence
<220> FEATURE:
<223> OTHER INFORMATION: Defensin like

<400> SEQUENCE: 129

```
Asn Leu Cys Glu Arg Ala Ser Lys Thr Trp Thr Gly Asn Cys Gly Asn
 1               5                  10                  15

Thr Lys His Cys Asp Asn Gln Cys Lys Ser Trp Glu Gly Ala Lys His
            20                  25                  30

Gly Ala Cys His Val Arg Ser Gly Lys His Lys Cys Phe Cys Tyr Phe
            35                  40                  45

Asn Cys
    50
```

<210> SEQ ID NO 130
<211> LENGTH: 50
<212> TYPE: PRT
<213> ORGANISM: Artificial Sequence
<220> FEATURE:
<223> OTHER INFORMATION: Defensin like

<400> SEQUENCE: 130

```
Asn Leu Cys Glu Lys Ala Ser Lys Thr Trp Ser Gly Asn Cys Gly Asn
 1               5                  10                  15

Thr Lys His Cys Asp Thr Lys Cys Arg Asn Trp Glu Gly Ala Lys His
            20                  25                  30

Gly Ala Cys His Val Arg Asn Gly Lys Trp Met Cys Phe Cys Tyr Phe
            35                  40                  45

Asn Cys
    50
```

<210> SEQ ID NO 131
<211> LENGTH: 50
<212> TYPE: PRT
<213> ORGANISM: Artificial Sequence
<220> FEATURE:
<223> OTHER INFORMATION: Defensin like

<400> SEQUENCE: 131

```
Asn Leu Cys Glu Arg Ala Ser Lys Thr Trp Ser Gly Asn Cys Gly Asn
 1               5                  10                  15

Thr Lys His Cys Asp Asn Gln Cys Arg Asn Trp Glu Gly Ala Lys His
            20                  25                  30

Gly Ala Cys His Val Arg Asn Gly Lys Trp Lys Cys Phe Cys Tyr Phe
            35                  40                  45

Asn Cys
    50
```

<210> SEQ ID NO 132
<211> LENGTH: 50
<212> TYPE: PRT
<213> ORGANISM: Artificial Sequence
<220> FEATURE:
<223> OTHER INFORMATION: Defensin like

<400> SEQUENCE: 132

```
Asn Leu Cys Glu Arg Ala Ser Lys Thr Trp Ser Gly Asn Cys Gly Asn
 1               5                  10                  15

Thr Gly His Cys Asp Thr Gln Cys Arg Ser Trp Glu Gly Ala Lys His
            20                  25                  30

Gly Ala Cys His Val Arg Asn Gly Lys His Lys Cys Phe Cys Tyr Phe
            35                  40                  45

Asn Cys
    50
```

```
<210> SEQ ID NO 133
<211> LENGTH: 50
<212> TYPE: PRT
<213> ORGANISM: Artificial Sequence
<220> FEATURE:
<223> OTHER INFORMATION: Defensin like

<400> SEQUENCE: 133

Asn Leu Cys Glu Arg Ala Ser Lys Thr Trp Ser Gly Asn Cys Gly Asn
 1               5                  10                  15

Thr Lys His Cys Asp Asn Gln Cys Arg Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 134
<211> LENGTH: 50
<212> TYPE: PRT
<213> ORGANISM: Artificial Sequence
<220> FEATURE:
<223> OTHER INFORMATION: Defensin like

<400> SEQUENCE: 134

Asn Leu Cys Glu Lys Ala Ser Lys Thr Trp Thr Gly Asn Cys Gly Asn
 1               5                  10                  15

Thr Lys His Cys Asp Thr Gln Cys Arg Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 135
<211> LENGTH: 50
<212> TYPE: PRT
<213> ORGANISM: Artificial Sequence
<220> FEATURE:
<223> OTHER INFORMATION: Defensin like

<400> SEQUENCE: 135

Asn Leu Cys Glu Arg Ala Ser Lys Thr Trp Thr Gly Asn Cys Gly Asn
 1               5                  10                  15

Thr Lys His Cys Asp Thr Gln Cys Arg Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 136
<211> LENGTH: 50
<212> TYPE: PRT
<213> ORGANISM: Artificial Sequence
<220> FEATURE:
<223> OTHER INFORMATION: Defensin like

<400> SEQUENCE: 136

Asn Leu Cys Glu Arg Ala Ser Lys Thr Trp Ser Gly Asn Cys Gly Asn
 1               5                  10                  15

Thr Lys His Cys Asp Asn Gln Cys Arg Ser Trp Glu Gly Ala Lys His
```

-continued

```
                20                  25                  30
Gly Ala Cys His Lys Arg Asn Gly Lys Trp Lys Cys Tyr Phe
        35                  40                  45
Asn Cys
    50

<210> SEQ ID NO 137
<211> LENGTH: 50
<212> TYPE: PRT
<213> ORGANISM: Artificial Sequence
<220> FEATURE:
<223> OTHER INFORMATION: Defensin like

<400> SEQUENCE: 137

Asn Leu Cys Glu Lys Ala Ser Lys Thr Trp Ser Gly Asn Cys Gly Asn
  1               5                  10                  15

Thr Lys His Cys Asp Thr Gln Cys Lys Ser Trp Glu Gly Ala Ala His
                20                  25                  30

Gly Ala Cys His Val Arg Ser Gly Lys His Lys Cys Phe Cys Tyr Phe
        35                  40                  45

Asn Cys
    50

<210> SEQ ID NO 138
<211> LENGTH: 50
<212> TYPE: PRT
<213> ORGANISM: Artificial Sequence
<220> FEATURE:
<223> OTHER INFORMATION: Defensin like

<400> SEQUENCE: 138

Asn Leu Cys Glu Arg Ala Ser Lys Thr Trp Ser Gly Asn Cys Gly Asn
  1               5                  10                  15

Thr Lys His Cys Asp Asn Gln Cys Lys Ser Trp Glu Gly Ala Lys His
                20                  25                  30

Gly Ala Cys His Val Arg Asn Gly Lys His Met Cys Phe Cys Tyr Phe
        35                  40                  45

Asn Cys
    50

<210> SEQ ID NO 139
<211> LENGTH: 50
<212> TYPE: PRT
<213> ORGANISM: Artificial Sequence
<220> FEATURE:
<223> OTHER INFORMATION: Defensin like

<400> SEQUENCE: 139

Asn Leu Cys Glu Lys Ala Ser Lys Thr Trp Thr Gly Asn Cys Gly Asn
  1               5                  10                  15

Thr Lys His Cys Asp Asn Gln Cys Lys Asn Trp Glu Gly Ala Lys His
                20                  25                  30

Gly Ala Cys His Lys Arg Ser Gly Lys Trp Lys Cys Phe Cys Tyr Phe
        35                  40                  45

Asn Cys
    50

<210> SEQ ID NO 140
<211> LENGTH: 50
<212> TYPE: PRT
<213> ORGANISM: Artificial Sequence
```

```
<220> FEATURE:
<223> OTHER INFORMATION: Defensin like

<400> SEQUENCE: 140

Asn Leu Cys Glu Lys Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 141
<211> LENGTH: 50
<212> TYPE: PRT
<213> ORGANISM: Artificial Sequence
<220> FEATURE:
<223> OTHER INFORMATION: Defensin like

<400> SEQUENCE: 141

Asn Leu Cys Glu Arg Ala Ser Lys Thr Trp Ser Gly Asn Cys Gly Asn
 1               5                  10                  15

Thr Gly His Cys Asp Thr Gln Cys Arg Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 142
<211> LENGTH: 50
<212> TYPE: PRT
<213> ORGANISM: Artificial Sequence
<220> FEATURE:
<223> OTHER INFORMATION: Defensin like

<400> SEQUENCE: 142

Asn Leu Cys Glu Lys Ala Ser Lys Thr Trp Ser Gly Asn Cys Gly Asn
 1               5                  10                  15

Thr Lys His Cys Asp Asn Gln Cys Arg Ser Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 143
<211> LENGTH: 50
<212> TYPE: PRT
<213> ORGANISM: Artificial Sequence
<220> FEATURE:
<223> OTHER INFORMATION: Defensin like

<400> SEQUENCE: 143

Asn Leu Cys Glu Lys Ala Ser Lys Thr Trp Ser Gly Asn Cys Gly Asn
 1               5                  10                  15

Thr Gly His Cys Asp Asn Gln Cys Lys Ser Trp Glu Gly Ala Ala His
            20                  25                  30

Gly Ala Cys His Val Arg Asn Gly Lys His Lys Cys Phe Cys Tyr Phe
        35                  40                  45
```

```
<210> SEQ ID NO 144
<211> LENGTH: 50
<212> TYPE: PRT
<213> ORGANISM: Artificial Sequence
<220> FEATURE:
<223> OTHER INFORMATION: Defensin like

<400> SEQUENCE: 144

Asn Leu Cys Glu Arg Ala Ser Lys Thr Trp Ser Gly Asn Cys Gly Asn
 1               5                  10                  15

Thr Lys His Cys Asp Asn Gln Cys Arg Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 145
<211> LENGTH: 50
<212> TYPE: PRT
<213> ORGANISM: Artificial Sequence
<220> FEATURE:
<223> OTHER INFORMATION: Defensin like

<400> SEQUENCE: 145

Asn Leu Cys Glu Arg Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 146
<211> LENGTH: 50
<212> TYPE: PRT
<213> ORGANISM: Artificial Sequence
<220> FEATURE:
<223> OTHER INFORMATION: Defensin like

<400> SEQUENCE: 146

Asn Leu Cys Glu Lys Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 147
<211> LENGTH: 50
<212> TYPE: PRT
<213> ORGANISM: Artificial Sequence
<220> FEATURE:
<223> OTHER INFORMATION: Defensin like

<400> SEQUENCE: 147
```

-continued

Asn Leu Cys Glu Arg Ala Ser Lys Thr Trp Ser Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Asn Gly Lys Trp Lys Cys Phe Cys Tyr Phe
            35                  40                  45

Asn Cys
    50

<210> SEQ ID NO 148
<211> LENGTH: 50
<212> TYPE: PRT
<213> ORGANISM: Artificial Sequence
<220> FEATURE:
<223> OTHER INFORMATION: Defensin like

<400> SEQUENCE: 148

Asn Leu Cys Glu Arg Ala Ser Lys Thr Trp Thr Gly Asn Cys Gly Asn
1               5                   10                  15

Thr Lys His Cys Asp Asn Gln Cys Arg Ser Trp Glu Gly Ala Ala His
            20                  25                  30

Gly Ala Cys His Lys Arg Asn Gly Lys Trp Lys Cys Phe Cys Tyr Phe
            35                  40                  45

Asn Cys
    50

<210> SEQ ID NO 149
<211> LENGTH: 50
<212> TYPE: PRT
<213> ORGANISM: Artificial Sequence
<220> FEATURE:
<223> OTHER INFORMATION: Defensin like

<400> SEQUENCE: 149

Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Val Arg Asn Gly Lys Trp Lys Cys Phe Cys Tyr Phe
            35                  40                  45

Asn Cys
    50

<210> SEQ ID NO 150
<211> LENGTH: 50
<212> TYPE: PRT
<213> ORGANISM: Artificial Sequence
<220> FEATURE:
<223> OTHER INFORMATION: Defensin like

<400> SEQUENCE: 150

Asn Leu Cys Glu Arg Ala Ser Lys Thr Trp Thr Gly Asn Cys Gly Asn
1               5                   10                  15

Thr Lys His Cys Asp Asn Gln Cys Lys Asn Trp Glu Gly Ala Lys His
            20                  25                  30

Gly Ala Cys His Val Arg Asn Gly Lys His Lys Cys Phe Cys Tyr Phe
            35                  40                  45

Asn Cys
    50

```
<210> SEQ ID NO 151
<211> LENGTH: 50
<212> TYPE: PRT
<213> ORGANISM: Artificial Sequence
<220> FEATURE:
<223> OTHER INFORMATION: Defensin like

<400> SEQUENCE: 151
```

Asn Leu Cys Glu Arg Ala Ser Lys Thr Trp Ser Gly Asn Cys Gly Asn
 1               5                  10                  15

Thr Lys His Cys Asp Thr Gln Cys Arg Asn Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

```
<210> SEQ ID NO 152
<211> LENGTH: 50
<212> TYPE: PRT
<213> ORGANISM: Artificial Sequence
<220> FEATURE:
<223> OTHER INFORMATION: Defensin like

<400> SEQUENCE: 152
```

Asn Leu Cys Glu Lys Ala Ser Lys Thr Trp Ser Gly Asn Cys Gly Asn
 1               5                  10                  15

Thr Lys His Cys Asp Thr Gln Cys Arg Asn Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

```
<210> SEQ ID NO 153
<211> LENGTH: 50
<212> TYPE: PRT
<213> ORGANISM: Artificial Sequence
<220> FEATURE:
<223> OTHER INFORMATION: Defensin like

<400> SEQUENCE: 153
```

Asn Leu Cys Glu Arg Ala Ser Lys Thr Trp Ser Gly Asn Cys Gly Asn
 1               5                  10                  15

Thr Lys His Cys Asp Thr Gln Cys Arg Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

```
<210> SEQ ID NO 154
<211> LENGTH: 50
<212> TYPE: PRT
<213> ORGANISM: Artificial Sequence
<220> FEATURE:
<223> OTHER INFORMATION: Defensin like

<400> SEQUENCE: 154
```

Asn Leu Cys Glu Lys Ala Ser Lys Thr Trp Thr Gly Asn Cys Gly Asn
 1               5                  10                  15

-continued

Thr Lys His Cys Asp Thr Gln Cys Lys Asn Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 155
<211> LENGTH: 50
<212> TYPE: PRT
<213> ORGANISM: Artificial Sequence
<220> FEATURE:
<223> OTHER INFORMATION: Defensin like

<400> SEQUENCE: 155

Asn Leu Cys Glu Arg Ala Ser Lys Thr Trp Thr Gly Asn Cys Gly Asn
 1               5                  10                  15

Thr Lys His Cys Asp Asn Gln Cys Arg Asn Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 156
<211> LENGTH: 50
<212> TYPE: PRT
<213> ORGANISM: Artificial Sequence
<220> FEATURE:
<223> OTHER INFORMATION: Defensin like

<400> SEQUENCE: 156

Asn Leu Cys Glu Arg Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 157
<211> LENGTH: 50
<212> TYPE: PRT
<213> ORGANISM: Artificial Sequence
<220> FEATURE:
<223> OTHER INFORMATION: Defensin like

<400> SEQUENCE: 157

Asn Leu Cys Glu Arg Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 158
<211> LENGTH: 50
<212> TYPE: PRT

```
<213> ORGANISM: Artificial Sequence
<220> FEATURE:
<223> OTHER INFORMATION: Defensin like

<400> SEQUENCE: 158

Asn Leu Cys Glu Arg Ala Ser Lys Thr Trp Ser Gly Asn Cys Gly Asn
1               5                   10                  15

Thr Lys His Cys Asp Thr Gln Cys Lys Ser Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 159
<211> LENGTH: 50
<212> TYPE: PRT
<213> ORGANISM: Artificial Sequence
<220> FEATURE:
<223> OTHER INFORMATION: Defensin like

<400> SEQUENCE: 159

Asn Leu Cys Glu Arg Ala Ser Lys Thr Trp Ser Gly Asn Cys Gly Asn
1               5                   10                  15

Thr Lys His Cys Asp Asn Gln Cys Lys Asn Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 160
<211> LENGTH: 50
<212> TYPE: PRT
<213> ORGANISM: Artificial Sequence
<220> FEATURE:
<223> OTHER INFORMATION: Defensin like

<400> SEQUENCE: 160

Asn Leu Cys Glu Lys Ala Ser Lys Thr Trp Thr Gly Asn Cys Gly Asn
1               5                   10                  15

Thr Lys His Cys Asp Asn Gln Cys Arg Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 161
<211> LENGTH: 50
<212> TYPE: PRT
<213> ORGANISM: Artificial Sequence
<220> FEATURE:
<223> OTHER INFORMATION: Defensin like

<400> SEQUENCE: 161

Asn Leu Cys Glu Lys Ala Ser Lys Thr Trp Thr Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Val Arg Asn Gly Lys Trp Lys Cys Phe Cys Tyr Phe
```

```
                35                  40                  45
Asn Cys
    50

<210> SEQ ID NO 162
<211> LENGTH: 50
<212> TYPE: PRT
<213> ORGANISM: Artificial Sequence
<220> FEATURE:
<223> OTHER INFORMATION: Defensin like

<400> SEQUENCE: 162

Asn Leu Cys Glu Lys Ala Ser Lys Thr Trp Thr Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 163
<211> LENGTH: 50
<212> TYPE: PRT
<213> ORGANISM: Artificial Sequence
<220> FEATURE:
<223> OTHER INFORMATION: Defensin like

<400> SEQUENCE: 163

Asn Leu Cys Glu Arg Ala Ser Lys Thr Trp Thr Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 164
<211> LENGTH: 50
<212> TYPE: PRT
<213> ORGANISM: Artificial Sequence
<220> FEATURE:
<223> OTHER INFORMATION: Defensin like

<400> SEQUENCE: 164

Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 165
<211> LENGTH: 50
<212> TYPE: PRT
<213> ORGANISM: Artificial Sequence
<220> FEATURE:
<223> OTHER INFORMATION: Defensin like
```

```
<400> SEQUENCE: 165

Asn Leu Cys Glu Arg Ala Ser Lys Thr Trp Ser Gly Asn Cys Gly Asn
 1               5                  10                  15

Thr Lys Asn Cys Asp Asn Gln Cys Arg Asn Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 166
<211> LENGTH: 50
<212> TYPE: PRT
<213> ORGANISM: Artificial Sequence
<220> FEATURE:
<223> OTHER INFORMATION: Defensin like

<400> SEQUENCE: 166

Asn Leu Cys Glu Arg Ala Ser Lys Thr Trp Thr Gly Asn Cys Gly Asn
 1               5                  10                  15

Thr Lys His Cys Asp Asn Gln Cys Lys Ser Trp Glu Gly Ala Ala His
            20                  25                  30

Gly Ala Cys His Val Arg Ser Gly Lys His Lys Cys Phe Cys Tyr Phe
        35                  40                  45

Asn Cys
    50

<210> SEQ ID NO 167
<211> LENGTH: 50
<212> TYPE: PRT
<213> ORGANISM: Artificial Sequence
<220> FEATURE:
<223> OTHER INFORMATION: Defensin like

<400> SEQUENCE: 167

Asn Leu Cys Glu Arg Ala Ser Lys Thr Trp Ser Gly Asn Cys Gly Asn
 1               5                  10                  15

Thr Lys His Cys Asp Asn Gln Cys Arg Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 168
<211> LENGTH: 50
<212> TYPE: PRT
<213> ORGANISM: Artificial Sequence
<220> FEATURE:
<223> OTHER INFORMATION: Defensin like

<400> SEQUENCE: 168

Asn Leu Cys Glu Arg Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50
```

<210> SEQ ID NO 169
<211> LENGTH: 50
<212> TYPE: PRT
<213> ORGANISM: Artificial Sequence
<220> FEATURE:
<223> OTHER INFORMATION: Defensin like

<400> SEQUENCE: 169

Asn Leu Cys Glu Arg Ala Ser Lys Thr Trp Thr Gly Asn Cys Gly Asn
1               5                   10                  15

Thr Lys His Cys Asp Thr Gln Cys Arg Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 170
<211> LENGTH: 50
<212> TYPE: PRT
<213> ORGANISM: Artificial Sequence
<220> FEATURE:
<223> OTHER INFORMATION: Defensin like

<400> SEQUENCE: 170

Asn Leu Cys Glu Lys Ala Ser Lys Thr Trp Ser Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 171
<211> LENGTH: 50
<212> TYPE: PRT
<213> ORGANISM: Artificial Sequence
<220> FEATURE:
<223> OTHER INFORMATION: Defensin like

<400> SEQUENCE: 171

Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 172
<211> LENGTH: 50
<212> TYPE: PRT
<213> ORGANISM: Artificial Sequence
<220> FEATURE:
<223> OTHER INFORMATION: Defensin like

<400> SEQUENCE: 172

Asn Leu Cys Glu Arg Ala Ser Lys Thr Trp Thr Gly Asn Cys Gly Asn
1               5                   10                  15

```
Thr Lys His Cys Asp Asn Gln Cys Lys Asn Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 173
<211> LENGTH: 50
<212> TYPE: PRT
<213> ORGANISM: Artificial Sequence
<220> FEATURE:
<223> OTHER INFORMATION: Defensin like

<400> SEQUENCE: 173

Asn Leu Cys Glu Lys Ala Ser Lys Thr Trp Ser Gly Asn Cys Gly Asn
1               5                   10                  15

Thr Lys His Cys Asp Asn Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 174
<211> LENGTH: 50
<212> TYPE: PRT
<213> ORGANISM: Artificial Sequence
<220> FEATURE:
<223> OTHER INFORMATION: Defensin like

<400> SEQUENCE: 174

Asn Leu Cys Glu Arg Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 175
<211> LENGTH: 50
<212> TYPE: PRT
<213> ORGANISM: Artificial Sequence
<220> FEATURE:
<223> OTHER INFORMATION: Defensin like

<400> SEQUENCE: 175

Asn Leu Cys Glu Lys Ala Ser Lys Thr Trp Thr Gly Asn Cys Gly Asn
1               5                   10                  15

Thr Lys His Cys Asp Asn Gln Cys Arg Asn Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 176
<211> LENGTH: 50
```

```
<212> TYPE: PRT
<213> ORGANISM: Artificial Sequence
<220> FEATURE:
<223> OTHER INFORMATION: Defensin like

<400> SEQUENCE: 176

Asn Leu Cys Glu Arg Ala Ser Lys Thr Trp Ser Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 177
<211> LENGTH: 50
<212> TYPE: PRT
<213> ORGANISM: Artificial Sequence
<220> FEATURE:
<223> OTHER INFORMATION: Defensin like

<400> SEQUENCE: 177

Asn Leu Cys Glu Arg Ala Ser Lys Thr Trp Ser Gly Asn Cys Gly Asn
1               5                   10                  15

Thr Lys His Cys Asp Thr Gln Cys Lys Asn Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 178
<211> LENGTH: 50
<212> TYPE: PRT
<213> ORGANISM: Artificial Sequence
<220> FEATURE:
<223> OTHER INFORMATION: Defensin like

<400> SEQUENCE: 178

Asn Leu Cys Glu Arg Ala Ser Lys Thr Trp Thr Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 179
<211> LENGTH: 50
<212> TYPE: PRT
<213> ORGANISM: Artificial Sequence
<220> FEATURE:
<223> OTHER INFORMATION: Defensin like

<400> SEQUENCE: 179

Asn Leu Cys Glu Arg Ala Ser Lys Thr Trp Ser Gly Asn Cys Gly Asn
1               5                   10                  15

Thr Lys His Cys Asp Asn Gln Cys Arg Asn Trp Glu Gly Ala Ala His
            20                  25                  30
```

-continued

```
Gly Ala Cys His Val Arg Asn Gly Lys His Lys Cys Phe Cys Tyr Phe
        35                  40                  45

Asn Cys
    50

<210> SEQ ID NO 180
<211> LENGTH: 50
<212> TYPE: PRT
<213> ORGANISM: Artificial Sequence
<220> FEATURE:
<223> OTHER INFORMATION: Defensin like

<400> SEQUENCE: 180

Asn Leu Cys Glu Arg Ala Ser Lys Thr Trp Ser Gly Asn Cys Gly Asn
1               5                   10                  15

Thr Lys His Cys Asp Asn Gln Cys Lys Asn Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 181
<211> LENGTH: 50
<212> TYPE: PRT
<213> ORGANISM: Artificial Sequence
<220> FEATURE:
<223> OTHER INFORMATION: Defensin like

<400> SEQUENCE: 181

Asn Leu Cys Glu Arg Ala Ser Lys Thr Trp Ser Gly Asn Cys Gly Asn
1               5                   10                  15

Thr Lys His Cys Asp Asn Gln Cys Lys Ser Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 182
<211> LENGTH: 50
<212> TYPE: PRT
<213> ORGANISM: Artificial Sequence
<220> FEATURE:
<223> OTHER INFORMATION: Defensin like

<400> SEQUENCE: 182

Asn Leu Cys Glu Arg Ala Ser Lys Thr Trp Thr Gly Asn Cys Gly Asn
1               5                   10                  15

Thr Lys His Cys Asp Thr Gln Cys Arg Ser Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 183
<211> LENGTH: 50
<212> TYPE: PRT
<213> ORGANISM: Artificial Sequence
<220> FEATURE:
<223> OTHER INFORMATION: Defensin like
```

```
<400> SEQUENCE: 183

Asn Leu Cys Glu Arg Ala Ser Lys Thr Trp Ser Gly Asn Cys Gly Asn
 1               5                  10                  15

Thr Lys His Cys Asp Thr Gln Cys Arg Asn Trp Glu Gly Ala Lys His
             20                  25                  30

Gly Ala Cys His Val Arg Asn Gly Lys His Lys Cys Phe Cys Tyr Phe
         35                  40                  45

Asn Cys
     50

<210> SEQ ID NO 184
<211> LENGTH: 50
<212> TYPE: PRT
<213> ORGANISM: Artificial Sequence
<220> FEATURE:
<223> OTHER INFORMATION: Defensin like

<400> SEQUENCE: 184

Asn Leu Cys Glu Lys Ala Ser Lys Thr Trp Ser Gly Asn Cys Gly Asn
 1               5                  10                  15

Thr Lys His Cys Asp Asn Gln Cys Arg Asn Trp Glu Gly Ala Ala His
             20                  25                  30

Gly Ala Cys His Val Arg Asn Gly Lys His Lys Cys Phe Cys Tyr Phe
         35                  40                  45

Asn Cys
     50

<210> SEQ ID NO 185
<211> LENGTH: 50
<212> TYPE: PRT
<213> ORGANISM: Artificial Sequence
<220> FEATURE:
<223> OTHER INFORMATION: Defensin like

<400> SEQUENCE: 185

Asn Leu Cys Glu Arg Ala Ser Lys Thr Trp Thr Gly Asn Cys Gly Asn
 1               5                  10                  15

Thr Lys His Cys Asp Asn Gln Cys Arg Ser Trp Glu Gly Ala Ala His
             20                  25                  30

Gly Ala Cys His Val Arg Asn Gly Lys His Lys Cys Phe Cys Tyr Phe
         35                  40                  45

Asn Cys
     50

<210> SEQ ID NO 186
<211> LENGTH: 50
<212> TYPE: PRT
<213> ORGANISM: Artificial Sequence
<220> FEATURE:
<223> OTHER INFORMATION: Defensin like

<400> SEQUENCE: 186

Asn Leu Cys Glu Lys Ala Ser Lys Thr Trp Thr Gly Asn Cys Gly Asn
 1               5                  10                  15

Thr Lys His Cys Asp Thr Gln Cys Lys Asn Trp Glu Gly Ala Lys His
             20                  25                  30

Gly Ala Cys His Val Arg Asn Gly Lys Trp Lys Cys Phe Cys Tyr Phe
         35                  40                  45

Asn Cys
```

50

<210> SEQ ID NO 187
<211> LENGTH: 50
<212> TYPE: PRT
<213> ORGANISM: Artificial Sequence
<220> FEATURE:
<223> OTHER INFORMATION: Defensin like

<400> SEQUENCE: 187

Asn Leu Cys Glu Lys Ala Ser Lys Thr Trp Ser Gly Asn Cys Gly Asn
 1               5                  10                  15

Thr Lys His Cys Asp Asn Gln Cys Lys Asn Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 188
<211> LENGTH: 50
<212> TYPE: PRT
<213> ORGANISM: Artificial Sequence
<220> FEATURE:
<223> OTHER INFORMATION: Defensin like

<400> SEQUENCE: 188

Asn Leu Cys Glu Arg Ala Ser Lys Thr Trp Thr Gly Asn Cys Gly Asn
 1               5                  10                  15

Thr Lys His Cys Asp Thr Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 189
<211> LENGTH: 50
<212> TYPE: PRT
<213> ORGANISM: Artificial Sequence
<220> FEATURE:
<223> OTHER INFORMATION: Defensin like

<400> SEQUENCE: 189

Asn Leu Cys Glu Lys Ala Ser Lys Thr Trp Ser Gly Asn Cys Gly Asn
 1               5                  10                  15

Thr Lys His Cys Asp Thr Gln Cys Arg Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 190
<211> LENGTH: 50
<212> TYPE: PRT
<213> ORGANISM: Artificial Sequence
<220> FEATURE:
<223> OTHER INFORMATION: Defensin like

<400> SEQUENCE: 190

Asn Leu Cys Glu Arg Ala Ser Lys Thr Trp Thr Gly Asn Cys Gly Asn

```
                1               5                  10                 15
Thr Lys His Cys Asp Asn Gln Cys Arg Ser Trp Glu Gly Ala Lys His
            20                 25                 30

Gly Ala Cys His Val Arg Asn Gly Lys His Lys Cys Phe Cys Tyr Phe
        35                 40                 45

Asn Cys
    50

<210> SEQ ID NO 191
<211> LENGTH: 50
<212> TYPE: PRT
<213> ORGANISM: Artificial Sequence
<220> FEATURE:
<223> OTHER INFORMATION: Defensin like

<400> SEQUENCE: 191

Asn Leu Cys Glu Arg Ala Ser Lys Thr Trp Thr Gly Asn Cys Gly Asn
1               5                  10                 15

Thr Lys His Cys Asp Thr Gln Cys Lys Asn Trp Glu Gly Ala Lys His
            20                 25                 30

Gly Ala Cys His Val Arg Asn Gly Lys Trp Lys Cys Phe Cys Tyr Phe
        35                 40                 45

Asn Cys
    50

<210> SEQ ID NO 192
<211> LENGTH: 50
<212> TYPE: PRT
<213> ORGANISM: Artificial Sequence
<220> FEATURE:
<223> OTHER INFORMATION: Defensin like

<400> SEQUENCE: 192

Asn Leu Cys Glu Arg Ala Ser Lys Thr Trp Ser Gly Asn Cys Gly Asn
1               5                  10                 15

Thr Lys His Cys Asp Thr Gln Cys Arg Asn Trp Glu Gly Ala Lys His
            20                 25                 30

Gly Ala Cys His Val Arg Asn Gly Lys His Lys Cys Phe Cys Tyr Phe
        35                 40                 45

Asn Cys
    50

<210> SEQ ID NO 193
<211> LENGTH: 50
<212> TYPE: PRT
<213> ORGANISM: Artificial Sequence
<220> FEATURE:
<223> OTHER INFORMATION: Defensin like

<400> SEQUENCE: 193

Asn Leu Cys Glu Arg Ala Ser Lys Thr Trp Ser Gly Asn Cys Gly Asn
1               5                  10                 15

Thr Lys His Cys Asp Thr Gln Cys Lys Asn Trp Glu Gly Ala Lys His
            20                 25                 30

Gly Ala Cys His Val Arg Asn Gly Lys His Lys Cys Phe Cys Tyr Phe
        35                 40                 45

Asn Cys
    50

<210> SEQ ID NO 194
```

```
<211> LENGTH: 50
<212> TYPE: PRT
<213> ORGANISM: Artificial Sequence
<220> FEATURE:
<223> OTHER INFORMATION: Defensin like

<400> SEQUENCE: 194

Asn Leu Cys Glu Arg Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 195
<211> LENGTH: 50
<212> TYPE: PRT
<213> ORGANISM: Artificial Sequence
<220> FEATURE:
<223> OTHER INFORMATION: Defensin like

<400> SEQUENCE: 195

Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Gly Ala Ala His
            20                  25                  30

Gly Ala Cys His Val Arg Ser Gly Lys His Lys Cys Phe Cys Tyr Phe
        35                  40                  45

Asn Cys
    50

<210> SEQ ID NO 196
<211> LENGTH: 50
<212> TYPE: PRT
<213> ORGANISM: Artificial Sequence
<220> FEATURE:
<223> OTHER INFORMATION: Defensin like

<400> SEQUENCE: 196

Asn Leu Cys Glu Arg Ala Ser Lys Thr Trp Ser Gly Asn Cys Gly Asn
1               5                   10                  15

Thr Lys His Cys Asp Asn Gln Cys Lys Asn Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 197
<211> LENGTH: 50
<212> TYPE: PRT
<213> ORGANISM: Artificial Sequence
<220> FEATURE:
<223> OTHER INFORMATION: Defensin like

<400> SEQUENCE: 197

Asn Leu Cys Glu Arg Ala Ser Lys Thr Trp Ser Gly Asn Cys Gly Asn
1               5                   10                  15

Thr Lys His Cys Asp Asn Gln Cys Lys Ser Trp Glu Gly Ala Lys His
            20                  25                  30
```

```
Gly Ala Cys His Lys Arg Asn Gly Lys Trp Lys Cys Phe Cys Tyr Phe
            35                  40                  45

Asn Cys
    50

<210> SEQ ID NO 198
<211> LENGTH: 50
<212> TYPE: PRT
<213> ORGANISM: Artificial Sequence
<220> FEATURE:
<223> OTHER INFORMATION: Defensin like

<400> SEQUENCE: 198

Asn Leu Cys Glu Arg Ala Ser Lys Thr Trp Thr Gly Asn Cys Gly Asn
1               5                   10                  15

Thr Lys His Cys Asp Asn Gln Cys Lys Ser Trp Glu Gly Ala Lys His
            20                  25                  30

Gly Ala Cys His Lys Arg Ser Gly Lys Trp Lys Cys Phe Cys Tyr Phe
            35                  40                  45

Asn Cys
    50

<210> SEQ ID NO 199
<211> LENGTH: 50
<212> TYPE: PRT
<213> ORGANISM: Artificial Sequence
<220> FEATURE:
<223> OTHER INFORMATION: Defensin like

<400> SEQUENCE: 199

Asn Leu Cys Glu Lys Ala Ser Lys Thr Trp Ser Gly Asn Cys Gly Asn
1               5                   10                  15

Thr Lys His Cys Asp Asn Gln Cys Lys Asn Trp Glu Gly Ala Lys His
            20                  25                  30

Gly Ala Cys His Val Arg Ser Gly Lys His Lys Cys Phe Cys Tyr Phe
            35                  40                  45

Asn Cys
    50

<210> SEQ ID NO 200
<211> LENGTH: 50
<212> TYPE: PRT
<213> ORGANISM: Artificial Sequence
<220> FEATURE:
<223> OTHER INFORMATION: Defensin like

<400> SEQUENCE: 200

Asn Leu Cys Glu Lys Ala Ser Lys Thr Trp Thr Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Ser Gly Lys Trp Lys Cys Phe Cys Tyr Phe
            35                  40                  45

Asn Cys
    50

<210> SEQ ID NO 201
<211> LENGTH: 50
<212> TYPE: PRT
<213> ORGANISM: Artificial Sequence
<220> FEATURE:
```

<223> OTHER INFORMATION: Defensin like

<400> SEQUENCE: 201

Asn Leu Cys Glu Lys Ala Ser Lys Thr Trp Ser Gly Asn Cys Gly Asn
1               5                   10                  15

Thr Lys His Cys Asp Asn Gln Cys Arg Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 202
<211> LENGTH: 50
<212> TYPE: PRT
<213> ORGANISM: Artificial Sequence
<220> FEATURE:
<223> OTHER INFORMATION: Defensin like

<400> SEQUENCE: 202

Asn Leu Cys Glu Lys Ala Ser Lys Thr Trp Ser Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 203
<211> LENGTH: 50
<212> TYPE: PRT
<213> ORGANISM: Artificial Sequence
<220> FEATURE:
<223> OTHER INFORMATION: Defensin like

<400> SEQUENCE: 203

Asn Leu Cys Glu Arg Ala Ser Lys Thr Trp Ser Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 204
<211> LENGTH: 50
<212> TYPE: PRT
<213> ORGANISM: Artificial Sequence
<220> FEATURE:
<223> OTHER INFORMATION: Defensin like

<400> SEQUENCE: 204

Asn Leu Cys Glu Arg Ala Ser Lys Thr Trp Ser Gly Asn Cys Gly Asn
1               5                   10                  15

Thr Lys His Cys Asp Asn Gln Cys Arg Ser Trp Glu Gly Ala Lys His
            20                  25                  30

Gly Ala Cys His Val Arg Ser Gly Lys Trp Lys Cys Phe Cys Tyr Phe
        35                  40                  45

Asn Cys
    50

<210> SEQ ID NO 205
<211> LENGTH: 50
<212> TYPE: PRT
<213> ORGANISM: Artificial Sequence
<220> FEATURE:
<223> OTHER INFORMATION: Defensin like

<400> SEQUENCE: 205

Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 206
<211> LENGTH: 50
<212> TYPE: PRT
<213> ORGANISM: Artificial Sequence
<220> FEATURE:
<223> OTHER INFORMATION: Defensin like

<400> SEQUENCE: 206

Asn Leu Cys Glu Arg Ala Ser Lys Thr Trp Ser Gly Asn Cys Gly Asn
1               5                   10                  15

Thr Lys His Cys Asp Thr Gln Cys Lys Asn Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 207
<211> LENGTH: 50
<212> TYPE: PRT
<213> ORGANISM: Artificial Sequence
<220> FEATURE:
<223> OTHER INFORMATION: Defensin like

<400> SEQUENCE: 207

Asn Leu Cys Glu Arg Ala Ser Lys Thr Trp Ser Gly Asn Cys Gly Asn
1               5                   10                  15

Thr Lys His Cys Asp Thr Gln Cys Arg Ser Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 208
<211> LENGTH: 50
<212> TYPE: PRT
<213> ORGANISM: Artificial Sequence
<220> FEATURE:
<223> OTHER INFORMATION: Defensin like

<400> SEQUENCE: 208

```
Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Lys Arg Ser Gly Lys Trp Lys Cys Phe Cys Tyr Phe
            35                  40                  45

Asn Cys
    50
```

<210> SEQ ID NO 209
<211> LENGTH: 50
<212> TYPE: PRT
<213> ORGANISM: Artificial Sequence
<220> FEATURE:
<223> OTHER INFORMATION: Defensin like

<400> SEQUENCE: 209

```
Asn Leu Cys Glu Arg Ala Ser Lys Thr Trp Ser Gly Asn Cys Gly Asn
1               5                   10                  15

Thr Lys His Cys Asp Asn Gln Cys Arg Ser Trp Glu Gly Ala Lys His
            20                  25                  30

Gly Ala Cys His Val Arg Ser Gly Lys His Lys Cys Phe Cys Tyr Phe
            35                  40                  45

Asn Cys
    50
```

<210> SEQ ID NO 210
<211> LENGTH: 50
<212> TYPE: PRT
<213> ORGANISM: Artificial Sequence
<220> FEATURE:
<223> OTHER INFORMATION: Defensin like

<400> SEQUENCE: 210

```
Asn Leu Cys Glu Arg Ala Ser Lys Thr Trp Ser Gly Asn Cys Gly Asn
1               5                   10                  15

Thr Lys His Cys Asp Asn Gln Cys Lys Ser Trp Glu Gly Ala Ala His
            20                  25                  30

Gly Ala Cys His Lys Arg Asn Gly Lys Trp Lys Cys Phe Cys Tyr Phe
            35                  40                  45

Asn Cys
    50
```

<210> SEQ ID NO 211
<211> LENGTH: 50
<212> TYPE: PRT
<213> ORGANISM: Artificial Sequence
<220> FEATURE:
<223> OTHER INFORMATION: Defensin like

<400> SEQUENCE: 211

```
Asn Leu Cys Glu Arg Ala Ser Lys Thr Trp Ser Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Asn Gly Lys His Lys Cys Phe Cys Tyr Phe
            35                  40                  45

Asn Cys
    50
```

<210> SEQ ID NO 212
<211> LENGTH: 50
<212> TYPE: PRT
<213> ORGANISM: Artificial Sequence
<220> FEATURE:
<223> OTHER INFORMATION: Defensin like

<400> SEQUENCE: 212

```
Asn Leu Cys Glu Lys Ala Ser Lys Thr Trp Thr Gly Asn Cys Gly Asn
 1               5                  10                  15

Thr Lys His Cys Asp Asn Gln Cys Arg Asn Trp Glu Gly Ala Lys His
            20                  25                  30

Gly Ala Cys His Val Arg Ser Gly Lys His Lys Cys Phe Cys Tyr Phe
        35                  40                  45

Asn Cys
    50
```

<210> SEQ ID NO 213
<211> LENGTH: 50
<212> TYPE: PRT
<213> ORGANISM: Artificial Sequence
<220> FEATURE:
<223> OTHER INFORMATION: Defensin like

<400> SEQUENCE: 213

```
Asn Leu Cys Glu Lys Ala Ser Lys Thr Trp Ser Gly Asn Cys Gly Asn
 1               5                  10                  15

Thr Lys His Cys Asp Asn Gln Cys Arg Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50
```

<210> SEQ ID NO 214
<211> LENGTH: 50
<212> TYPE: PRT
<213> ORGANISM: Artificial Sequence
<220> FEATURE:
<223> OTHER INFORMATION: Defensin like

<400> SEQUENCE: 214

```
Asn Leu Cys Glu Arg Ala Ser Lys Thr Trp Ser Gly Asn Cys Gly Asn
 1               5                  10                  15

Thr Lys His Cys Asp Thr Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50
```

<210> SEQ ID NO 215
<211> LENGTH: 50
<212> TYPE: PRT
<213> ORGANISM: Artificial Sequence
<220> FEATURE:
<223> OTHER INFORMATION: Defensin like

<400> SEQUENCE: 215

```
Asn Leu Cys Glu Arg Ala Ser Lys Thr Trp Ser Gly Asn Cys Gly Asn
 1               5                  10                  15

Thr Lys His Cys Asp Thr Gln Cys Arg Asn Trp Glu Gly Ala Lys His
```

Gly Ala Cys His Val Arg Ser Gly Lys His Lys Cys Phe Cys Tyr Phe
        35                  40                  45

Asn Cys
    50

<210> SEQ ID NO 216
<211> LENGTH: 50
<212> TYPE: PRT
<213> ORGANISM: Artificial Sequence
<220> FEATURE:
<223> OTHER INFORMATION: Defensin like

<400> SEQUENCE: 216

Asn Leu Cys Glu Lys Ala Ser Lys Thr Trp Thr Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 217
<211> LENGTH: 50
<212> TYPE: PRT
<213> ORGANISM: Artificial Sequence
<220> FEATURE:
<223> OTHER INFORMATION: Defensin like

<400> SEQUENCE: 217

Asn Leu Cys Glu Arg Ala Ser Lys Thr Trp Ser Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 218
<211> LENGTH: 50
<212> TYPE: PRT
<213> ORGANISM: Artificial Sequence
<220> FEATURE:
<223> OTHER INFORMATION: Defensin like

<400> SEQUENCE: 218

Asn Leu Cys Glu Arg Ala Ser Lys Thr Trp Ser Gly Asn Cys Gly Asn
1               5                   10                  15

Thr Lys His Cys Asp Thr Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 219
<211> LENGTH: 50
<212> TYPE: PRT
<213> ORGANISM: Artificial Sequence

```
<220> FEATURE:
<223> OTHER INFORMATION: Defensin like

<400> SEQUENCE: 219

Asn Leu Cys Glu Arg Ala Ser Lys Thr Trp Thr Gly Asn Cys Gly Asn
1               5                   10                  15

Thr Lys His Cys Asp Asn Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 220
<211> LENGTH: 50
<212> TYPE: PRT
<213> ORGANISM: Artificial Sequence
<220> FEATURE:
<223> OTHER INFORMATION: Defensin like

<400> SEQUENCE: 220

Asn Leu Cys Glu Lys Ala Ser Lys Thr Trp Thr Gly Asn Cys Gly Asn
1               5                   10                  15

Thr Lys His Cys Asp Asn Gln Cys Arg Asn Trp Glu Gly Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 221
<211> LENGTH: 50
<212> TYPE: PRT
<213> ORGANISM: Artificial Sequence
<220> FEATURE:
<223> OTHER INFORMATION: Defensin like

<400> SEQUENCE: 221

Asn Leu Cys Glu Arg Ala Ser Lys Thr Trp Ser Gly Asn Cys Gly Asn
1               5                   10                  15

Thr Lys His Cys Asp Thr Gln Cys Arg Ser Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 222
<211> LENGTH: 50
<212> TYPE: PRT
<213> ORGANISM: Artificial Sequence
<220> FEATURE:
<223> OTHER INFORMATION: Defensin like

<400> SEQUENCE: 222

Asn Leu Cys Glu Lys Ala Ser Lys Thr Trp Ser Gly Asn Cys Gly Asn
1               5                   10                  15

Thr Lys His Cys Asp Asn Gln Cys Arg Ser Trp Glu Gly Ala Ala His
            20                  25                  30

Gly Ala Cys His Val Arg Ser Gly Lys His Lys Cys Phe Cys Tyr Phe
        35                  40                  45
```

-continued

Asn Cys
    50

<210> SEQ ID NO 223
<211> LENGTH: 50
<212> TYPE: PRT
<213> ORGANISM: Artificial Sequence
<220> FEATURE:
<223> OTHER INFORMATION: Defensin like

<400> SEQUENCE: 223

Asn Leu Cys Glu Arg Ala Ser Lys Thr Trp Ser Gly Asn Cys Gly Asn
 1               5                  10                  15

Thr Lys His Cys Asp Thr Gln Cys Arg Ser Trp Glu Gly Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 224
<211> LENGTH: 50
<212> TYPE: PRT
<213> ORGANISM: Artificial Sequence
<220> FEATURE:
<223> OTHER INFORMATION: Defensin like

<400> SEQUENCE: 224

Asn Leu Cys Glu Lys Ala Ser Lys Thr Trp Thr Gly Asn Cys Gly Asn
 1               5                  10                  15

Thr Lys His Cys Asp Thr Gln Cys Lys Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 225
<211> LENGTH: 50
<212> TYPE: PRT
<213> ORGANISM: Artificial Sequence
<220> FEATURE:
<223> OTHER INFORMATION: Defensin like

<400> SEQUENCE: 225

Asn Leu Cys Glu Lys Ala Ser Lys Thr Trp Ser Gly Asn Cys Gly Asn
 1               5                  10                  15

Thr Lys His Cys Asp Thr Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 226
<211> LENGTH: 50
<212> TYPE: PRT
<213> ORGANISM: Artificial Sequence
<220> FEATURE:
<223> OTHER INFORMATION: Defensin like

<400> SEQUENCE: 226

```
Asn Leu Cys Glu Arg Ala Ser Lys Thr Trp Ser Gly Asn Cys Gly Asn
 1               5                  10                  15

Thr Lys His Cys Asp Thr Gln Cys Arg Ser Trp Glu Gly Ala Lys His
            20                  25                  30

Gly Ala Cys His Val Arg Asn Gly Lys His Lys Cys Phe Cys Tyr Phe
            35                  40                  45

Asn Cys
    50
```

<210> SEQ ID NO 227
<211> LENGTH: 50
<212> TYPE: PRT
<213> ORGANISM: Artificial Sequence
<220> FEATURE:
<223> OTHER INFORMATION: Defensin like

<400> SEQUENCE: 227

```
Asn Leu Cys Glu Lys Ala Ser Lys Thr Trp Ser Gly Asn Cys Gly Asn
 1               5                  10                  15

Thr Lys His Cys Asp Asn Gln Cys Arg Ser Trp Glu Gly Ala Lys His
            20                  25                  30

Gly Ala Cys His Val Arg Ser Gly Lys His Lys Cys Phe Cys Tyr Phe
            35                  40                  45

Asn Cys
    50
```

<210> SEQ ID NO 228
<211> LENGTH: 50
<212> TYPE: PRT
<213> ORGANISM: Artificial Sequence
<220> FEATURE:
<223> OTHER INFORMATION: Defensin like

<400> SEQUENCE: 228

```
Asn Leu Cys Glu Arg Ala Ser Lys Thr Trp Ser Gly Asn Cys Gly Asn
 1               5                  10                  15

Thr Lys His Cys Asp Asn Gln Cys Lys Ser Trp Glu Gly Ala Lys His
            20                  25                  30

Gly Ala Cys His Val Arg Asn Gly Lys Trp Lys Cys Phe Cys Tyr Phe
            35                  40                  45

Asn Cys
    50
```

<210> SEQ ID NO 229
<211> LENGTH: 50
<212> TYPE: PRT
<213> ORGANISM: Artificial Sequence
<220> FEATURE:
<223> OTHER INFORMATION: Defensin like

<400> SEQUENCE: 229

```
Asn Leu Cys Glu Lys Ala Ser Lys Thr Trp Ser Gly Asn Cys Gly Asn
 1               5                  10                  15

Thr Lys His Cys Asp Thr Gln Cys Lys Asn Trp Glu Gly Ala Lys His
            20                  25                  30

Gly Ala Cys His Lys Arg Asn Gly Lys Trp Lys Cys Phe Cys Tyr Phe
            35                  40                  45

Asn Cys
    50
```

```
<210> SEQ ID NO 230
<211> LENGTH: 50
<212> TYPE: PRT
<213> ORGANISM: Artificial Sequence
<220> FEATURE:
<223> OTHER INFORMATION: Defensin like

<400> SEQUENCE: 230
```

Asn Leu Cys Glu Lys Ala Ser Lys Thr Trp Ser Gly Asn Cys Gly Asn
 1               5                  10                  15

Thr Lys His Cys Asp Asn Gln Cys Lys Ser Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

```
<210> SEQ ID NO 231
<211> LENGTH: 50
<212> TYPE: PRT
<213> ORGANISM: Artificial Sequence
<220> FEATURE:
<223> OTHER INFORMATION: Defensin like

<400> SEQUENCE: 231
```

Asn Leu Cys Glu Arg Ala Ser Lys Thr Trp Ser Gly Asn Cys Gly Asn
 1               5                  10                  15

Thr Lys His Cys Asp Asn Gln Cys Lys Ser Trp Glu Gly Ala Gln His
            20                  25                  30

Gly Ala Cys His Val Arg Asn Gly Lys His Lys Cys Phe Cys Tyr Phe
        35                  40                  45

Asn Cys
    50

```
<210> SEQ ID NO 232
<211> LENGTH: 50
<212> TYPE: PRT
<213> ORGANISM: Artificial Sequence
<220> FEATURE:
<223> OTHER INFORMATION: Defensin like

<400> SEQUENCE: 232
```

Asn Leu Cys Glu Arg Ala Ser Lys Thr Trp Ser Gly Asn Cys Gly Asn
 1               5                  10                  15

Thr Lys His Cys Asp Thr Gln Cys Arg Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

```
<210> SEQ ID NO 233
<211> LENGTH: 50
<212> TYPE: PRT
<213> ORGANISM: Artificial Sequence
<220> FEATURE:
<223> OTHER INFORMATION: Defensin like

<400> SEQUENCE: 233
```

Asn Leu Cys Glu Arg Ala Ser Lys Thr Trp Thr Gly Asn Cys Gly Asn
 1               5                  10                  15

Thr Lys His Cys Asp Thr Gln Cys Arg Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 234
<211> LENGTH: 50
<212> TYPE: PRT
<213> ORGANISM: Artificial Sequence
<220> FEATURE:
<223> OTHER INFORMATION: Defensin like

<400> SEQUENCE: 234

Asn Leu Cys Glu Lys Ala Ser Lys Thr Trp Thr Gly Asn Cys Gly Asn
 1               5                  10                  15

Thr Lys His Cys Asp Asn Gln Cys Lys Ser Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 235
<211> LENGTH: 50
<212> TYPE: PRT
<213> ORGANISM: Artificial Sequence
<220> FEATURE:
<223> OTHER INFORMATION: Defensin like

<400> SEQUENCE: 235

Asn Leu Cys Glu Lys Ala Ser Lys Thr Trp Ser Gly Asn Cys Gly Asn
 1               5                  10                  15

Thr Lys His Cys Asp Thr Gln Cys Lys Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 236
<211> LENGTH: 50
<212> TYPE: PRT
<213> ORGANISM: Artificial Sequence
<220> FEATURE:
<223> OTHER INFORMATION: Defensin like

<400> SEQUENCE: 236

Asn Leu Cys Glu Arg Ala Ser Lys Thr Trp Ser Gly Asn Cys Gly Asn
 1               5                  10                  15

Thr Lys His Cys Asp Asn Gln Cys Ile Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 237
<211> LENGTH: 50
<212> TYPE: PRT

```
<213> ORGANISM: Artificial Sequence
<220> FEATURE:
<223> OTHER INFORMATION: Defensin like

<400> SEQUENCE: 237

Asn Leu Cys Glu Lys Ala Ser Lys Thr Trp Thr Gly Asn Cys Gly Asn
 1               5                  10                  15

Thr Lys His Cys Asp Thr Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 238
<211> LENGTH: 50
<212> TYPE: PRT
<213> ORGANISM: Artificial Sequence
<220> FEATURE:
<223> OTHER INFORMATION: Defensin like

<400> SEQUENCE: 238

Asn Leu Cys Glu Arg Ala Ser Lys Thr Trp Thr Gly Asn Cys Gly Asn
 1               5                  10                  15

Thr Lys His Cys Asp Asn Gln Cys Lys Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 239
<211> LENGTH: 50
<212> TYPE: PRT
<213> ORGANISM: Artificial Sequence
<220> FEATURE:
<223> OTHER INFORMATION: Defensin like

<400> SEQUENCE: 239

Asn Leu Cys Glu Arg Ala Ser Lys Thr Trp Ala Gly Asn Cys Gly Asn
 1               5                  10                  15

Thr Lys His Cys Asp Asn Gln Cys Arg Ser Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 240
<211> LENGTH: 50
<212> TYPE: PRT
<213> ORGANISM: Artificial Sequence
<220> FEATURE:
<223> OTHER INFORMATION: Defensin like

<400> SEQUENCE: 240

Asn Leu Cys Glu Lys Ala Ser Lys Thr Trp Ser Gly Asn Cys Gly Asn
 1               5                  10                  15

Thr Lys His Cys Asp Asn Gln Cys Lys Ser Trp Glu Gly Ala Ala His
            20                  25                  30

Gly Ala Cys His Lys Arg Ser Gly Lys Trp Lys Cys Phe Cys Tyr Phe
```

<210> SEQ ID NO 241
<211> LENGTH: 50
<212> TYPE: PRT
<213> ORGANISM: Artificial Sequence
<220> FEATURE:
<223> OTHER INFORMATION: Defensin like

<400> SEQUENCE: 241

Asn Leu Cys Glu Lys Ala Ser Lys Thr Trp Ser Gly Asn Cys Gly Asn
1               5                   10                  15

Thr Asn His Cys Asp Asn Gln Cys Arg Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 242
<211> LENGTH: 50
<212> TYPE: PRT
<213> ORGANISM: Artificial Sequence
<220> FEATURE:
<223> OTHER INFORMATION: Defensin like

<400> SEQUENCE: 242

Asn Leu Cys Glu Arg Ala Ser Lys Thr Trp Ser Gly Asn Cys Gly Ser
1               5                   10                  15

Thr Lys His Cys Asp Asn Gln Cys Lys Asn Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 243
<211> LENGTH: 50
<212> TYPE: PRT
<213> ORGANISM: Artificial Sequence
<220> FEATURE:
<223> OTHER INFORMATION: Defensin like

<400> SEQUENCE: 243

Asn Leu Cys Glu Arg Ala Ser Lys Thr Trp Ser Gly Asn Cys Gly Asn
1               5                   10                  15

Thr Lys His Cys Asp Thr Gln Cys Lys Ser Trp Glu Gly Ala Lys His
            20                  25                  30

Gly Ala Cys His Val Arg Asn Gly Lys His Lys Cys Phe Cys Tyr Phe
        35                  40                  45

Asn Cys
    50

<210> SEQ ID NO 244
<211> LENGTH: 50
<212> TYPE: PRT
<213> ORGANISM: Artificial Sequence
<220> FEATURE:
<223> OTHER INFORMATION: Defensin like

<400> SEQUENCE: 244

Asn Leu Cys Glu Arg Ala Ser Lys Thr Trp Ser Gly Asn Cys Gly Asn
1               5                   10                  15

Thr Lys His Cys Asp Asn Gln Cys Lys Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 245
<211> LENGTH: 50
<212> TYPE: PRT
<213> ORGANISM: Artificial Sequence
<220> FEATURE:
<223> OTHER INFORMATION: Defensin like

<400> SEQUENCE: 245

Asn Leu Cys Glu Arg Ala Ser Lys Thr Trp Thr Gly Asn Cys Gly Asn
1               5                   10                  15

Thr Lys His Cys Asp Asn Gln Cys Lys Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 246
<211> LENGTH: 50
<212> TYPE: PRT
<213> ORGANISM: Artificial Sequence
<220> FEATURE:
<223> OTHER INFORMATION: Defensin like

<400> SEQUENCE: 246

Asn Leu Cys Glu Arg Ala Ser Lys Thr Trp Thr Gly Asn Cys Gly Asn
1               5                   10                  15

Thr Lys His Cys Asp Thr Gln Cys Arg Ser Trp Glu Gly Ala Ala His
            20                  25                  30

Gly Ala Cys His Val Arg Gly Gly Lys His Lys Cys Phe Cys Tyr Phe
        35                  40                  45

Asn Cys
    50

<210> SEQ ID NO 247
<211> LENGTH: 50
<212> TYPE: PRT
<213> ORGANISM: Artificial Sequence
<220> FEATURE:
<223> OTHER INFORMATION: Defensin like

<400> SEQUENCE: 247

Asn Leu Cys Glu Lys Ala Ser Lys Thr Trp Thr Gly Asn Cys Gly Asn
1               5                   10                  15

Thr Lys His Cys Asp Asn Gln Cys Arg Ser Trp Glu Gly Ala Lys His
            20                  25                  30

Gly Ala Cys His Val Arg Ser Gly Lys His Lys Cys Phe Cys Tyr Phe
        35                  40                  45

Asn Cys
    50

<210> SEQ ID NO 248
<211> LENGTH: 50
<212> TYPE: PRT
<213> ORGANISM: Artificial Sequence
<220> FEATURE:
<223> OTHER INFORMATION: Defensin like

<400> SEQUENCE: 248

Asn Leu Cys Glu Arg Ala Ser Lys Thr Trp Ser Gly Asn Cys Gly Asn
1               5                   10                  15

Thr Lys His Cys Asp Asn Gln Cys Arg Ser Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 249
<211> LENGTH: 50
<212> TYPE: PRT
<213> ORGANISM: Artificial Sequence
<220> FEATURE:
<223> OTHER INFORMATION: Defensin like

<400> SEQUENCE: 249

Asn Leu Cys Glu Lys Ala Ser Lys Thr Trp Thr Gly Asn Cys Gly Asn
1               5                   10                  15

Thr Lys His Cys Asp Asn Gln Cys Lys Ser Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 250
<211> LENGTH: 50
<212> TYPE: PRT
<213> ORGANISM: Artificial Sequence
<220> FEATURE:
<223> OTHER INFORMATION: Defensin like

<400> SEQUENCE: 250

Asn Leu Cys Glu Arg Ala Ser Lys Thr Trp Ser Ser Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 251
<211> LENGTH: 50
<212> TYPE: PRT
<213> ORGANISM: Artificial Sequence
<220> FEATURE:
<223> OTHER INFORMATION: Defensin like

<400> SEQUENCE: 251

Asn Leu Cys Glu Arg Ala Ser Lys Thr Trp Ser Gly Asn Cys Gly Asn
1               5                   10                  15

-continued

```
Thr Lys His Cys Asp Thr Gln Cys Lys Asn Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 252
<211> LENGTH: 50
<212> TYPE: PRT
<213> ORGANISM: Artificial Sequence
<220> FEATURE:
<223> OTHER INFORMATION: Defensin like

<400> SEQUENCE: 252

Asn Leu Cys Glu Arg Ala Ser Lys Thr Trp Ser Gly Asp Cys Gly Asn
1               5                   10                  15

Thr Lys His Cys Asp Asn Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 253
<211> LENGTH: 50
<212> TYPE: PRT
<213> ORGANISM: Artificial Sequence
<220> FEATURE:
<223> OTHER INFORMATION: Defensin like

<400> SEQUENCE: 253

Asn Leu Cys Glu Lys Ala Ser Lys Thr Trp Thr Gly Asn Cys Gly Asn
1               5                   10                  15

Thr Lys His Cys Asp Asn Gln Cys Lys Ser Trp Glu Gly Ala Lys His
            20                  25                  30

Gly Ala Cys His Lys Arg Gly Gly Lys Trp Lys Cys Phe Cys Tyr Phe
        35                  40                  45

Asn Cys
    50

<210> SEQ ID NO 254
<211> LENGTH: 50
<212> TYPE: PRT
<213> ORGANISM: Artificial Sequence
<220> FEATURE:
<223> OTHER INFORMATION: Defensin like

<400> SEQUENCE: 254

Asn Leu Cys Glu Arg Ala Ser Lys Thr Trp Thr Gly Asn Cys Gly Asn
1               5                   10                  15

Thr Lys His Cys Asp Asn Gln Cys Lys Ser Trp Glu Gly Ala Lys His
            20                  25                  30

Gly Ala Cys His Val Arg Asn Gly Lys Trp Lys Cys Phe Cys Tyr Phe
        35                  40                  45

Asn Cys
    50

<210> SEQ ID NO 255
<211> LENGTH: 50
```

<212> TYPE: PRT
<213> ORGANISM: Artificial Sequence
<220> FEATURE:
<223> OTHER INFORMATION: Defensin like

<400> SEQUENCE: 255

Asn Leu Cys Glu Arg Ala Ser Lys Thr Trp Ser Gly Asn Cys Gly Asn
1               5                   10                  15

Thr Lys His Cys Asp Asn Gln Cys Lys Asn Trp Glu Gly Ala Ala His
            20                  25                  30

Gly Ala Cys His Val Arg Ser Gly Lys His Lys Cys Phe Cys Tyr Phe
        35                  40                  45

Asn Cys
    50

<210> SEQ ID NO 256
<211> LENGTH: 50
<212> TYPE: PRT
<213> ORGANISM: Artificial Sequence
<220> FEATURE:
<223> OTHER INFORMATION: Defensin like

<400> SEQUENCE: 256

Asn Leu Cys Glu Lys Ala Ser Lys Thr Trp Thr Gly Asn Cys Gly Asn
1               5                   10                  15

Thr Lys His Cys Asp Asn Gln Cys Lys Ser Trp Glu Gly Ala Ala His
            20                  25                  30

Gly Ala Cys His Val Arg Asn Gly Lys His Lys Cys Phe Cys Tyr Phe
        35                  40                  45

Asn Cys
    50

<210> SEQ ID NO 257
<211> LENGTH: 50
<212> TYPE: PRT
<213> ORGANISM: Artificial Sequence
<220> FEATURE:
<223> OTHER INFORMATION: Defensin like

<400> SEQUENCE: 257

Asn Leu Cys Glu Lys Ala Ser Lys Thr Trp Ser Gly Asn Cys Gly Asn
1               5                   10                  15

Thr Lys His Cys Asp Thr Gln Cys Lys Asn Trp Glu Gly Ala Lys His
            20                  25                  30

Gly Ala Cys His Val Arg Ser Gly Lys Trp Lys Cys Phe Cys Tyr Phe
        35                  40                  45

Asn Cys
    50

<210> SEQ ID NO 258
<211> LENGTH: 50
<212> TYPE: PRT
<213> ORGANISM: Artificial Sequence
<220> FEATURE:
<223> OTHER INFORMATION: Defensin like

<400> SEQUENCE: 258

Asn Leu Cys Glu Lys Ala Ser Lys Thr Trp Thr Gly Asn Cys Gly Asn
1               5                   10                  15

Thr Lys His Cys Asp Asn Gln Cys Arg Ser Trp Glu Gly Ala Ala His
            20                  25                  30

```
Gly Ala Cys His Val Arg Asn Gly Lys His Lys Cys Phe Cys Tyr Phe
        35                  40                  45

Asn Cys
    50

<210> SEQ ID NO 259
<211> LENGTH: 50
<212> TYPE: PRT
<213> ORGANISM: Artificial Sequence
<220> FEATURE:
<223> OTHER INFORMATION: Defensin like

<400> SEQUENCE: 259

Asn Leu Cys Glu Arg Ala Ser Lys Thr Trp Ser Gly Asn Cys Gly Asn
 1               5                  10                  15

Thr Lys His Cys Asp Asn Gln Cys Arg Asn Trp Glu Gly Ala Lys His
            20                  25                  30

Gly Ala Cys His Val Arg Ser Gly Lys Trp Lys Cys Phe Cys Tyr Phe
        35                  40                  45

Asn Cys
    50

<210> SEQ ID NO 260
<211> LENGTH: 50
<212> TYPE: PRT
<213> ORGANISM: Artificial Sequence
<220> FEATURE:
<223> OTHER INFORMATION: Defensin like

<400> SEQUENCE: 260

Asn Leu Cys Glu Arg Ala Ser Lys Thr Trp Thr Gly Asn Cys Gly Asn
 1               5                  10                  15

Thr Lys His Cys Asp Thr Gln Cys Arg Asn Trp Glu Gly Ala Arg His
            20                  25                  30

Gly Ala Cys His Val Arg Asn Gly Lys Trp Lys Cys Phe Cys Tyr Phe
        35                  40                  45

Asn Cys
    50

<210> SEQ ID NO 261
<211> LENGTH: 50
<212> TYPE: PRT
<213> ORGANISM: Artificial Sequence
<220> FEATURE:
<223> OTHER INFORMATION: Defensin like

<400> SEQUENCE: 261

Asn Leu Cys Glu Arg Ala Ser Lys Thr Trp Ser Gly Asn Cys Gly Asn
 1               5                  10                  15

Thr Lys His Cys Asp Asn Gln Cys Arg Ser Trp Glu Gly Ala Ala His
            20                  25                  30

Gly Ala Cys His Val Arg Asn Gly Lys Trp Lys Cys Phe Cys Tyr Phe
        35                  40                  45

Asn Cys
    50

<210> SEQ ID NO 262
<211> LENGTH: 50
<212> TYPE: PRT
<213> ORGANISM: Artificial Sequence
<220> FEATURE:
<223> OTHER INFORMATION: Defensin like
```

-continued

```
<400> SEQUENCE: 262

Asn Leu Cys Glu Lys Ala Ser Lys Thr Trp Thr Gly Asn Cys Gly Asn
1               5                   10                  15

Thr Lys His Cys Asp Asn Gln Cys Arg Ser Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 263
<211> LENGTH: 50
<212> TYPE: PRT
<213> ORGANISM: Artificial Sequence
<220> FEATURE:
<223> OTHER INFORMATION: Defensin like

<400> SEQUENCE: 263

Asn Leu Cys Glu Arg Ala Ser Lys Thr Trp Thr Gly Asn Cys Gly Asn
1               5                   10                  15

Thr Lys His Cys Asp Asn Gln Cys Arg Ser Trp Glu Gly Ala Lys His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 264
<211> LENGTH: 50
<212> TYPE: PRT
<213> ORGANISM: Artificial Sequence
<220> FEATURE:
<223> OTHER INFORMATION: Defensin like

<400> SEQUENCE: 264

Asn Leu Cys Glu Lys Ala Ser Lys Thr Trp Ser Gly Asn Cys Gly Asn
1               5                   10                  15

Thr Lys His Cys Asp Thr Gln Cys Lys Ser Trp Glu Gly Ala Ala His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 265
<211> LENGTH: 50
<212> TYPE: PRT
<213> ORGANISM: Artificial Sequence
<220> FEATURE:
<223> OTHER INFORMATION: Defensin like

<400> SEQUENCE: 265

Asn Leu Cys Glu Arg Ala Ser Lys Thr Trp Thr Gly Asn Cys Gly Asn
1               5                   10                  15

Thr Lys His Cys Asp Asn Gln Cys Arg Asn Trp Glu Gly Ala Lys His
            20                  25                  30

Gly Ala Cys His Val Arg Ser Gly Lys Trp Lys Cys Phe Cys Tyr Phe
        35                  40                  45

Asn Cys
```

50

<210> SEQ ID NO 266
<211> LENGTH: 50
<212> TYPE: PRT
<213> ORGANISM: Artificial Sequence
<220> FEATURE:
<223> OTHER INFORMATION: Defensin like

<400> SEQUENCE: 266

Asn Leu Cys Glu Arg Ala Ser Lys Thr Trp Thr Gly Asn Cys Gly Asn
1               5                   10                  15

Thr Lys His Cys Asp Asn Gln Cys Lys Asn Trp Glu Gly Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 267
<211> LENGTH: 50
<212> TYPE: PRT
<213> ORGANISM: Artificial Sequence
<220> FEATURE:
<223> OTHER INFORMATION: Defensin like

<400> SEQUENCE: 267

Asn Leu Cys Glu Arg Ala Ser Lys Thr Trp Thr Gly Asn Cys Gly Asn
1               5                   10                  15

Thr Lys His Cys Asp Asn Gln Cys Arg Ser Trp Glu Gly Ala Ala His
            20                  25                  30

Gly Ala Cys His Lys Arg Ser Gly Lys Trp Lys Cys Phe Cys Tyr Phe
        35                  40                  45

Asn Cys
    50

<210> SEQ ID NO 268
<211> LENGTH: 50
<212> TYPE: PRT
<213> ORGANISM: Artificial Sequence
<220> FEATURE:
<223> OTHER INFORMATION: Defensin like

<400> SEQUENCE: 268

Asn Leu Cys Glu Arg Ala Ser Lys Thr Trp Thr Gly Asn Cys Gly Asn
1               5                   10                  15

Thr Lys His Cys Asp Asn Gln Cys Lys Asn Trp Glu Gly Ala Ala His
            20                  25                  30

Gly Ala Cys His Val Arg Ser Gly Lys His Lys Cys Phe Cys Tyr Phe
        35                  40                  45

Asn Cys
    50

<210> SEQ ID NO 269
<211> LENGTH: 50
<212> TYPE: PRT
<213> ORGANISM: Artificial Sequence
<220> FEATURE:
<223> OTHER INFORMATION: Defensin like

<400> SEQUENCE: 269

Asn Leu Cys Glu Lys Ala Ser Lys Thr Trp Ser Gly Asn Cys Gly Asn

```
                1               5                  10                  15
Thr Lys His Cys Asp Asn Gln Cys Arg Asn Trp Glu Gly Ala Glu His
            20                  25                  30

Gly Ala Cys His Val Arg Asn Gly Lys His Lys Cys Phe Cys Tyr Phe
            35                  40                  45

Asn Cys
    50

<210> SEQ ID NO 270
<211> LENGTH: 50
<212> TYPE: PRT
<213> ORGANISM: Artificial Sequence
<220> FEATURE:
<223> OTHER INFORMATION: Defensin like

<400> SEQUENCE: 270

Asn Leu Cys Glu Arg Ala Ser Lys Thr Trp Ser Gly Asn Cys Gly Asn
1               5                  10                  15

Thr Lys His Cys Asp Asn Gln Cys Lys Ser Trp Glu Gly Ala Lys His
            20                  25                  30

Gly Ala Cys His Val Arg Asn Gly Lys His Lys Cys Phe Cys Tyr Phe
            35                  40                  45

Asn Cys
    50

<210> SEQ ID NO 271
<211> LENGTH: 50
<212> TYPE: PRT
<213> ORGANISM: Artificial Sequence
<220> FEATURE:
<223> OTHER INFORMATION: Defensin like

<400> SEQUENCE: 271

Asn Leu Cys Glu Lys Ala Ser Lys Thr Trp Ser Gly Asn Cys Gly Asn
1               5                  10                  15

Thr Lys His Cys Asp Asn Gln Cys Lys Ser Trp Glu Gly Ala Ala His
            20                  25                  30

Gly Ala Cys His Lys Arg Asn Gly Lys Trp Lys Cys Phe Cys Tyr Phe
            35                  40                  45

Asn Cys
    50

<210> SEQ ID NO 272
<211> LENGTH: 50
<212> TYPE: PRT
<213> ORGANISM: Artificial Sequence
<220> FEATURE:
<223> OTHER INFORMATION: Defensin like

<400> SEQUENCE: 272

Asn Leu Cys Glu Lys Ala Ser Lys Thr Trp Ser Gly Asn Cys Gly Asn
1               5                  10                  15

Thr Lys His Cys Asp Asn Gln Cys Lys Ser Trp Glu Gly Ala Lys His
            20                  25                  30

Gly Ala Cys His Lys Arg Asn Gly Lys Trp Lys Cys Phe Cys Tyr Phe
            35                  40                  45

Asn Cys
    50

<210> SEQ ID NO 273
```

```
<211> LENGTH: 50
<212> TYPE: PRT
<213> ORGANISM: Artificial Sequence
<220> FEATURE:
<223> OTHER INFORMATION: Defensin like

<400> SEQUENCE: 273
```

Asn Leu Cys Glu Arg Ala Ser Arg Thr Trp Ser Gly Asn Cys Gly Asn
1               5                   10                  15

Thr Lys His Cys Asp Asn Gln Cys Lys Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

```
<210> SEQ ID NO 274
<211> LENGTH: 50
<212> TYPE: PRT
<213> ORGANISM: Artificial Sequence
<220> FEATURE:
<223> OTHER INFORMATION: Defensin like

<400> SEQUENCE: 274
```

Asn Leu Cys Glu Arg Ala Ser Lys Thr Trp Ser Gly Asn Cys Gly Ile
1               5                   10                  15

Thr Lys His Cys Asp Asn Gln Cys Lys Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

```
<210> SEQ ID NO 275
<211> LENGTH: 50
<212> TYPE: PRT
<213> ORGANISM: Artificial Sequence
<220> FEATURE:
<223> OTHER INFORMATION: Defensin like

<400> SEQUENCE: 275
```

Asn Leu Cys Glu Arg Ala Ser Lys Thr Trp Ser Gly Asn Cys Ser Asn
1               5                   10                  15

Thr Lys His Cys Asp Asn Gln Cys Lys Ser Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

```
<210> SEQ ID NO 276
<211> LENGTH: 50
<212> TYPE: PRT
<213> ORGANISM: Artificial Sequence
<220> FEATURE:
<223> OTHER INFORMATION: Defensin like

<400> SEQUENCE: 276
```

Asn Leu Cys Glu Arg Ala Ser Lys Thr Trp Ser Gly Asn Cys Gly Asn
1               5                   10                  15

Thr Lys His Cys Asp Asn Gln Cys Lys Asn Trp Glu Gly Ala Lys His
            20                  25                  30

```
Gly Ala Cys His Lys Arg Asn Gly Lys Trp Lys Cys Phe Cys Tyr Phe
        35                  40                  45

Asn Cys
    50

<210> SEQ ID NO 277
<211> LENGTH: 50
<212> TYPE: PRT
<213> ORGANISM: Artificial Sequence
<220> FEATURE:
<223> OTHER INFORMATION: Defensin like

<400> SEQUENCE: 277

Asn Leu Cys Glu Lys Ala Ser Lys Thr Trp Ser Gly Asn Cys Gly Asn
1               5                   10                  15

Thr Lys His Cys Asp Asn Gln Cys Lys Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 278
<211> LENGTH: 50
<212> TYPE: PRT
<213> ORGANISM: Artificial Sequence
<220> FEATURE:
<223> OTHER INFORMATION: Defensin like

<400> SEQUENCE: 278

Asn Leu Cys Glu Arg Ala Ser Lys Thr Trp Ser Gly Asn Cys Gly Asn
1               5                   10                  15

Thr Lys His Cys Asp Asn Gln Cys Lys Gly Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 279
<211> LENGTH: 50
<212> TYPE: PRT
<213> ORGANISM: Artificial Sequence
<220> FEATURE:
<223> OTHER INFORMATION: Defensin like

<400> SEQUENCE: 279

Asn Leu Cys Glu Arg Ala Ser Lys Thr Trp Ser Gly Asn Cys Gly Asn
1               5                   10                  15

Thr Lys His Cys Asp Asn Gln Cys Lys Gly Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 280
<211> LENGTH: 53
<212> TYPE: PRT
<213> ORGANISM: Artificial Sequence
<220> FEATURE:
```

<223> OTHER INFORMATION: Defensin like

<400> SEQUENCE: 280

Asp Gly Val Lys Leu Cys Glu Arg Pro Ser Gln Thr Trp Thr Gly Asn
1               5                   10                  15

Cys Gly Asn Thr Lys His Cys Asp Lys Gln Cys Lys Ser Trp Glu Gly
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 281
<211> LENGTH: 53
<212> TYPE: PRT
<213> ORGANISM: Artificial Sequence
<220> FEATURE:
<223> OTHER INFORMATION: Defensin like

<400> SEQUENCE: 281

Asp Gly Val Lys Leu Cys Glu Lys Pro Ser Gln Thr Trp Thr Gly His
1               5                   10                  15

Cys Gly Asn Thr Lys His Cys Asp Thr Gln Cys Arg Ser Trp Glu Gly
            20                  25                  30

Ala Ala His Gly Ala Cys His Lys Arg Ser Gly Lys Trp Lys Cys Phe
        35                  40                  45

Cys Tyr Phe Asn Cys
    50

<210> SEQ ID NO 282
<211> LENGTH: 53
<212> TYPE: PRT
<213> ORGANISM: Artificial Sequence
<220> FEATURE:
<223> OTHER INFORMATION: Defensin like

<400> SEQUENCE: 282

Asp Gly Val Lys Leu Cys Glu Arg Ala Ser Lys Thr Trp Thr Gly Asn
1               5                   10                  15

Cys Gly Asn Thr Lys His Cys Asp Lys Gln Cys Lys Asn Trp Glu Gly
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 283
<211> LENGTH: 53
<212> TYPE: PRT
<213> ORGANISM: Artificial Sequence
<220> FEATURE:
<223> OTHER INFORMATION: Defensin like

<400> SEQUENCE: 283

Asp Gly Val Lys Leu Cys Glu Lys Ala Ser Lys Thr Trp Ser Gly Asn
1               5                   10                  15

Cys Gly Asn Thr Lys His Cys Asp Lys Gln Cys Arg Ser Trp Glu Lys
            20                  25                  30

Ala Lys His Gly Ala Cys His Val Arg Asn Gly Lys His Lys Cys Phe
        35                  40                  45

Cys Tyr Phe Asn Cys
    50

<210> SEQ ID NO 284
<211> LENGTH: 50
<212> TYPE: PRT
<213> ORGANISM: Artificial Sequence
<220> FEATURE:
<223> OTHER INFORMATION: Defensin like

<400> SEQUENCE: 284

Asn Leu Cys Glu Arg Ala Ser Lys Thr Trp Ser Gly His Cys Gly Asn
 1               5                  10                  15

Thr Lys His Cys Asp Asn Gln Cys Arg Asn Trp Glu Gly Ala Lys His
            20                  25                  30

Gly Ala Cys His Lys Arg Asn Gly Lys Trp Lys Cys Phe Cys Tyr Phe
        35                  40                  45

Asn Cys
    50

<210> SEQ ID NO 285
<211> LENGTH: 53
<212> TYPE: PRT
<213> ORGANISM: Artificial Sequence
<220> FEATURE:
<223> OTHER INFORMATION: Defensin like

<400> SEQUENCE: 285

Asp Gly Val Lys Leu Cys Glu Arg Pro Ser Lys Thr Trp Ser Gly Asn
 1               5                  10                  15

Cys Gly Asn Thr Lys His Cys Asp Lys Gln Cys Lys Asn Trp Glu Lys
            20                  25                  30

Ala Lys His Gly Ala Cys His Val Arg Asn Gly Lys Trp Lys Cys Phe
        35                  40                  45

Cys Tyr Phe Asn Cys
    50

<210> SEQ ID NO 286
<211> LENGTH: 53
<212> TYPE: PRT
<213> ORGANISM: Artificial Sequence
<220> FEATURE:
<223> OTHER INFORMATION: Defensin like

<400> SEQUENCE: 286

Asp Gly Val Lys Leu Cys Glu Lys Pro Ser Lys Thr Trp Ser Gly His
 1               5                  10                  15

Cys Gly Asn Thr Lys His Cys Asp Lys Gln Cys Lys Asn Trp Glu Lys
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 287
<211> LENGTH: 50
<212> TYPE: PRT
<213> ORGANISM: Artificial Sequence
<220> FEATURE:
<223> OTHER INFORMATION: Defensin like

<400> SEQUENCE: 287

-continued

Asn Leu Cys Glu Lys Ala Ser Gln Thr Trp Thr Gly His Cys Gly Asn
1               5                   10                  15

Thr Lys His Cys Asp Lys Gln Cys Lys Ser Trp Glu Gly Ala Ala His
            20                  25                  30

Gly Ala Cys His Val Arg Ser Gly Lys Trp Lys Cys Phe Cys Tyr Phe
            35                  40                  45

Asn Cys
    50

<210> SEQ ID NO 288
<211> LENGTH: 53
<212> TYPE: PRT
<213> ORGANISM: Artificial Sequence
<220> FEATURE:
<223> OTHER INFORMATION: Defensin like

<400> SEQUENCE: 288

Asp Gly Val Lys Leu Cys Glu Arg Pro Ser Gln Thr Trp Ser Gly Asn
1               5                   10                  15

Cys Gly Asn Thr Lys His Cys Asp Lys Gln Cys Arg Asn Trp Glu Lys
            20                  25                  30

Ala Lys His Gly Ala Cys His Lys Arg Asn Gly Lys Trp Lys Cys Phe
            35                  40                  45

Cys Tyr Phe Asn Cys
    50

<210> SEQ ID NO 289
<211> LENGTH: 53
<212> TYPE: PRT
<213> ORGANISM: Artificial Sequence
<220> FEATURE:
<223> OTHER INFORMATION: Defensin like

<400> SEQUENCE: 289

Asp Gly Val Lys Leu Cys Glu Lys Pro Ser Lys Thr Trp Thr Gly His
1               5                   10                  15

Cys Gly Asn Thr Lys His Cys Asp Asn Gln Cys Lys Asn Trp Glu Lys
            20                  25                  30

Ala Ala His Gly Ala Cys His Val Arg Ser Gly Lys Trp Lys Cys Phe
            35                  40                  45

Cys Tyr Phe Asn Cys
    50

<210> SEQ ID NO 290
<211> LENGTH: 53
<212> TYPE: PRT
<213> ORGANISM: Artificial Sequence
<220> FEATURE:
<223> OTHER INFORMATION: Defensin like

<400> SEQUENCE: 290

Asp Gly Val Lys Leu Cys Glu Lys Pro Ser Lys Thr Trp Thr Gly His
1               5                   10                  15

Cys Gly Asn Thr Lys His Cys Asp Lys Gln Cys Lys Asn Trp Glu Lys
            20                  25                  30

Ala Ala His Gly Ala Cys His Val Arg Asn Gly Lys Trp Lys Cys Phe
            35                  40                  45

Cys Tyr Phe Asn Cys
    50

<210> SEQ ID NO 291
<211> LENGTH: 53
<212> TYPE: PRT
<213> ORGANISM: Artificial Sequence
<220> FEATURE:
<223> OTHER INFORMATION: Defensin like

<400> SEQUENCE: 291

```
Asp Gly Val Lys Leu Cys Glu Arg Ala Ser Gln Thr Trp Ser Gly His
1               5                   10                  15

Cys Gly Asn Thr Lys His Cys Asp Lys Gln Cys Lys Asn Trp Glu Lys
            20                  25                  30

Ala Ala His Gly Ala Cys His Val Arg Ser Gly Lys Trp Lys Cys Phe
        35                  40                  45

Cys Tyr Phe Asn Cys
        50
```

<210> SEQ ID NO 292
<211> LENGTH: 53
<212> TYPE: PRT
<213> ORGANISM: Artificial Sequence
<220> FEATURE:
<223> OTHER INFORMATION: Defensin like

<400> SEQUENCE: 292

```
Asp Gly Val Lys Leu Cys Glu Arg Ala Ser Gln Thr Trp Thr Gly His
1               5                   10                  15

Cys Gly Asn Thr Lys His Cys Asp Lys Gln Cys Lys Ser Trp Glu Lys
            20                  25                  30

Ala Lys His Gly Ala Cys His Val Arg Asn Gly Lys Trp Lys Cys Phe
        35                  40                  45

Cys Tyr Phe Asn Cys
        50
```

<210> SEQ ID NO 293
<211> LENGTH: 53
<212> TYPE: PRT
<213> ORGANISM: Artificial Sequence
<220> FEATURE:
<223> OTHER INFORMATION: Defensin like

<400> SEQUENCE: 293

```
Asp Gly Val Lys Leu Cys Glu Arg Ala Ser Gln Thr Trp Ser Gly His
1               5                   10                  15

Cys Gly Asn Thr Lys His Cys Asp Lys Gln Cys Arg Asn Trp Glu Gly
            20                  25                  30

Ala Ala His Gly Ala Cys His Val Arg Asn Gly Lys Trp Lys Cys Phe
        35                  40                  45

Cys Tyr Phe Asn Cys
        50
```

<210> SEQ ID NO 294
<211> LENGTH: 53
<212> TYPE: PRT
<213> ORGANISM: Artificial Sequence
<220> FEATURE:
<223> OTHER INFORMATION: Defensin like

<400> SEQUENCE: 294

```
Asp Gly Val Lys Leu Cys Glu Lys Ala Ser Gln Thr Trp Ser Gly Asn
1               5                   10                  15

Cys Gly Asn Thr Lys His Cys Asp Thr Gln Cys Arg Asn Trp Glu Gly
```

-continued

```
                20                  25                  30
Ala Lys His Gly Ala Cys His Lys Arg Asn Gly Lys Trp Lys Cys Phe
        35                  40                  45

Cys Tyr Phe Asn Cys
    50

<210> SEQ ID NO 295
<211> LENGTH: 53
<212> TYPE: PRT
<213> ORGANISM: Artificial Sequence
<220> FEATURE:
<223> OTHER INFORMATION: Defensin like

<400> SEQUENCE: 295

Asp Gly Val Lys Leu Cys Glu Arg Ala Ser Gln Thr Trp Thr Gly His
1               5                   10                  15

Cys Gly Asn Thr Lys His Cys Asp Asn Gln Cys Lys Asn Trp Glu Gly
                20                  25                  30

Ala Lys His Gly Ala Cys His Lys Arg Ser Gly Lys Trp Lys Cys Phe
        35                  40                  45

Cys Tyr Phe Asn Cys
    50

<210> SEQ ID NO 296
<211> LENGTH: 53
<212> TYPE: PRT
<213> ORGANISM: Artificial Sequence
<220> FEATURE:
<223> OTHER INFORMATION: Defensin like

<400> SEQUENCE: 296

Asp Gly Val Lys Leu Cys Glu Lys Pro Ser Gln Thr Trp Thr Gly His
1               5                   10                  15

Cys Gly Asn Thr Lys His Cys Asp Lys Gln Cys Lys Asn Trp Glu Gly
                20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 297
<211> LENGTH: 53
<212> TYPE: PRT
<213> ORGANISM: Artificial Sequence
<220> FEATURE:
<223> OTHER INFORMATION: Defensin like

<400> SEQUENCE: 297

Asp Gly Val Lys Leu Cys Glu Arg Ala Ser Gln Thr Trp Thr Gly His
1               5                   10                  15

Cys Gly Asn Thr Lys His Cys Asp Lys Gln Cys Arg Asn Trp Glu Gly
                20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 298
<211> LENGTH: 50
<212> TYPE: PRT
<213> ORGANISM: Artificial Sequence
```

```
<220> FEATURE:
<223> OTHER INFORMATION: Defensin like

<400> SEQUENCE: 298

Asn Leu Cys Glu Arg Ala Ser His Thr Trp Ser Gly His Cys Gly Asn
 1               5                  10                  15

Thr Lys His Cys Asp Lys Gln Cys Arg Ser Trp Glu Gly Ala Ala His
            20                  25                  30

Gly Ala Cys His Val Arg Asn Gly Lys Arg Lys Cys Phe Cys Tyr Phe
        35                  40                  45

Asn Cys
    50

<210> SEQ ID NO 299
<211> LENGTH: 53
<212> TYPE: PRT
<213> ORGANISM: Artificial Sequence
<220> FEATURE:
<223> OTHER INFORMATION: Defensin like

<400> SEQUENCE: 299

Asp Gly Val Lys Leu Cys Glu Lys Pro Ser Lys Thr Trp Ser Gly His
 1               5                  10                  15

Cys Gly Asn Thr Lys His Cys Asp Asn Gln Cys Arg Asn Trp Glu Lys
            20                  25                  30

Ala Ala His Gly Ala Cys His Val Arg Asn Gly Lys Trp Lys Cys Phe
        35                  40                  45

Cys Tyr Phe Asn Cys
    50

<210> SEQ ID NO 300
<211> LENGTH: 51
<212> TYPE: PRT
<213> ORGANISM: Artificial Sequence
<220> FEATURE:
<223> OTHER INFORMATION: Defensin like

<400> SEQUENCE: 300

Gln Lys Leu Cys Glu Lys Ala Ser Gln Thr Trp Thr Gly His Cys Gly
 1               5                  10                  15

Asn Thr Lys His Cys Asp Asn Gln Cys Arg Asn Trp Glu Lys Ala Ala
            20                  25                  30

His Gly Ala Cys His Val Arg Asn Gly Lys Trp Lys Cys Phe Cys Tyr
        35                  40                  45

Phe Asn Cys
    50

<210> SEQ ID NO 301
<211> LENGTH: 53
<212> TYPE: PRT
<213> ORGANISM: Artificial Sequence
<220> FEATURE:
<223> OTHER INFORMATION: Defensin like

<400> SEQUENCE: 301

Asp Gly Val Lys Leu Cys Glu Arg Ala Ser Gln Thr Trp Thr Gly His
 1               5                  10                  15

Cys Gly Asn Thr Lys His Cys Asp Thr Gln Cys Arg Ser Trp Glu Gly
            20                  25                  30

Ala Ala His Gly Ala Cys His Lys Arg Asn Gly Lys Trp Lys Cys Phe
        35                  40                  45
```

Cys Tyr Phe Asn Cys
    50

<210> SEQ ID NO 302
<211> LENGTH: 53
<212> TYPE: PRT
<213> ORGANISM: Artificial Sequence
<220> FEATURE:
<223> OTHER INFORMATION: Defensin like

<400> SEQUENCE: 302

Asp Gly Val Lys Leu Cys Glu Arg Ala Ser Lys Thr Trp Ser Gly His
1               5                   10                  15

Cys Gly Asn Thr Lys His Cys Asp Asn Gln Cys Arg Ser Trp Glu Gly
            20                  25                  30

Ala Lys His Gly Ala Cys His Val Arg Ser Gly Lys His Lys Cys Phe
        35                  40                  45

Cys Tyr Phe Asn Cys
    50

<210> SEQ ID NO 303
<211> LENGTH: 53
<212> TYPE: PRT
<213> ORGANISM: Artificial Sequence
<220> FEATURE:
<223> OTHER INFORMATION: Defensin like

<400> SEQUENCE: 303

Asp Gly Val Lys Leu Cys Glu Arg Ala Ser Lys Thr Trp Ser Gly His
1               5                   10                  15

Cys Gly Asn Thr Lys His Cys Asp Lys Gln Cys Lys Asn Trp Glu Lys
            20                  25                  30

Ala Lys His Gly Ala Cys His Lys Arg Ser Gly Lys Trp Lys Cys Phe
        35                  40                  45

Cys Tyr Phe Asn Cys
    50

<210> SEQ ID NO 304
<211> LENGTH: 52
<212> TYPE: PRT
<213> ORGANISM: Artificial Sequence
<220> FEATURE:
<223> OTHER INFORMATION: Defensin like

<400> SEQUENCE: 304

Asp Gly Val Lys Leu Cys Glu Lys Pro Ser Gln Thr Trp Ser His Cys
1               5                   10                  15

Gly Asn Thr Lys His Cys Asp Asn Gln Cys Lys Asn Trp Glu Gly Ala
            20                  25                  30

Ala His Gly Ala Cys His Lys Arg Ser Gly Lys Trp Lys Cys Phe Cys
        35                  40                  45

Tyr Phe Asn Cys
    50

<210> SEQ ID NO 305
<211> LENGTH: 53
<212> TYPE: PRT
<213> ORGANISM: Artificial Sequence
<220> FEATURE:
<223> OTHER INFORMATION: Defensin like

<400> SEQUENCE: 305

Asp Gly Val Lys Leu Cys Glu Arg Ala Ser Gln Thr Trp Thr Gly His
1               5                   10                  15

Cys Gly Asn Thr Lys His Cys Asp Asn Gln Cys Arg Asn Trp Glu Gly
                20                  25                  30

Ala Lys His Gly Ala Cys His Lys Arg Asn Gly Lys Trp Lys Cys Phe
            35                  40                  45

Cys Tyr Phe Asn Cys
        50

<210> SEQ ID NO 306
<211> LENGTH: 53
<212> TYPE: PRT
<213> ORGANISM: Artificial Sequence
<220> FEATURE:
<223> OTHER INFORMATION: Defensin like

<400> SEQUENCE: 306

Asp Gly Val Lys Leu Cys Glu Lys Ala Ser Gln Thr Trp Ser Gly His
1               5                   10                  15

Cys Gly Asn Thr Lys His Cys Asp Asn Gln Cys Lys Asn Trp Glu Gly
                20                  25                  30

Ala Lys His Gly Ala Cys His Lys Arg Asn Gly Lys Trp Lys Cys Phe
            35                  40                  45

Cys Tyr Phe Asn Cys
        50

<210> SEQ ID NO 307
<211> LENGTH: 53
<212> TYPE: PRT
<213> ORGANISM: Artificial Sequence
<220> FEATURE:
<223> OTHER INFORMATION: Defensin like

<400> SEQUENCE: 307

Asp Gly Val Lys Leu Cys Glu Lys Pro Ser Lys Thr Trp Ser Gly His
1               5                   10                  15

Cys Gly Asn Thr Lys His Cys Asp Thr Gln Cys Arg Asn Trp Glu Lys
                20                  25                  30

Ala Lys His Gly Ala Cys His Val Arg Asn Gly Lys Trp Lys Cys Phe
            35                  40                  45

Cys Tyr Phe Asn Cys
        50

<210> SEQ ID NO 308
<211> LENGTH: 53
<212> TYPE: PRT
<213> ORGANISM: Artificial Sequence
<220> FEATURE:
<223> OTHER INFORMATION: Defensin like

<400> SEQUENCE: 308

Asp Gly Val Lys Leu Cys Glu Lys Ala Ser Gln Thr Trp Ser Gly His
1               5                   10                  15

Cys Gly Asn Thr Lys His Cys Asp Asn Gln Cys Lys Asn Trp Glu Gly
                20                  25                  30

Ala Lys His Gly Ala Cys His Lys Arg Ser Gly Lys Trp Lys Cys Phe
            35                  40                  45

Cys Tyr Phe Asn Cys
        50

```
<210> SEQ ID NO 309
<211> LENGTH: 53
<212> TYPE: PRT
<213> ORGANISM: Artificial Sequence
<220> FEATURE:
<223> OTHER INFORMATION: Defensin like

<400> SEQUENCE: 309

Asp Gly Val Lys Leu Cys Glu Lys Pro Ser Gln Thr Trp Thr Gly Asn
 1               5                  10                  15

Cys Gly Asn Thr Lys His Cys Asp Thr Gln Cys Arg Asn Trp Glu Gly
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 310
<211> LENGTH: 53
<212> TYPE: PRT
<213> ORGANISM: Artificial Sequence
<220> FEATURE:
<223> OTHER INFORMATION: Defensin like

<400> SEQUENCE: 310

Asp Gly Val Lys Leu Cys Glu Arg Ala Ser Gln Thr Trp Thr Gly His
 1               5                  10                  15

Cys Gly Asn Thr Lys His Cys Asp Lys Gln Cys Lys Asn Trp Glu Gly
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 311
<211> LENGTH: 53
<212> TYPE: PRT
<213> ORGANISM: Artificial Sequence
<220> FEATURE:
<223> OTHER INFORMATION: Defensin like

<400> SEQUENCE: 311

Asp Gly Val Lys Leu Cys Glu Lys Ala Ser Gln Thr Trp Ser Gly His
 1               5                  10                  15

Cys Gly Asn Thr Lys His Cys Asp Asn Gln Cys Lys Asn Trp Glu Gly
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 312
<211> LENGTH: 53
<212> TYPE: PRT
<213> ORGANISM: Artificial Sequence
<220> FEATURE:
<223> OTHER INFORMATION: Defensin like

<400> SEQUENCE: 312

Asp Gly Val Lys Leu Cys Glu Arg Ala Ser Lys Thr Trp Thr Gly Asn
 1               5                  10                  15
```

```
Cys Gly Asn Thr Lys His Cys Asp Lys Gln Cys Lys Asn Trp Glu Gly
                20                  25                  30

Ala Lys His Gly Ala Cys His Val Arg Asn Gly Lys Trp Lys Cys Phe
             35                  40                  45

Cys Tyr Phe Asn Cys
         50

<210> SEQ ID NO 313
<211> LENGTH: 53
<212> TYPE: PRT
<213> ORGANISM: Artificial Sequence
<220> FEATURE:
<223> OTHER INFORMATION: Defensin like

<400> SEQUENCE: 313

Asp Gly Val Lys Leu Cys Glu Arg Ala Ser Lys Thr Trp Ser Gly His
 1               5                  10                  15

Cys Gly Asn Thr Lys His Cys Asp Asn Gln Cys Arg Ser Trp Glu Gly
                20                  25                  30

Ala Lys His Gly Ala Cys His Val Arg Asn Gly Lys Trp Lys Cys Phe
             35                  40                  45

Cys Tyr Phe Asn Cys
         50

<210> SEQ ID NO 314
<211> LENGTH: 53
<212> TYPE: PRT
<213> ORGANISM: Artificial Sequence
<220> FEATURE:
<223> OTHER INFORMATION: Defensin like

<400> SEQUENCE: 314

Asp Gly Val Lys Leu Cys Glu Arg Pro Ser Gln Thr Trp Thr Gly Asn
 1               5                  10                  15

Cys Gly Asn Thr Lys His Cys Asp Lys Gln Cys Lys Asn Trp Glu Lys
                20                  25                  30

Ala Lys His Gly Ala Cys His Val Arg Asn Gly Lys Trp Lys Cys Phe
             35                  40                  45

Cys Tyr Phe Asn Cys
         50

<210> SEQ ID NO 315
<211> LENGTH: 50
<212> TYPE: PRT
<213> ORGANISM: Artificial Sequence
<220> FEATURE:
<223> OTHER INFORMATION: Defensin like

<400> SEQUENCE: 315

Asn Leu Cys Glu Arg Pro Ser Lys Thr Trp Thr Gly His Cys Gly Asn
 1               5                  10                  15

Thr Lys His Cys Asp Lys Gln Cys Lys Ser Trp Glu Gly Ala Lys His
                20                  25                  30

Gly Ala Cys His Val Arg Ser Gly Lys Trp Lys Cys Phe Cys Tyr Phe
             35                  40                  45

Asn Cys
     50

<210> SEQ ID NO 316
<211> LENGTH: 53
<212> TYPE: PRT
```

<213> ORGANISM: Artificial Sequence
<220> FEATURE:
<223> OTHER INFORMATION: Defensin like

<400> SEQUENCE: 316

Asp Gly Val Lys Leu Cys Glu Lys Pro Ser Gln Thr Trp Ser Gly Asn
1               5                   10                  15

Cys Gly Asn Thr Lys His Cys Asp Lys Gln Cys Lys Ser Trp Glu Gly
            20                  25                  30

Ala Lys His Gly Ala Cys His Val Arg Asn Gly Lys Trp Lys Cys Phe
        35                  40                  45

Cys Tyr Phe Asn Cys
    50

<210> SEQ ID NO 317
<211> LENGTH: 53
<212> TYPE: PRT
<213> ORGANISM: Artificial Sequence
<220> FEATURE:
<223> OTHER INFORMATION: Defensin like

<400> SEQUENCE: 317

Asp Gly Val Lys Leu Cys Glu Lys Ala Ser Gln Thr Trp Thr Gly His
1               5                   10                  15

Cys Gly Asn Thr Lys His Cys Asp Lys Gln Cys Lys Ser Trp Glu Gly
            20                  25                  30

Ala Lys His Gly Ala Cys His Lys Arg Ser Gly Lys Trp Lys Cys Phe
        35                  40                  45

Cys Tyr Phe Asn Cys
    50

<210> SEQ ID NO 318
<211> LENGTH: 51
<212> TYPE: PRT
<213> ORGANISM: Artificial Sequence
<220> FEATURE:
<223> OTHER INFORMATION: Defensin like

<400> SEQUENCE: 318

Gln Lys Leu Cys Glu Arg Ala Ser Lys Thr Trp Thr Gly His Cys Gly
1               5                   10                  15

Asn Thr Lys His Cys Asp Lys Gln Cys Lys Asn Trp Glu Lys Ala Lys
            20                  25                  30

His Gly Ala Cys His Val Arg Asn Gly Lys Trp Lys Cys Phe Cys Tyr
        35                  40                  45

Phe Asn Cys
    50

<210> SEQ ID NO 319
<211> LENGTH: 53
<212> TYPE: PRT
<213> ORGANISM: Artificial Sequence
<220> FEATURE:
<223> OTHER INFORMATION: Defensin like

<400> SEQUENCE: 319

Asp Gly Val Lys Leu Cys Glu Arg Pro Ser Gln Thr Trp Thr Gly Asn
1               5                   10                  15

Cys Gly Asn Thr Lys His Cys Asp Lys Gln Cys Arg Asn Trp Glu Gly
            20                  25                  30

Ala Lys His Gly Ala Cys His Val Arg Asn Gly Lys Trp Lys Cys Phe

```
                35                  40                  45

Cys Tyr Phe Asn Cys
    50

<210> SEQ ID NO 320
<211> LENGTH: 53
<212> TYPE: PRT
<213> ORGANISM: Artificial Sequence
<220> FEATURE:
<223> OTHER INFORMATION: Defensin like

<400> SEQUENCE: 320

Asp Gly Val Lys Leu Cys Glu Lys Ala Ser Gln Thr Trp Thr Gly Asn
1               5                   10                  15

Cys Gly Asn Thr Lys His Cys Asp Asn Gln Cys Lys Asn Trp Glu Lys
            20                  25                  30

Ala Lys His Gly Ala Cys His Lys Arg Ser Gly Lys Trp Lys Cys Phe
        35                  40                  45

Cys Tyr Phe Asn Cys
    50

<210> SEQ ID NO 321
<211> LENGTH: 51
<212> TYPE: PRT
<213> ORGANISM: Artificial Sequence
<220> FEATURE:
<223> OTHER INFORMATION: Defensin like

<400> SEQUENCE: 321

Gln Lys Leu Cys Glu Arg Pro Ser Gln Thr Trp Thr Gly His Cys Gly
1               5                   10                  15

Asn Thr Lys His Cys Asp Thr Gln Cys Lys Ser Trp Glu Gly Ala Lys
            20                  25                  30

His Gly Ala Cys His Lys Arg Asn Gly Lys Trp Lys Cys Phe Cys Tyr
        35                  40                  45

Phe Asn Cys
    50

<210> SEQ ID NO 322
<211> LENGTH: 53
<212> TYPE: PRT
<213> ORGANISM: Artificial Sequence
<220> FEATURE:
<223> OTHER INFORMATION: Defensin like

<400> SEQUENCE: 322

Asp Gly Val Lys Leu Cys Glu Lys Pro Ser Gln Thr Trp Thr Gly Asn
1               5                   10                  15

Cys Gly Asn Thr Lys His Cys Asp Lys Gln Cys Arg Asn Trp Glu Lys
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 323
<211> LENGTH: 53
<212> TYPE: PRT
<213> ORGANISM: Artificial Sequence
<220> FEATURE:
<223> OTHER INFORMATION: Defensin like
```

```
<400> SEQUENCE: 323

Asp Gly Val Lys Leu Cys Glu Lys Pro Ser Lys Thr Trp Ser Gly Asn
1               5                   10                  15

Cys Gly Asn Thr Lys His Cys Asp Asn Gln Cys Arg Ser Trp Glu Lys
            20                  25                  30

Ala Lys His Gly Ala Cys His Lys Arg Ser Gly Lys Trp Lys Cys Phe
        35                  40                  45

Cys Tyr Phe Asn Cys
    50

<210> SEQ ID NO 324
<211> LENGTH: 53
<212> TYPE: PRT
<213> ORGANISM: Artificial Sequence
<220> FEATURE:
<223> OTHER INFORMATION: Defensin like

<400> SEQUENCE: 324

Asp Gly Val Lys Leu Cys Glu Arg Pro Ser Lys Thr Trp Ser Gly Asn
1               5                   10                  15

Cys Gly Asn Thr Lys His Cys Asp Lys Gln Cys Arg Ser Trp Glu Gly
            20                  25                  30

Ala Lys His Gly Ala Cys His Val Arg Ser Gly Lys His Lys Cys Phe
        35                  40                  45

Cys Tyr Phe Asn Cys
    50

<210> SEQ ID NO 325
<211> LENGTH: 53
<212> TYPE: PRT
<213> ORGANISM: Artificial Sequence
<220> FEATURE:
<223> OTHER INFORMATION: Defensin like

<400> SEQUENCE: 325

Asp Gly Val Lys Leu Cys Glu Arg Ala Ser Gln Thr Trp Ser Gly His
1               5                   10                  15

Cys Gly Asn Thr Lys His Cys Asp Asn Gln Cys Lys Ser Trp Glu Lys
            20                  25                  30

Ala Lys His Gly Ala Cys His Val Arg Ser Gly Lys His Lys Cys Phe
        35                  40                  45

Cys Tyr Phe Asn Cys
    50

<210> SEQ ID NO 326
<211> LENGTH: 51
<212> TYPE: PRT
<213> ORGANISM: Artificial Sequence
<220> FEATURE:
<223> OTHER INFORMATION: Defensin like

<400> SEQUENCE: 326

Gln Lys Leu Cys Glu Lys Ala Ser Lys Thr Trp Thr Gly Asn Cys Gly
1               5                   10                  15

Asn Thr Lys His Cys Asp Lys Gln Cys Arg Ser Trp Glu Lys Ala Lys
            20                  25                  30

His Gly Ala Cys His Val Arg Asn Gly Lys Trp Lys Cys Phe Cys Tyr
        35                  40                  45

Phe Asn Cys
    50
```

```
<210> SEQ ID NO 327
<211> LENGTH: 53
<212> TYPE: PRT
<213> ORGANISM: Artificial Sequence
<220> FEATURE:
<223> OTHER INFORMATION: Defensin like

<400> SEQUENCE: 327

Asp Gly Val Lys Leu Cys Glu Lys Ala Ser Lys Thr Trp Ser Gly Asn
1               5                   10                  15

Cys Gly Asn Thr Lys His Cys Asp Lys Gln Cys Arg Ser Trp Glu Lys
            20                  25                  30

Ala Ala His Gly Ala Cys His Val Arg Ser Gly Lys Trp Lys Cys Phe
        35                  40                  45

Cys Tyr Phe Asn Cys
    50

<210> SEQ ID NO 328
<211> LENGTH: 53
<212> TYPE: PRT
<213> ORGANISM: Artificial Sequence
<220> FEATURE:
<223> OTHER INFORMATION: Defensin like

<400> SEQUENCE: 328

Asp Gly Val Lys Leu Cys Glu Lys Ala Ser Lys Thr Trp Thr Gly His
1               5                   10                  15

Cys Gly Asn Thr Lys His Cys Asp Lys Gln Cys Lys Asn Trp Glu Gly
            20                  25                  30

Ala Lys His Gly Ala Cys His Lys Arg Ser Gly Lys Trp Lys Cys Phe
        35                  40                  45

Cys Tyr Phe Asn Cys
    50

<210> SEQ ID NO 329
<211> LENGTH: 53
<212> TYPE: PRT
<213> ORGANISM: Artificial Sequence
<220> FEATURE:
<223> OTHER INFORMATION: Defensin like

<400> SEQUENCE: 329

Asp Gly Val Lys Leu Cys Glu Lys Ala Ser Lys Thr Trp Ser Gly Asn
1               5                   10                  15

Cys Gly Asn Thr Lys His Cys Asp Lys Gln Cys Lys Asn Trp Glu Gly
            20                  25                  30

Ala Ala His Gly Ala Cys His Lys Arg Asn Gly Lys Trp Lys Cys Phe
        35                  40                  45

Cys Tyr Phe Asn Cys
    50

<210> SEQ ID NO 330
<211> LENGTH: 53
<212> TYPE: PRT
<213> ORGANISM: Artificial Sequence
<220> FEATURE:
<223> OTHER INFORMATION: Defensin like

<400> SEQUENCE: 330

Asp Gly Val Lys Leu Cys Glu Lys Ala Ser Gln Thr Trp Thr Gly His
1               5                   10                  15
```

```
Cys Gly Asn Thr Lys His Cys Asp Lys Gln Cys Lys Ser Trp Glu Gly
            20                  25                  30

Ala Lys His Gly Ala Cys His Lys Arg Asn Gly Lys Trp Lys Cys Phe
        35                  40                  45

Cys Tyr Phe Asn Cys
    50

<210> SEQ ID NO 331
<211> LENGTH: 53
<212> TYPE: PRT
<213> ORGANISM: Artificial Sequence
<220> FEATURE:
<223> OTHER INFORMATION: Defensin like

<400> SEQUENCE: 331

Asp Gly Val Lys Leu Cys Glu Arg Ala Ser Lys Thr Trp Thr Gly Asn
1               5                   10                  15

Cys Gly Asn Thr Lys His Cys Asp Asn Gln Cys Lys Ser Trp Glu Gly
            20                  25                  30

Ala Lys His Gly Ala Cys His Val Arg Asn Gly Lys His Lys Cys Phe
        35                  40                  45

Cys Tyr Phe Asn Cys
    50

<210> SEQ ID NO 332
<211> LENGTH: 53
<212> TYPE: PRT
<213> ORGANISM: Artificial Sequence
<220> FEATURE:
<223> OTHER INFORMATION: Defensin like

<400> SEQUENCE: 332

Asp Gly Val Lys Leu Cys Glu Arg Pro Ser Lys Thr Trp Thr Gly His
1               5                   10                  15

Cys Gly Asn Thr Lys His Cys Asp Lys Gln Cys Arg Asn Trp Glu Gly
            20                  25                  30

Ala Ala His Gly Ala Cys His Val Arg Asn Gly Lys His Lys Cys Phe
        35                  40                  45

Cys Tyr Phe Asn Cys
    50

<210> SEQ ID NO 333
<211> LENGTH: 53
<212> TYPE: PRT
<213> ORGANISM: Artificial Sequence
<220> FEATURE:
<223> OTHER INFORMATION: Defensin like

<400> SEQUENCE: 333

Asp Gly Val Lys Leu Cys Glu Arg Pro Ser Lys Thr Trp Ser Gly Asn
1               5                   10                  15

Cys Gly Asn Thr Lys His Cys Asp Asn Gln Cys Arg Asn Trp Glu Gly
            20                  25                  30

Ala Lys His Gly Ala Cys His Lys Arg Ser Gly Lys Trp Lys Cys Phe
        35                  40                  45

Cys Tyr Phe Asn Cys
    50

<210> SEQ ID NO 334
<211> LENGTH: 53
```

```
<212> TYPE: PRT
<213> ORGANISM: Artificial Sequence
<220> FEATURE:
<223> OTHER INFORMATION: Defensin like

<400> SEQUENCE: 334

Asp Gly Val Lys Leu Cys Glu Arg Ala Ser Gln Thr Trp Thr Gly His
1               5                   10                  15

Cys Gly Asn Thr Lys His Cys Asp Asn Gln Cys Arg Ser Trp Glu Gly
            20                  25                  30

Ala Ala His Gly Ala Cys His Lys Arg Ser Gly Lys Trp Lys Cys Phe
        35                  40                  45

Cys Tyr Phe Asn Cys
    50

<210> SEQ ID NO 335
<211> LENGTH: 53
<212> TYPE: PRT
<213> ORGANISM: Artificial Sequence
<220> FEATURE:
<223> OTHER INFORMATION: Defensin like

<400> SEQUENCE: 335

Asp Gly Val Lys Leu Cys Glu Arg Pro Ser Gln Thr Trp Thr Gly His
1               5                   10                  15

Cys Gly Asn Thr Lys His Cys Asp Lys Gln Cys Arg Asn Trp Glu Gly
            20                  25                  30

Ala Ala His Gly Ala Cys His Lys Arg Ser Gly Lys Trp Lys Cys Phe
        35                  40                  45

Cys Tyr Phe Asn Cys
    50

<210> SEQ ID NO 336
<211> LENGTH: 53
<212> TYPE: PRT
<213> ORGANISM: Artificial Sequence
<220> FEATURE:
<223> OTHER INFORMATION: Defensin like

<400> SEQUENCE: 336

Asp Gly Val Lys Leu Cys Glu Arg Pro Ser Gln Thr Trp Ser Gly His
1               5                   10                  15

Cys Gly Asn Thr Lys His Cys Asp Lys Gln Cys Arg Asn Trp Glu Gly
            20                  25                  30

Ala Lys His Gly Ala Cys His Val Arg Asn Gly Lys Trp Lys Cys Phe
        35                  40                  45

Cys Tyr Phe Asn Cys
    50

<210> SEQ ID NO 337
<211> LENGTH: 51
<212> TYPE: PRT
<213> ORGANISM: Artificial Sequence
<220> FEATURE:
<223> OTHER INFORMATION: Defensin like

<400> SEQUENCE: 337

Gln Lys Leu Cys Glu Arg Pro Ser Gln Thr Trp Thr Gly His Cys Gly
1               5                   10                  15

Asn Thr Lys His Cys Asp Lys Gln Cys Lys Asn Trp Glu Gly Ala Lys
            20                  25                  30
```

His Gly Ala Cys His Val Arg Asn Gly Lys Trp Lys Cys Phe Cys Tyr
        35                  40                  45

Phe Asn Cys
    50

<210> SEQ ID NO 338
<211> LENGTH: 53
<212> TYPE: PRT
<213> ORGANISM: Artificial Sequence
<220> FEATURE:
<223> OTHER INFORMATION: Defensin like

<400> SEQUENCE: 338

Asp Gly Val Lys Leu Cys Glu Arg Ala Ser Lys Thr Trp Ser Gly His
1               5                   10                  15

Cys Gly Asn Thr Lys His Cys Asp Lys Gln Cys Lys Asn Trp Glu Lys
            20                  25                  30

Ala Ala His Gly Ala Cys His Val Arg Asn Gly Lys Trp Lys Cys Phe
        35                  40                  45

Cys Tyr Phe Ser Cys
    50

<210> SEQ ID NO 339
<211> LENGTH: 53
<212> TYPE: PRT
<213> ORGANISM: Artificial Sequence
<220> FEATURE:
<223> OTHER INFORMATION: Defensin like

<400> SEQUENCE: 339

Asp Gly Val Lys Leu Cys Glu Arg Pro Ser Lys Thr Trp Ser Gly His
1               5                   10                  15

Cys Gly Asn Thr Lys His Cys Asp Lys Gln Cys Arg Ser Trp Glu Gly
            20                  25                  30

Ala Ala His Gly Ala Cys His Val Arg Asn Gly Lys Trp Lys Cys Phe
        35                  40                  45

Cys Tyr Phe Asn Cys
    50

<210> SEQ ID NO 340
<211> LENGTH: 50
<212> TYPE: PRT
<213> ORGANISM: Aesculus hippocastanum

<400> SEQUENCE: 340

Leu Cys Asn Glu Arg Pro Ser Gln Thr Trp Ser Gly Asn Cys Gly Asn
1               5                   10                  15

Thr Ala His Cys Asp Lys Gln Cys Gln Asp Trp Glu Lys Ala Ser His
            20                  25                  30

Gly Ala Cys His Lys Arg Glu Asn His Trp Lys Cys Phe Cys Tyr Phe
        35                  40                  45

Asn Cys
    50

<210> SEQ ID NO 341
<211> LENGTH: 51
<212> TYPE: PRT
<213> ORGANISM: Arabidopasis thaiana

<400> SEQUENCE: 341

Gln Lys Leu Cys Glu Lys Pro Ser Gly Thr Trp Ser Gly Val Cys Gly

```
                1               5                   10                  15
Asn Ser Asn Ala Cys Lys Asn Gln Cys Ile Asn Leu Glu Gly Ala Lys
            20                  25                  30

His Gly Ser Cys Asn Tyr Val Phe Pro Ala His Lys Cys Ile Cys Tyr
            35                  40                  45

Phe Pro Cys
    50

<210> SEQ ID NO 342
<211> LENGTH: 51
<212> TYPE: PRT
<213> ORGANISM: Arabidopasis thaiana

<400> SEQUENCE: 342

Gln Lys Leu Cys Glu Lys Pro Ser Gly Thr Trp Ser Gly Val Cys Gly
1               5                   10                  15

Asn Ser Asn Ala Cys Lys Asn Gln Cys Ile Asn Leu Glu Gly Ala Lys
            20                  25                  30

His Gly Ser Cys Asn Tyr Val Phe Pro Ala His Lys Cys Ile Cys Tyr
            35                  40                  45

Val Pro Cys
    50

<210> SEQ ID NO 343
<211> LENGTH: 51
<212> TYPE: PRT
<213> ORGANISM: Raphanus sativus

<400> SEQUENCE: 343

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
            35                  40                  45

Phe Pro Cys
    50

<210> SEQ ID NO 344
<211> LENGTH: 51
<212> TYPE: PRT
<213> ORGANISM: Raphanus sativus

<400> SEQUENCE: 344

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
            35                  40                  45

Phe Pro Cys
    50

<210> SEQ ID NO 345
<211> LENGTH: 51
<212> TYPE: PRT
<213> ORGANISM: Raphanus sativus

<400> SEQUENCE: 345
```

```
Gln Lys Leu Cys Glu Arg Ser Ser Gly Thr Trp Ser Gly Val Cys Gly
1               5                   10                  15

Asn Asn Asn Ala Cys Lys Asn Gln Cys Ile Arg Leu Glu Gly Ala Gln
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 346
<211> LENGTH: 51
<212> TYPE: PRT
<213> ORGANISM: Raphanus sativus

<400> SEQUENCE: 346

Gln Lys Leu Cys Glu Arg Ser Ser Gly Thr Trp Ser Gly Val Cys Gly
1               5                   10                  15

Asn Asn Asn Ala Cys Lys Asn Gln Cys Ile Asn Leu Glu Gly Ala Arg
            20                  25                  30

His Gly Ser Cys Asn Tyr Ile Phe Pro Tyr His Arg Cys Ile Cys Tyr
        35                  40                  45

Phe Pro Cys
    50

<210> SEQ ID NO 347
<211> LENGTH: 50
<212> TYPE: PRT
<213> ORGANISM: Dahlia merckii

<400> SEQUENCE: 347

Glu Leu Cys Glu Lys Ala Ser Lys Thr Trp Ser Gly Asn Cys Gly Asn
1               5                   10                  15

Thr Gly His Cys Asp Asn Gln Cys Lys Ser Trp Glu Gly Ala Ala His
            20                  25                  30

Gly Ala Cys His Val Arg Asn Gly Lys His Met Cys Phe Cys Tyr Phe
        35                  40                  45

Asn Cys
    50

<210> SEQ ID NO 348
<211> LENGTH: 49
<212> TYPE: PRT
<213> ORGANISM: Clitoria ternatea

<400> SEQUENCE: 348

Asn Leu Cys Glu Arg Ala Ser Leu Thr Trp Thr Gly Asn Cys Gly Asn
1               5                   10                  15

Thr Gly His Cys Asp Thr Gln Cys Arg Asn Trp Glu Ser Ala Lys His
            20                  25                  30

Gly Ala Cys His Lys Arg Gly Asn Trp Lys Cys Phe Cys Tyr Phe Asn
        35                  40                  45

Cys

<210> SEQ ID NO 349
<211> LENGTH: 51
<212> TYPE: PRT
<213> ORGANISM: Cnicus benedictus

<400> SEQUENCE: 349
```

```
Glu Leu Cys Glu Lys Ala Ser Lys Thr Trp Ser Gly Asn Cys Gly Asn
1               5                   10                  15

Thr Lys His Cys Asp Asp Gln Cys Lys Ser Trp Glu Gly Ala Ala His
            20                  25                  30

Gly Ala Cys His Val Arg Asn Gly Lys His Met Cys Phe Cys Tyr Phe
            35                  40                  45

Asn Cys Asn
    50

<210> SEQ ID NO 350
<211> LENGTH: 50
<212> TYPE: PRT
<213> ORGANISM: Cnicus benedictus

<400> SEQUENCE: 350

Glu Leu Cys Glu Lys Ala Ser Lys Thr Trp Ser Gly Asn Cys Gly Asn
1               5                   10                  15

Thr Lys His Cys Asp Asn Lys Cys Lys Ser Trp Glu Gly Ala Ala His
            20                  25                  30

Gly Ala Cys His Val Arg Ser Gly Lys His Met Cys Phe Cys Tyr Phe
            35                  40                  45

Asn Cys
    50

<210> SEQ ID NO 351
<211> LENGTH: 51
<212> TYPE: PRT
<213> ORGANISM: Raphanus sativus

<400> SEQUENCE: 351

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
            35                  40                  45

Phe Pro Cys
    50

<210> SEQ ID NO 352
<211> LENGTH: 54
<212> TYPE: PRT
<213> ORGANISM: Heuchera sanguinea

<400> SEQUENCE: 352

Asp Gly Val Lys Leu Cys Asp Val Pro Ser Gly Thr Trp Ser Gly His
1               5                   10                  15

Cys Gly Ser Ser Ser Lys Cys Ser Gln Gln Cys Lys Asp Arg Glu His
            20                  25                  30

Phe Ala Tyr Gly Gly Ala Cys His Tyr Gln Phe Pro Ser Val Lys Cys
            35                  40                  45

Phe Cys Lys Arg Gln Cys
    50

<210> SEQ ID NO 353
<211> LENGTH: 51
<212> TYPE: PRT
<213> ORGANISM: Raphanus sativus

<400> SEQUENCE: 353
```

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 354
<211> LENGTH: 51
<212> TYPE: PRT
<213> ORGANISM: Artificial Sequence
<220> FEATURE:
<223> OTHER INFORMATION: Synthetic Construct

<400> SEQUENCE: 354

Gln Lys Leu Cys Glu Arg Pro Ser Arg Thr Trp Ser Gly Val Cys Gly
1               5                   10                  15

Asn Asn Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 355
<211> LENGTH: 51
<212> TYPE: PRT
<213> ORGANISM: Artificial Sequence
<220> FEATURE:
<223> OTHER INFORMATION: Synthetic Construct

<400> SEQUENCE: 355

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 356
<211> LENGTH: 51
<212> TYPE: PRT
<213> ORGANISM: Artificial Sequence
<220> FEATURE:
<223> OTHER INFORMATION: Synthetic Construct

<400> SEQUENCE: 356

Gln Lys Leu Cys Glu Arg Pro Ser Arg Thr Trp Ser Gly Val Cys Gly
1               5                   10                  15

Asn Asn Asn Ala Cys Lys Asn Gln Cys Ile Asn Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 357
<211> LENGTH: 51
<212> TYPE: PRT
<213> ORGANISM: Artificial Sequence
<220> FEATURE:
<223> OTHER INFORMATION: Synthetic Construct

<400> SEQUENCE: 357

```
Gln Lys Leu Cys Met Arg Pro Ser Gly Thr Trp Ser Gly Val Cys Gly
 1               5                  10                  15

Asn Asn Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50
```

<210> SEQ ID NO 358
<211> LENGTH: 51
<212> TYPE: PRT
<213> ORGANISM: Artificial Sequence
<220> FEATURE:
<223> OTHER INFORMATION: Synthetic Construct

<400> SEQUENCE: 358

```
Gln Lys Leu Cys Glu Arg Pro Ser Gly Thr Trp Ser Gly Val Cys Met
 1               5                  10                  15

Asn Asn Asn Ala Cys Lys Asn Gln Cys Ile Asn Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50
```

<210> SEQ ID NO 359
<211> LENGTH: 51
<212> TYPE: PRT
<213> ORGANISM: Artificial Sequence
<220> FEATURE:
<223> OTHER INFORMATION: Synthetic Construct

<400> SEQUENCE: 359

```
Gln Lys Leu Cys Gln Arg Pro Ser Arg Thr Trp Ser Gly Val Cys Gly
 1               5                  10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50
```

<210> SEQ ID NO 360
<211> LENGTH: 51
<212> TYPE: PRT
<213> ORGANISM: Artificial Sequence
<220> FEATURE:
<223> OTHER INFORMATION: Synthetic Construct

<400> SEQUENCE: 360

```
Gln Lys Leu Cys Gln Arg Pro Ser Gly Thr Trp Ser Gly Val Cys Gly
 1               5                  10                  15
```

```
Asn Asn Asn Ala Cys Lys Asn Gln Cys Ile Arg Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 361
<211> LENGTH: 51
<212> TYPE: PRT
<213> ORGANISM: Artificial Sequence
<220> FEATURE:
<223> OTHER INFORMATION: Synthetic Construct

<400> SEQUENCE: 361

Gln Lys Leu Cys Gln Arg Pro Ser Arg Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Arg Phe Pro Ala His Lys Cys Ile Cys Tyr
        35                  40                  45

Phe Pro Cys
    50

<210> SEQ ID NO 362
<211> LENGTH: 51
<212> TYPE: PRT
<213> ORGANISM: Artificial Sequence
<220> FEATURE:
<223> OTHER INFORMATION: Synthetic Construct

<400> SEQUENCE: 362

Gln Lys Leu Cys Met Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 363
<211> LENGTH: 51
<212> TYPE: PRT
<213> ORGANISM: Artificial Sequence
<220> FEATURE:
<223> OTHER INFORMATION: Synthetic Construct

<400> SEQUENCE: 363

Gln Lys Leu Cys Gln Arg Pro Ser Gly Thr Trp Ser Gly Val Cys Met
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Lys Cys Ile Cys Tyr
        35                  40                  45

Phe Pro Cys
    50

<210> SEQ ID NO 364
<211> LENGTH: 50
<212> TYPE: PRT
```

```
<213> ORGANISM: Artificial Sequence
<220> FEATURE:
<223> OTHER INFORMATION: Synthetic Construct

<400> SEQUENCE: 364

Lys Leu Cys Glu Arg Ser Ser Arg Thr Trp Ser Gly Val Cys Gly Asn
 1               5                  10                  15

Asn Asn Ala Cys Lys Asn Gln Cys Ile Arg Leu Glu Gly Ala Gln His
             20                  25                  30

Gly Ser Cys Asn Tyr Val Phe Pro Ala His Lys Cys Ile Cys Tyr Phe
         35                  40                  45

Pro Cys
     50

<210> SEQ ID NO 365
<211> LENGTH: 50
<212> TYPE: PRT
<213> ORGANISM: Artificial Sequence
<220> FEATURE:
<223> OTHER INFORMATION: Synthetic Construct

<400> SEQUENCE: 365

Lys Leu Cys Glu Arg Ser Ser Gly Thr Trp Ser Gly Val Cys Gly Asn
 1               5                  10                  15

Asn Asn Ala Cys Lys Asn Gln Cys Ile Arg Leu Glu Gly Ala Gln His
             20                  25                  30

Gly Ser Cys Asn Tyr Arg Phe Pro Ala His Lys Cys Ile Cys Tyr Phe
         35                  40                  45

Pro Cys
     50

<210> SEQ ID NO 366
<211> LENGTH: 50
<212> TYPE: PRT
<213> ORGANISM: Artificial Sequence
<220> FEATURE:
<223> OTHER INFORMATION: Synthetic Construct

<400> SEQUENCE: 366

Lys Leu Cys Glu Arg Ser Ser Arg Thr Trp Ser Gly Val Cys Gly Asn
 1               5                  10                  15

Asn Asn Ala Cys Lys Asn Gln Cys Ile Arg Leu Glu Gly Ala Gln His
             20                  25                  30

Gly Ser Cys Asn Tyr Arg Phe Pro Ala His Lys Cys Ile Cys Tyr Phe
         35                  40                  45

Pro Cys
     50

<210> SEQ ID NO 367
<211> LENGTH: 50
<212> TYPE: PRT
<213> ORGANISM: Artificial Sequence
<220> FEATURE:
<223> OTHER INFORMATION: Synthetic Construct

<400> SEQUENCE: 367

Lys Leu Cys Met Arg Ser Ser Gly Thr Trp Ser Gly Val Cys Gly Asn
 1               5                  10                  15

Asn Asn Ala Cys Lys Asn Gln Cys Ile Arg Leu Glu Gly Ala Gln His
             20                  25                  30

Gly Ser Cys Asn Tyr Val Phe Pro Ala His Lys Cys Ile Cys Tyr Phe
```

-continued

<210> SEQ ID NO 368
<211> LENGTH: 50
<212> TYPE: PRT
<213> ORGANISM: Artificial Sequence
<220> FEATURE:
<223> OTHER INFORMATION: Synthetic Construct

<400> SEQUENCE: 368

Lys Leu Cys Glu Arg Ser Ser Gly Thr Trp Ser Gly Val Cys Met Asn
1               5                   10                  15

Asn Asn Ala Cys Lys Asn Gln Cys Ile Arg Leu Glu Gly Ala Gln His
            20                  25                  30

Gly Ser Cys Asn Tyr Val Phe Pro Ala His Lys Cys Ile Cys Tyr Phe
        35                  40                  45

Pro Cys
    50

<210> SEQ ID NO 369
<211> LENGTH: 51
<212> TYPE: PRT
<213> ORGANISM: Artificial Sequence
<220> FEATURE:
<223> OTHER INFORMATION: Synthetic Construct

<400> SEQUENCE: 369

Gln Lys Leu Cys Glu Arg Ser Ser Arg Thr Trp Ser Gly Val Cys Gly
1               5                   10                  15

Asn Asn Asn Ala Cys Lys Asn Gln Cys Ile Asn Leu Glu Gly Ala Arg
            20                  25                  30

His Gly Ser Cys Asn Tyr Ile Phe Pro Tyr His Arg Cys Ile Cys Tyr
        35                  40                  45

Phe Pro Cys
    50

<210> SEQ ID NO 370
<211> LENGTH: 51
<212> TYPE: PRT
<213> ORGANISM: Artificial Sequence
<220> FEATURE:
<223> OTHER INFORMATION: Synthetic Construct

<400> SEQUENCE: 370

Gln Lys Leu Cys Glu Arg Ser Ser Gly Thr Trp Ser Gly Val Cys Gly
1               5                   10                  15

Asn Asn Asn Ala Cys Lys Asn Gln Cys Ile Asn Leu Glu Gly Ala Arg
            20                  25                  30

His Gly Ser Cys Asn Tyr Arg Phe Pro Tyr His Arg Cys Ile Cys Tyr
        35                  40                  45

Phe Pro Cys
    50

<210> SEQ ID NO 371
<211> LENGTH: 51
<212> TYPE: PRT
<213> ORGANISM: Artificial Sequence
<220> FEATURE:
<223> OTHER INFORMATION: Synthetic Construct -continued

```
<400> SEQUENCE: 371

Gln Lys Leu Cys Glu Arg Ser Ser Arg Thr Trp Ser Gly Val Cys Gly
 1               5                  10                  15

Asn Asn Asn Ala Cys Lys Asn Gln Cys Ile Asn Leu Glu Gly Ala Arg
             20                  25                  30

His Gly Ser Cys Asn Tyr Arg Phe Pro Tyr His Arg Cys Ile Cys Tyr
         35                  40                  45

Phe Pro Cys
         50

<210> SEQ ID NO 372
<211> LENGTH: 51
<212> TYPE: PRT
<213> ORGANISM: Artificial Sequence
<220> FEATURE:
<223> OTHER INFORMATION: Synthetic Construct

<400> SEQUENCE: 372

Gln Lys Leu Cys Met Arg Ser Ser Gly Thr Trp Ser Gly Val Cys Gly
 1               5                  10                  15

Asn Asn Asn Ala Cys Lys Asn Gln Cys Ile Asn Leu Glu Gly Ala Arg
             20                  25                  30

His Gly Ser Cys Asn Tyr Ile Phe Pro Tyr His Arg Cys Ile Cys Tyr
         35                  40                  45

Phe Pro Cys
         50

<210> SEQ ID NO 373
<211> LENGTH: 51
<212> TYPE: PRT
<213> ORGANISM: Artificial Sequence
<220> FEATURE:
<223> OTHER INFORMATION: Synthetic Construct

<400> SEQUENCE: 373

Gln Lys Leu Cys Glu Arg Ser Ser Gly Thr Trp Ser Gly Val Cys Met
 1               5                  10                  15

Asn Asn Asn Ala Cys Lys Asn Gln Cys Ile Asn Leu Glu Gly Ala Arg
             20                  25                  30

His Gly Ser Cys Asn Tyr Ile Phe Pro Tyr His Arg Cys Ile Cys Tyr
         35                  40                  45

Phe Pro Cys
         50

<210> SEQ ID NO 374
<211> LENGTH: 80
<212> TYPE: PRT
<213> ORGANISM: Brassica oleracea

<400> SEQUENCE: 374

Met Ala Lys Val Ala Ser Ile Val Ala Leu Leu Phe Pro Ala Leu Val
 1               5                  10                  15

Ile Phe Ala Ala Phe Glu Ala Pro Thr Met Val Glu Ala Gln Lys Leu
             20                  25                  30

Cys Glu Arg Pro Ser Gly Thr Trp Ser Gly Val Cys Gly Asn Asn Asn
         35                  40                  45

Ala Cys Lys Asn Gln Cys Ile Arg Leu Glu Lys Ala Arg His Gly Ser
     50                  55                  60

Cys Asn Tyr Val Phe Pro Ala His Lys Cys Ile Cys Tyr Phe Pro Cys
```

```
            65                  70                  75                  80

<210> SEQ ID NO 375
<211> LENGTH: 80
<212> TYPE: PRT
<213> ORGANISM: Arabidopsis thaliana

<400> SEQUENCE: 375

Met Ala Lys Ser Ala Ala Ile Ile Thr Phe Leu Phe Ala Ala Leu Val
1               5                   10                  15

Leu Phe Ala Ala Phe Glu Ala Pro Ile Met Val Glu Ala Gln Lys Leu
            20                  25                  30

Cys Glu Lys Pro Ser Gly Thr Trp Ser Gly Val Cys Gly Asn Ser Asn
        35                  40                  45

Ala Cys Lys Asn Gln Cys Ile Asn Leu Glu Gly Ala Lys His Gly Ser
    50                  55                  60

Cys Asn Tyr Val Phe Pro Ala His Lys Cys Ile Cys Tyr Phe Pro Cys
65                  70                  75                  80

<210> SEQ ID NO 376
<211> LENGTH: 80
<212> TYPE: PRT
<213> ORGANISM: Brassica rapa

<400> SEQUENCE: 376

Met Ala Lys Phe Val Ser Ile Ile Thr Leu Phe Phe Ala Ala Leu Val
1               5                   10                  15

Leu Phe Ala Ala Phe Glu Ala Pro Thr Met Val Lys Ala Gln Lys Leu
            20                  25                  30

Cys Glu Arg Ser Ser Gly Thr Trp Ser Gly Val Cys Gly Asn Asn Asn
        35                  40                  45

Ala Cys Lys Asn Gln Cys Ile Asn Leu Glu Gly Ala Arg His Gly Ser
    50                  55                  60

Cys Asn Tyr Val Phe Pro Tyr His Arg Cys Ile Cys Tyr Phe Pro Cys
65                  70                  75                  80

<210> SEQ ID NO 377
<211> LENGTH: 80
<212> TYPE: PRT
<213> ORGANISM: Wasabia japonica

<400> SEQUENCE: 377

Met Ala Lys Phe Ala Ser Ile Ile Ala Leu Leu Phe Ala Ala Leu Val
1               5                   10                  15

Leu Phe Ser Ala Phe Glu Ala Pro Ser Met Val Glu Ala Gln Lys Leu
            20                  25                  30

Cys Glu Lys Ser Ser Gly Thr Trp Ser Gly Val Cys Gly Asn Asn Asn
        35                  40                  45

Ala Cys Lys Asn Gln Cys Ile Asn Leu Glu Gly Ala Arg His Gly Ser
    50                  55                  60

Cys Asn Tyr Ile Phe Pro Tyr His Arg Cys Ile Cys Tyr Phe Pro Cys
65                  70                  75                  80

<210> SEQ ID NO 378
<211> LENGTH: 79
<212> TYPE: PRT
<213> ORGANISM: Brassica napus

<400> SEQUENCE: 378
```

```
Met Ala Lys Phe Ala Ser Ile Ile Thr Leu Leu Phe Ala Ala Leu Val
 1               5                  10                  15

Val Phe Ala Ala Phe Glu Ala Pro Thr Met Val Glu Ala Lys Leu Cys
                20                  25                  30

Glu Arg Ser Ser Gly Thr Trp Ser Gly Val Cys Gly Asn Asn Asn Ala
            35                  40                  45

Cys Lys Asn Gln Cys Ile Arg Leu Glu Gly Ala Gln His Gly Ser Cys
 50                  55                  60

Asn Tyr Val Phe Pro Ala His Lys Cys Ile Cys Tyr Phe Pro Cys
 65                  70                  75
```

<210> SEQ ID NO 379
<211> LENGTH: 51
<212> TYPE: PRT
<213> ORGANISM: Sinapis alba

<400> SEQUENCE: 379

```
Gln Lys Leu Cys Gln Arg Pro Ser Gly Thr Trp Ser Gly Val Cys Gly
 1               5                  10                  15

Asn Asn Asn Ala Cys Arg Asn Gln Cys Ile Asn Leu Glu Lys Ala Arg
                20                  25                  30

His Gly Ser Cys Asn Tyr Val Phe Pro Ala His Lys Cys Ile Cys Tyr
            35                  40                  45

Phe Pro Cys
    50
```

<210> SEQ ID NO 380
<211> LENGTH: 80
<212> TYPE: PRT
<213> ORGANISM: Arabidopsis thaliana

<400> SEQUENCE: 380

```
Met Ala Lys Ser Ala Thr Ile Val Thr Leu Phe Phe Ala Ala Leu Val
 1               5                  10                  15

Phe Phe Ala Ala Leu Glu Ala Pro Met Val Val Glu Ala Gln Lys Leu
                20                  25                  30

Cys Glu Arg Pro Ser Gly Thr Trp Ser Gly Val Cys Gly Asn Ser Asn
            35                  40                  45

Ala Cys Lys Asn Gln Cys Ile Asn Leu Glu Lys Ala Arg His Gly Ser
 50                  55                  60

Cys Asn Tyr Val Phe Pro Ala His Lys Cys Ile Cys Tyr Phe Pro Cys
 65                  70                  75                  80
```

<210> SEQ ID NO 381
<211> LENGTH: 80
<212> TYPE: PRT
<213> ORGANISM: Arabidopsis thaliana

<400> SEQUENCE: 381

```
Met Ala Lys Phe Ala Ser Ile Ile Thr Leu Ile Phe Ala Ala Leu Val
 1               5                  10                  15

Leu Phe Ala Ala Phe Asp Ala Pro Met Val Glu Ala Gln Lys Leu
                20                  25                  30

Cys Glu Lys Pro Ser Gly Thr Trp Ser Gly Val Cys Gly Asn Ser Asn
            35                  40                  45

Ala Cys Lys Asn Gln Cys Ile Asn Leu Glu Gly Ala Lys His Gly Ser
 50                  55                  60

Cys Asn Tyr Val Phe Pro Ala His Lys Cys Ile Cys Tyr Val Pro Cys
```

```
                65                  70                  75                  80

<210> SEQ ID NO 382
<211> LENGTH: 51
<212> TYPE: PRT
<213> ORGANISM: Sinapsis alba

<400> SEQUENCE: 382

Gln Lys Leu Cys Glu Arg Pro Ser Gly Thr Trp Ser Gly Val Cys Gly
  1               5                  10                  15

Asn Asn Asn Ala Cys Lys Asn Gln Cys Ile Asn Leu Glu Lys Ala Arg
             20                  25                  30

His Gly Ser Cys Asn Tyr Val Phe Pro Ala His Lys Cys Ile Cys Tyr
         35                  40                  45

Phe Pro Cys
     50

<210> SEQ ID NO 383
<211> LENGTH: 51
<212> TYPE: PRT
<213> ORGANISM: Descurainia sophia

<400> SEQUENCE: 383

Gln Lys Leu Cys Glu Lys Pro Ser Gly Thr Trp Ser Gly Val Cys Gly
  1               5                  10                  15

Asn Ser Asn Ala Cys Lys Asn Gln Cys Ile Asn Leu Glu Arg Ala Arg
             20                  25                  30

His Gly Ser Cys Asn Tyr Val Phe Pro Ala His Lys Cys Ile Cys Tyr
         35                  40                  45

Phe Pro Cys
     50

<210> SEQ ID NO 384
<211> LENGTH: 50
<212> TYPE: PRT
<213> ORGANISM: Helianthus annuus

<400> SEQUENCE: 384

Glu Leu Cys Glu Lys Ala Ser Lys Thr Trp Ser Gly Lys Cys Gly Asn
  1               5                  10                  15

Thr Arg His Cys Asp Asp Gln Cys Lys Ser Trp Glu Gly Ala Ala His
             20                  25                  30

Gly Ala Cys His Val Arg Gly Gly Lys His Met Cys Phe Cys Tyr Phe
         35                  40                  45

Asn Cys
     50

<210> SEQ ID NO 385
<211> LENGTH: 108
<212> TYPE: PRT
<213> ORGANISM: Helianthus annuus

<400> SEQUENCE: 385

Met Ala Lys Ile Ser Val Ala Phe Asn Ala Phe Leu Leu Leu Leu Phe
  1               5                  10                  15

Val Leu Ala Ile Ser Glu Ile Gly Ser Val Lys Gly Glu Leu Cys Glu
             20                  25                  30

Lys Ala Ser Gln Thr Trp Ser Gly Thr Cys Gly Lys Thr Lys His Cys
         35                  40                  45
```

```
Asp Asp Gln Cys Lys Ser Trp Glu Gly Ala Ala His Gly Ala Cys His
    50                  55                  60

Val Arg Asp Gly Lys His Met Cys Phe Cys Tyr Phe Asn Cys Ser Lys
 65                  70                  75                  80

Ala Gln Lys Leu Ala Gln Asp Lys Leu Arg Ala Glu Glu Leu Ala Lys
                 85                  90                  95

Glu Lys Ile Glu Pro Glu Lys Ala Thr Ala Lys Pro
            100                 105

<210> SEQ ID NO 386
<211> LENGTH: 161
<212> TYPE: PRT
<213> ORGANISM: Helianthus annuus

<400> SEQUENCE: 386

Leu Val Phe Val Val Ala Ile Ser Asp Ile Ala Thr Val Asn Gly Lys
 1               5                  10                  15

Ile Cys Glu Lys Pro Ser Lys Thr Trp Phe Gly Asn Cys Lys Asp Thr
                20                  25                  30

Asp Lys Cys Asp Lys Arg Cys Ile Asp Trp Glu Gly Ala Lys His Gly
             35                  40                  45

Ala Cys His Gln Arg Glu Ala Lys His Met Cys Phe Cys Tyr Phe Asp
 50                  55                  60

Cys Asp Pro Gln Lys Asn Pro Gly Pro Pro Gly Ala Pro Gly Thr
 65                  70                  75                  80

Pro Gly Thr Pro Pro Ala Pro Pro Gly Lys Gly Glu Gly Asp Ala Pro
                 85                  90                  95

His Pro Pro Pro Thr Pro Ser Pro Pro Gly Gly Asp Gly Gly Ser Gly
            100                 105                 110

Pro Ala Pro Pro Ala Gly Gly Ser Pro Pro Ala Gly Gly Asp
        115                 120                 125

Gly Gly Gly Gly Ala Pro Pro Ala Gly Gly Asp Gly Gly Gly
    130                 135                 140

Ala Pro Pro Pro Ala Gly Gly Asp Gly Gly Ala Pro Pro Gly
145                 150                 155                 160

Ala

<210> SEQ ID NO 387
<211> LENGTH: 50
<212> TYPE: PRT
<213> ORGANISM: Lactuca sativa

<400> SEQUENCE: 387

Glu Leu Cys Glu Lys Pro Ser Lys Thr Trp Ser Gly Asn Cys Gly Asn
 1               5                  10                  15

Thr Gly His Cys Asp Gly Gln Cys Lys Ser Trp Glu Gly Gly Ala His
                20                  25                  30

Gly Ala Cys His Val Arg Gly Gly Lys His Met Cys Phe Cys Tyr Phe
             35                  40                  45

Asn Cys
     50

<210> SEQ ID NO 388
<211> LENGTH: 50
<212> TYPE: PRT
<213> ORGANISM: Lactuca sativa
<220> FEATURE:
<221> NAME/KEY: VARIANT
```

```
<222> LOCATION: 6, 7, 15
<223> OTHER INFORMATION: Xaa = Any Amino Acid

<400> SEQUENCE: 388

Glu Leu Cys Glu Lys Xaa Xaa Lys Lys Trp Ser Gly Asn Cys Xaa Asn
 1               5                  10                  15

Thr Gly His Cys Asp Gly Gln Cys Lys Ser Trp Glu Gly Gly Ala His
             20                  25                  30

Gly Ala Cys His Val Arg Gly Lys His Met Cys Phe Cys Tyr Phe
         35                  40                  45

Asn Cys
    50

<210> SEQ ID NO 389
<211> LENGTH: 162
<212> TYPE: DNA
<213> ORGANISM: Artificial Sequence
<220> FEATURE:
<223> OTHER INFORMATION: Defensin like

<400> SEQUENCE: 389
gatggcgtga aactgtgcga aagaccgagc aaaacctgga gcggcaactg cggcaacacc      60
aaacattgcg ataaccagtg cagaaactgg gaaggcgcca acatggtgc ttgccacaaa     120 cgcagcggca aatggaaatg cttttgctat tttaactgct ga                       162

<210> SEQ ID NO 390
<211> LENGTH: 162
<212> TYPE: DNA
<213> ORGANISM: Artificial Sequence
<220> FEATURE:
<223> OTHER INFORMATION: Defensin like

<400> SEQUENCE: 390
gatggcgtga aactgtgcga aagagcgagc caaacctgga ccggccactg cggcaacacc      60
aaacattgcg ataaccagtg cagaagctgg gaaggcgccg cccatggtgc ttgccacaaa     120
cgcagcggca aatggaaatg cttttgctat tttaactgct ga                       162

<210> SEQ ID NO 391
<211> LENGTH: 162
<212> TYPE: DNA
<213> ORGANISM: Artificial Sequence
<220> FEATURE:
<223> OTHER INFORMATION: Defensin like

<400> SEQUENCE: 391
gatggcgtga aactgtgcga aagaccgagc caaacctgga ccggccactg cggcaacacc      60
aaacattgcg ataaacagtg cagaaactgg gaaggcgccg cccatggtgc ttgccacaaa     120
cgcagcggca aatggaaatg cttttgctat tttaactgct ga                       162

<210> SEQ ID NO 392
<211> LENGTH: 162
<212> TYPE: DNA
<213> ORGANISM: Artificial Sequence
<220> FEATURE:
<223> OTHER INFORMATION: Defensin like

<400> SEQUENCE: 392
gatggcgtga aactgtgcga aagaccgagc caaacctgga gcggccactg cggcaacacc      60
aaacattgcg ataaacagtg cagaaactgg gaaggcgcca acatggtgc ttgccacgtg     120
```

```
cgcaacggca aatggaaatg cttttgctat tttaactgct ga                 162
```

<210> SEQ ID NO 393
<211> LENGTH: 156
<212> TYPE: DNA
<213> ORGANISM: Artificial Sequence
<220> FEATURE:
<223> OTHER INFORMATION: Defensin like

<400> SEQUENCE: 393

```
cagaaactgt gcgaaagacc gagccaaacc tggaccggcc actgcggcaa caccaaacat    60
tgcgataaac agtgcaaaaa ctgggaaggc gccaaacatg gtgcttgcca cgtgcgcaac   120
ggcaaatgga atgcttttg ctattttaac tgctga                              156
```

<210> SEQ ID NO 394
<211> LENGTH: 153
<212> TYPE: DNA
<213> ORGANISM: Artificial Sequence
<220> FEATURE:
<223> OTHER INFORMATION: Defensin like

<400> SEQUENCE: 394

```
aacctgtgcg aaagagcgag caaaacctgg agcggccact gcggcaacac caaacattgc    60
gataaccagt gcagaaactg ggaaggcgcc aaacatggtg cttgccacaa acgcaacggc   120
aaatggaaat gcttttgcta ttttaactgc tga                                153
```

<210> SEQ ID NO 395
<211> LENGTH: 162
<212> TYPE: DNA
<213> ORGANISM: Artificial Sequence
<220> FEATURE:
<223> OTHER INFORMATION: Defensin like

<400> SEQUENCE: 395

```
gatggcgtga aactgtgcga aagagcgagc aaaacctgga gcggccactg cggcaacacc    60
aaacattgcg ataaacagtg caaaaactgg gaaaaagccg cccatggtgc ttgccacgtg   120
cgcaacggca aatggaaatg cttttgctat tttagctgct ga                      162
```

<210> SEQ ID NO 396
<211> LENGTH: 162
<212> TYPE: DNA
<213> ORGANISM: Artificial Sequence
<220> FEATURE:
<223> OTHER INFORMATION: Defensin like

<400> SEQUENCE: 396

```
gatggcgtga aactgtgcga aagaccgagc aaaacctgga gcggccactg cggcaacacc    60
aaacattgcg ataaacagtg cagaagctgg gaaggcgccg cccatggtgc ttgccacgtg   120
cgcaacggca aatggaaatg cttttgctat tttaactgct ga                      162
```

<210> SEQ ID NO 397
<211> LENGTH: 162
<212> TYPE: DNA
<213> ORGANISM: Artificial Sequence
<220> FEATURE:
<223> OTHER INFORMATION: Defensin like

<400> SEQUENCE: 397

```
gatggcgtga aactgtgcga aagaccgagc caaacctgga ccggcaactg cggcaacacc    60
aaacattgcg ataaacagtg caaaagctgg gaaggcgcca aacatggtgc ttgccacaaa   120
```

```
cgcaacggca aatggaaatg cttttgctat tttaactgct ga                        162

<210> SEQ ID NO 398
<211> LENGTH: 159
<212> TYPE: DNA
<213> ORGANISM: Artificial Sequence
<220> FEATURE:
<223> OTHER INFORMATION: Defensin like

<400> SEQUENCE: 398
gatggcgtga aactgtgcga aagagcgagc caaacctgga ccggccactg cggcaacacc     60
aaacattgcg ataaacagtg cagaaactgg gaaggcgcca acatggtgc ttgccacaaa    120 cgcaacggca aatggaaatg cttttgctat tttaactgc                          159

<210> SEQ ID NO 399
<211> LENGTH: 159
<212> TYPE: DNA
<213> ORGANISM: Artificial Sequence
<220> FEATURE:
<223> OTHER INFORMATION: Defensin like

<400> SEQUENCE: 399
gatggcgtga aactgtgcga aaagcgagc caaacctgga gcggccactg cggcaacacc      60
aaacattgcg ataaccagtg caaaaactgg gaaggcgcca acatggtgc ttgccacaaa    120 cgcaacggca aatggaaatg cttttgctat tttaactgc                          159

<210> SEQ ID NO 400
<211> LENGTH: 153
<212> TYPE: DNA
<213> ORGANISM: Artificial Sequence
<220> FEATURE:
<223> OTHER INFORMATION: Defensin like

<400> SEQUENCE: 400
cagaaacttt gcgaacgtcc aagcggtacc tggtctggtg tctgcggcaa caacaacgcc     60
tgcaagaacc agtgcatccg tctggaaaaa gcccgtcacg gctcctgcaa ctatcgcttc    120
ccggcgcata agtgcatttg ctattttccg tgc                                153

<210> SEQ ID NO 401
<211> LENGTH: 153
<212> TYPE: DNA
<213> ORGANISM: Artificial Sequence
<220> FEATURE:
<223> OTHER INFORMATION: Defensin like

<400> SEQUENCE: 401
cagaaactgt gccaaaaacc aagccgtacc tggtctggtg tctgcggcaa caacaacgcc     60
tgcaagaacc agtgcatccg tctggaaaaa gcccgtcacg gctcctgcaa ctatgttttc    120
ccggcgcata agtgcatttg ctattttccg tgc                                153

<210> SEQ ID NO 402
<211> LENGTH: 153
<212> TYPE: DNA
<213> ORGANISM: Artificial Sequence
<220> FEATURE:
<223> OTHER INFORMATION: Defensin like

<400> SEQUENCE: 402
cagaaactgt gccaacgttc aagccgtacc tggtctggtg tctgcggcaa cagcaacgcc     60
```

```
tgcaagaacc agtgcatccg tctggaaggc gcccgtcacg gctcctgcaa ctatgttttc     120
ccggcgcata agtgcatttg ctattttccg tgc                                  153
```

<210> SEQ ID NO 403
<211> LENGTH: 153
<212> TYPE: DNA
<213> ORGANISM: Artificial Sequence
<220> FEATURE:
<223> OTHER INFORMATION: Defensin like

<400> SEQUENCE: 403

```
cagaaactgt gccaacgtcc aagccgtacc tggtctggtg tctgcggcaa cagcaacgcc     60
tgcaagaacc agtgcatcaa tctggaaggc gccaaacacg gctcctgcaa ctatcgcttc    120
ccggcgcata agtgcatttg ctatgttccg tgc                                  153
```

<210> SEQ ID NO 404
<211> LENGTH: 153
<212> TYPE: DNA
<213> ORGANISM: Artificial Sequence
<220> FEATURE:
<223> OTHER INFORMATION: Defensin like

<400> SEQUENCE: 404

```
cagaaactgt gcgaacgtcc aagcggtacc tggtctggtg tctgcggcaa cagcaacgcc     60
tgcaagaacc agtgcatccg tctggaaaaa gcccgtcacg gctcctgcaa ctatcgcttc    120
ccggcgcata agtgcatttg ctattttccg tgc                                  153
```

<210> SEQ ID NO 405
<211> LENGTH: 153
<212> TYPE: DNA
<213> ORGANISM: Artificial Sequence
<220> FEATURE:
<223> OTHER INFORMATION: Defensin like

<400> SEQUENCE: 405

```
cagaaactgt gccaacgtcc aagcggtacc tggtctggtg tctgcatgaa caacaacgcc     60
tgcaagaacc agtgcatccg tctggaaaaa gccaaacacg gctcctgcaa ctatgttttc    120
ccggcgcata agtgcatttg ctattttccg tgc                                  153
```

<210> SEQ ID NO 406
<211> LENGTH: 153
<212> TYPE: DNA
<213> ORGANISM: Artificial Sequence
<220> FEATURE:
<223> OTHER INFORMATION: Defensin like

<400> SEQUENCE: 406

```
cagaaactgt gcgaacgtcc aagccgtacc tggtctggtg tctgcggcaa cagcaacgcc     60
tgcaagaacc agtgcatcaa tctggaaggc gcccgtcacg gctcctgcaa ctatcgcttc    120
ccggcgcata agtgcatttg ctattttccg tgc                                  153
```

<210> SEQ ID NO 407
<211> LENGTH: 153
<212> TYPE: DNA
<213> ORGANISM: Artificial Sequence
<220> FEATURE:
<223> OTHER INFORMATION: Defensin like

<400> SEQUENCE: 407

```
cagaaactgt gcgaacgtcc aagcggtacc tggtctggtg tctgcggcaa cagcaacgcc     60
```
tgcaagaacc agtgcatccg tctggaaggc gcccgtcacg gctcctgcaa ctatcgcttc    120
ccggcgcata agtgcatttg ctattttccg tgc                                153

<210> SEQ ID NO 408
<211> LENGTH: 153
<212> TYPE: DNA
<213> ORGANISM: Artificial Sequence
<220> FEATURE:
<223> OTHER INFORMATION: Defensin like

<400> SEQUENCE: 408
cagaaactgt gcgaaaaacc aagcggtacc tggtctggtg tctgcggcaa cagcaacgcc    60
tgcaagaacc agtgcatccg tctggaaaaa gcccgtcacg gctcctgcaa ctatcgcttc    120
ccggcgcata agtgcatttg ctattttccg tgc                                153

<210> SEQ ID NO 409
<211> LENGTH: 153
<212> TYPE: DNA
<213> ORGANISM: Artificial Sequence
<220> FEATURE:
<223> OTHER INFORMATION: Defensin like

<400> SEQUENCE: 409
cagaaactgt gccaacgtcc aagcggtacc tggtctggtg tctgcggcaa caacaacgcc    60
tgcaagaacc agtgcatccg tctggaaggc gccaaacacg gctcctgcaa ctatattttc    120
ccggcgcata agtgcatttg ctattttccg tgc                                153

<210> SEQ ID NO 410
<211> LENGTH: 153
<212> TYPE: DNA
<213> ORGANISM: Artificial Sequence
<220> FEATURE:
<223> OTHER INFORMATION: Defensin like

<400> SEQUENCE: 410
cagaaactgt gccaacgtcc aagccgtacc tggtctggtg tctgcggcaa cagcaacgcc    60
tgcaagaacc agtgcatcaa tctggaaaaa gcccgtcacg gctcctgcaa ctatcgcttc    120
ccggcgcata agtgcatttg ctattttccg tgc                                153

<210> SEQ ID NO 411
<211> LENGTH: 153
<212> TYPE: DNA
<213> ORGANISM: Artificial Sequence
<220> FEATURE:
<223> OTHER INFORMATION: Defensin like

<400> SEQUENCE: 411
cagaaactgt gccaacgttc aagccgtacc tggtctggtg tctgcggcaa caacaacgcc    60
tgcaagaacc agtgcatccg tctggaaggc gcccgtcacg gctcctgcaa ctatcgcttc    120
ccggcgcata agtgcatttg ctattttccg tgc                                153

<210> SEQ ID NO 412
<211> LENGTH: 153
<212> TYPE: DNA
<213> ORGANISM: Artificial Sequence
<220> FEATURE:
<223> OTHER INFORMATION: Defensin like

<400> SEQUENCE: 412

```
cagaaactgt gccaacgtcc aagcggtacc tggtctggtg tctgcggcaa caacaacgcc      60
tgcaagaacc agtgcatccg tctggaaaaa gcccgtcacg gctcctgcaa ctatcgcttc     120
ccggcgcata agtgcatttg ctattttccg tgc                                  153
```

<210> SEQ ID NO 413
<211> LENGTH: 153
<212> TYPE: DNA
<213> ORGANISM: Artificial Sequence
<220> FEATURE:
<223> OTHER INFORMATION: Defensin like

<400> SEQUENCE: 413

```
cagaaactgt gccaacgtcc aagccgtacc tggtctggtg tctgcatgaa caacaacgcc      60
tgcaagaacc agtgcatccg tctggaaggc gcccgtcacg gctcctgcaa ctatcgcttc     120
ccggcgcata agtgcatttg ctattttccg tgc                                  153
```

<210> SEQ ID NO 414
<211> LENGTH: 153
<212> TYPE: DNA
<213> ORGANISM: Artificial Sequence
<220> FEATURE:
<223> OTHER INFORMATION: Defensin like

<400> SEQUENCE: 414

```
cagaaactgt gcgaacgtcc aagcggtacc tggtctggtg tctgcatgaa cagcaacgcc      60
tgcaagaacc agtgcatccg tctggaaggc gcccgtcacg gctcctgcaa ctatgttttc     120
ccggcgcata agtgcatttg ctattttccg tgc                                  153
```

<210> SEQ ID NO 415
<211> LENGTH: 153
<212> TYPE: DNA
<213> ORGANISM: Artificial Sequence
<220> FEATURE:
<223> OTHER INFORMATION: Defensin like

<400> SEQUENCE: 415

```
cagaaactgt gccaacgtcc aagccgtacc tggtctggtg tctgcggcaa cagcaacgcc      60
tgcaagaacc agtgcatccg tctggaaaaa gcccgtcacg gctcctgcaa ctatcgcttc     120
ccggcgcata agtgcatttg ctattttccg tgc                                  153
```

<210> SEQ ID NO 416
<211> LENGTH: 153
<212> TYPE: DNA
<213> ORGANISM: Artificial Sequence
<220> FEATURE:
<223> OTHER INFORMATION: Defensin like

<400> SEQUENCE: 416

```
cagaaactgt gccaaaaacc aagccgtacc tggtctggtg tctgcggcaa cagcaacgcc      60
tgcaagaacc agtgcatccg tctggaaaaa gcccgtcacg gctcctgcaa ctatgttttc     120
ccggcgcata agtgcatttg ctatgttccg tgc                                  153
```

<210> SEQ ID NO 417
<211> LENGTH: 153
<212> TYPE: DNA
<213> ORGANISM: Artificial Sequence
<220> FEATURE:
<223> OTHER INFORMATION: Defensin like

<400> SEQUENCE: 417
cagaaactgt gccaacgtcc aagcggtacc tggtctggtg tctgcggcaa caacaacgcc     60
tgcaagaacc agtgcatcaa tctggaaggc gcccgtcacg gctcctgcaa ctatcgcttc    120
ccggcgcata agtgcatttg ctattttccg tgc                                 153

<210> SEQ ID NO 418
<211> LENGTH: 153
<212> TYPE: DNA
<213> ORGANISM: Artificial Sequence
<220> FEATURE:
<223> OTHER INFORMATION: Defensin like

<400> SEQUENCE: 418
cagaaactgt gccaacgtcc aagcggtacc tggtctggtg tctgcatgaa caacaacgcc     60
tgcaagaacc agtgcatccg tctggaaaaa gcccgtcacg gctcctgcaa ctatcgcttc    120
ccggcgcata agtgcatttg ctattttccg tgc                                 153

<210> SEQ ID NO 419
<211> LENGTH: 153
<212> TYPE: DNA
<213> ORGANISM: Artificial Sequence
<220> FEATURE:
<223> OTHER INFORMATION: Defensin like

<400> SEQUENCE: 419
cagaaactgt gccaacgtcc aagccgtacc tggtctggtg tctgcggcaa caacaacgcc     60
tgcaagaacc agtgcatccg tctggaaaaa gcccgtcacg gctcctgcaa ctatcgcttc    120
ccggcgcata agtgcatttg ctatgttccg tgc                                 153

<210> SEQ ID NO 420
<211> LENGTH: 153
<212> TYPE: DNA
<213> ORGANISM: Artificial Sequence
<220> FEATURE:
<223> OTHER INFORMATION: Defensin like

<400> SEQUENCE: 420
cagaaactgt gcgaacgttc aagccgtacc tggtctggtg tctgcggcaa cagcaacgcc     60
tgcaagaacc agtgcatccg tctggaaggc gcccgtcacg gctcctgcaa ctatgttttc    120
ccggcgcata agtgcatttg ctattttccg tgc                                 153

<210> SEQ ID NO 421
<211> LENGTH: 153
<212> TYPE: DNA
<213> ORGANISM: Artificial Sequence
<220> FEATURE:
<223> OTHER INFORMATION: Defensin like

<400> SEQUENCE: 421
caaaaactgt gccaacgtcc aagcggtacc tggtctggtg tctgcggcaa cagcaacgcc     60
tgcaagaacc agtgcatccg tctggaaggc gcccgtcacg gctcctgcaa ctatcgcttc    120
ccggcgcata agtgcatttg ctattttccg tgc                                 153

<210> SEQ ID NO 422
<211> LENGTH: 153
<212> TYPE: DNA
<213> ORGANISM: Artificial Sequence
<220> FEATURE:
<223> OTHER INFORMATION: Defensin like

```
<400> SEQUENCE: 422
cagaaactgt gccaacgtcc aagccgtacc tggtctggtg tctgcatgaa cagcaacgcc      60
tgcaagaacc agtgcatccg tctggaaaaa gcccgtcacg gctcctgcaa ctatcgcttc     120
ccggcgcata agtgcatttg ctatttccg tgc                                   153

<210> SEQ ID NO 423
<211> LENGTH: 153
<212> TYPE: DNA
<213> ORGANISM: Artificial Sequence
<220> FEATURE:
<223> OTHER INFORMATION: Defensin like

<400> SEQUENCE: 423
cagcaactgt gccaacgtcc aagccgtacc tggtctggtg tctgcatgaa caacaacgcc      60
tgcaagaacc agtgcatccg tctggaaggc gcccgtcacg gctcctgcaa ctatcgcttc     120
ccggcgcata agtgcatttg ctatgttccg tgc                                   153

<210> SEQ ID NO 424
<211> LENGTH: 153
<212> TYPE: DNA
<213> ORGANISM: Artificial Sequence
<220> FEATURE:
<223> OTHER INFORMATION: Defensin like

<400> SEQUENCE: 424
cagaaactgt gcgaaaaacc aagccgtacc tggtctggtg tctgcggcaa caacaacgcc      60
tgcaagaacc agtgcatccg tctggaaaaa gcccgtcacg gctcctgcaa ctatcgcttc     120
ccggcgcata agtgcatttg ctatgttccg tgc                                   153

<210> SEQ ID NO 425
<211> LENGTH: 150
<212> TYPE: DNA
<213> ORGANISM: Artificial Sequence
<220> FEATURE:
<223> OTHER INFORMATION: Defensin like

<400> SEQUENCE: 425
aacctgtgcg aaagagcgag caaaacctgg agcggcaact gcggcaacac caaacattgc      60
gatacccagt gcagaaactg ggaaggcgcc aaacatggtg cttgccacaa acgcagcggc     120
aaatggaagt gcttttgcta ttttaactgc                                       150

<210> SEQ ID NO 426
<211> LENGTH: 150
<212> TYPE: DNA
<213> ORGANISM: Artificial Sequence
<220> FEATURE:
<223> OTHER INFORMATION: Defensin like

<400> SEQUENCE: 426
gaactgtgcg aaaaagcgag caagacctgg agcggcaact gcggcaacac caagcactgc      60
gataaccagt gccgcagctg ggaaggcgcc gcccatggtg cttgccacaa acgtagcggg     120
aagtggaagt gcttttgcta ttttaactgc                                       150

<210> SEQ ID NO 427
<211> LENGTH: 150
<212> TYPE: DNA
<213> ORGANISM: Artificial Sequence
<220> FEATURE:
<223> OTHER INFORMATION: Defensin like
```

<400> SEQUENCE: 427
aacctgtgcg aacgcgcgag caagacctgg agcggcaact gcggcaacac caagcactgc    60
gatactcagt gccgcaactg ggaaggcgcc aaacatggtg cttgccacaa acgtagcggg    120
aagtggaagt gcttttgcta ttttaactgc                                     150

<210> SEQ ID NO 428
<211> LENGTH: 153
<212> TYPE: DNA
<213> ORGANISM: Artificial Sequence
<220> FEATURE:
<223> OTHER INFORMATION: Defensin like

<400> SEQUENCE: 428
aacctgtgcg aacgcgcgag caagacctgg agcggcaact gcggcaacac caagcactgc    60
gatgaccagt gcaaaagctg ggaaggcgcc gcccatggtg cttgccacaa acgtagcggg    120
aagtggaagt gcttttgcta ttttaactgc tga                                 153

<210> SEQ ID NO 429
<211> LENGTH: 153
<212> TYPE: DNA
<213> ORGANISM: Artificial Sequence
<220> FEATURE:
<223> OTHER INFORMATION: Defensin like

<400> SEQUENCE: 429
aacctgtgcg aaaaagcgag taagacctgg accggcaact gcggcaacac caagcactgc    60
gataaccagt gcaaaagctg ggaaggcgcc gcccatggtg cttgccacgt tcgtagcggg    120
aagcatatgt gcttttgcta ttttaactgc tga                                 153

<210> SEQ ID NO 430
<211> LENGTH: 153
<212> TYPE: DNA
<213> ORGANISM: Artificial Sequence
<220> FEATURE:
<223> OTHER INFORMATION: Defensin like

<400> SEQUENCE: 430
aaactgtgcg aacgcgcgag caagacctgg agcggcaact gcggcaacac caagcactgc    60
gatgaccagt gcaaaaactg ggaaagcgcc gcccatggtg cttgccacgt tcgtagcggg    120
aaccataagt gcttttgcta ttttaactgc tga                                 153

<210> SEQ ID NO 431
<211> LENGTH: 153
<212> TYPE: DNA
<213> ORGANISM: Artificial Sequence
<220> FEATURE:
<223> OTHER INFORMATION: Defensin like

<400> SEQUENCE: 431
aacctgtgcg aaaaagcgag ccttacctgg accggcaact gcggcaacac caagcactgc    60
gatactcagt gcaaaaactg ggaaggcgcc aaacatggtg cttgccacgt tcgtagcggg    120
aagtggaagt gcttttgcta ttttaactgc tga                                 153

<210> SEQ ID NO 432
<211> LENGTH: 153
<212> TYPE: DNA
<213> ORGANISM: Artificial Sequence
<220> FEATURE:

<223> OTHER INFORMATION: Defensin like

<400> SEQUENCE: 432
aacctgtgcg aaaaagcgag ccttacctgg accggcaact gcggcaacac caagcactgc    60
gatactcagt gcaaaaactg ggaaggcgcc aaacatggtg cttgccacgt tcgtaacggg   120
aaccataagt gcttttgcta ttttaactgc tga                                153

<210> SEQ ID NO 433
<211> LENGTH: 153
<212> TYPE: DNA
<213> ORGANISM: Artificial Sequence
<220> FEATURE:
<223> OTHER INFORMATION: Defensin like

<400> SEQUENCE: 433
gaactgtgcg aacgcgcgag ccttacctgg accggcaact gcggcaacac caagcactgc    60
gatactcagt gcaaaaactg ggaaggcgcc gcccatggtg cttgccacgt atgtagcggg   120
aagcataagt gcttttgcta ttttaactgc tga                                153

<210> SEQ ID NO 434
<211> LENGTH: 153
<212> TYPE: DNA
<213> ORGANISM: Artificial Sequence
<220> FEATURE:
<223> OTHER INFORMATION: Defensin like

<400> SEQUENCE: 434
aacctgtgcg aaaaagcgag ccttacctgg agcggcaact gcggcaacac caagcactgc    60
gataacaagt gcaaaaactg ggaaggcgcc gcccatggtg cttgccacaa acgtaacggg   120
aagtggaagt gcttttgcta ttttaactgc tga                                153

<210> SEQ ID NO 435
<211> LENGTH: 153
<212> TYPE: DNA
<213> ORGANISM: Artificial Sequence
<220> FEATURE:
<223> OTHER INFORMATION: Defensin like

<400> SEQUENCE: 435
aacctgtgcg aacgcgcgag ccttacctgg agcggcaact gcggcaacac caagcactgc    60
gatactcagt gcaaaagctg ggaaagcgcc aaacatggtg cttgccacgt tcgtagcggg   120
aagcatatgt gcttttgcta ttttaactgc tga                                153

<210> SEQ ID NO 436
<211> LENGTH: 153
<212> TYPE: DNA
<213> ORGANISM: Artificial Sequence
<220> FEATURE:
<223> OTHER INFORMATION: Defensin like

<400> SEQUENCE: 436
aacctgtgcg aaaaagcgag ccttacctgg agcggcaact gcggcaacac ccgccactgc    60
gatactcagt gccgcagctg ggaaggcgcc gcccatggtg cttgccacgt tcgtagcggg   120
aaccataagt gcttttgcta ttttaactgc tga                                153

<210> SEQ ID NO 437
<211> LENGTH: 153
<212> TYPE: DNA
<213> ORGANISM: Artificial Sequence

```
<220> FEATURE:
<223> OTHER INFORMATION: Defensin like

<400> SEQUENCE: 437
aaactgtgcg aacgcgcgag caagacctgg agcggcaact gcggcaacac caagcactgc    60
gataaccagt gccgcagctg ggaaggcgcc aaacatggtg cttgccacgt tcgtagcggg   120
aagtggatgt gcttttgcta ttttaactgc tga                                153

<210> SEQ ID NO 438
<211> LENGTH: 153
<212> TYPE: DNA
<213> ORGANISM: Artificial Sequence
<220> FEATURE:
<223> OTHER INFORMATION: Defensin like
<220> FEATURE:
<221> NAME/KEY: misc_feature
<222> LOCATION: 23
<223> OTHER INFORMATION: n = A, C, G, or T

<400> SEQUENCE: 438
aacctgtgcg aaaaagcgag cangacctgg agcggcaact gcggcaacac caagcactgc    60
gatgaccagt gccgcaactg ggaaggcgcc aaacatggtg cttgccacgt tcgtaacggg   120
aagtggaagt gcttttgcta ttttaactgc tga                                153

<210> SEQ ID NO 439
<211> LENGTH: 153
<212> TYPE: DNA
<213> ORGANISM: Artificial Sequence
<220> FEATURE:
<223> OTHER INFORMATION: Defensin like

<400> SEQUENCE: 439
gaactgtgcg aaaaagcgag caagacctgg agcggcaact gcggcaacac caagcactgc    60
gatactcagt gcaaaaactg ggaaggcgcc aaacatggtg cttgccacgt tcgtagcggg   120
aagcataagt gcttttgcta ttttaactgc tga                                153

<210> SEQ ID NO 440
<211> LENGTH: 153
<212> TYPE: DNA
<213> ORGANISM: Artificial Sequence
<220> FEATURE:
<223> OTHER INFORMATION: Defensin like

<400> SEQUENCE: 440
gaactgtgcg aaaaagcgag caagacctgg agcggcaact gcggcaacac caagcactgc    60
gatactaagt gcaaaaactg ggaaggcgcc aaacatggtg cttgccacaa acgtaacggg   120
aagtggatgt gcttttgcta ttttaactgc tga                                153

<210> SEQ ID NO 441
<211> LENGTH: 153
<212> TYPE: DNA
<213> ORGANISM: Artificial Sequence
<220> FEATURE:
<223> OTHER INFORMATION: Defensin like

<400> SEQUENCE: 441
gaactgtgcg aaaaagcgag caagacctgg accggcaact gcggcaacac caagcactgc    60
gatactcagt gcaaaaactg ggaaagcgcc aaacatggtg cttgccacgt tcgtaacggg   120
aagcataagt gcttttgcta ttttaactgc tga                                153
```

<210> SEQ ID NO 442
<211> LENGTH: 150
<212> TYPE: DNA
<213> ORGANISM: Artificial Sequence
<220> FEATURE:
<223> OTHER INFORMATION: Defensin like

<400> SEQUENCE: 442

```
aacctgtgcg aacgcgcgag caagacctgg accggcaact gcggcaacac cggccactgc      60
gataacaagt gcaaaagctg ggaaggcgcc aaacatggtg cttgccacgt tcgtaacggg     120
aagtggatgt gcttttgcta ttttaactgc                                       150
```

<210> SEQ ID NO 443
<211> LENGTH: 153
<212> TYPE: DNA
<213> ORGANISM: Artificial Sequence
<220> FEATURE:
<223> OTHER INFORMATION: Defensin like

<400> SEQUENCE: 443

```
aacctgtgcg aaaaagcgag caagacctgg agcggcaact gcggcaacac caagcactgc      60
gatgaccagt gccgcaactg ggaaggcgcc aaacatggtg cttgccacgt tcgtaacggg     120
aagtggaagt gcttttgcta ttttaactgc tga                                   153
```

<210> SEQ ID NO 444
<211> LENGTH: 153
<212> TYPE: DNA
<213> ORGANISM: Artificial Sequence
<220> FEATURE:
<223> OTHER INFORMATION: Defensin like

<400> SEQUENCE: 444

```
aacctgtgcg aacgcgcgag caagacctgg agcggcaact gcggcaacac caagcactgc      60
gatactcagt gcaaaaactg ggaaggcgcc aaacatggtg cttgccacaa acgtagcggg     120
aagtggatgt gcttttgcta ttttaactgc tga                                   153
```

<210> SEQ ID NO 445
<211> LENGTH: 153
<212> TYPE: DNA
<213> ORGANISM: Artificial Sequence
<220> FEATURE:
<223> OTHER INFORMATION: Defensin like

<400> SEQUENCE: 445

```
gaactgtgcg aaaaagcgag caagacctgg accggcaact gcggcaacac caagcactgc      60
gataaccagt gcaaaagctg ggaaggcgcc gcccatggtg cttgccacaa acgtagcggg     120
aagtggatgt gcttttgcta ttttaactgc tga                                   153
```

<210> SEQ ID NO 446
<211> LENGTH: 150
<212> TYPE: DNA
<213> ORGANISM: Artificial Sequence
<220> FEATURE:
<223> OTHER INFORMATION: Defensin like

<400> SEQUENCE: 446

```
gaactgtgcg aaaaagcgag caagacctgg agcggcaact gcggcaacac caaacactgc      60
gataaccagt gcaaaagctg ggaaggcgcc aaacatggtg cttgccacaa acgtagcggg     120
aagcataagt gcttttgcta ttttaactgc                                       150
```

<210> SEQ ID NO 447
<211> LENGTH: 150
<212> TYPE: DNA
<213> ORGANISM: Artificial Sequence
<220> FEATURE:
<223> OTHER INFORMATION: Defensin like

<400> SEQUENCE: 447
aacctgtgcg aacgcgcgag caagacctgg accggcaact gcggcaacac caagcactgc      60
gatactcagt gcaaaaactg ggaaagcgcc aaacatggtg cttgccacgt tcgtagcggg     120
aagcataagt gcttttgcta ttttaactgc                                      150

<210> SEQ ID NO 448
<211> LENGTH: 150
<212> TYPE: DNA
<213> ORGANISM: Artificial Sequence
<220> FEATURE:
<223> OTHER INFORMATION: Defensin like

<400> SEQUENCE: 448
aacctgtgcg aacgcgcgag caagacctgg agcggcaact gcggcaacac caagcactgc      60
gatactcagt gccgcaactg ggaaagcgcc gcccatggtg cttgccacaa acgtaacggg     120
aagtggaagt gcttttgcta ttttaactgc                                      150

<210> SEQ ID NO 449
<211> LENGTH: 150
<212> TYPE: DNA
<213> ORGANISM: Artificial Sequence
<220> FEATURE:
<223> OTHER INFORMATION: Defensin like

<400> SEQUENCE: 449
aacctgtgcg aacgcgcgag caagacctgg accggcaact gcggcaacac cggccactgc      60
aataaccagt gccgcagctg ggaaggcgcc aaacatggtg cttgccacgt tcgtagcggg     120
aagcataagt gcttttgcta ttttaactgc                                      150

<210> SEQ ID NO 450
<211> LENGTH: 150
<212> TYPE: DNA
<213> ORGANISM: Artificial Sequence
<220> FEATURE:
<223> OTHER INFORMATION: Defensin like

<400> SEQUENCE: 450
aacctgtgcg aacgcgcgag caagacctgg agcggcaact gcggcaacac caagcactgc      60
gatactcagt gccgcaagtg ggaaggcgcc aaacatggtg cttgccacaa acgtaacggg     120
aagtggatgt gcttttgcta ttttaactgc                                      150

<210> SEQ ID NO 451
<211> LENGTH: 150
<212> TYPE: DNA
<213> ORGANISM: Artificial Sequence
<220> FEATURE:
<223> OTHER INFORMATION: Defensin like

<400> SEQUENCE: 451
aacctgtgcg aacgcgcgag caagacctgg accggcaact gcggcaacac caagcactgc      60
gatactcagt gcaaaaactg ggaaggcgcc aaacatggtg cttgccacaa acgtaacggg     120

```
aagtggaagt gcttttgcta ttttaactgc                                     150
```

<210> SEQ ID NO 452
<211> LENGTH: 150
<212> TYPE: DNA
<213> ORGANISM: Artificial Sequence
<220> FEATURE:
<223> OTHER INFORMATION: Defensin like

<400> SEQUENCE: 452

```
aacctgtgcg aacgcgcgag ccttacctgg accggcaact gcggcaacac cggccactgc    60
gatactaagt gccgcaactg ggaaggcgcc aaacatggtg cttgccacaa acgtaacggg   120
aagtggaagt gcttttgcta ttttaactgc                                    150
```

<210> SEQ ID NO 453
<211> LENGTH: 150
<212> TYPE: DNA
<213> ORGANISM: Artificial Sequence
<220> FEATURE:
<223> OTHER INFORMATION: Defensin like

<400> SEQUENCE: 453

```
aacctgtgcg aacgcgcgag caagacctgg accggcaact gcggcaacac caagcactgc    60
gatactaagt gccgcagctg ggaaagcgcc aaacatggtg cttgccacaa acgtaacggg   120
aagtggaagt gcttttgcta ttttaactgc                                    150
```

<210> SEQ ID NO 454
<211> LENGTH: 150
<212> TYPE: DNA
<213> ORGANISM: Artificial Sequence
<220> FEATURE:
<223> OTHER INFORMATION: Defensin like

<400> SEQUENCE: 454

```
aacctgtgcg aaaaagcgag caagacctgg accggcaact gcggcaacac caagcactgc    60
gatactcagt gcaaaagctg ggaaggcgcc gcccatggtg cttgccacaa acgtagcggg   120
aagtggaagt gcttttgcta ttttaactgc                                    150
```

<210> SEQ ID NO 455
<211> LENGTH: 150
<212> TYPE: DNA
<213> ORGANISM: Artificial Sequence
<220> FEATURE:
<223> OTHER INFORMATION: Defensin like

<400> SEQUENCE: 455

```
aacctgtgcg aacgcgcgag caagacctgg accggcaact gcggcaacac caagcactgc    60
gatacgcagt gcaaaagctg ggaaggcgcc gcccatggtg cttgccacgt tcgtagcggg   120
aagcataagt gcttttgcta ttttaactgc                                    150
```

<210> SEQ ID NO 456
<211> LENGTH: 150
<212> TYPE: DNA
<213> ORGANISM: Artificial Sequence
<220> FEATURE:
<223> OTHER INFORMATION: Defensin like

<400> SEQUENCE: 456

```
aacctgtgcg aaaaagcgag caagacctgg accggcaact gcggcaacac cggccactgc    60
gatactcagt gccgcaactg ggaaggcgcc aaacatggtg cttgccacaa acgtaacggg   120
```
aagcataagt gctttgcta ttttaactgc                                              150

<210> SEQ ID NO 457
<211> LENGTH: 150
<212> TYPE: DNA
<213> ORGANISM: Artificial Sequence
<220> FEATURE:
<223> OTHER INFORMATION: Defensin like

<400> SEQUENCE: 457
gaactgtgcg aaaaagcgag caagacctgg accggcaact gcggcaacac caagcactgc    60
gataaccagt gcaaaaactg ggaaggcgcc aaacatggtg cttgccacgt tcgtagcggg   120
aagtggaagt gctttgcta ttttaactgc                                      150

<210> SEQ ID NO 458
<211> LENGTH: 150
<212> TYPE: DNA
<213> ORGANISM: Artificial Sequence
<220> FEATURE:
<223> OTHER INFORMATION: Defensin like

<400> SEQUENCE: 458
aacctgtgcg aacgcgcgag caagacctgg accggcaact gcggcaacac caagcactgc    60
gatactcagt gcaaaagctg ggaaagcgcc aaacatggtg cttgccacgt tcgtagcggg   120
aagcataagt gctttgcta ttttaactgc                                      150

<210> SEQ ID NO 459
<211> LENGTH: 150
<212> TYPE: DNA
<213> ORGANISM: Artificial Sequence
<220> FEATURE:
<223> OTHER INFORMATION: Defensin like

<400> SEQUENCE: 459
gaactgtgcg aaaaagcgag ccttacctgg accggcaact gcggcaacac caagcactgc    60
gatactcagt gccgcaactg ggaaggcgcc aaacatggtg cttgccacaa acgtagcggg   120
aagtggaagt gctttgcta ttttaactgc                                      150

<210> SEQ ID NO 460
<211> LENGTH: 150
<212> TYPE: DNA
<213> ORGANISM: Artificial Sequence
<220> FEATURE:
<223> OTHER INFORMATION: Defensin like

<400> SEQUENCE: 460
aacctgtgcg aaaaagcgag caagacctgg accggcaact gcggcaacac caagcactgc    60
gataaccagt gccgcaactg ggaaggcgcc gcccatggtg cttgccacaa acgtaacggg   120
aagtggaagt gctttgcta ttttaactgc                                      150

<210> SEQ ID NO 461
<211> LENGTH: 150
<212> TYPE: DNA
<213> ORGANISM: Artificial Sequence
<220> FEATURE:
<223> OTHER INFORMATION: Defensin like

<400> SEQUENCE: 461
aacctgtgcg aacgcgcgag caagacctgg accggcaact gcggcaacac caagcactgc    60

```
gatactcagt gcaaaatctg ggaaggcgcc aaacatggtg cttgccacaa acgtagcggg    120
aagtggaagt gcttttgcta ttttaactgc                                    150
```

<210> SEQ ID NO 462
<211> LENGTH: 150
<212> TYPE: DNA
<213> ORGANISM: Artificial Sequence
<220> FEATURE:
<223> OTHER INFORMATION: Defensin like

<400> SEQUENCE: 462

```
aacctgtgcg aaaaagcgag caagacctgg accggcaact gcggcaacac caagcactgc    60
gataaccagt gcaaaaactg ggaaagcgcc gcccatggtg cttgccacaa acgtaacggg   120
aagtggaagt gcttttgcta ttttaactgc                                    150
```

<210> SEQ ID NO 463
<211> LENGTH: 150
<212> TYPE: DNA
<213> ORGANISM: Artificial Sequence
<220> FEATURE:
<223> OTHER INFORMATION: Defensin like

<400> SEQUENCE: 463

```
aacctgtgcg aacgcgcgag ccttacctgg agcggcaact gcggcaacac caagcactgc    60
gatgaccagt gcaaaagctg ggaaagcgcc aaacatggtg cttgccacaa acgtaacggg   120
aagcataagt gcttttgcta ttttaactgc                                    150
```

<210> SEQ ID NO 464
<211> LENGTH: 150
<212> TYPE: DNA
<213> ORGANISM: Artificial Sequence
<220> FEATURE:
<223> OTHER INFORMATION: Defensin like

<400> SEQUENCE: 464

```
aacctgtgcg aacgcgcgag caagacctgg agcggcaact gcggcaacac caagcactgc    60
gatgacaagt gcaaaagctg ggaaggcgcc aaacatggtg cttgccacgt tcgtaacggg   120
aagcataagt gcttttgcta ttttaactgc                                    150
```

<210> SEQ ID NO 465
<211> LENGTH: 150
<212> TYPE: DNA
<213> ORGANISM: Artificial Sequence
<220> FEATURE:
<223> OTHER INFORMATION: Defensin like

<400> SEQUENCE: 465

```
gaactgtgcg aacgcgcgag caagacctgg accggcaact gcggcaacac caagcactgc    60
gataaccagt gccgcagctg ggaaagcgcc gcccatggtg cttgccacaa acgtagcggg   120
aagtggaagt gcttttgcta ttttaactgc                                    150
```

<210> SEQ ID NO 466
<211> LENGTH: 150
<212> TYPE: DNA
<213> ORGANISM: Artificial Sequence
<220> FEATURE:
<223> OTHER INFORMATION: Defensin like

<400> SEQUENCE: 466

```
aacctgtgcg aacgcgcgag caagacctgg accggcaact gcggcaacac cggccactgc    60
```
gatactcagt gcaaaaactg ggaaggcgcc aaacatggtg cttgccacaa acgtagcggg    120
aagtggaagt gcttttgcta ttttaactgc                                    150

<210> SEQ ID NO 467
<211> LENGTH: 150
<212> TYPE: DNA
<213> ORGANISM: Artificial Sequence
<220> FEATURE:
<223> OTHER INFORMATION: Defensin like

<400> SEQUENCE: 467
aacctgtgcg aacgcgcgag caagacctgg accggcaact gcggcaacac caagcactgc    60
gatactcagt gcaaaaactg ggaaggcgcc aaacatggtg cttgccacgt tcgtagcggg    120
aagcatatgt gcttttgcta ttttaactgc                                    150

<210> SEQ ID NO 468
<211> LENGTH: 153
<212> TYPE: DNA
<213> ORGANISM: Artificial Sequence
<220> FEATURE:
<223> OTHER INFORMATION: Defensin like

<400> SEQUENCE: 468
aacctgtgcg aaaaagcgag caagacctgg accggcaact gcggcaacac caagcactgc    60
gatgaccagt gcaaaaactg ggaaggcgcc aaacatggtg cttgccacaa acgtaacggg    120
aagtggatgt gcttttgcta ttttaactgc tga                                153

<210> SEQ ID NO 469
<211> LENGTH: 153
<212> TYPE: DNA
<213> ORGANISM: Artificial Sequence
<220> FEATURE:
<223> OTHER INFORMATION: Defensin like

<400> SEQUENCE: 469
aacctgtgcg aacgcgcgag caagacctgg agcggcaact gcggcaacac caagcactgc    60
gatactcagt gcaaaaactg ggaaagcgcc aaacatggtg cttgccacaa acgtaacggg    120
aagcataagt gcttttgcta ttttaactgc tga                                153

<210> SEQ ID NO 470
<211> LENGTH: 153
<212> TYPE: DNA
<213> ORGANISM: Artificial Sequence
<220> FEATURE:
<223> OTHER INFORMATION: Defensin like

<400> SEQUENCE: 470
gaactgtgcg aacgcgcgag ccttacctgg accggcaact gcggcaacac caagcactgc    60
gatactcagt gcaaaagctg ggaaggcgcc aaacatggtg cttgccacaa acgtagcggg    120
aagtggaagt gcttttgcta ttttaactgc tga                                153

<210> SEQ ID NO 471
<211> LENGTH: 153
<212> TYPE: DNA
<213> ORGANISM: Artificial Sequence
<220> FEATURE:
<223> OTHER INFORMATION: Defensin like

<400> SEQUENCE: 471

-continued aaactgtgcg aacgcgcgag ccttacctgg agcggcaact gcggcaacac caagcactgc    60
gatactaagt gcaaaaactg ggaaggcgcc aaacatggtc cttgccacaa acgtaacggg   120
aagtggaagt gcttttgcta ttttaactgc tga                                153

<210> SEQ ID NO 472
<211> LENGTH: 153
<212> TYPE: DNA
<213> ORGANISM: Artificial Sequence
<220> FEATURE:
<223> OTHER INFORMATION: Defensin like

<400> SEQUENCE: 472
aacctgtgcg aacgcgcgag caagacctgg accggcaact gcggcaacac caagcactgc    60
gataaccagt gccgcaactg ggaaagcgcc gcccatggtg cttgccacaa acgtagcggg   120
aagtggaagt gcttttgcta ttttaactgc tga                                153

<210> SEQ ID NO 473
<211> LENGTH: 153
<212> TYPE: DNA
<213> ORGANISM: Artificial Sequence
<220> FEATURE:
<223> OTHER INFORMATION: Defensin like

<400> SEQUENCE: 473
aacctgtggg aaaagcgag ccttacctgg accggcaact gcggcaacac caagcactgc     60
gataaccagt gcaaaaactg ggaaagcgcc gcccatggtg cttgccacaa acgtagcggg   120
aagtggatgt gcttttgcta ttttaactgc tga                                153

<210> SEQ ID NO 474
<211> LENGTH: 153
<212> TYPE: DNA
<213> ORGANISM: Artificial Sequence
<220> FEATURE:
<223> OTHER INFORMATION: Defensin like

<400> SEQUENCE: 474
aacctgtgcg aacgcgcgag caagacctgg accggcaact gcggcaacac cggccactgc    60
gataacaagt gcaaaagctg ggaaggcgcc aaacatggtg cttgccacgt tcgtagcggg   120
aagtggatgt gcttttgcta ttttaactgc tga                                153

<210> SEQ ID NO 475
<211> LENGTH: 153
<212> TYPE: DNA
<213> ORGANISM: Artificial Sequence
<220> FEATURE:
<223> OTHER INFORMATION: Defensin like

<400> SEQUENCE: 475
gaactgtgcg aacgcgcgag caagacctgg agcggcaact gcggcaacac caagcactgc    60
gatactcagt gccgcaactg ggaaagcgcc aaacatggtg cttgccacgt tcgtagcggg   120
aagtggaagt gcttttgcta ttttaactgc tga                                153

<210> SEQ ID NO 476
<211> LENGTH: 153
<212> TYPE: DNA
<213> ORGANISM: Artificial Sequence
<220> FEATURE:
<223> OTHER INFORMATION: Defensin like

<400> SEQUENCE: 476

```
aaactgtgcg aaaaagcgag caagacctgg accggcaact gcggcaacac caagcactgc    60
gatactcagt gcaaaagctg ggaaggcgcc aaacatggtg cttgccacaa acgtaacggg   120
aagtggatgt gctttggcta ttttaactgc tga                                153

<210> SEQ ID NO 477
<211> LENGTH: 153
<212> TYPE: DNA
<213> ORGANISM: Artificial Sequence
<220> FEATURE:
<223> OTHER INFORMATION: Defensin like

<400> SEQUENCE: 477
aacctgtgcg aaaaagcgag caagacctgg accggcaact gcggcaacac cggccactgc    60
gataacaagt gcaaaagctg ggaaggcgcc aaacatggtg cttgccacat tcgtagcggg   120
aagtggaagt gctttggcta ttttaactgc tga                                153

<210> SEQ ID NO 478
<211> LENGTH: 153
<212> TYPE: DNA
<213> ORGANISM: Artificial Sequence
<220> FEATURE:
<223> OTHER INFORMATION: Defensin like

<400> SEQUENCE: 478
aacctgtgcg aaaaagcgag ccttacctgg agcggcaact gcggcaacac caagcactgc    60
gatactcagt gcaaaagctg ggaaagcgcc gcccatggtg cttgccacaa acgtagcggg   120
aagcataagt gctttggcta ttttaactgc tga                                153

<210> SEQ ID NO 479
<211> LENGTH: 153
<212> TYPE: DNA
<213> ORGANISM: Artificial Sequence
<220> FEATURE:
<223> OTHER INFORMATION: Defensin like

<400> SEQUENCE: 479
aacctgtgcg aacgcgcgag caagacctgg agcggcaact gcggcaacac caagcactgc    60
gatactcagt gccgcagctg ggaaggcgcc gcccatggtg cttgccacaa acgtagcggg   120
aagcatatgt gttttggcta ttttaactgc tga                                153

<210> SEQ ID NO 480
<211> LENGTH: 153
<212> TYPE: DNA
<213> ORGANISM: Artificial Sequence
<220> FEATURE:
<223> OTHER INFORMATION: Defensin like

<400> SEQUENCE: 480
gaactgtgcg aaaaagcgag caagacctgg agcggcaact gcggcaacac caagcactgc    60
gatactaagt gcaaaagctg ggaaagcgcc aaacatggtg cttgccacaa acgtagcggg   120
aactggaagt gctttggcta ttttaactgc tga                                153

<210> SEQ ID NO 481
<211> LENGTH: 153
<212> TYPE: DNA
<213> ORGANISM: Artificial Sequence
<220> FEATURE:
<223> OTHER INFORMATION: Defensin like
```

<400> SEQUENCE: 481
gaactgtgcg aaaaagcgag caagacctgg accggcaact gcggcaacac caagcactgc      60
gatactcagt gcaaaagctg ggaaggcgcc gcccatggtg cttgccacaa acgtaacggg     120
aagtggatgt gcttttgcta ttttaactgc tga                                 153

<210> SEQ ID NO 482
<211> LENGTH: 153
<212> TYPE: DNA
<213> ORGANISM: Artificial Sequence
<220> FEATURE:
<223> OTHER INFORMATION: Defensin like

<400> SEQUENCE: 482
aacctgtgcg aacgcgcgag ccttacctgg accggcaact gcggcaacac caagcactgc      60
gataaccagt gcaaaagctg ggaaggcgcc gcccatggtg cttgccacgt tcgtaacggg     120
aagcataagt gcttttgcta ttttaactgc tga                                 153

<210> SEQ ID NO 483
<211> LENGTH: 153
<212> TYPE: DNA
<213> ORGANISM: Artificial Sequence
<220> FEATURE:
<223> OTHER INFORMATION: Defensin like

<400> SEQUENCE: 483
gaactgtgcg aacgcgcgag caagacctgg accggcaact gcggcaacac caagcactgc      60
gatactcagt gcaaaagctg ggaaggcgcc gcccatggtg cttgccacgt tcgtagcggg     120
aagcataagt gcttttgcta ttttaactgc tga                                 153

<210> SEQ ID NO 484
<211> LENGTH: 153
<212> TYPE: DNA
<213> ORGANISM: Artificial Sequence
<220> FEATURE:
<223> OTHER INFORMATION: Defensin like

<400> SEQUENCE: 484
gaactgtgcg aaaaagcgag ccttacctgg agcggcaact gcggcaacac caagcactgc      60
gatactcagt gccgcaactg ggaaggcgcc aaacatggtg cttgccacaa acgtaacggg     120
aagtggatgt gcttttgcta ttttaactgc tga                                 153

<210> SEQ ID NO 485
<211> LENGTH: 153
<212> TYPE: DNA
<213> ORGANISM: Artificial Sequence
<220> FEATURE:
<223> OTHER INFORMATION: Defensin like

<400> SEQUENCE: 485
aacctgtgcg aacgcgcgag ccttacctgg accggcaact gcggcaacac cggccactgc      60
gatactcagt gcaaaagctg ggaaggcgcc aaacatggtg cttgccacaa acgtaacggg     120
aagtggaagt gcttttgcta ttttaactgc tga                                 153

<210> SEQ ID NO 486
<211> LENGTH: 153
<212> TYPE: DNA
<213> ORGANISM: Artificial Sequence
<220> FEATURE:
<223> OTHER INFORMATION: Defensin like

```
<400> SEQUENCE: 486
aacctgtgcg aaaaagcgag caagacctgg agcggcaact gcggcaacac caagcactgc      60
gatactcagt gccgcaactg ggaaagcgcc gcccatggtg cttgccacaa acgtaacggg     120
aagtggaagt gcttttgcta ttttaactgc tga                                 153

<210> SEQ ID NO 487
<211> LENGTH: 153
<212> TYPE: DNA
<213> ORGANISM: Artificial Sequence
<220> FEATURE:
<223> OTHER INFORMATION: Defensin like

<400> SEQUENCE: 487
aacctgtgcg aacgcgcgag caagacctgg agcggcaact gcggcaacac caagcactgc      60
gataacaagt gcaaaaactg ggaaagcgcc gcccatggtg cttgccacgt tcgtaacggg     120
aagcatatgt gcttttgcta ttttaactgc tga                                 153

<210> SEQ ID NO 488
<211> LENGTH: 153
<212> TYPE: DNA
<213> ORGANISM: Artificial Sequence
<220> FEATURE:
<223> OTHER INFORMATION: Defensin like

<400> SEQUENCE: 488
aacctgtgcg aacgcgcgag caagacctgg agcggcaact gcggcaacac caagcactgc      60
gatgaccagt gccgcagctg ggaaggcgcc aaacatggtg cttgccacaa acgtagcggg     120
aagtggatgt gcttttgcta ttttaactgc tga                                 153

<210> SEQ ID NO 489
<211> LENGTH: 153
<212> TYPE: DNA
<213> ORGANISM: Artificial Sequence
<220> FEATURE:
<223> OTHER INFORMATION: Defensin like

<400> SEQUENCE: 489
aacctgtgcg aaaagcgag caaaacctgg accggcaact gcggcaacac caaacattgc      60
gatacccagt gcagaagctg ggaaggcgcc aaacatggtg cttgccacgt gcgcaacggc     120
aaacataagt gcttttgcta ttttaactgc tga                                 153

<210> SEQ ID NO 490
<211> LENGTH: 153
<212> TYPE: DNA
<213> ORGANISM: Artificial Sequence
<220> FEATURE:
<223> OTHER INFORMATION: Defensin like

<400> SEQUENCE: 490
aacctgtgcg aaaaagcgag caaaacctgg agcggcaact gcggcaacac caaacattgc      60
gatacccagt gcagaaactg ggaaggcgcc gcccatggtg cttgccacaa acgcagcggc     120
aaatggaagt gcttttgcta ttttaactgc tga                                 153

<210> SEQ ID NO 491
<211> LENGTH: 153
<212> TYPE: DNA
<213> ORGANISM: Artificial Sequence
<220> FEATURE:
```

<223> OTHER INFORMATION: Defensin like
<220> FEATURE:
<221> NAME/KEY: misc_feature
<222> LOCATION: 70
<223> OTHER INFORMATION: n = A, C, G, or T

<400> SEQUENCE: 491

```
aacctgtgcg aaaaagcgag caaaacctgg agcggcaact gcggcaacac cggccattgc    60
gatacccagn gcaaaaactg ggaaggcgcc aaacatggtg cttgccacgt gcgcaacggc   120
aaacataagt gcttttgcta ttttaactgc tga                                153
```

<210> SEQ ID NO 492
<211> LENGTH: 153
<212> TYPE: DNA
<213> ORGANISM: Artificial Sequence
<220> FEATURE:
<223> OTHER INFORMATION: Defensin like

<400> SEQUENCE: 492

```
aacctgtgcg aaaaagcgag caaaacctgg agcggcaact gcggcaacac caaacattgc    60
gatacccagt gcaaaagctg ggaaggcgcc aaacatggtg cttgccacgt gcgcaacggc   120
aaacataagt gcttttgcta ttttaactgc tga                                153
```

<210> SEQ ID NO 493
<211> LENGTH: 153
<212> TYPE: DNA
<213> ORGANISM: Artificial Sequence
<220> FEATURE:
<223> OTHER INFORMATION: Defensin like

<400> SEQUENCE: 493

```
aacctgtgcg aaaaagcgag caaaacctgg accggcaact gcggcaacac caaacattgc    60
gataaccagt gcagaagctg ggaaggcgcc gcccatggtg cttgccacaa acgcaacggc   120
aaatggaagt gcttttgcta ttttaactgc tga                                153
```

<210> SEQ ID NO 494
<211> LENGTH: 153
<212> TYPE: DNA
<213> ORGANISM: Artificial Sequence
<220> FEATURE:
<223> OTHER INFORMATION: Defensin like

<400> SEQUENCE: 494

```
aacctgtgcg aaaaagcgag caaaacctgg accggcaact gcggcaacac caaacattgc    60
gataaccagt gcaaaagctg ggaaggcgcc aaacatggtg cttgccacaa acgcagcggc   120
aaatggaagt gcttttgcta ttttaactgc tga                                153
```

<210> SEQ ID NO 495
<211> LENGTH: 153
<212> TYPE: DNA
<213> ORGANISM: Artificial Sequence
<220> FEATURE:
<223> OTHER INFORMATION: Defensin like

<400> SEQUENCE: 495

```
aacctgtgcg aaagagcgag caaaacctgg agcggcaact gcggcaacac caaacattgc    60
gataccaagt gcagaagctg ggaaggcgcc aaacatggtg cttgccacgt gcgcaacggc   120
aaatggaagt gcttttgcta ttttaactgc tga                                153
```

<210> SEQ ID NO 496
<211> LENGTH: 153
<212> TYPE: DNA
<213> ORGANISM: Artificial Sequence
<220> FEATURE:
<223> OTHER INFORMATION: Defensin like

<400> SEQUENCE: 496

```
aacctgtgcg aaaaagcgag caaaacctgg accggcaact gcggcaacac caaacattgc      60
gatacccagt gcaaaagctg ggaaggcgcc aaacatggtg cttgccacgt gcgcaacggc     120
aaacataagt gcttttgcta ttttaactgc tga                                  153
```

<210> SEQ ID NO 497
<211> LENGTH: 153
<212> TYPE: DNA
<213> ORGANISM: Artificial Sequence
<220> FEATURE:
<223> OTHER INFORMATION: Defensin like

<400> SEQUENCE: 497

```
aacctgtgcg aaagagcgag caaaacctgg agcggcaact gcggcaacac caaacattgc      60
gatacccagt gcaaaagctg ggaaggcgcc gcccatggtg cttgccacaa acgcaacggc     120
aaatggaagt gcttttgcta ttttaactgc tga                                  153
```

<210> SEQ ID NO 498
<211> LENGTH: 153
<212> TYPE: DNA
<213> ORGANISM: Artificial Sequence
<220> FEATURE:
<223> OTHER INFORMATION: Defensin like

<400> SEQUENCE: 498

```
aacctgtgcg aaagagcgag caaaacctgg agcggcaact gcggcaacac caaacattgc      60
gataaccagt gcaaaagctg ggaaggcgcc gcccatggtg cttgccacaa acgcagcggc     120
aaacataagt gcttttgcta ttttaactgc tga                                  153
```

<210> SEQ ID NO 499
<211> LENGTH: 153
<212> TYPE: DNA
<213> ORGANISM: Artificial Sequence
<220> FEATURE:
<223> OTHER INFORMATION: Defensin like

<400> SEQUENCE: 499

```
aacctgtgcg aaagagcgag caaaacctgg accggcaact gcggcaacac caaacattgc      60
gatacccagt gcaaaagctg ggaaggcgcc aaacatggtg cttgccacaa acgcagcggc     120
aaatggaagt gcttttgcta ttttaactgc tga                                  153
```

<210> SEQ ID NO 500
<211> LENGTH: 153
<212> TYPE: DNA
<213> ORGANISM: Artificial Sequence
<220> FEATURE:
<223> OTHER INFORMATION: Defensin like

<400> SEQUENCE: 500

```
aacctgtgcg aaaaagcgag caaaacctgg accggcaact gcggcaacac caaacattgc      60
gatacccagt gcaaaagctg ggaaggcgcc aaacatggtg cttgccacaa acgcaacggc     120
aaatggaagt gcttttgcta ttttaactgc tga                                  153
```

<210> SEQ ID NO 501
<211> LENGTH: 153
<212> TYPE: DNA
<213> ORGANISM: Artificial Sequence
<220> FEATURE:
<223> OTHER INFORMATION: Defensin like

<400> SEQUENCE: 501
aacctgtgcg aaagagcgag caaaacctgg accggcaact gcggcaacac caaacattgc    60
gatacccagt gcagaagctg ggaaggcgcc gcccatggtg cttgccacgt gcgcagcggc    120
aaacataagt gcttttgcta ttttaactgc tga    153

<210> SEQ ID NO 502
<211> LENGTH: 153
<212> TYPE: DNA
<213> ORGANISM: Artificial Sequence
<220> FEATURE:
<223> OTHER INFORMATION: Defensin like

<400> SEQUENCE: 502
aacctgtgcg aaagagcgag caaaacctgg accggcaact gcggcaacac caaacattgc    60
gataaccagt gcaaaagctg ggaaggcgcc gcccatggtg cttgccacgt gcgcaacggc    120
aaacataagt gcttttgcta ttttaactgc tga    153

<210> SEQ ID NO 503
<211> LENGTH: 153
<212> TYPE: DNA
<213> ORGANISM: Artificial Sequence
<220> FEATURE:
<223> OTHER INFORMATION: Defensin like

<400> SEQUENCE: 503
aacctgtgcg aaagagcgag caaaacctgg agcggcaact gcggcaacac caaacattgc    60
gatacccagt gcaaaagctg ggaaggcgcc gcccatggtg cttgccacgt gcgcagcggc    120
aaacataagt gcttttgcta ttttaactgc tga    153

<210> SEQ ID NO 504
<211> LENGTH: 153
<212> TYPE: DNA
<213> ORGANISM: Artificial Sequence
<220> FEATURE:
<223> OTHER INFORMATION: Defensin like

<400> SEQUENCE: 504
aacctgtgcg aaagagcgag caaaacctgg agcggcaact gcggcaacac caaacattgc    60
gatacccagt gcaaaagctg ggaaggcgcc aaacatggtg cttgccacgt gcgcagcggc    120
aaacataagt gcttttgcta ttttaactgc tga    153

<210> SEQ ID NO 505
<211> LENGTH: 153
<212> TYPE: DNA
<213> ORGANISM: Artificial Sequence
<220> FEATURE:
<223> OTHER INFORMATION: Defensin like

<400> SEQUENCE: 505
aacctgtgcg aaagagcgag caaaacctgg accggcaact gcggcaacac caaacattgc    60
gatacccagt gcagaagctg ggaaggcgcc aaacatggtg cttgccacgt gcgcagcggc    120
aaacataagt gcttttgcta ttttaactgc tga    153

```
<210> SEQ ID NO 506
<211> LENGTH: 153
<212> TYPE: DNA
<213> ORGANISM: Artificial Sequence
<220> FEATURE:
<223> OTHER INFORMATION: Defensin like

<400> SEQUENCE: 506
aacctgtgcg aaagagcgag caaaacctgg accggcaact gcggcaacac caaacattgc      60
gatacccagt gcaaaaactg ggaaggcgcc gcccatggtg cttgccacgt gcgcaacggc     120
aaacataagt gcttttgcta ttttaactgc tga                                  153

<210> SEQ ID NO 507
<211> LENGTH: 153
<212> TYPE: DNA
<213> ORGANISM: Artificial Sequence
<220> FEATURE:
<223> OTHER INFORMATION: Defensin like

<400> SEQUENCE: 507
aacctgtgcg aaagagcgag caaaacctgg agcggcaact gcggcaacac cggccattgc      60
gatacccagt gcaaaagctg ggaaggcgcc aaacatggtg cttgccacgt gcgcaacggc     120
aaacataagt gcttttgcta ttttaactgc tga                                  153

<210> SEQ ID NO 508
<211> LENGTH: 153
<212> TYPE: DNA
<213> ORGANISM: Artificial Sequence
<220> FEATURE:
<223> OTHER INFORMATION: Defensin like

<400> SEQUENCE: 508
aacctgtgcg aaagagcgag caaaacctgg accggcaact gcggcaacac caaacattgc      60
gatacccagt gcaaaagctg ggaaggcgcc aaacatggtg cttgccacgt gcgcagcggc     120
aaacataagt gcttttgcta ttttaactgc tga                                  153

<210> SEQ ID NO 509
<211> LENGTH: 153
<212> TYPE: DNA
<213> ORGANISM: Artificial Sequence
<220> FEATURE:
<223> OTHER INFORMATION: Defensin like

<400> SEQUENCE: 509
aacctgtgcg aaagagcgag caaaacctgg accggcaact gcggcaacac caaacattgc      60
gataaccagt gcaaaagctg ggaaggcgcc aaacatggtg cttgccacgt gcgcagcggc     120
aaacataagt gcttttgcta ttttaactgc tga                                  153

<210> SEQ ID NO 510
<211> LENGTH: 153
<212> TYPE: DNA
<213> ORGANISM: Artificial Sequence
<220> FEATURE:
<223> OTHER INFORMATION: Defensin like

<400> SEQUENCE: 510
aacctgtgcg aaaagcgag caaaacctgg agcggcaact gcggcaacac caaacattgc      60
gataccaagt gcagaaactg ggaaggcgcc aaacatggtg cttgccacgt gcgcaacggc     120
```

```
aaatggatgt gcttttgcta ttttaactgc tga                                153
```

<210> SEQ ID NO 511
<211> LENGTH: 153
<212> TYPE: DNA
<213> ORGANISM: Artificial Sequence
<220> FEATURE:
<223> OTHER INFORMATION: Defensin like

<400> SEQUENCE: 511

```
aacctgtgcg aaagagcgag caaaacctgg agcggcaact gcggcaacac caaacattgc    60
gataaccagt gcagaaactg ggaaggcgcc aaacatggtg cttgccacgt gcgcaacggc   120
aaatggaagt gcttttgcta ttttaactgc tga                                153
```

<210> SEQ ID NO 512
<211> LENGTH: 153
<212> TYPE: DNA
<213> ORGANISM: Artificial Sequence
<220> FEATURE:
<223> OTHER INFORMATION: Defensin like

<400> SEQUENCE: 512

```
aacctgtgcg aaagagcgag caaaacctgg agcggcaact gcggcaacac cggccattgc    60
gatacccagt gcagaagctg ggaaggcgcc aaacatggtg cttgccacgt gcgcaacggc   120
aaacataagt gcttttgcta ttttaactgc tga                                153
```

<210> SEQ ID NO 513
<211> LENGTH: 153
<212> TYPE: DNA
<213> ORGANISM: Artificial Sequence
<220> FEATURE:
<223> OTHER INFORMATION: Defensin like

<400> SEQUENCE: 513

```
aacctgtgcg aaagagcgag caaaacctgg agcggcaact gcggcaacac caaacattgc    60
gataaccagt gcagaaactg ggaaggcgcc aaacatggtg cttgccacgt gcgcaacggc   120
aaatggaagt gcttttgcta ttttaactgc tga                                153
```

<210> SEQ ID NO 514
<211> LENGTH: 153
<212> TYPE: DNA
<213> ORGANISM: Artificial Sequence
<220> FEATURE:
<223> OTHER INFORMATION: Defensin like

<400> SEQUENCE: 514

```
aacctgtgcg aaaaagcgag caaaacctgg accggcaact gcggcaacac caaacattgc    60
gatacccagt gcagaagctg ggaaggcgcc aaacatggtg cttgccacgt gcgcagcggc   120
aaacataagt gcttttgcta ttttaactgc tga                                153
```

<210> SEQ ID NO 515
<211> LENGTH: 153
<212> TYPE: DNA
<213> ORGANISM: Artificial Sequence
<220> FEATURE:
<223> OTHER INFORMATION: Defensin like

<400> SEQUENCE: 515

```
aacctgtgcg aaagagcgag caaaacctgg accggcaact gcggcaacac caaacattgc    60
gatacccagt gcagaaactg ggaaggcgcc aaacatggtg cttgccacgt gcgcaacggc   120
```

```
aaatggaagt gcttttgcta ttttaactgc tga                                  153

<210> SEQ ID NO 516
<211> LENGTH: 153
<212> TYPE: DNA
<213> ORGANISM: Artificial Sequence
<220> FEATURE:
<223> OTHER INFORMATION: Defensin like

<400> SEQUENCE: 516
aacctgtgcg aaagagcgag caaaacctgg agcggcaact gcggcaacac caaacattgc     60
gataaccagt gcagaagctg ggaaggcgcc aaacatggtg cttgccacaa acgcaacggc    120
aaatggaagt gcttttgcta ttttaactgc tga                                  153

<210> SEQ ID NO 517
<211> LENGTH: 153
<212> TYPE: DNA
<213> ORGANISM: Artificial Sequence
<220> FEATURE:
<223> OTHER INFORMATION: Defensin like

<400> SEQUENCE: 517
aacctgtgcg aaaagcgag caaaacctgg agcggcaact gcggcaacac caaacattgc      60
gatacccagt gcaaaagctg ggaaggcgcc gcccatggtg cttgccacgt gcgcagcggc    120
aaacataagt gcttttgcta ttttaactgc tga                                  153

<210> SEQ ID NO 518
<211> LENGTH: 153
<212> TYPE: DNA
<213> ORGANISM: Artificial Sequence
<220> FEATURE:
<223> OTHER INFORMATION: Defensin like

<400> SEQUENCE: 518
aacctgtgcg aaagagcgag caaaacctgg agcggcaact gcggcaacac caaacattgc     60
gataaccagt gcaaaagctg ggaaggcgcc aaacatggtg cttgccacgt gcgcaacggc    120
aaacatatgt gcttttgcta ttttaactgc tga                                  153

<210> SEQ ID NO 519
<211> LENGTH: 153
<212> TYPE: DNA
<213> ORGANISM: Artificial Sequence
<220> FEATURE:
<223> OTHER INFORMATION: Defensin like

<400> SEQUENCE: 519
aacctgtgcg aaaagcgag caaaacctgg accggcaact gcggcaacac caaacattgc      60
gataaccagt gcaaaaactg ggaaggcgcc aaacatggtg cttgccacaa acgcagcggc    120
aaatggaagt gcttttgcta ttttaactgc tga                                  153

<210> SEQ ID NO 520
<211> LENGTH: 153
<212> TYPE: DNA
<213> ORGANISM: Artificial Sequence
<220> FEATURE:
<223> OTHER INFORMATION: Defensin like

<400> SEQUENCE: 520
aacctgtgcg aaaagcgag caaaacctgg accggcaact gcggcaacac caaacattgc      60
```

```
gataaccagt gcaaaaactg ggaaggcgcc aaacatggtg cttgccacgt gcgcaacggc       120
aaatggaagt gcttttgcta ttttaactgc tga                                   153

<210> SEQ ID NO 521
<211> LENGTH: 153
<212> TYPE: DNA
<213> ORGANISM: Artificial Sequence
<220> FEATURE:
<223> OTHER INFORMATION: Defensin like

<400> SEQUENCE: 521
aacctgtgcg aaagagcgag caaaacctgg agcggcaact gcggcaacac cggccattgc        60
gatacccagt gcagaagctg ggaaggcgcc aaacatggtg cttgccacgt gcgcagcggc       120
aaacataagt gcttttgcta ttttaactgc tga                                   153

<210> SEQ ID NO 522
<211> LENGTH: 153
<212> TYPE: DNA
<213> ORGANISM: Artificial Sequence
<220> FEATURE:
<223> OTHER INFORMATION: Defensin like

<400> SEQUENCE: 522
aacctgtgcg aaaagcgag caaaacctgg agcggcaact gcggcaacac caaacattgc        60
gataaccagt gcagaagctg ggaaggcgcc aaacatggtg cttgccacgt gcgcaacggc       120
aaatggaagt gcttttgcta ttttaactgc tga                                   153

<210> SEQ ID NO 523
<211> LENGTH: 153
<212> TYPE: DNA
<213> ORGANISM: Artificial Sequence
<220> FEATURE:
<223> OTHER INFORMATION: Defensin like

<400> SEQUENCE: 523
aacctgtgcg aaaagcgag caaaacctgg agcggcaact gcggcaacac cggccattgc        60
gataaccagt gcaaaagctg ggaaggcgcc gcccatggtg cttgccacgt gcgcaacggc       120
aaacataagt gcttttgcta ttttaactgc tga                                   153

<210> SEQ ID NO 524
<211> LENGTH: 153
<212> TYPE: DNA
<213> ORGANISM: Artificial Sequence
<220> FEATURE:
<223> OTHER INFORMATION: Defensin like
<220> FEATURE:
<221> NAME/KEY: misc_feature
<222> LOCATION: 32, 65
<223> OTHER INFORMATION: n = A, C, G, or T

<400> SEQUENCE: 524
aacctgtgcg aaagagcgag caaaacctgg ancggcaact gcggcaacac caaacattgc        60
gatanccagt gcagaagctg ggaaggcgcc aaacatggtg cttgccacgt gcgcaacggc       120
aaacataagt gcttttgcta ttttaactgc tga                                   153

<210> SEQ ID NO 525
<211> LENGTH: 153
<212> TYPE: DNA
<213> ORGANISM: Artificial Sequence
<220> FEATURE:
<223> OTHER INFORMATION: Defensin like
```

-continued

<400> SEQUENCE: 525
aacctgtgcg aaagagcgag caaaacctgg accggcaact gcggcaacac caaacattgc    60
gataaccagt gcaaaaactg ggaaggcgcc aaacatggtg cttgccacgt gcgcaacggc   120
aaatggaaat gcttttgcta ttttaactgc tga                                153

<210> SEQ ID NO 526
<211> LENGTH: 153
<212> TYPE: DNA
<213> ORGANISM: Artificial Sequence
<220> FEATURE:
<223> OTHER INFORMATION: Defensin like

<400> SEQUENCE: 526
aacctgtgcg aaaagcgag caaaacctgg accggcaact gcggcaacac caaacattgc    60
gataaccagt gcaaaaactg ggaaggcgcc aaacatggtg cttgccacgt gcgcaacggc   120
aaacataaat gcttttgcta ttttaactgc tga                                153

<210> SEQ ID NO 527
<211> LENGTH: 153
<212> TYPE: DNA
<213> ORGANISM: Artificial Sequence
<220> FEATURE:
<223> OTHER INFORMATION: Defensin like

<400> SEQUENCE: 527
aacctgtgcg aaagagcgag caaaacctgg agcggcaact gcggcaacac caaacattgc    60
gatacccagt gcaaaaactg ggaaggcgcc aaacatggtg cttgccacgt gcgcaacggc   120
aaatggaaat gcttttgcta ttttaactgc tga                                153

<210> SEQ ID NO 528
<211> LENGTH: 153
<212> TYPE: DNA
<213> ORGANISM: Artificial Sequence
<220> FEATURE:
<223> OTHER INFORMATION: Defensin like

<400> SEQUENCE: 528
aacctgtgcg aaagagcgag caaaacctgg accggcaact gcggcaacac caaacattgc    60
gataaccagt gcagaagctg ggaaggcgcc gcccatggtg cttgccacaa acgcaacggc   120
aaatggaaat gcttttgcta ttttaactgc tga                                153

<210> SEQ ID NO 529
<211> LENGTH: 153
<212> TYPE: DNA
<213> ORGANISM: Artificial Sequence
<220> FEATURE:
<223> OTHER INFORMATION: Defensin like

<400> SEQUENCE: 529
aacctgtgcg aaagagcgag caaaacctgg accggcaact gcggcaacac caaacactgc    60
gataaccagt gcagaaactg ggaaggcgcc aaacatggtg cttgccacgt gcgcaacggc   120
aaatggaaat gcttttgcta ttttaactgc tga                                153

<210> SEQ ID NO 530
<211> LENGTH: 153
<212> TYPE: DNA
<213> ORGANISM: Artificial Sequence
<220> FEATURE:

<223> OTHER INFORMATION: Defensin like

<400> SEQUENCE: 530

```
aacttgtgcg aaagagcgag caaaacctgg accggcaact gcggcaacac caaacattgc    60
gataaccagt gcaaaaactg ggaaggcgcc aaacatggtg cttgccacgt gcgcaacggc   120
aaacataaat gcttttgcta ttttaactgc tga                                153
```

<210> SEQ ID NO 531
<211> LENGTH: 153
<212> TYPE: DNA
<213> ORGANISM: Artificial Sequence
<220> FEATURE:
<223> OTHER INFORMATION: Defensin like

<400> SEQUENCE: 531

```
aacctgtgcg aaagagcgag caaaacctgg agcggcaact gcggcaacac caaacattgc    60
gatacccagt gcagaaactg ggaaggcgcc gcccatggtg cttgccacaa acgcaacggc   120
aaatggaaat gcttttgcta ttttaactgc tga                                153
```

<210> SEQ ID NO 532
<211> LENGTH: 153
<212> TYPE: DNA
<213> ORGANISM: Artificial Sequence
<220> FEATURE:
<223> OTHER INFORMATION: Defensin like

<400> SEQUENCE: 532

```
aacctgtgcg aaaagcgag caaaacctgg agcggcaact gcggcaacac caaacattgc    60
gatacccagt gcagaaactg ggaaggcgcc aaacatggtg cttgccacgt gcgcaacggc   120
aaacataaat gcttttgcta ttttaactgc tga                                153
```

<210> SEQ ID NO 533
<211> LENGTH: 153
<212> TYPE: DNA
<213> ORGANISM: Artificial Sequence
<220> FEATURE:
<223> OTHER INFORMATION: Defensin like

<400> SEQUENCE: 533

```
aacctgtgcg aaagagcgag caaaacctgg agcggcaact gcggcaacac caaacattgc    60
gatacccagt gcagaagctg ggaaggcgcc aaacatggtg cttgccacgt gcgcagcggc   120
aaacataaat gcttttgcta ttttaactgc tga                                153
```

<210> SEQ ID NO 534
<211> LENGTH: 153
<212> TYPE: DNA
<213> ORGANISM: Artificial Sequence
<220> FEATURE:
<223> OTHER INFORMATION: Defensin like

<400> SEQUENCE: 534

```
aacctgtgcg aaaagcgag caaaacctgg accggcaact gcggcaacac caaacattgc    60
gatacccagt gcaaaaactg ggaaggcgcc aaacatggtg cttgccacgt gcgcaacggc   120
aaacataaat gcttttgcta ttttaactgc tga                                153
```

<210> SEQ ID NO 535
<211> LENGTH: 153
<212> TYPE: DNA
<213> ORGANISM: Artificial Sequence

```
<220> FEATURE:
<223> OTHER INFORMATION: Defensin like

<400> SEQUENCE: 535
aacctgtgcg aaagagcgag caaaacctgg accggcaact gcggcaacac caaacattgc      60
gataaccagt gcagaaactg ggaaggcgcc aaacatggtg cttgccacgt gcgcagcggc     120
aaacataaat gcttttgcta ttttaactgc tga                                  153

<210> SEQ ID NO 536
<211> LENGTH: 150
<212> TYPE: DNA
<213> ORGANISM: Artificial Sequence
<220> FEATURE:
<223> OTHER INFORMATION: Defensin like

<400> SEQUENCE: 536
aacctgtgcg aaagagcgag caaaacctgg agcggcaact gcggcaacac caaacattgc      60
gataaccagt gcagaaactg ggaaggcgcc aaacatggtg cttgccacgt gcgcaacggc     120
aaatggaaat gcttttgcta ttttaactgc                                      150

<210> SEQ ID NO 537
<211> LENGTH: 153
<212> TYPE: DNA
<213> ORGANISM: Artificial Sequence
<220> FEATURE:
<223> OTHER INFORMATION: Defensin like

<400> SEQUENCE: 537
aacctgtgcg aaagagcgag caaaacctgg accggcaact gcggcaacac caaacattgc      60
gataaccagt gcaaaaactg ggaaggcgcc aaacatggtg cttgccacgt gcgcagcggc     120
aaacataaat gcttttgcta ttttaactgc tga                                  153

<210> SEQ ID NO 538
<211> LENGTH: 153
<212> TYPE: DNA
<213> ORGANISM: Artificial Sequence
<220> FEATURE:
<223> OTHER INFORMATION: Defensin like

<400> SEQUENCE: 538
aacctgtgcg aaagagcgag caaaacctgg agcggcaact gcggcaacac caaacattgc      60
gatacccagt gcaaaagctg ggaaggcgcc gcccatggtg cttgccacgt gcgcaacggc     120
aaacataaat gcttttgcta ttttaactgc tga                                  153

<210> SEQ ID NO 539
<211> LENGTH: 153
<212> TYPE: DNA
<213> ORGANISM: Artificial Sequence
<220> FEATURE:
<223> OTHER INFORMATION: Defensin like

<400> SEQUENCE: 539
aacctgtgcg aaagagcgag caaaacctgg agcggcaact gcggcaacac caaacattgc      60
gataaccagt gcaaaaactg ggaaggcgcc aaacatggtg cttgccacgt gcgcaacggc     120
aaacataaat gcttttgcta ttttaactgc tga                                  153

<210> SEQ ID NO 540
<211> LENGTH: 153
<212> TYPE: DNA
```

```
<213> ORGANISM: Artificial Sequence
<220> FEATURE:
<223> OTHER INFORMATION: Defensin like

<400> SEQUENCE: 540
aacctgtgcg aaaaagcgag caaaacctgg accggcaact gcggcaacac caaacattgc      60
gataaccagt gcagaagctg ggaaggcgcc aaacatggtg cttgccacgt gcgcaacggc     120
aaacataaat gcttttgcta ttttaactgc tga                                  153

<210> SEQ ID NO 541
<211> LENGTH: 153
<212> TYPE: DNA
<213> ORGANISM: Artificial Sequence
<220> FEATURE:
<223> OTHER INFORMATION: Defensin like

<400> SEQUENCE: 541
aacctgtgcg aaaaagcgag caaaacctgg accggcaact gcggcaacac caaacattgc      60
gataaccagt gcagaaactg ggaaggcgcc aaacatggtg cttgccacgt gcgcaacggc     120
aaatggaaat gcttttgcta ttttaactgc tga                                  153

<210> SEQ ID NO 542
<211> LENGTH: 150
<212> TYPE: DNA
<213> ORGANISM: Artificial Sequence
<220> FEATURE:
<223> OTHER INFORMATION: Defensin like

<400> SEQUENCE: 542
aacctgtgcg aaaaagcgag caaaacctgg accggcaact gcggcaacac caaacattgc      60
gatacccagt gcagaaactg ggaaggcgcc aaacatggtg cttgccacaa acgcaacggc     120
aaatggaaat gcttttgcta ttttaactgc                                      150

<210> SEQ ID NO 543
<211> LENGTH: 153
<212> TYPE: DNA
<213> ORGANISM: Artificial Sequence
<220> FEATURE:
<223> OTHER INFORMATION: Defensin like

<400> SEQUENCE: 543
aacctgtgcg aaagagcgag caaaacctgg accggcaact gcggcaacac caaacattgc      60
gatacccagt gcagaaactg ggaaggcgcc aaacatggtg cttgccacaa acgcagcggc     120
aaatggaaat gcttttgcta ttttaactgc tga                                  153

<210> SEQ ID NO 544
<211> LENGTH: 153
<212> TYPE: DNA
<213> ORGANISM: Artificial Sequence
<220> FEATURE:
<223> OTHER INFORMATION: Defensin like

<400> SEQUENCE: 544
aacctgtgcg aaagagcgag caaaacctgg accggcaact gcggcaacac caaacattgc      60
gataaccagt gcagaaactg ggaaggcgcc aaacatggtg cttgccacgt gcgcaacggc     120
aaacataaat gcttttgcta ttttaactgc tga                                  153

<210> SEQ ID NO 545
<211> LENGTH: 153
```

```
<212> TYPE: DNA
<213> ORGANISM: Artificial Sequence
<220> FEATURE:
<223> OTHER INFORMATION: Defensin like

<400> SEQUENCE: 545
aacctgtgcg aaagagcgag caaaacctgg agcggcaact gcggcaacac caaaaattgc    60
gataaccagt gcagaaactg ggaaggcgcc aaacatggtg cttgccacgt gcgcagcggc   120
aaacataaat gcttttgcta ttttaactgc tga                                153

<210> SEQ ID NO 546
<211> LENGTH: 153
<212> TYPE: DNA
<213> ORGANISM: Artificial Sequence
<220> FEATURE:
<223> OTHER INFORMATION: Defensin like

<400> SEQUENCE: 546
aacctgtgcg aaagagcgag caaaacctgg accggcaact gcggcaacac caaacattgc    60
gataaccagt gcaaaagctg ggaaggcgcc gcccatggtg cttgccacgt gcgcagcggc   120
aaacataaat gcttttgcta ttttaactgc tga                                153

<210> SEQ ID NO 547
<211> LENGTH: 150
<212> TYPE: DNA
<213> ORGANISM: Artificial Sequence
<220> FEATURE:
<223> OTHER INFORMATION: Defensin like

<400> SEQUENCE: 547
aacctgtgcg aaagagcgag caaaacctgg agcggcaact gcggcaacac caaacattgc    60
gataaccagt gcaaaaactg ggaaggcgcc aaacatggtg cttgccacgt gcgcaacggc   120
aaacataaat gcttttgcta ttttaactgc                                    150

<210> SEQ ID NO 548
<211> LENGTH: 150
<212> TYPE: DNA
<213> ORGANISM: Artificial Sequence
<220> FEATURE:
<223> OTHER INFORMATION: Defensin like

<400> SEQUENCE: 548
aacctgtgcg aaagagcgag caaaacctgg accggcaact gcggcaacac caaacattgc    60
gataaccagt gcaaaaactg ggaaggcgcc aaacatggtg cttgccacgt gcgcaacggc   120
aaatggaaat gcttttgcta ttttaactgc                                    150

<210> SEQ ID NO 549
<211> LENGTH: 153
<212> TYPE: DNA
<213> ORGANISM: Artificial Sequence
<220> FEATURE:
<223> OTHER INFORMATION: Defensin like

<400> SEQUENCE: 549
aacctgtgcg aaagagcgag caaaacctgg accggcaact gcggcaacac caaacattgc    60
gatacccagt gcagaagctg ggaaggcgcc aaacatggtg cttgccacgt gcgcaacggc   120
aaacataaat gcttttgcta ttttaactgc tga                                153

<210> SEQ ID NO 550
```

<211> LENGTH: 153
<212> TYPE: DNA
<213> ORGANISM: Artificial Sequence
<220> FEATURE:
<223> OTHER INFORMATION: Defensin like

<400> SEQUENCE: 550
aacctgtgcg aaaaagcgag caaaacctgg agcggcaact gcggcaacac caaacattgc    60
gatacccagt gcagaaactg ggaaggcgcc aaacatggtg cttgccacgt gcgcaacggc   120
aaatggaaat gcttttgcta ttttaactgc tga                                153

<210> SEQ ID NO 551
<211> LENGTH: 153
<212> TYPE: DNA
<213> ORGANISM: Artificial Sequence
<220> FEATURE:
<223> OTHER INFORMATION: Defensin like

<400> SEQUENCE: 551
aacctgtgcg aaagagcgag caaaacctgg accggcaact gcggcaacac caaacattgc    60
gataaccagt gcagaaactg ggaaggcgcc gcccatggtg cttgccacaa acgcaacggc   120
aaatggaaat gcttttgcta ttttaactgc tga                                153

<210> SEQ ID NO 552
<211> LENGTH: 153
<212> TYPE: DNA
<213> ORGANISM: Artificial Sequence
<220> FEATURE:
<223> OTHER INFORMATION: Defensin like

<400> SEQUENCE: 552
aacctgtgcg aaagagcgag caaaacctgg accggcaact gcggcaacac caaacattgc    60
gataaccagt gcaaaaactg ggaaggcgcc gcccatggtg cttgccacgt gcgcaacggc   120
aaacataaat gcttttgcta ttttaactgc tga                                153

<210> SEQ ID NO 553
<211> LENGTH: 153
<212> TYPE: DNA
<213> ORGANISM: Artificial Sequence
<220> FEATURE:
<223> OTHER INFORMATION: Defensin like

<400> SEQUENCE: 553
aacctgtgcg aaaaagcgag caaaacctgg agcggcaact gcggcaacac caaacattgc    60
gataaccagt gcaaaagctg ggaaggcgcc aaacatggtg cttgccacgt gcgcaacggc   120
aaacataaat gcttttgcta ttttaactgc tga                                153

<210> SEQ ID NO 554
<211> LENGTH: 153
<212> TYPE: DNA
<213> ORGANISM: Artificial Sequence
<220> FEATURE:
<223> OTHER INFORMATION: Defensin like

<400> SEQUENCE: 554
aacctgtgcg aaagagcgag caaaacctgg accggcaact gcggcaacac caaacattgc    60
gatacccagt gcaaaagctg ggaaggcgcc aaacatggtg cttgccacgt gcgcaacggc   120
aaatggaaat gcttttgcta ttttaactgc tga                                153

```
<210> SEQ ID NO 555
<211> LENGTH: 153
<212> TYPE: DNA
<213> ORGANISM: Artificial Sequence
<220> FEATURE:
<223> OTHER INFORMATION: Defensin like

<400> SEQUENCE: 555
aacctgtgcg aaaaagcgag caaaacctgg accggcaact gcggcaacac caaacattgc    60
gataaccagt gcagaaactg ggaaggcgcc gcccatggtg cttgccacgt gcgcaacggc   120
aaacataaat gcttttgcta ttttaactgc tga                                 153

<210> SEQ ID NO 556
<211> LENGTH: 153
<212> TYPE: DNA
<213> ORGANISM: Artificial Sequence
<220> FEATURE:
<223> OTHER INFORMATION: Defensin like

<400> SEQUENCE: 556
aacctgtgcg aaagagcgag caaaacctgg agcggcaact gcggcaacac caaacattgc    60
gataaccagt gcagaaactg ggaaggcgcc aaacatggtg cttgccacaa acgcaacggc   120
aaatggaaat gcttttgcta ttttaactgc tga                                 153

<210> SEQ ID NO 557
<211> LENGTH: 153
<212> TYPE: DNA
<213> ORGANISM: Artificial Sequence
<220> FEATURE:
<223> OTHER INFORMATION: Defensin like

<400> SEQUENCE: 557
aacctgtgcg aaagagcgag caaaacctgg agcggcaact gcggcaacac caaacattgc    60
gatacccagt gcaaaaactg ggaaggcgcc gcccatggtg cttgccacgt gcgcaacggc   120
aaacataaat gcttttgcta ttttaactgc tga                                 153

<210> SEQ ID NO 558
<211> LENGTH: 153
<212> TYPE: DNA
<213> ORGANISM: Artificial Sequence
<220> FEATURE:
<223> OTHER INFORMATION: Defensin like

<400> SEQUENCE: 558
aacctgtgcg aaagagcgag caaaacctgg accggcaact gcggcaacac caaacattgc    60
gatacccagt gcaaaaactg ggaaggcgcc aaacatggtg cttgccacgt gcgcagcggc   120
aaacataaat gcttttgcta ttttaactgc tga                                 153

<210> SEQ ID NO 559
<211> LENGTH: 153
<212> TYPE: DNA
<213> ORGANISM: Artificial Sequence
<220> FEATURE:
<223> OTHER INFORMATION: Defensin like

<400> SEQUENCE: 559
aacctgtgcg aaagagcgag caaaacctgg agcggcaact gcggcaacac caaacattgc    60
gataaccagt gcagaaactg ggaaggcgcc gcccatggtg cttgccacgt gcgcaacggc   120
aaacataaat gcttttgcta ttttaactgc tga                                 153
```

<210> SEQ ID NO 560
<211> LENGTH: 150
<212> TYPE: DNA
<213> ORGANISM: Artificial Sequence
<220> FEATURE:
<223> OTHER INFORMATION: Defensin like

<400> SEQUENCE: 560
aacctgtgcg aaagagcgag caaaacctgg accggcaact gcggcaacac caaacattgc      60
gataaccagt gcaaaaactg ggaaggcgcc aaacatggtg cttgccacgt gcgcaacggc     120
aaatggaaat gcttttgcta ttttaactgc                                     150

<210> SEQ ID NO 561
<211> LENGTH: 153
<212> TYPE: DNA
<213> ORGANISM: Artificial Sequence
<220> FEATURE:
<223> OTHER INFORMATION: Defensin like

<400> SEQUENCE: 561
aacctgtgcg aaagagcgag caaaacctgg agcggcaact gcggcaacac caaacattgc      60
gataaccagt gcaaaagctg ggaaggcgcc gcccatggtg cttgccacgt gcgcaacggc     120
aaacataaat gcttttgcta ttttaactgc tga                                 153

<210> SEQ ID NO 562
<211> LENGTH: 153
<212> TYPE: DNA
<213> ORGANISM: Artificial Sequence
<220> FEATURE:
<223> OTHER INFORMATION: Defensin like

<400> SEQUENCE: 562
aacctgtgcg aaagagcgag caaaacctgg accggcaact gcggcaacac caaacattgc      60
gatacccagt gcagaagctg ggaaggcgcc aaacatggtg cttgccacgt gcgcaacggc     120
aaatggaaat gcttttgcta ttttaactgc tga                                 153

<210> SEQ ID NO 563
<211> LENGTH: 153
<212> TYPE: DNA
<213> ORGANISM: Artificial Sequence
<220> FEATURE:
<223> OTHER INFORMATION: Defensin like

<400> SEQUENCE: 563
aacctgtgcg aaagagcgag caaaacctgg agcggcaact gcggcaacac caaacattgc      60
gatacccagt gcagaaactg ggaaggcgcc aaacatggtg cttgccacgt gcgcaacggc     120
aaacataaat gcttttgcta ttttaactgc tga                                 153

<210> SEQ ID NO 564
<211> LENGTH: 153
<212> TYPE: DNA
<213> ORGANISM: Artificial Sequence
<220> FEATURE:
<223> OTHER INFORMATION: Defensin like

<400> SEQUENCE: 564
aacctgtgcg aaaaagcgag caaaacctgg agcggcaact gcggcaacac caaacattgc      60
gataaccagt gcagaaactg ggaaggcgcc gcccatggtg cttgccacgt gcgcaacggc     120
aaacataaat gcttttgcta ttttaactgc tga                                 153

<210> SEQ ID NO 565
<211> LENGTH: 153
<212> TYPE: DNA
<213> ORGANISM: Artificial Sequence
<220> FEATURE:
<223> OTHER INFORMATION: Defensin like

<400> SEQUENCE: 565

```
aacctgtgcg aaagagcgag caaaacctgg accggcaact gcggcaacac caaacattgc      60
gataaccagt gcagaagctg ggaaggcgcc gcccatggtg cttgccacgt gcgcaacggc     120
aaacataaat gcttttgcta ttttaactgc tga                                  153
```

<210> SEQ ID NO 566
<211> LENGTH: 153
<212> TYPE: DNA
<213> ORGANISM: Artificial Sequence
<220> FEATURE:
<223> OTHER INFORMATION: Defensin like

<400> SEQUENCE: 566

```
aacctgtgcg aaaaagcgag caaaacctgg accggcaact gcggcaacac caaacattgc      60
gatacccagt gcaaaaactg ggaaggcgcc aaacatggtg cttgccacgt gcgcaacggc     120
aaatggaaat gcttttgcta ttttaactgc tga                                  153
```

<210> SEQ ID NO 567
<211> LENGTH: 153
<212> TYPE: DNA
<213> ORGANISM: Artificial Sequence
<220> FEATURE:
<223> OTHER INFORMATION: Defensin like

<400> SEQUENCE: 567

```
aacctgtgcg aaaaagcgag caaaacctgg agcggcaact gcggcaacac caaacattgc      60
gataaccagt gcaaaaactg ggaaggcgcc gcccatggtg cttgccacgt gcgcaacggc     120
aaacataaat gcttttgcta ttttaactgc tga                                  153
```

<210> SEQ ID NO 568
<211> LENGTH: 153
<212> TYPE: DNA
<213> ORGANISM: Artificial Sequence
<220> FEATURE:
<223> OTHER INFORMATION: Defensin like

<400> SEQUENCE: 568

```
aacctgtgcg aaagagcgag caaaacctgg accggcaact gcggcaacac caaacattgc      60
gatacccagt gcaaaagctg ggaaggcgcc aaacatggtg cttgccacgt gcgcaacggc     120
aaacataaat gcttttgcta ttttaactgc tga                                  153
```

<210> SEQ ID NO 569
<211> LENGTH: 153
<212> TYPE: DNA
<213> ORGANISM: Artificial Sequence
<220> FEATURE:
<223> OTHER INFORMATION: Defensin like

<400> SEQUENCE: 569

```
aacctgtgcg aaaaagcgag caaaacctgg agcggcaact gcggcaacac caaacattgc      60
gatacccagt gcagaagctg ggaaggcgcc aaacatggtg cttgccacgt gcgcagcggc     120
```

```
aaacataaat gcttttgcta ttttaactgc tga                                153
```

<210> SEQ ID NO 570
<211> LENGTH: 153
<212> TYPE: DNA
<213> ORGANISM: Artificial Sequence
<220> FEATURE:
<223> OTHER INFORMATION: Defensin like

<400> SEQUENCE: 570

```
aacctgtgcg aaagagcgag caaaacctgg accggcaact gcggcaacac caaacattgc     60
gataaccagt gcagaagctg ggaaggcgcc aaacatggtg cttgccacgt gcgcaacggc    120
aaacataaat gcttttgcta ttttaactgc tga                                153
```

<210> SEQ ID NO 571
<211> LENGTH: 153
<212> TYPE: DNA
<213> ORGANISM: Artificial Sequence
<220> FEATURE:
<223> OTHER INFORMATION: Defensin like

<400> SEQUENCE: 571

```
aacctgtgcg aaagagcgag caaaacctgg accggcaact gcggcaacac caaacattgc     60
gatacccagt gcaaaaactg ggaaggcgcc aaacatggtg cttgccacgt gcgcaacggc    120
aaatggaaat gcttttgcta ttttaactgc tga                                153
```

<210> SEQ ID NO 572
<211> LENGTH: 153
<212> TYPE: DNA
<213> ORGANISM: Artificial Sequence
<220> FEATURE:
<223> OTHER INFORMATION: Defensin like

<400> SEQUENCE: 572

```
aacctgtgcg aaagagcgag caaaacctgg agcggcaact gcggcaacac caaacattgc     60
gatacccagt gcagaaactg ggaaggcgcc aaacatggtg cttgccacgt gcgcaacggc    120
aaacataaat gcttttgcta ttttaactgc tga                                153
```

<210> SEQ ID NO 573
<211> LENGTH: 153
<212> TYPE: DNA
<213> ORGANISM: Artificial Sequence
<220> FEATURE:
<223> OTHER INFORMATION: Defensin like

<400> SEQUENCE: 573

```
aacctgtgcg aaagagcgag caaaacctgg agcggcaact gcggcaacac caaacattgc     60
gatacccagt gcaaaaactg ggaaggcgcc aaacatggtg cttgccacgt gcgcaacggc    120
aaacataaat gcttttgcta ttttaactgc tga                                153
```

<210> SEQ ID NO 574
<211> LENGTH: 150
<212> TYPE: DNA
<213> ORGANISM: Artificial Sequence
<220> FEATURE:
<223> OTHER INFORMATION: Defensin like

<400> SEQUENCE: 574

```
aacctgtgcg aaagagcgag caaaacctgg agcggcaact gcggcaacac caaacattgc     60
gatacccagt gcaaaaactg ggaaggcgcc aaacatggtg cttgccacgt gcgcaacggc    120
```

```
aaacataagt gctttgcta ttttaactgc                                          150

<210> SEQ ID NO 575
<211> LENGTH: 153
<212> TYPE: DNA
<213> ORGANISM: Artificial Sequence
<220> FEATURE:
<223> OTHER INFORMATION: Defensin like

<400> SEQUENCE: 575
aacctgtgcg aaagagcgag caaaacctgg accggcaact gcggcaacac caaacattgc         60
gataaccagt gcagaaactg ggaaggcgcc gcccatggtg cttgccacgt gcgcagcggc        120
aaacataaat gctttgcta ttttaactgc tga                                      153

<210> SEQ ID NO 576
<211> LENGTH: 153
<212> TYPE: DNA
<213> ORGANISM: Artificial Sequence
<220> FEATURE:
<223> OTHER INFORMATION: Defensin like

<400> SEQUENCE: 576
aacctgtgcg aaagagcgag caaaacctgg agcggcaact gcggcaacac caaacattgc         60
gataaccagt gcaaaaactg ggaaggcgcc gcccatggtg cttgccacgt gcgcaacggc        120
aaacataagt gctttgcta ttttaactgc tga                                      153

<210> SEQ ID NO 577
<211> LENGTH: 153
<212> TYPE: DNA
<213> ORGANISM: Artificial Sequence
<220> FEATURE:
<223> OTHER INFORMATION: Defensin like

<400> SEQUENCE: 577
aacctgtgcg aaagagcgag caaaacctgg agcggcaact gcggcaacac caaacattgc         60
gataaccagt gcaaaagctg ggaaggcgcc aaacatggtg cttgccacaa acgcaacggc        120
aaatggaagt gctttgcta ttttaactgc tga                                      153

<210> SEQ ID NO 578
<211> LENGTH: 153
<212> TYPE: DNA
<213> ORGANISM: Artificial Sequence
<220> FEATURE:
<223> OTHER INFORMATION: Defensin like

<400> SEQUENCE: 578
aacctgtgcg aaagagcgag caaaacctgg accggcaact gcggcaacac caaacattgc         60
gataaccagt gcaaaagctg ggaaggcgcc aaacatggtg cttgccacaa acgcagcggc        120
aaatggaagt gctttgcta ttttaactgc tga                                      153

<210> SEQ ID NO 579
<211> LENGTH: 153
<212> TYPE: DNA
<213> ORGANISM: Artificial Sequence
<220> FEATURE:
<223> OTHER INFORMATION: Defensin like

<400> SEQUENCE: 579
aacctgtgcg aaaaagcgag caaaacctgg agcggcaact gcggcaacac caaacattgc         60
```

```
gataaccagt gcaaaaactg ggaaggcgcc aaacatggtg cttgccacgt gcgcagcggc    120
aaacataagt gcttttgcta ttttaactgc tga                                 153
```

<210> SEQ ID NO 580
<211> LENGTH: 153
<212> TYPE: DNA
<213> ORGANISM: Artificial Sequence
<220> FEATURE:
<223> OTHER INFORMATION: Defensin like

<400> SEQUENCE: 580

```
aacctgtgcg aaaaagcgag caaaacctgg accggcaact gcggcaacac caaacattgc     60
gatacccagt gcagaaactg ggaaggcgcc aaacatggtg cttgccacaa acgcagcggc    120
aaatggaagt gcttttgcta ttttaactgc tga                                 153
```

<210> SEQ ID NO 581
<211> LENGTH: 153
<212> TYPE: DNA
<213> ORGANISM: Artificial Sequence
<220> FEATURE:
<223> OTHER INFORMATION: Defensin like

<400> SEQUENCE: 581

```
aacctgtgcg aaaaagcgag caaaacctgg agcggcaact gcggcaacac caaacattgc     60
gataaccagt gcagaagctg ggaaggcgcc aaacatggtg cttgccacaa acgcaacggc    120
aaatggaagt gcttttgcta ttttaactgc tga                                 153
```

<210> SEQ ID NO 582
<211> LENGTH: 153
<212> TYPE: DNA
<213> ORGANISM: Artificial Sequence
<220> FEATURE:
<223> OTHER INFORMATION: Defensin like

<400> SEQUENCE: 582

```
aacctgtgcg aaaaagcgag caaaacctgg agcggcaact gcggcaacac caaacattgc     60
gatacccagt gcaaaagctg ggaaggcgcc aaacatggtg cttgccacaa acgcagcggc    120
aaatggaagt gcttttgcta ttttaactgc tga                                 153
```

<210> SEQ ID NO 583
<211> LENGTH: 150
<212> TYPE: DNA
<213> ORGANISM: Artificial Sequence
<220> FEATURE:
<223> OTHER INFORMATION: Defensin like

<400> SEQUENCE: 583

```
aacctgtgcg aaagagcgag caaaacctgg accggcaact gcggcaacac caaacattgc     60
gatacccagt gcaaaagctg ggaaggcgcc aaacatggtg cttgccacgt gcgcaacggc    120
aaacataaat gcttttgcta ttttaactgc                                     150
```

<210> SEQ ID NO 584
<211> LENGTH: 153
<212> TYPE: DNA
<213> ORGANISM: Artificial Sequence
<220> FEATURE:
<223> OTHER INFORMATION: Defensin like

<400> SEQUENCE: 584

```
aacctgtgcg aaagagcgag caaaacctgg agcggcaact gcggcaacac caaacattgc     60
```

```
gataaccagt gcagaagctg ggaaggcgcc aaacatggtg cttgccacgt gcgcagcggc       120
aaatggaagt gcttttgcta ttttaactgc tga                                    153

<210> SEQ ID NO 585
<211> LENGTH: 153
<212> TYPE: DNA
<213> ORGANISM: Artificial Sequence
<220> FEATURE:
<223> OTHER INFORMATION: Defensin like

<400> SEQUENCE: 585
aacctgtgcg aaagagcgag caaaacctgg accggcaact gcggcaacac caaacattgc       60
gataaccagt gcagaaactg ggaaggcgcc aaacatggtg cttgccacaa acgcaacggc      120
aaatggaagt gcttttgcta ttttaactgc tga                                    153

<210> SEQ ID NO 586
<211> LENGTH: 153
<212> TYPE: DNA
<213> ORGANISM: Artificial Sequence
<220> FEATURE:
<223> OTHER INFORMATION: Defensin like

<400> SEQUENCE: 586
aacctgtgcg aaagagcgag caaaacctgg agcggcaact gcggcaacac caaacattgc       60
gatacccagt gcaaaaactg ggaaggcgcc gcccatggtg cttgccataa acgcaacggc      120
aaatggaagt gcttttgcta ttttaactgc tga                                    153

<210> SEQ ID NO 587
<211> LENGTH: 153
<212> TYPE: DNA
<213> ORGANISM: Artificial Sequence
<220> FEATURE:
<223> OTHER INFORMATION: Defensin like

<400> SEQUENCE: 587
aacctgtgcg aaagagcgag caaaacctgg agcggcaact gcggcaacac caaacattgc       60
gatacccagt gcagaagctg ggaaggcgcc gcccatggtg cttgccacaa acgcaacggc      120
aaatggaagt gcttttgcta ttttaactgc tga                                    153

<210> SEQ ID NO 588
<211> LENGTH: 153
<212> TYPE: DNA
<213> ORGANISM: Artificial Sequence
<220> FEATURE:
<223> OTHER INFORMATION: Defensin like

<400> SEQUENCE: 588
aacctgtgcg aaagagcgag caaaacctgg accggcaact gcggcaacac caaacattgc       60
gataaccagt gcagaaactg ggaaggcgcc aaacatggtg cttgccacaa acgcagcggc      120
aaatggaagt gttttgcta ttttaactgc tga                                     153

<210> SEQ ID NO 589
<211> LENGTH: 153
<212> TYPE: DNA
<213> ORGANISM: Artificial Sequence
<220> FEATURE:
<223> OTHER INFORMATION: Defensin like

<400> SEQUENCE: 589
```
aacctgtgcg aaagagcgag caaaacctgg agcggcaact gcggcaacac caaacattgc    60
gataaccagt gcagaagctg ggaaggcgcc aaacatggtg cttgccacgt gcgcagcggc    120
aaacataagt gcttttgcta ttttaactgc tga                                153

<210> SEQ ID NO 590
<211> LENGTH: 153
<212> TYPE: DNA
<213> ORGANISM: Artificial Sequence
<220> FEATURE:
<223> OTHER INFORMATION: Defensin like

<400> SEQUENCE: 590
aacctgtgcg aaagagcgag caaaacctgg agcggcaact gcggcaacac caaacattgc    60
gataaccagt gcaaaagctg ggaaggcgcc gcccatggtg cttgccacaa acgcaacggc    120
aaatggaagt gcttttgcta ttttaactgc tga                                153

<210> SEQ ID NO 591
<211> LENGTH: 150
<212> TYPE: DNA
<213> ORGANISM: Artificial Sequence
<220> FEATURE:
<223> OTHER INFORMATION: Defensin like

<400> SEQUENCE: 591
aacctgtgcg aaagagcgag caaaacctgg agcggcaact gcggcaacac caaacattgc    60
gatacccagt gcaaaagctg ggaaggcgcc aaacatggtg cttgccacgt gcgcaacggc    120
aaacataagt gcttttgcta ttttaactgc                                    150

<210> SEQ ID NO 592
<211> LENGTH: 153
<212> TYPE: DNA
<213> ORGANISM: Artificial Sequence
<220> FEATURE:
<223> OTHER INFORMATION: Defensin like

<400> SEQUENCE: 592
aacctgtgcg aaaaagcgag caaaacctgg accggcaact gcggcaacac caaacattgc    60
gataaccagt gcagaaactg ggaaggcgcc aaacatggtg cttgccacgt gcgcagcggc    120
aaacataagt gcttttgcta ttttaactgc tga                                153

<210> SEQ ID NO 593
<211> LENGTH: 153
<212> TYPE: DNA
<213> ORGANISM: Artificial Sequence
<220> FEATURE:
<223> OTHER INFORMATION: Defensin like

<400> SEQUENCE: 593
aacctgtgcg aaaagcgag caaaacctgg agcggcaact gcggcaacac caaacattgc    60
gataaccagt gcagaagctg ggaaggcgcc aaacatggtg cttgccacgt gcgcaacggc    120
aaacataagt gcttttgcta ttttaactgc tga                                153

<210> SEQ ID NO 594
<211> LENGTH: 150
<212> TYPE: DNA
<213> ORGANISM: Artificial Sequence
<220> FEATURE:
<223> OTHER INFORMATION: Defensin like

<400> SEQUENCE: 594

```
aacctgtgcg aacgcgcgag ccttacctgg accggcaact gcggcaacac caagcactgc    60
gatactcagt gcaaaaactg ggaaggcgcc aaacatggtg cttgccacgt tcgtaacggg   120
aagtggaagt gcttttgcta ttttaactgc                                    150
```

<210> SEQ ID NO 595
<211> LENGTH: 153
<212> TYPE: DNA
<213> ORGANISM: Artificial Sequence
<220> FEATURE:
<223> OTHER INFORMATION: Defensin like

<400> SEQUENCE: 595

```
aacctgtgcg aaagagcgag caaaacctgg agcggcaact gcggcaacac caaacattgc    60 gataccagt gcagaaactg ggaaggcgcc aaacatggtg cttgccacgt gcgcagcggc    120
aaacataagt gcttttgcta ttttaactgc tga                                153
```

<210> SEQ ID NO 596
<211> LENGTH: 153
<212> TYPE: DNA
<213> ORGANISM: Artificial Sequence
<220> FEATURE:
<223> OTHER INFORMATION: Defensin like

<400> SEQUENCE: 596

```
aacctgtgcg aaaaagcgag caaaacctgg accggcaact gcggcaacac caaacattgc    60 gataccagt gcaaaagctg ggaaggcgcc aaacatggtg cttgccacgt gcgcagcggc    120
aaacataagt gcttttgcta ttttaactgc tga                                153
```

<210> SEQ ID NO 597
<211> LENGTH: 153
<212> TYPE: DNA
<213> ORGANISM: Artificial Sequence
<220> FEATURE:
<223> OTHER INFORMATION: Defensin like

<400> SEQUENCE: 597

```
aacctgtgcg aaagagcgag caaaacctgg agcggcaact gcggcaacac caaacattgc    60
gataaccagt gcagaaactg ggaaggcgcc aaacatggtg cttgccacaa acgcagcggc   120
aaatggaagt gcttttgcta ttttaactgc tga                                153
```

<210> SEQ ID NO 598
<211> LENGTH: 153
<212> TYPE: DNA
<213> ORGANISM: Artificial Sequence
<220> FEATURE:
<223> OTHER INFORMATION: Defensin like

<400> SEQUENCE: 598

```
aacctgtgcg aaagagcgag caaaacctgg agcggcaact gcggcaacac taaacattgc    60 gataccagt gcagaaactg ggaaggcgcc aaacatggtg cttgccacaa acgcaacggc    120
aaatggaagt gcttttgcta ttttaactgc tga                                153
```

<210> SEQ ID NO 599
<211> LENGTH: 153
<212> TYPE: DNA
<213> ORGANISM: Artificial Sequence
<220> FEATURE:
<223> OTHER INFORMATION: Defensin like

<400> SEQUENCE: 599

```
aacctgtgcg aaagagcgag caaaacctgg accggcaact gcggcaacac caaacattgc    60
gataaccagt gcaaaagctg ggaaggcgcc aaacatggtg cttgccacgt gcgcaacggc   120
aaacataagt gcttttgcta ttttaactgc tga                                153
```

<210> SEQ ID NO 600
<211> LENGTH: 153
<212> TYPE: DNA
<213> ORGANISM: Artificial Sequence
<220> FEATURE:
<223> OTHER INFORMATION: Defensin like

<400> SEQUENCE: 600

```
aacctgtgcg aaaagcgag caaaacctgg accggcaact gcggcaacac caaacattgc    60
gataaccagt gcagaaactg ggaaggcgcc gcccatggtg cttgccacaa acgcagcggc   120
aaatggaagt gcttttgcta ttttaactgc tga                                153
```

<210> SEQ ID NO 601
<211> LENGTH: 153
<212> TYPE: DNA
<213> ORGANISM: Artificial Sequence
<220> FEATURE:
<223> OTHER INFORMATION: Defensin like

<400> SEQUENCE: 601

```
aacctgtgcg aaagagcgag caaaacctgg agcggcaact gcggcaacac caaacattgc    60
gatacccagt gcagaagctg ggaaggcgcc aaacatggtg cttgccacaa acgcagcggc   120
aaatggaagt gcttttgcta ttttaactgc tga                                153
```

<210> SEQ ID NO 602
<211> LENGTH: 153
<212> TYPE: DNA
<213> ORGANISM: Artificial Sequence
<220> FEATURE:
<223> OTHER INFORMATION: Defensin like

<400> SEQUENCE: 602

```
aacctgtgcg aaaagcgag caaaacctgg agcggcaact gcggcaacac caaacattgc    60
gataaccagt gcagaagctg ggaaggcgcc gcccatggtg cttgccacgt gcgcagcggc   120
aaacataagt gcttttgcta ttttaactgc tga                                153
```

<210> SEQ ID NO 603
<211> LENGTH: 153
<212> TYPE: DNA
<213> ORGANISM: Artificial Sequence
<220> FEATURE:
<223> OTHER INFORMATION: Defensin like

<400> SEQUENCE: 603

```
aacctgtgcg aaagagcgag caaaacctgg agcggcaact gcggcaacac caaacattgc    60
gatacccagt gcagaagctg ggaaggcgcc gcccatggtg cttgccacaa acgcagcggc   120
aaatggaagt gcttttgcta ttttaactgc tga                                153
```

<210> SEQ ID NO 604
<211> LENGTH: 153
<212> TYPE: DNA
<213> ORGANISM: Artificial Sequence
<220> FEATURE:
<223> OTHER INFORMATION: Defensin like

<400> SEQUENCE: 604
aacctgtgcg aaaaagcgag caaaacctgg accggcaact gcggcaacac caaacattgc    60
gatacccagt gcaaaaactg ggaaggcgcc aaacatggtg cttgccacaa acgcaacggc   120
aaatggaagt gcttttgcta ttttaactgc tga                                153

<210> SEQ ID NO 605
<211> LENGTH: 153
<212> TYPE: DNA
<213> ORGANISM: Artificial Sequence
<220> FEATURE:
<223> OTHER INFORMATION: Defensin like

<400> SEQUENCE: 605
aacttgtgcg aaaaagcgag caaaacctgg agcggcaact gcggcaacac caaacattgc    60
gatacccagt gcagaaactg ggaaggcgcc aaacatggtg cttgccacaa acgcaacggc   120
aaatggaagt gcttttgcta ttttaactgc tga                                153

<210> SEQ ID NO 606
<211> LENGTH: 153
<212> TYPE: DNA
<213> ORGANISM: Artificial Sequence
<220> FEATURE:
<223> OTHER INFORMATION: Defensin like

<400> SEQUENCE: 606
aacctgtgcg aaagagcgag caaaacctgg agcggcaact gcggcaacac caaacattgc    60
gatacccagt gcagaagctg ggaaggcgcc aaacatggtg cttgccacgt gcgcaacggc   120
aaacataagt gcttttgcta ttttaactgc tga                                153

<210> SEQ ID NO 607
<211> LENGTH: 153
<212> TYPE: DNA
<213> ORGANISM: Artificial Sequence
<220> FEATURE:
<223> OTHER INFORMATION: Defensin like

<400> SEQUENCE: 607
aacctgtgcg aaaaagcgag caaaacctgg agcggcaact gcggcaacac caaacattgc    60
gataaccagt gcagaagctg ggaaggcgcc aaacatggtg cttgccacgt gcgcagcggc   120
aaacataagt gcttttgcta ttttaactgc tga                                153

<210> SEQ ID NO 608
<211> LENGTH: 153
<212> TYPE: DNA
<213> ORGANISM: Artificial Sequence
<220> FEATURE:
<223> OTHER INFORMATION: Defensin like

<400> SEQUENCE: 608
aacctgtgcg aaagagcgag caaaacctgg agcggcaact gcggcaacac caaacattgc    60
gataaccagt gcaaaagctg ggaaggcgcc aaacatggtg cttgccacgt gcgcaacggc   120
aaatggaagt gcttttgcta ttttaactgc tga                                153

<210> SEQ ID NO 609
<211> LENGTH: 153
<212> TYPE: DNA
<213> ORGANISM: Artificial Sequence
<220> FEATURE:

<223> OTHER INFORMATION: Defensin like

<400> SEQUENCE: 609
aacctgtgcg aaaaagcgag caaaacctgg agcggcaact gcggcaacac caaacattgc    60
gatacccagt gcaaaaactg ggaaggcgcc aaacatggtg cttgccacaa acgcaacggc   120
aaatggaagt gcttttgcta ttttaactgc tga                                153

<210> SEQ ID NO 610
<211> LENGTH: 153
<212> TYPE: DNA
<213> ORGANISM: Artificial Sequence
<220> FEATURE:
<223> OTHER INFORMATION: Defensin like

<400> SEQUENCE: 610
aacctgtgcg aaaaagcgag caaaacctgg agcggcaact gcggcaacac caaacattgc    60
gataaccagt gcaaaagctg ggaaggcgcc gcccatggtg cttgccacgt gcgcaacggc   120
aaacataagt gcttttgcta ttttaactgc tga                                153

<210> SEQ ID NO 611
<211> LENGTH: 153
<212> TYPE: DNA
<213> ORGANISM: Artificial Sequence
<220> FEATURE:
<223> OTHER INFORMATION: Defensin like

<400> SEQUENCE: 611
aacctgtgcg aaagagcgag caaaacctgg agcggtaact gcggcaacac caaacattgc    60
gataaccagt gcaaaagctg ggaaggcgcc caacatggtg cttgccacgt gcgcaacggc   120
aaacataagt gcttttgcta ttttaactgc tga                                153

<210> SEQ ID NO 612
<211> LENGTH: 153
<212> TYPE: DNA
<213> ORGANISM: Artificial Sequence
<220> FEATURE:
<223> OTHER INFORMATION: Defensin like

<400> SEQUENCE: 612
aacctgtgcg aaagagcgag caaaacctgg agcggcaact gcggcaacac caaacattgc    60
gatacccagt gcagaaactg ggaaggcgcc aaacatggtg cttgccacgt gcgcaacggc   120
aaatggaagt gcttttgcta ttttaactgc tga                                153

<210> SEQ ID NO 613
<211> LENGTH: 153
<212> TYPE: DNA
<213> ORGANISM: Artificial Sequence
<220> FEATURE:
<223> OTHER INFORMATION: Defensin like

<400> SEQUENCE: 613
aacctgtgcg aaagagcgag caaaacctgg accggcaact gcggcaacac caaacattgc    60
gatacccagt gcagaagctg ggaaggcgcc aaacatggtg cttgccacaa acgcaacggc   120
aaatggaagt gcttttgcta ttttaactgc tga                                153

<210> SEQ ID NO 614
<211> LENGTH: 153
<212> TYPE: DNA
<213> ORGANISM: Artificial Sequence

```
<220> FEATURE:
<223> OTHER INFORMATION: Defensin like

<400> SEQUENCE: 614
aacctgtgcg aaaaagcgag caaaacctgg accggcaact gcggcaacac caaacattgc      60
gataaccagt gcaaaagctg ggaaggcgcc aaacatggtg cttgccacgt gcgcaacggc     120
aaatggaagt gcttttgcta ttttaactgc tga                                  153

<210> SEQ ID NO 615
<211> LENGTH: 153
<212> TYPE: DNA
<213> ORGANISM: Artificial Sequence
<220> FEATURE:
<223> OTHER INFORMATION: Defensin like

<400> SEQUENCE: 615
aacctgtgcg aaaaagcgag caaaacctgg agcggcaact gcggcaacac caaacattgc      60
gatacccagt gcaaaagctg ggaaggcgcc aaacatggtg cctgccacgt gcgcagcggc     120
aaacataagt gcttttgcta ttttaactgc tga                                  153

<210> SEQ ID NO 616
<211> LENGTH: 153
<212> TYPE: DNA
<213> ORGANISM: Artificial Sequence
<220> FEATURE:
<223> OTHER INFORMATION: Defensin like

<400> SEQUENCE: 616
aacctgtgcg aaagagcgag caaaacctgg agcggcaact gcggcaacac caaacattgc      60
gataaccagt gcataagctg ggaaggcgcc aaacatggtg cttgccacaa acgcaacggc     120
aaatggaagt gcttttgcta ttttaactgc tga                                  153

<210> SEQ ID NO 617
<211> LENGTH: 153
<212> TYPE: DNA
<213> ORGANISM: Artificial Sequence
<220> FEATURE:
<223> OTHER INFORMATION: Defensin like

<400> SEQUENCE: 617
aacctgtgcg aaaaagcgag caaaacctgg accggcaact gcggcaacac caagcattgc      60
gatacccagt gcagaaactg ggaaggcgcc aaacatggtg cttgccacaa acgcaacggc     120
aaatggaagt gcttttgcta ttttaactgc tga                                  153

<210> SEQ ID NO 618
<211> LENGTH: 153
<212> TYPE: DNA
<213> ORGANISM: Artificial Sequence
<220> FEATURE:
<223> OTHER INFORMATION: Defensin like

<400> SEQUENCE: 618
aacctgtgcg aaagagcgag caaaacctgg accggcaact gcggcaacac caaacattgc      60
gataaccagt gcaaaaactg ggaaggcgcc aaacatggtg cttgccacaa acgcagcggc     120
aaatggaagt gcttttgcta ttttaactgc tga                                  153

<210> SEQ ID NO 619
<211> LENGTH: 153
<212> TYPE: DNA
```

```
<213> ORGANISM: Artificial Sequence
<220> FEATURE:
<223> OTHER INFORMATION: Defensin like

<400> SEQUENCE: 619
aacctgtgcg aaagagcgag caaaacctgg gccggcaact gcggcaacac caaacattgc     60
gataaccagt gcagaagctg ggaaggcgcc aaacatggtg cttgccacgt gcgcaacggc    120
aaatggaagt gcttttgcta ttttaactgc tga                                 153

<210> SEQ ID NO 620
<211> LENGTH: 153
<212> TYPE: DNA
<213> ORGANISM: Artificial Sequence
<220> FEATURE:
<223> OTHER INFORMATION: Defensin like

<400> SEQUENCE: 620
aacctgtgcg aaaaagcgag caaaacctgg agcggcaact gcggcaacac caaacattgc     60
gataaccagt gcaaaagctg ggaaggcgcc gcccatggtg cttgccacaa acgcagcggc    120
aaatggaagt gcttttgcta ttttaactgc tga                                 153

<210> SEQ ID NO 621
<211> LENGTH: 153
<212> TYPE: DNA
<213> ORGANISM: Artificial Sequence
<220> FEATURE:
<223> OTHER INFORMATION: Defensin like

<400> SEQUENCE: 621
aacctgtgcg aaaaagcgag caaaacctgg agcggcaact gcggcaacac caatcattgc     60
gataaccagt gcaggagctg ggagggcgcc aaacatggtg cttgccacgt gcgcagcggc    120
aaacataagt gcttttgcta ttttaactgc tga                                 153

<210> SEQ ID NO 622
<211> LENGTH: 153
<212> TYPE: DNA
<213> ORGANISM: Artificial Sequence
<220> FEATURE:
<223> OTHER INFORMATION: Defensin like

<400> SEQUENCE: 622
aacctgtgcg aaagagcgag caaaacctgg agcggcaact gcggcagcac caaacattgc     60
gataaccagt gcaaaaactg ggaaggcgcc aaacatggtg cttgccacgt gcgcagcggc    120
aaacataagt gcttttgcta ttttaactgc tga                                 153

<210> SEQ ID NO 623
<211> LENGTH: 153
<212> TYPE: DNA
<213> ORGANISM: Artificial Sequence
<220> FEATURE:
<223> OTHER INFORMATION: Defensin like

<400> SEQUENCE: 623
aacctgtgcg aaagagcgag caaaacctgg agcggcaact gcggcaacac caaacattgc     60
gatacccagt gcaaaagctg ggaaggcgcc aaacatggtg cttgccacgt gcgcaacggc    120
aaacataagt gcttttgcta ttttaactgc tga                                 153

<210> SEQ ID NO 624
<211> LENGTH: 153
```

```
<212> TYPE: DNA
<213> ORGANISM: Artificial Sequence
<220> FEATURE:
<223> OTHER INFORMATION: Defensin like

<400> SEQUENCE: 624
aacctgtgcg aaagagcgag caaaacctgg agcggcaact gcggcaacac caaacattgc      60
gataaccagt gcaaaaactg ggaaggcgcc aaacatggtg cttgccacgt gcgcaacggc     120
aaatggaagt gcttttgcta ttttaactgc tga                                  153

<210> SEQ ID NO 625
<211> LENGTH: 153
<212> TYPE: DNA
<213> ORGANISM: Artificial Sequence
<220> FEATURE:
<223> OTHER INFORMATION: Defensin like

<400> SEQUENCE: 625
aacctgtgcg aaagagcgag caaaacctgg accggcaact gcggcaacac caaacattgc      60
gataaccagt gcaaaagctg ggaaggcgcc aaacatggtg cttgccacaa acgcaacggc     120
aaatggaagt gcttttgcta ttttaactgc tga                                  153

<210> SEQ ID NO 626
<211> LENGTH: 153
<212> TYPE: DNA
<213> ORGANISM: Artificial Sequence
<220> FEATURE:
<223> OTHER INFORMATION: Defensin like

<400> SEQUENCE: 626
aacctgtgcg aaagagcgag caaaacctgg accggcaatt gcggcaacac caaacattgc      60
gatacccagt gcagaagctg ggaaggcgcc gcccacggtg cttgccacgt gcgcggcggc     120
aaacataagt gcttttgcta ttttaactgc tga                                  153

<210> SEQ ID NO 627
<211> LENGTH: 153
<212> TYPE: DNA
<213> ORGANISM: Artificial Sequence
<220> FEATURE:
<223> OTHER INFORMATION: Defensin like

<400> SEQUENCE: 627
aacctgtgcg aaaagcgag caaaacctgg accggcaact gcggcaacac caaacattgc       60
gataaccagt gcagaagctg ggaaggcgcc aaacatggtg cttgccacgt gcgcagcggc     120
aaacataagt gcttttgcta ttttaactgc tga                                  153

<210> SEQ ID NO 628
<211> LENGTH: 153
<212> TYPE: DNA
<213> ORGANISM: Artificial Sequence
<220> FEATURE:
<223> OTHER INFORMATION: Defensin like

<400> SEQUENCE: 628
aacctgtgcg aaagagcgag caaaacctgg agcggcaact gcggcaacac caaacattgc      60
gataaccagt gcagaagctg ggaaggcgcc gcccatggtg cttgccacaa acgcaacggc     120
aaatggaagt gcttttgcta ttttaactgc tga                                  153

<210> SEQ ID NO 629
```

```
<211> LENGTH: 153
<212> TYPE: DNA
<213> ORGANISM: Artificial Sequence
<220> FEATURE:
<223> OTHER INFORMATION: Defensin like

<400> SEQUENCE: 629
aacctgtgcg aaaaagcgag caaaacctgg accggcaact gcggcaacac caaacattgc      60
gataaccagt gcaaaagctg ggaaggcgcc gcccatggtg cttgccacaa acgcaacggc     120
aaatggaagt gcttttgcta ttttaactgc tga                                  153

<210> SEQ ID NO 630
<211> LENGTH: 153
<212> TYPE: DNA
<213> ORGANISM: Artificial Sequence
<220> FEATURE:
<223> OTHER INFORMATION: Defensin like

<400> SEQUENCE: 630
aacctgtgcg aaagagcgag caaaacctgg agcagcaact gcggcaacac caaacattgc      60
gatacccagt gcaaaaactg ggaaggcgcc aaacatggtg cttgccacgt gcgcaacggc     120
aaatggaagt gcttttgcta ttttaactgc tga                                  153

<210> SEQ ID NO 631
<211> LENGTH: 153
<212> TYPE: DNA
<213> ORGANISM: Artificial Sequence
<220> FEATURE:
<223> OTHER INFORMATION: Defensin like

<400> SEQUENCE: 631
aacctgtgcg aaagagcgag caaaacctgg agcggcaact gcggcaacac caaacattgc      60
gatacccagt gcaaaaactg ggaaggcgcc aaacatggtg cttgccacaa acgcagcggc     120
aaatggaagt gcttttgcta ttttaactgc tga                                  153

<210> SEQ ID NO 632
<211> LENGTH: 153
<212> TYPE: DNA
<213> ORGANISM: Artificial Sequence
<220> FEATURE:
<223> OTHER INFORMATION: Defensin like

<400> SEQUENCE: 632
aacctgtgcg aaagagcaag caaaacctgg agcggcgact gcggcaacac caaacattgc      60
gataaccagt gcagaaactg ggaaggcgcc aaacatggtg cttgccacaa acgcaacggc     120
aaatggaagt gcttttgcta ttttaactgc tga                                  153

<210> SEQ ID NO 633
<211> LENGTH: 153
<212> TYPE: DNA
<213> ORGANISM: Artificial Sequence
<220> FEATURE:
<223> OTHER INFORMATION: Defensin like

<400> SEQUENCE: 633
aacctgtgcg aaaaagcgag caaaacctgg accggcaact gcggcaacac caaacattgc      60
gataaccagt gcaaaagctg ggaaggcgcc aaacatggtg cttgccacaa acgcggcggc     120
aaatggaagt gcttttgcta ttttaactgc tga                                  153
```

```
<210> SEQ ID NO 634
<211> LENGTH: 153
<212> TYPE: DNA
<213> ORGANISM: Artificial Sequence
<220> FEATURE:
<223> OTHER INFORMATION: Defensin like

<400> SEQUENCE: 634
aacctgtgcg aaagagcgag caaaacctgg accggcaact gcggcaacac caaacattgc    60
gataaccagt gcaaaagctg ggaaggcgcc aaacatggtg cttgccacgt gcgcaacggc   120
aaatggaagt gcttttgcta ttttaactgc tga                                153

<210> SEQ ID NO 635
<211> LENGTH: 153
<212> TYPE: DNA
<213> ORGANISM: Artificial Sequence
<220> FEATURE:
<223> OTHER INFORMATION: Defensin like

<400> SEQUENCE: 635
aacctgtgcg aaagagcgag caaaacctgg agcggcaact gcggcaacac caaacattgc    60
gataaccagt gcaagaactg ggaaggcgcc gcccatggtg cttgccacgt gcgcagcggc   120
aaacataagt gcttttgcta ttttaactgc tga                                153

<210> SEQ ID NO 636
<211> LENGTH: 153
<212> TYPE: DNA
<213> ORGANISM: Artificial Sequence
<220> FEATURE:
<223> OTHER INFORMATION: Defensin like

<400> SEQUENCE: 636
aacctgtgcg aaaaagcgag caaaacctgg accggcaact gcggcaacac caaacattgc    60
gataaccagt gcaaaagctg ggaaggcgcc gcccatggcg cttgccacgt gcgcaacggc   120
aaacataagt gcttttgcta ttttaactgc tga                                153

<210> SEQ ID NO 637
<211> LENGTH: 153
<212> TYPE: DNA
<213> ORGANISM: Artificial Sequence
<220> FEATURE:
<223> OTHER INFORMATION: Defensin like

<400> SEQUENCE: 637
aacctgtgcg aaaaagcgag caaaacctgg agcggcaact gcggcaacac caaacattgc    60
gatacccagt gcaaaaactg ggaaggcgcc aaacatggtg cttgccacgt gcgcagcggc   120
aaatggaagt gcttttgcta ttttaactgc tga                                153

<210> SEQ ID NO 638
<211> LENGTH: 153
<212> TYPE: DNA
<213> ORGANISM: Artificial Sequence
<220> FEATURE:
<223> OTHER INFORMATION: Defensin like

<400> SEQUENCE: 638
aacctgtgcg aaaaagcgag caaaacctgg accggcaact gcggcaacac caaacattgc    60
gataaccagt gcagaagctg ggaaggcgcc gcccatggtg cttgccacgt gcgcaacggc   120
aaacataagt gcttttgcta ttttaactgc tga                                153
```

<210> SEQ ID NO 639
<211> LENGTH: 153
<212> TYPE: DNA
<213> ORGANISM: Artificial Sequence
<220> FEATURE:
<223> OTHER INFORMATION: Defensin like

<400> SEQUENCE: 639
aacctgtgcg aaagagcgag caaaacctgg agcggcaact gcggcaacac caaacattgc      60
gataaccagt gcagaaactg ggaaggcgcc aaacatggtg cttgccacgt gcgcagcggc     120
aaatggaagt gcttttgcta ttttaactgc tga                                 153

<210> SEQ ID NO 640
<211> LENGTH: 153
<212> TYPE: DNA
<213> ORGANISM: Artificial Sequence
<220> FEATURE:
<223> OTHER INFORMATION: Defensin like

<400> SEQUENCE: 640
aacctgtgcg aaagagcgag caaaacctgg accggcaact gcggcaacac caaacattgc      60
gatacccagt gcagaaactg ggaaggcgcc agacatggtg cttgccacgt gcgcaacggc     120
aaatggaagt gcttttgcta ttttaactgc tga                                 153

<210> SEQ ID NO 641
<211> LENGTH: 153
<212> TYPE: DNA
<213> ORGANISM: Artificial Sequence
<220> FEATURE:
<223> OTHER INFORMATION: Defensin like

<400> SEQUENCE: 641
aacctgtgcg aaagagcgag caaaacctgg agcggcaact gcggcaacac caaacattgc      60
gataaccagt gcagaagctg ggaaggcgcc gcccatggtg cttgccacgt gcgcaacggc     120
aaatggaagt gcttttgcta ttttaactgc tga                                 153

<210> SEQ ID NO 642
<211> LENGTH: 153
<212> TYPE: DNA
<213> ORGANISM: Artificial Sequence
<220> FEATURE:
<223> OTHER INFORMATION: Defensin like

<400> SEQUENCE: 642
aacctgtgcg aaaagcgag caaaacctgg accggcaact gcggcaacac caaacattgc      60
gataaccagt gcagaagctg ggaaggcgcc aaacatggtg cttgccacaa acgcagcggc     120
aaatggaagt gcttttgcta ttttaactgc tga                                 153

<210> SEQ ID NO 643
<211> LENGTH: 153
<212> TYPE: DNA
<213> ORGANISM: Artificial Sequence
<220> FEATURE:
<223> OTHER INFORMATION: Defensin like

<400> SEQUENCE: 643
aacctgtgcg aaagagcgag caaaacctgg accggcaact gcggcaacac caaacattgc      60
gataaccagt gcagaagctg ggaaggcgcc aaacatggtg cttgccacaa acgcagcggc     120
aaatggaagt gcttttgcta ttttaactgc tga                                 153

<210> SEQ ID NO 644
<211> LENGTH: 153
<212> TYPE: DNA
<213> ORGANISM: Artificial Sequence
<220> FEATURE:
<223> OTHER INFORMATION: Defensin like

<400> SEQUENCE: 644
aacctgtgcg aaaaagcgag caaaacctgg agcggcaact gcggcaacac caaacattgc    60
gatacccagt gcaaaagctg ggaaggcgcc gcccatggtg cttgccacaa acgcaacggc   120
aaatggaagt gcttttgcta ttttaactgc tga                                153

<210> SEQ ID NO 645
<211> LENGTH: 153
<212> TYPE: DNA
<213> ORGANISM: Artificial Sequence
<220> FEATURE:
<223> OTHER INFORMATION: Defensin like

<400> SEQUENCE: 645
aacctgtgcg aaagagcgag caaaacctgg accggcaact gcggcaacac caaacattgc    60
gataaccagt gcagaaactg ggaaggcgcc aaacatggtg cttgccacgt gcgcagcggc   120
aaatggaagt gcttttgcta ttttaactgc tga                                153

<210> SEQ ID NO 646
<211> LENGTH: 153
<212> TYPE: DNA
<213> ORGANISM: Artificial Sequence
<220> FEATURE:
<223> OTHER INFORMATION: Defensin like

<400> SEQUENCE: 646
aacctgtgcg aaagagcgag caaaacctgg accggcaact gcggcaacac caaacattgc    60
gataaccagt gcaaaaactg ggaaggcgcc gcccatggtg cttgccacaa acgcagcggc   120
aaatggaagt gcttttgcta ttttaactgc tga                                153

<210> SEQ ID NO 647
<211> LENGTH: 153
<212> TYPE: DNA
<213> ORGANISM: Artificial Sequence
<220> FEATURE:
<223> OTHER INFORMATION: Defensin like

<400> SEQUENCE: 647
aacctgtgcg aaagagcgag caaaacctgg accggcaact gcggcaacac caaacattgc    60
gataaccagt gcagaagctg ggaaggcgcc gcccatggtg cttgccacaa acgcagcggc   120
aaatggaagt gcttttgcta ttttaactgc tga                                153

<210> SEQ ID NO 648
<211> LENGTH: 153
<212> TYPE: DNA
<213> ORGANISM: Artificial Sequence
<220> FEATURE:
<223> OTHER INFORMATION: Defensin like

<400> SEQUENCE: 648
aacctgtgcg aaagagcgag caaaacctgg accggcaact gcggcaacac caaacactgc    60
gataaccagt gcaaaaactg ggaaggcgcc gcccatggtg cttgccacgt gcgcagcggc   120

```
aaacataagt gcttttgcta ttttaactgc tga                              153
```

<210> SEQ ID NO 649
<211> LENGTH: 153
<212> TYPE: DNA
<213> ORGANISM: Artificial Sequence
<220> FEATURE:
<223> OTHER INFORMATION: Defensin like

<400> SEQUENCE: 649

```
aacctgtgcg aaaaagcgag caaaacctgg agcggcaact gcggcaacac caagcattgc    60
gataaccagt gcaggaactg ggaaggcgcc aacatggtg cttgccacgt acgcaacggc   120
aaacataagt gcttttgcta ttttaactgc tgt                              153
```

<210> SEQ ID NO 650
<211> LENGTH: 153
<212> TYPE: DNA
<213> ORGANISM: Artificial Sequence
<220> FEATURE:
<223> OTHER INFORMATION: Defensin like

<400> SEQUENCE: 650

```
aacctgtgcg aaagagcgag caaaacctgg agcggcaact gcggcaacac caaacattgc    60
gataaccagt gcaaaagctg ggaaggcgcc aacatggtg cttgccacgt gcgcaacggc   120
aaacataagt gcttttgcta ttttaactgc tga                              153
```

<210> SEQ ID NO 651
<211> LENGTH: 153
<212> TYPE: DNA
<213> ORGANISM: Artificial Sequence
<220> FEATURE:
<223> OTHER INFORMATION: Defensin like

<400> SEQUENCE: 651

```
aacctgtgcg aaaaagcgag caaaacctgg agcggcaact gcggcaacac caaacattgc    60
gataaccagt gcaaaagctg ggaaggcgcc gcccatggtg cttgccacaa acgcaacggc   120
aaatggaagt gcttttgcta ttttaactgc tga                              153
```

<210> SEQ ID NO 652
<211> LENGTH: 153
<212> TYPE: DNA
<213> ORGANISM: Artificial Sequence
<220> FEATURE:
<223> OTHER INFORMATION: Defensin like

<400> SEQUENCE: 652

```
aacctgtgcg aaaaagcgag caaaacctgg agcggcaact gcggcaacac caaacattgc    60
gataaccagt gcaaaagctg ggaaggcgcc aacatggtg cttgccacaa acgcaacggc   120
aaatggaagt gcttttgcta ttttaactgc tga                              153
```

<210> SEQ ID NO 653
<211> LENGTH: 153
<212> TYPE: DNA
<213> ORGANISM: Artificial Sequence
<220> FEATURE:
<223> OTHER INFORMATION: Defensin like

<400> SEQUENCE: 653

```
aacctgtgcg aaagagcgag tagaacctgg agcggcaact gcggcaacac caaacattgc    60
gataaccagt gcaaaagttg ggaaggcgcc aacatggtg cttgccacaa acgcaacggc   120
```
aaatggaagt gcttttgcta ttttaactgc tga 33

<210> SEQ ID NO 654
<211> LENGTH: 153
<212> TYPE: DNA
<213> ORGANISM: Artificial Sequence
<220> FEATURE:
<223> OTHER INFORMATION: Defensin like

<400> SEQUENCE: 654
aacctgtgcg aaagagcgag caaaacctgg agcggcaact gcggcatcac caaacattgt 60
gataaccagt gcaaaagctg ggaaggcgcc aaacatggtg cttgccacaa acgcaacggc 120
aaatggaagt gcttttgcta ttttaactgc tga 153

<210> SEQ ID NO 655
<211> LENGTH: 153
<212> TYPE: DNA
<213> ORGANISM: Artificial Sequence
<220> FEATURE:
<223> OTHER INFORMATION: Defensin like

<400> SEQUENCE: 655
aacctgtgcg aaagagcgag caaaacctgg agcggcaact gcagcaacac caaacattgc 60
gataaccagt gcaaaagctg ggaaggcgcc aaacatggtg cttgccacaa acgcaacggc 120
aaatggaagt gcttttgcta ttttaactgc tga 153

<210> SEQ ID NO 656
<211> LENGTH: 153
<212> TYPE: DNA
<213> ORGANISM: Artificial Sequence
<220> FEATURE:
<223> OTHER INFORMATION: Defensin like

<400> SEQUENCE: 656
aacctgtgcg aaagagcgag caaaacctgg agcggcaact gcggcaacac caaacattgc 60
gataaccagt gcaaaaactg ggaaggcgcc aaacatggtg cttgccacaa acgcaacggc 120
aaatggaagt gcttttgcta ttttaactgc tga 153

<210> SEQ ID NO 657
<211> LENGTH: 153
<212> TYPE: DNA
<213> ORGANISM: Artificial Sequence
<220> FEATURE:
<223> OTHER INFORMATION: Defensin like

<400> SEQUENCE: 657
aacctgtgcg aaaaagcgag caaaacctgg agcggcaact gcggcaacac caaacattgc 60
gataaccagt gcaaaaactg ggaaggcgcc aaacatggtg cttgccacaa acgcaacggc 120
aaatggaagt gcttttgcta ttttaactgc tga 153

<210> SEQ ID NO 658
<211> LENGTH: 153
<212> TYPE: DNA
<213> ORGANISM: Artificial Sequence
<220> FEATURE:
<223> OTHER INFORMATION: Defensin like

<400> SEQUENCE: 658
aacctgtgcg aaagagcgag caaaacctgg agcggcaact gcggcaacac caaacattgc 60

```
gataaccagt gcaaaggctg ggaaggcgcc aaacatggtg cttgccacaa acgcaacggc    120
aaatggaagt gcttttgcta ttttaactgc tga                                153

<210> SEQ ID NO 659
<211> LENGTH: 150
<212> TYPE: DNA
<213> ORGANISM: Artificial Sequence
<220> FEATURE:
<223> OTHER INFORMATION: Defensin like

<400> SEQUENCE: 659
aacctgtgcg aaagagcgag caaaacctgg agcggcaact gcggcaacac caaacattgc    60
gataaccagt gcaaaggctg ggaaggcgcc aaacatggtg cttgccacaa acgcaacggc    120
aaatggaagt gcttttgcta ttttaactgc                                     150

<210> SEQ ID NO 660
<211> LENGTH: 162
<212> TYPE: DNA
<213> ORGANISM: Artificial Sequence
<220> FEATURE:
<223> OTHER INFORMATION: Defensin like

<400> SEQUENCE: 660
gatggcgtga aactgtgcga aaaaccgagc caaacctgga ccggccactg cggcaacacc    60
aaacattgcg atacccagtg cagaagctgg gaaggcgccg cccatggtgc ttgccacaaa    120
cgcagcggca aatggaaatg cttttgctat tttaactgct ga                       162

<210> SEQ ID NO 661
<211> LENGTH: 162
<212> TYPE: DNA
<213> ORGANISM: Artificial Sequence
<220> FEATURE:
<223> OTHER INFORMATION: Defensin like

<400> SEQUENCE: 661
gatggcgtga aactgtgcga aagagcgagc aaaacctgga ccggcaactg cggcaacacc    60
aaacattgcg ataaacagtg caaaaactgg gaaggcgcca acatggtgc ttgccacaaa    120 cgcaacggca aatggaaatg cttttgctat tttaactgct ga                       162

<210> SEQ ID NO 662
<211> LENGTH: 162
<212> TYPE: DNA
<213> ORGANISM: Artificial Sequence
<220> FEATURE:
<223> OTHER INFORMATION: Defensin like

<400> SEQUENCE: 662
gatggcgtga aactgtgcga aaaagcgagc aaaacctgga gcggcaactg cggcaacacc    60
aaacattgcg ataaacagtg cagaagctgg gaaaaagcca acatggtgc ttgccacgtg     120 cgcaacggca aacataaatg cttttgctat tttaactgct ga                       162

<210> SEQ ID NO 663
<211> LENGTH: 162
<212> TYPE: DNA
<213> ORGANISM: Artificial Sequence
<220> FEATURE:
<223> OTHER INFORMATION: Defensin like

<400> SEQUENCE: 663
gatggcgtga aactgtgcga agaccgagc aaaacctgga gcggcaactg cggcaacacc     60
```

```
aaacattgcg ataaacagtg caaaaactgg gaaaaagcca acatggtgc ttgccacgtg      120 cgcaacggca aatggaaatg cttttgctat tttaactgct ga                       162
```

<210> SEQ ID NO 664
<211> LENGTH: 162
<212> TYPE: DNA
<213> ORGANISM: Artificial Sequence
<220> FEATURE:
<223> OTHER INFORMATION: Defensin like

<400> SEQUENCE: 664

```
gatggcgtga aactgtgcga aaaccgagc aaaacctgga gcggccactg cggcaacacc      60
aaacattgcg ataaacagtg caaaaactgg gaaaaagcca acatggtgc ttgccacaaa     120 cgcaacggca aatggaaatg cttttgctat tttaactgct ga                       162
```

<210> SEQ ID NO 665
<211> LENGTH: 153
<212> TYPE: DNA
<213> ORGANISM: Artificial Sequence
<220> FEATURE:
<223> OTHER INFORMATION: Defensin like

<400> SEQUENCE: 665

```
aacctgtgcg aaaaagcgag ccaaacctgg accggccact gcggcaacac caaacattgc     60
gataaacagt gcaaaagctg ggaaggcgcc gcccatggtg cttgccacgt gcgcagcggc    120
aaatggaaat gcttttgcta ttttaactgc tga                                 153
```

<210> SEQ ID NO 666
<211> LENGTH: 162
<212> TYPE: DNA
<213> ORGANISM: Artificial Sequence
<220> FEATURE:
<223> OTHER INFORMATION: Defensin like

<400> SEQUENCE: 666

```
gatggcgtga aactgtgcga aagaccgagc caaacctgga gcggcaactg cggcaacacc      60
aaacattgcg ataaacagtg cagaaactgg gaaaaagcca acatggtgc ttgccacaaa     120 cgcaacggca aatggaaatg cttttgctat tttaactgct ga                       162
```

<210> SEQ ID NO 667
<211> LENGTH: 162
<212> TYPE: DNA
<213> ORGANISM: Artificial Sequence
<220> FEATURE:
<223> OTHER INFORMATION: Defensin like

<400> SEQUENCE: 667

```
gatggcgtga aactgtgcga aaaccgagc aaaacctgga ccggccactg cggcaacacc      60
aaacattgcg ataaccagtg caaaaactgg gaaaaagccg cccatggtgc ttgccacgtg    120
cgcagcggca aatggaaatg cttttgctat tttaactgct ga                       162
```

<210> SEQ ID NO 668
<211> LENGTH: 162
<212> TYPE: DNA
<213> ORGANISM: Artificial Sequence
<220> FEATURE:
<223> OTHER INFORMATION: Defensin like

<400> SEQUENCE: 668

```
gatggcgtga aactgtgcga aaaaccgagc aaaacctgga ccggccactg cggcaacacc    60
aaacattgcg ataaacagtg caaaaactgg gaaaaagccg cccatggtgc ttgccacgtg   120
cgcaacggca aatggaaatg cttttgctat tttaactgct ga                     162
```

<210> SEQ ID NO 669
<211> LENGTH: 162
<212> TYPE: DNA
<213> ORGANISM: Artificial Sequence
<220> FEATURE:
<223> OTHER INFORMATION: Defensin like

<400> SEQUENCE: 669

```
gatggcgtga aactgtgcga aagagcgagc caaacctgga gcggccactg cggcaacacc    60
aaacattgcg ataaacagtg caaaaactgg gaaaaagccg cccatggtgc ttgccacgtg   120
cgcagcggca aatggaaatg cttttgctat tttaactgct ga                     162
```

<210> SEQ ID NO 670
<211> LENGTH: 162
<212> TYPE: DNA
<213> ORGANISM: Artificial Sequence
<220> FEATURE:
<223> OTHER INFORMATION: Defensin like

<400> SEQUENCE: 670

```
gatggcgtga aactgtgcga aagagcgagc caaacctgga ccggccactg cggcaacacc    60
aaacattgcg ataaacagtg cagaaactgg gaaggcgcca acatggtgc ttgccacaaa   120 cgcaacggca aatggaaatg cttttgctat tttaactgct ga                     162
```

<210> SEQ ID NO 671
<211> LENGTH: 162
<212> TYPE: DNA
<213> ORGANISM: Artificial Sequence
<220> FEATURE:
<223> OTHER INFORMATION: Defensin like

<400> SEQUENCE: 671

```
gatggcgtga aactgtgcga aagagcgagc caaacctgga ccggccactg cggcaacacc    60
aaacattgcg ataaacagtg caaaagctgg gaaaaagcca acatggtgc ttgccacgtg   120 cgcaacggca aatggaaatg cttttgctat tttaactgct ga                     162
```

<210> SEQ ID NO 672
<211> LENGTH: 162
<212> TYPE: DNA
<213> ORGANISM: Artificial Sequence
<220> FEATURE:
<223> OTHER INFORMATION: Defensin like

<400> SEQUENCE: 672

```
gatggcgtga aactgtgcga aagagcgagc caaacctgga gcggccactg cggcaacacc    60
aaacattgcg ataaacagtg cagaaactgg gaaggcgccg cccatggtgc ttgccacgtg   120
cgcaacggca aatggaaatg cttttgctat tttaactgct ga                     162
```

<210> SEQ ID NO 673
<211> LENGTH: 162
<212> TYPE: DNA
<213> ORGANISM: Artificial Sequence
<220> FEATURE:
<223> OTHER INFORMATION: Defensin like

<400> SEQUENCE: 673

-continued gatggcgtga aactgtgcga aaaagcgagc caaacctgga gcggcaactg cggcaacacc      60
aaacattgcg atacccagtg cagaaactgg gaaggcgcca acatggtgc ttgccacaaa      120 cgcaacggca aatggaaatg cttttgctat tttaactgct ga      162

<210> SEQ ID NO 674
<211> LENGTH: 162
<212> TYPE: DNA
<213> ORGANISM: Artificial Sequence
<220> FEATURE:
<223> OTHER INFORMATION: Defensin like

<400> SEQUENCE: 674
gatggcgtga aactgtgcga aagagcgagc caaacctgga ccggccactg cggcaacacc      60
aaacattgcg ataaccagtg caaaaactgg gaaggcgcca acatggtgc ttgccacaaa      120 cgcagcggca aatggaaatg cttttgctat tttaactgct ga      162

<210> SEQ ID NO 675
<211> LENGTH: 162
<212> TYPE: DNA
<213> ORGANISM: Artificial Sequence
<220> FEATURE:
<223> OTHER INFORMATION: Defensin like

<400> SEQUENCE: 675
gatggcgtga aactgtgcga aaaccgagc caaacctgga ccggccactg cggcaacacc      60
aaacattgcg ataaacagtg caaaaactgg gaaggcgcca acatggtgc ttgccacaaa      120 cgcaacggca aatggaaatg cttttgctat tttaactgct ga      162

<210> SEQ ID NO 676
<211> LENGTH: 153
<212> TYPE: DNA
<213> ORGANISM: Artificial Sequence
<220> FEATURE:
<223> OTHER INFORMATION: Defensin like

<400> SEQUENCE: 676
aacctgtgcg aaagagcgag ccatacctgg agcggccact gcggcaacac caaacattgc      60
gataaacagt gcagaagctg ggaaggcgcc gcccatggtg cttgccacgt gcgcaacggc      120
aaacggaaat gcttttgcta ttttaactgc tga      153

<210> SEQ ID NO 677
<211> LENGTH: 162
<212> TYPE: DNA
<213> ORGANISM: Artificial Sequence
<220> FEATURE:
<223> OTHER INFORMATION: Defensin like

<400> SEQUENCE: 677
gatggcgtga aactgtgcga aaaccgagc aaaacctgga gcggccactg cggcaacacc      60
aaacattgcg ataaccagtg cagaaactgg gaaaaagccg cccatggtgc ttgccacgtg      120
cgcaacggca aatggaaatg cttttgctat tttaactgct ga      162

<210> SEQ ID NO 678
<211> LENGTH: 156
<212> TYPE: DNA
<213> ORGANISM: Artificial Sequence
<220> FEATURE:
<223> OTHER INFORMATION: Defensin like

<400> SEQUENCE: 678

```
cagaaactgt gcgaaaaagc gagccaaacc tggaccggcc actgcggcaa caccaaacat    60
tgcgataacc agtgcagaaa ctgggaaaaa gccgcccatg gtgcttgcca cgtgcgcaac   120
ggcaaatgga aatgcttttg ctattttaac tgctga                             156
```

<210> SEQ ID NO 679
<211> LENGTH: 162
<212> TYPE: DNA
<213> ORGANISM: Artificial Sequence
<220> FEATURE:
<223> OTHER INFORMATION: Defensin like

<400> SEQUENCE: 679

```
gatggcgtga aactgtgcga aagagcgagc caaacctgga ccggccactg cggcaacacc    60
aaacattgcg atacccagtg cagaagctgg gaaggcgccg cccatggtgc ttgccacaaa   120
cgcaacggca aatggaaatg cttttgctat ttaactgct ga                       162
```

<210> SEQ ID NO 680
<211> LENGTH: 162
<212> TYPE: DNA
<213> ORGANISM: Artificial Sequence
<220> FEATURE:
<223> OTHER INFORMATION: Defensin like

<400> SEQUENCE: 680

```
gatggcgtga aactgtgcga aagagcgagc aaaacctgga gcggccactg cggcaacacc    60
aaacattgcg ataaccagtg cagaagctgg gaaggcgcca acatggtgc ttgccacgtg   120
cgcagcggca aacataaatg cttttgctat ttaactgct ga                       162
```

<210> SEQ ID NO 681
<211> LENGTH: 162
<212> TYPE: DNA
<213> ORGANISM: Artificial Sequence
<220> FEATURE:
<223> OTHER INFORMATION: Defensin like

<400> SEQUENCE: 681

```
gatggcgtga aactgtgcga aagagcgagc aaaacctgga gcggccactg cggcaacacc    60
aaacattgcg ataaacagtg caaaaactgg gaaaaagcca acatggtgc ttgccacaaa   120
cgcagcggca aatggaaatg cttttgctat ttaactgct ga                       162
```

<210> SEQ ID NO 682
<211> LENGTH: 162
<212> TYPE: DNA
<213> ORGANISM: Artificial Sequence
<220> FEATURE:
<223> OTHER INFORMATION: Defensin like

<400> SEQUENCE: 682

```
gatggcgtga aactgtgcga aaaccgagc caaacctgga gcggccactg cggcaacacc     60
aaacattgcg ataaccagtg caaaaactgg gaaggcgccg cccatggtgc ttgccacaaa   120
cgcagcggca aatggaaatg cttttgctat ttaactgct ga                       162
```

<210> SEQ ID NO 683
<211> LENGTH: 153
<212> TYPE: DNA
<213> ORGANISM: Artificial Sequence
<220> FEATURE:
<223> OTHER INFORMATION: Defensin like -continued

<400> SEQUENCE: 683
aacctgtgcg aaagaccgag caaaacctgg accggccact gcggcaacac caaacattgc    60
gataaacagt gcaaaagctg ggaaggcgcc aaacatggtg cttgccacgt gcgcagcggc   120
aaatggaaat gcttttgcta ttttaactgc tga                                153

<210> SEQ ID NO 684
<211> LENGTH: 162
<212> TYPE: DNA
<213> ORGANISM: Artificial Sequence
<220> FEATURE:
<223> OTHER INFORMATION: Defensin like

<400> SEQUENCE: 684
gatggcgtga aactgtgcga aaaccgagc caaacctgga gcggcaactg cggcaacacc     60
aaacattgcg ataaacagtg caaaagctgg gaaggcgcca acatggtgc ttgccacgtg    120 cgcaacggca aatggaaatg cttttgctat tttaactgct ga                      162

<210> SEQ ID NO 685
<211> LENGTH: 162
<212> TYPE: DNA
<213> ORGANISM: Artificial Sequence
<220> FEATURE:
<223> OTHER INFORMATION: Defensin like

<400> SEQUENCE: 685
gatggcgtga aactgtgcga aaagcgagc caaacctgga ccggccactg cggcaacacc     60
aaacattgcg ataaacagtg caaaagctgg gaaggcgcca acatggtgc ttgccacaaa    120 cgcagcggca aatggaaatg cttttgctat tttaactgct ga                      162

<210> SEQ ID NO 686
<211> LENGTH: 162
<212> TYPE: DNA
<213> ORGANISM: Artificial Sequence
<220> FEATURE:
<223> OTHER INFORMATION: Defensin like

<400> SEQUENCE: 686
gatggcgtga aactgtgcga aagaccgagc aaaacctgga gcggccactg cggcaacacc     60
aaacattgcg ataaccagtg cagaaactgg gaaaaagccg cccatggtgc ttgccacgtg    120
cgcaacggca aacataaatg cttttgctat tttaactgct ga                       162

<210> SEQ ID NO 687
<211> LENGTH: 162
<212> TYPE: DNA
<213> ORGANISM: Artificial Sequence
<220> FEATURE:
<223> OTHER INFORMATION: Defensin like

<400> SEQUENCE: 687
gatggcgtga aactgtgcga aagaccgagc aaaacctgga gcggcaactg cggcaacacc     60
aaacattgcg ataaccagtg caaaaactgg gaaggcgccg cccatggtgc ttgccacaaa    120
cgcaacggca aatggaaatg cttttgctat tttaactgct ga                       162

<210> SEQ ID NO 688
<211> LENGTH: 162
<212> TYPE: DNA
<213> ORGANISM: Artificial Sequence
<220> FEATURE:

<223> OTHER INFORMATION: Defensin like

<400> SEQUENCE: 688

```
gatggcgtga aactgtgcga aaaagcgagc caaacctgga gcggccactg cggcaacacc    60
aaacattgcg ataaacagtg cagaaactgg gaaaaagcca acatggtgc ttgccacaaa    120
cgcaacggca aatggaaatg cttttgctat tttaactgct ga                      162
```

<210> SEQ ID NO 689
<211> LENGTH: 162
<212> TYPE: DNA
<213> ORGANISM: Artificial Sequence
<220> FEATURE:
<223> OTHER INFORMATION: Defensin like

<400> SEQUENCE: 689

```
gatggcgtga aactgtgcga aagagcgagc caaacctgga ccggccactg cggcaacacc    60
aaacattgcg ataaccagtg cagaaactgg gaaggcgcca acatggtgc ttgccacaaa    120
cgcagcggca aatggaaatg cttttgctat tttaactgct ga                      162
```

<210> SEQ ID NO 690
<211> LENGTH: 156
<212> TYPE: DNA
<213> ORGANISM: Artificial Sequence
<220> FEATURE:
<223> OTHER INFORMATION: Defensin like

<400> SEQUENCE: 690

```
cagaaactgt gcgaaaaacc gagccaaacc tggagcggca actgcggcaa caccaaacat    60
tgcgataaac agtgcaaaaa ctgggaaggc gccgcccatg gtgcttgcca caaacgcaac    120
ggcaaatgga aatgctttg ctattttaac tgctga                              156
```

<210> SEQ ID NO 691
<211> LENGTH: 162
<212> TYPE: DNA
<213> ORGANISM: Artificial Sequence
<220> FEATURE:
<223> OTHER INFORMATION: Defensin like

<400> SEQUENCE: 691

```
gatggcgtga aactgtgcga aagagcgagc caaacctgga gcggcaactg cggcaacacc    60
aaacattgcg ataaacagtg cagaaactgg gaaaaagcca acatggtgc ttgccacgtg    120
cgcaacggca aatggaaatg cttttgctat tttaactgct ga                      162
```

<210> SEQ ID NO 692
<211> LENGTH: 162
<212> TYPE: DNA
<213> ORGANISM: Artificial Sequence
<220> FEATURE:
<223> OTHER INFORMATION: Defensin like

<400> SEQUENCE: 692

```
gatggcgtga aactgtgcga aaaagcgagc aaaacctgga ccggccactg cggcaacacc    60
aaacattgcg atacccagtg cagaaactgg gaaggcgcca acatggtgc ttgccacaaa    120
cgcaacggca aatggaaatg cttttgctat tttaactgct ga                      162
```

<210> SEQ ID NO 693
<211> LENGTH: 162
<212> TYPE: DNA
<213> ORGANISM: Artificial Sequence
<220> FEATURE:
<223> OTHER INFORMATION: Defensin like

<400> SEQUENCE: 693
gatggcgtga aactgtgcga aagagcgagc caaacctgga ccggccactg cggcaacacc    60
aaacattgcg ataaacagtg cagaaactgg aaggcgcca aacatggtgc ttgccacaaa   120
cgcagcggca aatggaaatg cttttgctat tttaactgct ga                      162

<210> SEQ ID NO 694
<211> LENGTH: 162
<212> TYPE: DNA
<213> ORGANISM: Artificial Sequence
<220> FEATURE:
<223> OTHER INFORMATION: Defensin like

<400> SEQUENCE: 694
gatggcgtga aactgtgcga aagaccgagc caaacctgga ccggccactg cggcaacacc    60
aaacattgcg ataaacagtg cagaagctgg gaaaaagcca aacatggtgc ttgccacaaa   120
cgcaacggca aatggaaatg cttttgctat tttaactgct ga                      162

<210> SEQ ID NO 695
<211> LENGTH: 162
<212> TYPE: DNA
<213> ORGANISM: Artificial Sequence
<220> FEATURE:
<223> OTHER INFORMATION: Defensin like

<400> SEQUENCE: 695
gatggcgtga aactgtgcga aagagcgagc aaaacctgga gcggcaactg cggcaacacc    60
aaacattgcg ataaacagtg cagaagctgg gaaggcgcca aacatggtgc ttgccacgtg   120
cgcaacggca aacataaatg cttttgctat tttaactgct ga                      162

<210> SEQ ID NO 696
<211> LENGTH: 162
<212> TYPE: DNA
<213> ORGANISM: Artificial Sequence
<220> FEATURE:
<223> OTHER INFORMATION: Defensin like

<400> SEQUENCE: 696
gatggcgtga aactgtgcga aaaaccgagc caaacctgga gcggccactg cggcaacacc    60
aaacattgcg ataaacagtg cagaaactgg gaaggcgcca aacatggtgc ttgccacaaa   120
cgcaacggca aatggaaatg cttttgctat tttaactgct ga                      162

<210> SEQ ID NO 697
<211> LENGTH: 162
<212> TYPE: DNA
<213> ORGANISM: Artificial Sequence
<220> FEATURE:
<223> OTHER INFORMATION: Defensin like

<400> SEQUENCE: 697
gatggcgtga aactgtgcga aaaaccgagc caaacctgga gcggccactg cggcaacacc    60
aaacattgcg ataaccagtg caaaagctgg gaaaaagcca aacatggtgc ttgccacaaa   120
cgcaacggca aatggaaatg cttttgctat tttaactgct ga                      162

<210> SEQ ID NO 698
<211> LENGTH: 162
<212> TYPE: DNA

<213> ORGANISM: Artificial Sequence
<220> FEATURE:
<223> OTHER INFORMATION: Defensin like

<400> SEQUENCE: 698
gatggcgtga aactgtgcga aagaccgagc aaaacctgga gcggccactg cggcaacacc    60
aaacattgcg ataaccagtg cagaaactgg gaaaaagcca acatggtgc ttgccacaaa    120 cgcaacggca aatggaaatg cttttgctat tttaactgct ga                      162

<210> SEQ ID NO 699
<211> LENGTH: 162
<212> TYPE: DNA
<213> ORGANISM: Artificial Sequence
<220> FEATURE:
<223> OTHER INFORMATION: Defensin like

<400> SEQUENCE: 699
gatggcgtga aactgtgcga aagaccgagc caaacctgga gcggccactg cggcaacacc    60
aaacattgcg ataaacagtg caaaagctgg gaaggcgcca acatggtgc ttgccacaaa    120 cgcaacggca aatggaaatg cttttgctat tttaactgct ga                      162

<210> SEQ ID NO 700
<211> LENGTH: 162
<212> TYPE: DNA
<213> ORGANISM: Artificial Sequence
<220> FEATURE:
<223> OTHER INFORMATION: Defensin like

<400> SEQUENCE: 700
gatggcgtga aactgtgcga aagaccgagc caaacctgga gcggcaactg cggcaacacc    60
aaacattgcg ataaacagtg cagaaactgg gaaaaagcca acatggtgc ttgccacgtg    120 cgcaacggca aatggaaatg cttttgctat tttaactgct ga                      162

<210> SEQ ID NO 701
<211> LENGTH: 162
<212> TYPE: DNA
<213> ORGANISM: Artificial Sequence
<220> FEATURE:
<223> OTHER INFORMATION: Defensin like
<220> FEATURE:
<221> NAME/KEY: misc_feature
<222> LOCATION: 101, 102
<223> OTHER INFORMATION: n = A, C, G, or T

<400> SEQUENCE: 701
gatggcgtga aactgtgcga aagagcgagc aaaacctgga ccggccactg cggcaacacc    60
aaacattgcg ataaacagtg cagaaactgg gaaggcgcca nncatggtgc ttgccacgtg    120
cgcaacggca aatggaaatg cttttgctat tttaactgct ga                      162

<210> SEQ ID NO 702
<211> LENGTH: 162
<212> TYPE: DNA
<213> ORGANISM: Artificial Sequence
<220> FEATURE:
<223> OTHER INFORMATION: Defensin like

<400> SEQUENCE: 702
gatggcgtga aactgtgcga aagagcgagc caaacctgga ccggccactg cggcaacacc    60
aaacattgcg ataaccagtg cagaaactgg gaaggcgcca acatggtgc ttgccacaaa    120 cgcaacggca aatggaaatg cttttgctat tttaactgct ga                      162

<210> SEQ ID NO 703
<211> LENGTH: 156
<212> TYPE: DNA
<213> ORGANISM: Artificial Sequence
<220> FEATURE:
<223> OTHER INFORMATION: Defensin like

<400> SEQUENCE: 703
cagaaactgt gcgaaagagc gagcaaaacc tggaccggcc actgcggcaa caccaaacat    60
tgcgataaac agtgcaaaaa ctgggaaaaa gccaaacatg gtgcttgcca cgtgcgcaac   120
ggcaaatgga atgcttttg ctattttaac tgctga                              156

<210> SEQ ID NO 704
<211> LENGTH: 162
<212> TYPE: DNA
<213> ORGANISM: Artificial Sequence
<220> FEATURE:
<223> OTHER INFORMATION: Defensin like

<400> SEQUENCE: 704
gatggcgtga aactgtgcga aagagcgagc caaacctgga ccggcaactg cggcaacacc    60
aaacattgcg atacccagtg caaaaactgg gaaaagccg cccatggtgc ttgccacaaa    120
cgcagcggca aatggaaatg cttttgctat tttaactgct ga                      162

<210> SEQ ID NO 705
<211> LENGTH: 162
<212> TYPE: DNA
<213> ORGANISM: Artificial Sequence
<220> FEATURE:
<223> OTHER INFORMATION: Defensin like

<400> SEQUENCE: 705
gatggcgtga aactgtgcga aaagcgagc caaacctgga gcggccactg cggcaacacc    60
aaacattgcg ataaccagtg caaaaactgg gaaggcgcca acatggtgc ttgccacaaa    120 cgcaacggca aatggaaatg cttttgctat tttaactgct ga                      162

<210> SEQ ID NO 706
<211> LENGTH: 162
<212> TYPE: DNA
<213> ORGANISM: Artificial Sequence
<220> FEATURE:
<223> OTHER INFORMATION: Defensin like

<400> SEQUENCE: 706
gatggcgtga aactgtgcga aaagcgagc caaacctgga gcggccactg cggcaacacc    60
aaacattgcg atacccagtg caaaaactgg gaaaaagcca acatggtgc ttgccacgtg   120 cgcagcggca aacataaatg cttttgctat tttaactgct ga                      162

<210> SEQ ID NO 707
<211> LENGTH: 162
<212> TYPE: DNA
<213> ORGANISM: Artificial Sequence
<220> FEATURE:
<223> OTHER INFORMATION: Defensin like

<400> SEQUENCE: 707
gatggcgtga aactgtgcga aagagcgagc aaaacctgga ccggccactg cggcaacacc    60
aaacattgcg ataaacagtg caaaaactgg gaaggcgcca acatggtgc ttgccacaaa   120

-continued

```
cgcagcggca aatggaaatg cttttgctat tttaactgct ga                    162

<210> SEQ ID NO 708
<211> LENGTH: 162
<212> TYPE: DNA
<213> ORGANISM: Artificial Sequence
<220> FEATURE:
<223> OTHER INFORMATION: Defensin like

<400> SEQUENCE: 708
gatggcgtga aactgtgcga aagagcgagc aaaacctgga ccggccactg cggcaacacc    60
aaacattgcg ataaacagtg caaaagctgg gaaggcgcca acatggtgc ttgccacaaa    120 cgcaacggca aatggaaatg cttttgctat tttaactgct ga                     162

<210> SEQ ID NO 709
<211> LENGTH: 162
<212> TYPE: DNA
<213> ORGANISM: Artificial Sequence
<220> FEATURE:
<223> OTHER INFORMATION: Defensin like

<400> SEQUENCE: 709
gatggcgtga aactgtgcga aaaccgagc caaacctgga gcggccactg cggcaacacc     60
aaacattgcg atacccagtg cagaaactgg gaaggcgcca acatggtgc ttgccacaaa    120 cgcagcggca aatggaaatg cttttgctat tttaactgct ga                     162

<210> SEQ ID NO 710
<211> LENGTH: 162
<212> TYPE: DNA
<213> ORGANISM: Artificial Sequence
<220> FEATURE:
<223> OTHER INFORMATION: Defensin like

<400> SEQUENCE: 710
gatggcgtga aactgtgcga aagagcgagc caaacctgga gcggccactg cggcaacacc    60
aaacattgcg ataaacagtg cagaagctgg gaaggcgcca acatggtgc ttgccacaaa    120 cgcaacggca aatggaaatg cttttgctat tttaactgct ga                     162

<210> SEQ ID NO 711
<211> LENGTH: 162
<212> TYPE: DNA
<213> ORGANISM: Artificial Sequence
<220> FEATURE:
<223> OTHER INFORMATION: Defensin like

<400> SEQUENCE: 711
gatggcgtga aactgtgcga aagaccgagc caaacctgga ccggccactg cggcaacacc    60
aaacattgcg ataaacagtg cagaaactgg gaaaaagcca acatggtgc ttgccacaaa    120 cgcaacggca aatggaaatg cttttgctat tttaactgct ga                     162

<210> SEQ ID NO 712
<211> LENGTH: 156
<212> TYPE: DNA
<213> ORGANISM: Artificial Sequence
<220> FEATURE:
<223> OTHER INFORMATION: Defensin like

<400> SEQUENCE: 712
cagaaactgt gcgaaaaacc gagccaaacc tggaccggca actgcggcaa caccaaacat    60
tgcgataaac agtgcagaaa ctgggaaaaa gccgcccatg gtgcttgcca cgtgcgtaac   120
```

```
ggcaaatgga aatgcttttg ctattttaac tgctga                               156

<210> SEQ ID NO 713
<211> LENGTH: 162
<212> TYPE: DNA
<213> ORGANISM: Artificial Sequence
<220> FEATURE:
<223> OTHER INFORMATION: Defensin like

<400> SEQUENCE: 713
gatggcgtga aactgtgcga aagaccgagc aaaacctgga gcggccactg cggcaacacc    60
aaacattgcg ataaccagtg cagaaactgg gaaaaagcca acatggtgc ttgccacgtg    120 cgcaacggca aatggaaatg cttttgctat ttaactgct ga                        162

<210> SEQ ID NO 714
<211> LENGTH: 162
<212> TYPE: DNA
<213> ORGANISM: Artificial Sequence
<220> FEATURE:
<223> OTHER INFORMATION: Defensin like

<400> SEQUENCE: 714
gatggcgtga aactgtgcga aagaccgagc caaacctgga ccggcaactg cggcaacacc    60
aaacattgcg ataaacagtg caaaaactgg gaaaaagccg cccatggtgc ttgccacaaa    120
cgcaacggca aatggaaatg cttttgctat ttaactgct ga                        162

<210> SEQ ID NO 715
<211> LENGTH: 162
<212> TYPE: DNA
<213> ORGANISM: Artificial Sequence
<220> FEATURE:
<223> OTHER INFORMATION: Defensin like

<400> SEQUENCE: 715
gatggcgtga aactgtgcga aagaccgagc ataacctgga gcggcaactg cggcaacacc    60
aaacattgcg atacccagtg cagaagctgg gaaggcgccg cccatggtgc ttgccacgtg    120
cgcagcggca aacataaatg cttttgctat ttaactgct ga                        162

<210> SEQ ID NO 716
<211> LENGTH: 162
<212> TYPE: DNA
<213> ORGANISM: Artificial Sequence
<220> FEATURE:
<223> OTHER INFORMATION: Defensin like

<400> SEQUENCE: 716
gatggcgtga aactgtgcga aagaccgagc caaacctgga gcggccactg cggcaacacc    60
aaacattgcg ataaacagtg caaaaactgg gaaggcgcca acatggtgc ttgccacaaa    120 cgcaacggca aatggaaatg cttttgctat ttaactgct ga                        162

<210> SEQ ID NO 717
<211> LENGTH: 162
<212> TYPE: DNA
<213> ORGANISM: Artificial Sequence
<220> FEATURE:
<223> OTHER INFORMATION: Defensin like

<400> SEQUENCE: 717
gatggcgtga aactgtacga aaaaccgagc aaaacctgga ccggccactg cggcaacacc    60
```

```
aaacattgcg ataaccagtg caaaagctgg gaaggcgccg cccatggtgc ttgccacaaa    120
cgcaacggca aatggaaatg cttttgctat tttaactgct ga                      162
```

<210> SEQ ID NO 718
<211> LENGTH: 162
<212> TYPE: DNA
<213> ORGANISM: Artificial Sequence
<220> FEATURE:
<223> OTHER INFORMATION: Defensin like

<400> SEQUENCE: 718

```
gatggcgtga aactgtgcga aaaagcgagc caaacctgga gcggccactg cggcaacacc    60
aaacattgcg ataaacagtg caaaagctgg gaaggcgcca acatggtgc ttgccacaaa    120 cgcagcggca aatggaaatg cttttgctat tttaactgct ga                      162
```

<210> SEQ ID NO 719
<211> LENGTH: 162
<212> TYPE: DNA
<213> ORGANISM: Artificial Sequence
<220> FEATURE:
<223> OTHER INFORMATION: Defensin like

<400> SEQUENCE: 719

```
gatggcgtga aactgtgcga aagagcgagc caaacctgga gcggccactg cggcaacacc    60
aaacattgcg ataaacagtg caaaaactgg gaaaaagcca acatggtgc ttgccacaaa    120 cgcaacggca aatggaaatg cttttgctat tttaactgct ga                      162
```

<210> SEQ ID NO 720
<211> LENGTH: 162
<212> TYPE: DNA
<213> ORGANISM: Artificial Sequence
<220> FEATURE:
<223> OTHER INFORMATION: Defensin like

<400> SEQUENCE: 720

```
gatggcgtga aactgtgcga aaaagcgagc aaaacctgga ccggcaactg cggcaacacc    60
aaacattgcg ataaacagtg caaaaactgg gaaggcgcca acatggtgc ttgccacaaa    120 cgcagcggca aatggaaatg cttttgctat tttaactgct ga                      162
```

<210> SEQ ID NO 721
<211> LENGTH: 162
<212> TYPE: DNA
<213> ORGANISM: Artificial Sequence
<220> FEATURE:
<223> OTHER INFORMATION: Defensin like

<400> SEQUENCE: 721

```
gatggcgtga aactgtgcga aagagcgagc aaaacctgga gcggccactg cggcaacacc    60
aaacattgcg ataaacagtg cagaaactgg gaaggcgccg cccatggtgc ttgccacaaa    120
cgcaacggca aacataaatg cttttgctat tttaactgct ga                      162
```

<210> SEQ ID NO 722
<211> LENGTH: 162
<212> TYPE: DNA
<213> ORGANISM: Artificial Sequence
<220> FEATURE:
<223> OTHER INFORMATION: Defensin like

<400> SEQUENCE: 722

```
gatggcgtga aactgtgcga aagagcgagc caaacctgga gcggcaactg cggcaacacc    60
```

```
aaacattgcg ataaccagtg caaaaactgg aaggcgcca acatggtgc ttgccacaaa      120 cgcagcggca aatggaaatg cttttgctat tttaactgct ga                      162

<210> SEQ ID NO 723
<211> LENGTH: 162
<212> TYPE: DNA
<213> ORGANISM: Artificial Sequence
<220> FEATURE:
<223> OTHER INFORMATION: Defensin like

<400> SEQUENCE: 723
gatggcgtga aactgtgcga aagaccgagc caaacctgga ccggcaactg cggcaacacc    60
aaacattgcg ataaacagtg cagaaactgg gaaggcgcca acatggtgc ttgccacgtg    120 cgcaacggca aatggaaatg cttttgctat tttaactgct ga                      162

<210> SEQ ID NO 724
<211> LENGTH: 156
<212> TYPE: DNA
<213> ORGANISM: Artificial Sequence
<220> FEATURE:
<223> OTHER INFORMATION: Defensin like

<400> SEQUENCE: 724
cagaaactgt gcgaaaaagc gagcaaaacc tggagcggca actgcggcaa caccaaacat    60
tgcgataccc agtgcagaaa ctgggaaggc gccaaacatg gtgcttgcca cgtgcgcaac   120
ggcaaatgga aatgcttttg ctattttaac tgctga                             156

<210> SEQ ID NO 725
<211> LENGTH: 162
<212> TYPE: DNA
<213> ORGANISM: Artificial Sequence
<220> FEATURE:
<223> OTHER INFORMATION: Defensin like

<400> SEQUENCE: 725
gatggcgtga aactgtgcga aaaaccgagc aaaacctgga gcggccactg cggcaacacc    60
aaacattgcg atacccagtg cagaaactgg gaaaaagcca acatggtgc ttgccacgtg    120 cgcaacggca aatggaaatg cttttgctat tttaactgct ga                      162

<210> SEQ ID NO 726
<211> LENGTH: 162
<212> TYPE: DNA
<213> ORGANISM: Artificial Sequence
<220> FEATURE:
<223> OTHER INFORMATION: Defensin like

<400> SEQUENCE: 726
gatggcgtga aactgtgcga aagaccgagc aaaacctgga gcggcaactg cggcaacacc    60
aaacattgcg ataaacagtg caaaagctgg gaaggcgcca acatggtgc ttgccacaaa    120 cgcagcggca aatggaaatg cttttgctat tttaactgct ga                      162

<210> SEQ ID NO 727
<211> LENGTH: 156
<212> TYPE: DNA
<213> ORGANISM: Artificial Sequence
<220> FEATURE:
<223> OTHER INFORMATION: Defensin like

<400> SEQUENCE: 727
```

```
cagaaactgt gcgaaagagc gagccaaacc tggagcggca actgcggcaa caccaaacat    60
tgcgataaac agtgcaaaaa ctgggaaggc gccaaacatg gtgcttgcca caaacgcaac   120
ggcaaatgga aatgcttttg ctattttaac tgctga                             156
```

```
<210> SEQ ID NO 728
<211> LENGTH: 162
<212> TYPE: DNA
<213> ORGANISM: Artificial Sequence
<220> FEATURE:
<223> OTHER INFORMATION: Defensin like

<400> SEQUENCE: 728
gatggcgtga aactgtgcga agagcgagc caaacctgga gcggcaactg cggcaacacc    60
aaacattgcg ataaacagtg caaaaactgg gaaaaagcca acatggtgc ttgccacgtg   120 cgcagcggca aacataaatg cttttgctat ttaactgct ga                      162
```

```
<210> SEQ ID NO 729
<211> LENGTH: 162
<212> TYPE: DNA
<213> ORGANISM: Artificial Sequence
<220> FEATURE:
<223> OTHER INFORMATION: Defensin like

<400> SEQUENCE: 729
gatggcgtga aactgtgcga aaagcgagc aaaacctgga ccggcaactg cggcaacacc    60
aaacattgcg ataaacagtg caaaaactgg gaaggcgcca acatggtgc ttgccacgtg   120 cgcaacggca aatggaaatg cttttgctat tttaactgct ga                     162
```

```
<210> SEQ ID NO 730
<211> LENGTH: 162
<212> TYPE: DNA
<213> ORGANISM: Artificial Sequence
<220> FEATURE:
<223> OTHER INFORMATION: Defensin like

<400> SEQUENCE: 730
gatggcgtga aactgtgcga agagcgagc caaacctgga gcggccactg cggcaacacc    60
aaacattgcg ataaccagtg caaaaactgg gaaggcgccg cccatggtgc ttgccacaaa   120
cgcaacggca aatggaaatg cttttgctat tttaactgct ga                     162
```

```
<210> SEQ ID NO 731
<211> LENGTH: 153
<212> TYPE: DNA
<213> ORGANISM: Artificial Sequence
<220> FEATURE:
<223> OTHER INFORMATION: Defensin like

<400> SEQUENCE: 731
aacctgtgcg aaagagcgag caaaacctgg agcggccact gcggcaacac caaacattgc    60
gataaccagt gcaaaaactg ggaaggcgcc aaacatggtg cttgccacaa acgcaacggc   120
aaatggaaat gctttgcta ttttaactgc tga                                 153
```

```
<210> SEQ ID NO 732
<211> LENGTH: 162
<212> TYPE: DNA
<213> ORGANISM: Artificial Sequence
<220> FEATURE:
<223> OTHER INFORMATION: Defensin like

<400> SEQUENCE: 732
```

```
gatggcgtga aactgtgcga aagaccgagc aaaacctgga ccggccactg cggcaacacc    60
aaacattgcg ataaacagtg cagaaactgg aaaaagcca acatggtgc ttgccacgtg    120 cgcaacggca aatggaaatg cttttgctat tttaactgct ga                      162
```

<210> SEQ ID NO 733
<211> LENGTH: 162
<212> TYPE: DNA
<213> ORGANISM: Artificial Sequence
<220> FEATURE:
<223> OTHER INFORMATION: Defensin like

<400> SEQUENCE: 733

```
gatggcgtga aactgtgcga aagaccgagc caaacctgga ccggcaactg cggcaacacc    60
aaacattgcg ataaccagtg cagaaactgg gaaggcgcca acatggtgc ttgccacaaa    120 cgcagcggca aatggaaatg cttttgctat tttaactgct ga                      162
```

<210> SEQ ID NO 734
<211> LENGTH: 162
<212> TYPE: DNA
<213> ORGANISM: Artificial Sequence
<220> FEATURE:
<223> OTHER INFORMATION: Defensin like

<400> SEQUENCE: 734

```
gatggcgtga aactgtgcga aaaagcgagc aaaacctgga ccggccactg cggcaacacc    60
aaacattgcg ataaacagtg caaaaactgg gaaaaagcca acatggtgc ttgccacgtg    120 cgcagcggca aatggaaatg cttttgctat tttaactgct ga                      162
```

<210> SEQ ID NO 735
<211> LENGTH: 162
<212> TYPE: DNA
<213> ORGANISM: Artificial Sequence
<220> FEATURE:
<223> OTHER INFORMATION: Defensin like

<400> SEQUENCE: 735

```
gatggcgtga aactgtgcga aaaagcgagc caaacctgga gcggccactg cggcaacacc    60
aaacattgcg ataaccagtg cagaaactgg gaaaaagccg cccatggtgc ttgccacaaa    120
cgcagcggca aatggaaatg cttttgctat tttaactgct ga                      162
```

<210> SEQ ID NO 736
<211> LENGTH: 162
<212> TYPE: DNA
<213> ORGANISM: Artificial Sequence
<220> FEATURE:
<223> OTHER INFORMATION: Defensin like

<400> SEQUENCE: 736

```
gatggcgtga aactgtgcga aagagcgagc caaacctgga ccggcaactg cggcaacacc    60
aaacattgcg ataaacagtg caaaaactgg gaaggcgccg cccatggtgc ttgccacaaa    120
cgcagcggca aatggaaatg cttttgctat tttaactgct ga                      162
```

<210> SEQ ID NO 737
<211> LENGTH: 162
<212> TYPE: DNA
<213> ORGANISM: Artificial Sequence
<220> FEATURE:
<223> OTHER INFORMATION: Defensin like -continued

<400> SEQUENCE: 737
gatggcgtga aactgtgcga aagagcgagc caaacctgga gcggcaactg cggcaacacc    60
aaacattgcg ataaacagtg cagaagctgg gaaaaagcca acatggtgc ttgccacaaa    120 cgcaacggca aatggaaatg cttttgctat tttaactgct ga                      162

<210> SEQ ID NO 738
<211> LENGTH: 162
<212> TYPE: DNA
<213> ORGANISM: Artificial Sequence
<220> FEATURE:
<223> OTHER INFORMATION: Defensin like

<400> SEQUENCE: 738
gatggcgtga aactgtgcga aagaccgagc caaacctgga gcggcaactg cggcaacacc    60
aaacattgcg ataaacagtg caaaaactgg gaaaaagccg cccatggtgc ttgccacaaa    120
cgcagcggca aatggaaatg cttttgctat tttaactgct ga                      162

<210> SEQ ID NO 739
<211> LENGTH: 162
<212> TYPE: DNA
<213> ORGANISM: Artificial Sequence
<220> FEATURE:
<223> OTHER INFORMATION: Defensin like

<400> SEQUENCE: 739
gatggcgtga aactgtgcga aaaaccgagc caaacctgga ccggccactg cggcaacacc    60
aaacattgcg ataaacagtg caaaaactgg gaaggcgccg cccatggtgc ttgccacaaa    120
cgcaacggca aatggaaatg cttttgctat tttaactgct ga                      162

<210> SEQ ID NO 740
<211> LENGTH: 162
<212> TYPE: DNA
<213> ORGANISM: Artificial Sequence
<220> FEATURE:
<223> OTHER INFORMATION: Defensin like

<400> SEQUENCE: 740
gatggcgtga aactgtgcga aaaaccgagc caaacctgga ccggccactg cggcaacacc    60
aaacattgcg ataaacagtg cagaaactgg gaaggcgccg cccatggtgc ttgccacaaa    120
cgcaacggca aatggaaatg cttttgctat tttaactgct ga                      162

<210> SEQ ID NO 741
<211> LENGTH: 162
<212> TYPE: DNA
<213> ORGANISM: Artificial Sequence
<220> FEATURE:
<223> OTHER INFORMATION: Defensin like

<400> SEQUENCE: 741
gatggcgtga aactgtgcga aagaccgagc caaacctgga ccggccactg cggcaacacc    60
aaacattgcg ataaccagtg caaaaactgg gaaaaagcca acatggtgc ttgccacaaa    120 cgcaacggca aatggaaatg cttttgctat tttaactgct ga                      162

<210> SEQ ID NO 742
<211> LENGTH: 162
<212> TYPE: DNA
<213> ORGANISM: Artificial Sequence
<220> FEATURE:
<223> OTHER INFORMATION: Defensin like

<400> SEQUENCE: 742
gatggcgtga aactgtgcga aaaagcgagc caaacctgga ccggcaactg cggcaacacc     60
aaacattgcg ataaacagtg caaaagctgg aaggcgcca acatggtgc ttgccacaaa    120 cgcaacggca aatggaaatg cttttgctat tttaactgct ga                      162

<210> SEQ ID NO 743
<211> LENGTH: 162
<212> TYPE: DNA
<213> ORGANISM: Artificial Sequence
<220> FEATURE:
<223> OTHER INFORMATION: Defensin like

<400> SEQUENCE: 743
gatggcgtga aactgtgcga aaaagcgagc caaacctgga ccggcaactg cggcaacacc     60
aaacattgcg ataaccagtg caaaaactgg gaaaaagcca acatggtgc ttgccacaaa    120 cgcagcggca aatggaaatg cttttgctat tttaactgct ga                      162

<210> SEQ ID NO 744
<211> LENGTH: 162
<212> TYPE: DNA
<213> ORGANISM: Artificial Sequence
<220> FEATURE:
<223> OTHER INFORMATION: Defensin like

<400> SEQUENCE: 744
gatggcgtga aactgtgcga aagagcgagc aaaacctgga gcggccactg cggcaacacc     60
aaacattgcg ataaacagtg caaaagctgg gaaggcgcca acatggtgc ttgccacaaa    120 cgcagcggca aatggaaatg cttttgctat tttaactgct ga                      162

<210> SEQ ID NO 745
<211> LENGTH: 162
<212> TYPE: DNA
<213> ORGANISM: Artificial Sequence
<220> FEATURE:
<223> OTHER INFORMATION: Defensin like

<400> SEQUENCE: 745
gatggcgtga aactgtgcga aaaagcgagc caaacctgga gcggccactg cggcaacacc     60
aaacattgcg ataaccagtg caaaaactgg gaaggcgcca acatggtgc ttgccacaaa    120 cgcagcggca aatggaaatg cttttgctat tttaactgct ga                      162

<210> SEQ ID NO 746
<211> LENGTH: 162
<212> TYPE: DNA
<213> ORGANISM: Artificial Sequence
<220> FEATURE:
<223> OTHER INFORMATION: Defensin like

<400> SEQUENCE: 746
gatggcgtga aactgtgcga aagaccgagc aaaacctgga gcggcaactg cggcaacacc     60
aaacattgcg ataaacagtg caaaaactgg gaaggcgcca acatggtgc ttgccacaaa    120 cgcaacggca aatggaaatg cttttgctat tttaactgct ga                      162

<210> SEQ ID NO 747
<211> LENGTH: 162
<212> TYPE: DNA
<213> ORGANISM: Artificial Sequence
<220> FEATURE:

<223> OTHER INFORMATION: Defensin like

<400> SEQUENCE: 747

| gatggcgtga aactgtgcga aaaaccgagc caaacctgga gcggcaactg cggcaacacc | 60 |
| aaacattgcg ataaacagtg cagaaactgg aaaaagccaa acatggtgc ttgccacaaa | 120 |
| cgcaacggca aatggaaatg cttttgctat tttaactgct ga | 162 |

<210> SEQ ID NO 748
<211> LENGTH: 162
<212> TYPE: DNA
<213> ORGANISM: Artificial Sequence
<220> FEATURE:
<223> OTHER INFORMATION: Defensin like

<400> SEQUENCE: 748

| gatggcgtga aactgtgcga aaaaccgagc caaacctgga ccggcaactg cggcaacacc | 60 |
| aaacattgcg atacccagtg cagaaactgg aaggcgccaa acatggtgc ttgccacaaa | 120 |
| cgcaacggca aatggaaatg cttttgctat tttaactgct ga | 162 |

<210> SEQ ID NO 749
<211> LENGTH: 162
<212> TYPE: DNA
<213> ORGANISM: Artificial Sequence
<220> FEATURE:
<223> OTHER INFORMATION: Defensin like

<400> SEQUENCE: 749

| gatggcgtga aactgtgcga aagaccgagc aaaacctgga gcggccactg cggcaacacc | 60 |
| aaacattgcg ataaacagtg cagaaactgg aaggcgcca acatggtgc ttgccacgtg | 120 |
| cgcatcggca aatggaaatg cttttgctat tttaactgct ga | 162 |

<210> SEQ ID NO 750
<211> LENGTH: 162
<212> TYPE: DNA
<213> ORGANISM: Artificial Sequence
<220> FEATURE:
<223> OTHER INFORMATION: Defensin like

<400> SEQUENCE: 750

| gatggcgtga aactgtgcga aaaagcgagc aaaacctgga gcggccactg cggcaacacc | 60 |
| aaacattgcg ataaacagtg caaaaactgg gaaggcgccg cccatggtgc ttgccacgtg | 120 |
| cgcagcggca aatggaaatg cttttgctat tttaactgct ga | 162 |

<210> SEQ ID NO 751
<211> LENGTH: 162
<212> TYPE: DNA
<213> ORGANISM: Artificial Sequence
<220> FEATURE:
<223> OTHER INFORMATION: Defensin like

<400> SEQUENCE: 751

| gatggcgtga aactgtgcga aagagcgagc caaacctgga ccggccactg cggcaacacc | 60 |
| aaacattgcg ataaacagtg caaaaactgg gaaggcgcca acatggtgc ttgccacaaa | 120 |
| cgcaacggca aatggaaatg cttttgctat tttaactgct ga | 162 |

<210> SEQ ID NO 752
<211> LENGTH: 162
<212> TYPE: DNA
<213> ORGANISM: Artificial Sequence

```
<220> FEATURE:
<223> OTHER INFORMATION: Defensin like

<400> SEQUENCE: 752
gatggcgtga aactgtgcga aaaaccgagc caaacctgga gcggcaactg cggcaacacc      60
aaacattgcg ataaacagtg caaaagctgg gaaggcgcca acatggtgc ttgccacaaa      120 cgcaacggca aatggaaatg cttttgctat tttaactgct ga                        162

<210> SEQ ID NO 753
<211> LENGTH: 162
<212> TYPE: DNA
<213> ORGANISM: Artificial Sequence
<220> FEATURE:
<223> OTHER INFORMATION: Defensin like

<400> SEQUENCE: 753
gatggcgtga aactgtgcga aagaccgagc aaaacctgga gcggcaactg cggcaacacc      60
aaacattgcg atacccagtg cagaaactgg gaaggcgcca acatggtgc ttgccacgtg      120 cgcaacggca aacataaatg cttttgctat tttaactgct ga                        162

<210> SEQ ID NO 754
<211> LENGTH: 162
<212> TYPE: DNA
<213> ORGANISM: Artificial Sequence
<220> FEATURE:
<223> OTHER INFORMATION: Defensin like

<400> SEQUENCE: 754
gatggcgtga aactgtgcga aagagcgagc aaaacctgga ccggccactg cggcaacacc      60
aaacattgcg ataaacagtg caaaaactgg gaaggcgccg cccatggtgc ttgccacgtg      120
cgcagcggca aatggaaatg cttttgctat tttaactgct ga                        162

<210> SEQ ID NO 755
<211> LENGTH: 162
<212> TYPE: DNA
<213> ORGANISM: Artificial Sequence
<220> FEATURE:
<223> OTHER INFORMATION: Defensin like

<400> SEQUENCE: 755
gatggcgtga aactgtgcga aagagcgagc caaacctgga ccggcaactg cggcaacacc      60
aaacattgcg ataaacagtg cagaagctgg gaaggcgcca acatggtgc ttgccacaaa      120 cgcagcggca aatggaaatg cttttgctat tttaactgct ga                        162

<210> SEQ ID NO 756
<211> LENGTH: 162
<212> TYPE: DNA
<213> ORGANISM: Artificial Sequence
<220> FEATURE:
<223> OTHER INFORMATION: Defensin like

<400> SEQUENCE: 756
gatggcgtga aactgtgcga aagagcgagc caaacctgga ccggccactg cggcaacacc      60
aaacattgcg ataaacagtg caaaaactgg gaaaaagcca acatggtgc ttgccacaaa      120 cgcaacggca aatggaaatg cttttgctat tttaactgct ga                        162

<210> SEQ ID NO 757
<211> LENGTH: 162
<212> TYPE: DNA
```

```
<213> ORGANISM: Artificial Sequence
<220> FEATURE:
<223> OTHER INFORMATION: Defensin like

<400> SEQUENCE: 757
gatggcgtga aactgtgcga aagagcgagc aaaacctgga ccggcaactg cggcaacacc      60
aaacattgcg atacccagtg cagaaactgg aaggcgcca acatggtgc ttgccacaaa       120 cgcagcggca aatggaaatg cttttgctat tttaactgct ga                        162

<210> SEQ ID NO 758
<211> LENGTH: 156
<212> TYPE: DNA
<213> ORGANISM: Artificial Sequence
<220> FEATURE:
<223> OTHER INFORMATION: Defensin like

<400> SEQUENCE: 758
cagaaactgt gcgaaagacc gagccaaacc tggaccggcc actgcggcaa caccaaacat      60
tgcgataccc agtgcaaaag ctgggaaggc gccaaacatg gtgcttgcca caaacgcaac     120
ggcaaatgga atgcttttg ctattttaac tgctga                                156

<210> SEQ ID NO 759
<211> LENGTH: 162
<212> TYPE: DNA
<213> ORGANISM: Artificial Sequence
<220> FEATURE:
<223> OTHER INFORMATION: Defensin like

<400> SEQUENCE: 759
gatggcgtga aactgtgcga aaagcgagc caaacctgga gcggccactg cggcaacacc       60
aaacattgcg ataaccagtg caaaaactgg aaaaagcca acatggtgc ttgccacgtg       120 cgcaacggca aatggaaatg cttttgctat tttaactgct ga                        162

<210> SEQ ID NO 760
<211> LENGTH: 162
<212> TYPE: DNA
<213> ORGANISM: Artificial Sequence
<220> FEATURE:
<223> OTHER INFORMATION: Defensin like

<400> SEQUENCE: 760
gatggcgtga aactgtgcga aagagcgagc caaacctgga ccggccactg cggcaacacc      60
aaacattgcg ataaccagtg cagaaactgg aaggcgcca acatggtgc ttgccacgtg       120 cgcaacggca aatggaaatg cttttgctat tttaactgct ga                        162

<210> SEQ ID NO 761
<211> LENGTH: 153
<212> TYPE: DNA
<213> ORGANISM: Artificial Sequence
<220> FEATURE:
<223> OTHER INFORMATION: Defensin like

<400> SEQUENCE: 761
aacctgtgcg aaagagcgag ccaaacctgg accggcaact gcggcaacac caaacattgc      60
gataaacagt gcaaaaactg ggaaggcgcc aaacatggtg cttgccacgt gcgcagcggc     120
aaatggaaat gcttttgcta ttttaactgc tga                                   153

<210> SEQ ID NO 762
<211> LENGTH: 162
```

```
<212> TYPE: DNA
<213> ORGANISM: Artificial Sequence
<220> FEATURE:
<223> OTHER INFORMATION: Defensin like

<400> SEQUENCE: 762
gatggcgtga aactgtgcga aagagcgagc aaaacctgga ccggccactg cggcaacacc      60
aaacattgcg ataaacagtg cagaaactgg aaggcgccg cccatggtgc ttgccacgtg      120
cgcaacggca aatggaaatg cttttgctat tttaactgct ga                        162

<210> SEQ ID NO 763
<211> LENGTH: 162
<212> TYPE: DNA
<213> ORGANISM: Artificial Sequence
<220> FEATURE:
<223> OTHER INFORMATION: Defensin like

<400> SEQUENCE: 763
gatggcgtga aactgtgcga aagaccgagc caaacctgga gcggccactg cggcaacacc      60
aaacattgcg ataaccagtg cagaaactgg gaaaaagcca acatggtgc ttgccacaaa      120
cgcaacggca aatggaaatg cttttgctat tttaactgct ga                        162

<210> SEQ ID NO 764
<211> LENGTH: 162
<212> TYPE: DNA
<213> ORGANISM: Artificial Sequence
<220> FEATURE:
<223> OTHER INFORMATION: Defensin like

<400> SEQUENCE: 764
gatggcgtga aactgtgcga aaaagcgagc caaacctgga gcggcaactg cggcaacacc      60
aaacattgcg ataaacagtg cagaaactgg gaaggcgccg cccatggtgc ttgccacaaa      120
cgcagcggca aatggaaatg cttttgctat tttaactgct ga                        162

<210> SEQ ID NO 765
<211> LENGTH: 162
<212> TYPE: DNA
<213> ORGANISM: Artificial Sequence
<220> FEATURE:
<223> OTHER INFORMATION: Defensin like

<400> SEQUENCE: 765
gatggcgtga aactgtgcga aagagcgagc aaaacctgga ccggcaactg cggcaacacc      60
aaacattgcg ataaacagtg caaaaactgg gaaggcgcca acatggtgc ttgccacgtg       120
cgcaacggca aatggaaatg cttttgctat tttaactgct ga                        162

<210> SEQ ID NO 766
<211> LENGTH: 162
<212> TYPE: DNA
<213> ORGANISM: Artificial Sequence
<220> FEATURE:
<223> OTHER INFORMATION: Defensin like

<400> SEQUENCE: 766
gatggcgtga aactgtgcga aagaccgagc caaacctgga ccggcaactg cggcaacacc      60
aaacattgcg ataccagtg caaaagctgg gaaaaagccg cccatggtgc ttgccacaaa      120
cgcaacggca aatggaaatg cttttgctat tttaactgct ga                        162

<210> SEQ ID NO 767
```

```
<211> LENGTH: 162
<212> TYPE: DNA
<213> ORGANISM: Artificial Sequence
<220> FEATURE:
<223> OTHER INFORMATION: Defensin like

<400> SEQUENCE: 767
gatggcgtga aactgtgcga aagaccgagc aaaacctgga ccggcaactg cggcaacacc    60
aaacattgcg ataaccagtg cagaaactgg gaaggcgccg cccatggtgc ttgccacaaa   120
cgcaacggca aatggaaatg cttttgctat tttaactgct ga                      162

<210> SEQ ID NO 768
<211> LENGTH: 162
<212> TYPE: DNA
<213> ORGANISM: Artificial Sequence
<220> FEATURE:
<223> OTHER INFORMATION: Defensin like

<400> SEQUENCE: 768
gatggcgtga aactgtgcga aagagcgagc aaaacctgga gcggccactg cggcaacacc    60
aaacattgcg ataaccagtg cagaagctgg gaaggcgcca acatggtgc ttgccacgtg    120 cgcaacggca aatggaaatg cttttgctat tttaactgct ga                      162

<210> SEQ ID NO 769
<211> LENGTH: 162
<212> TYPE: DNA
<213> ORGANISM: Artificial Sequence
<220> FEATURE:
<223> OTHER INFORMATION: Defensin like

<400> SEQUENCE: 769
gatggcgtga aactgtgcga aagagcgagc aaaacctgga gcggcaactg cggcaacacc    60
aaacattgcg ataaacagtg cagaaactgg gaaaaagcca acatggtgc ttgccacaaa    120 cgcaacggca aatggaaatg cttttgctat tttaactgct ga                      162

<210> SEQ ID NO 770
<211> LENGTH: 162
<212> TYPE: DNA
<213> ORGANISM: Artificial Sequence
<220> FEATURE:
<223> OTHER INFORMATION: Defensin like

<400> SEQUENCE: 770
gatggcgtga aactgtgcga aagagcgagc caaacctgga gcggcaactg cggcaacacc    60
aaacattgcg ataaacagtg caaaaactgg gaaggcgcca acatggtgc ttgccacgtg    120 cgcagcggca aatggaaatg cttttgctat tttaactgct ga                      162

<210> SEQ ID NO 771
<211> LENGTH: 162
<212> TYPE: DNA
<213> ORGANISM: Artificial Sequence
<220> FEATURE:
<223> OTHER INFORMATION: Defensin like

<400> SEQUENCE: 771
gatggcgtga aactgtgcga aagaccgagc caaacctgga ccggcaactg cggcaacacc    60
aaacattgcg ataaacagtg caaaaactgg gaaaaagcca acatggtgc ttgccacgtg    120 cgcaacggca aatggaaatg cttttgctat tttaactgct ga                      162
```

<210> SEQ ID NO 772
<211> LENGTH: 162
<212> TYPE: DNA
<213> ORGANISM: Artificial Sequence
<220> FEATURE:
<223> OTHER INFORMATION: Defensin like

<400> SEQUENCE: 772

```
gatggcatga aactgtgcga agagcgagc aaaacctgga gcggcaactg cggcaacacc      60
aaacattgcg ataaacagtg caaaaactgg gaaaaagccg cccatggtgc ttgccacgtg    120
cgcaacggca aatggaaatg cttttgctat tttaactgct ga                       162
```

<210> SEQ ID NO 773
<211> LENGTH: 162
<212> TYPE: DNA
<213> ORGANISM: Artificial Sequence
<220> FEATURE:
<223> OTHER INFORMATION: Defensin like

<400> SEQUENCE: 773

```
gatggcgtga aactgtgcga aaaccgagc caaacctgga gcggccactg cggcaacacc      60
aaacattgcg ataccagtg cagaaactgg gaaaaagccg cccatggtgc ttgccacaaa    120
cgcagcggca aatggaaatg cttttgctat tttaactgct ga                       162
```

<210> SEQ ID NO 774
<211> LENGTH: 162
<212> TYPE: DNA
<213> ORGANISM: Artificial Sequence
<220> FEATURE:
<223> OTHER INFORMATION: Defensin like

<400> SEQUENCE: 774

```
gatggcgtga aactgtgcga aaaccgagc caaacctgga ccggcaactg cggcaacacc      60
aaacattgcg ataaacagtg cagaaactgg gaaaaagcca acatggtgc ttgccacaaa     120
cgcaacggca aatggaaatg cttttgctat tttaactgct ga                       162
```

<210> SEQ ID NO 775
<211> LENGTH: 162
<212> TYPE: DNA
<213> ORGANISM: Artificial Sequence
<220> FEATURE:
<223> OTHER INFORMATION: Defensin like

<400> SEQUENCE: 775

```
gatggcgtga aactgtgcga agagcgagc aaaacctgga ccggcaactg cggcaacacc      60
aaacattgcg ataaacagtg cagaaactgg gaaggcgcca acatggtgc ttgccacgtg     120
cgcagcggca aatggaaatg cttttgctat tttaactgct ga                       162
```

<210> SEQ ID NO 776
<211> LENGTH: 162
<212> TYPE: DNA
<213> ORGANISM: Artificial Sequence
<220> FEATURE:
<223> OTHER INFORMATION: Defensin like

<400> SEQUENCE: 776

```
gatggcgtga aactgtgcga agagcgagc aaaacctgga gcggccactg cggcaacacc      60
aaacattgcg ataaccagtg cagaagctgg gaaaaagccg cccatggtgc ttgccacaaa    120
cgcaacggca aatggaaatg cttttgctat tttaactgct ga                       162
```

<210> SEQ ID NO 777
<211> LENGTH: 162
<212> TYPE: DNA
<213> ORGANISM: Artificial Sequence
<220> FEATURE:
<223> OTHER INFORMATION: Defensin like

<400> SEQUENCE: 777

```
gatggcgtga aactgtgcga aaaaccgagc caaacctgga gcggcaactg cggcaacacc      60
aaacattgcg ataaacagtg caaaaactgg gaaaaagcca acatggtgc ttgccacgtg      120
cgcagcggca aatggaaatg cttttgctat tttaactgct ga                         162
```

<210> SEQ ID NO 778
<211> LENGTH: 162
<212> TYPE: DNA
<213> ORGANISM: Artificial Sequence
<220> FEATURE:
<223> OTHER INFORMATION: Defensin like

<400> SEQUENCE: 778

```
gatggcgtga aactgtgcga aagaccgagc caaacctgga gcggccactg cggcaacacc      60
aaacattgcg ataaacagtg caaaagctgg gaaaaagcca acatggtgc ttgccacgtg      120
cgcaacggca aacataaatg cttttgctat tttaactgct ga                         162
```

<210> SEQ ID NO 779
<211> LENGTH: 162
<212> TYPE: DNA
<213> ORGANISM: Artificial Sequence
<220> FEATURE:
<223> OTHER INFORMATION: Defensin like

<400> SEQUENCE: 779

```
gatggcgtga aactgtgcga aaaagcgagc aaaacctgga gcggcaactg cggcaacacc      60
aaacattgcg ataaccagtg caaaaactgg gaaggcgcca acatggtgc ttgccacaaa      120
cgcaacggca aatggaaatg cttttgctat tttaactgct ga                         162
```

<210> SEQ ID NO 780
<211> LENGTH: 162
<212> TYPE: DNA
<213> ORGANISM: Artificial Sequence
<220> FEATURE:
<223> OTHER INFORMATION: Defensin like

<400> SEQUENCE: 780

```
gatggcgtga aactgtgcga aaaaccgagc aaaacctgga gcggcaactg cggcaacacc      60
aaacattgcg ataaccagtg cagaagctgg gaaaaagcca acatggtgc ttgccacaaa      120
cgcagcggca aatggaaatg cttttgctat tttaactgct ga                         162
```

<210> SEQ ID NO 781
<211> LENGTH: 162
<212> TYPE: DNA
<213> ORGANISM: Artificial Sequence
<220> FEATURE:
<223> OTHER INFORMATION: Defensin like

<400> SEQUENCE: 781

```
gatggcgtga aactgtgcga aaaaccgagc caaacctgga gcggccactg cggcaacacc      60
aaacattgcg ataaacagtg cagaaactgg gaaggcgcca acatggtgc ttgccacaaa      120
cgcagcggca aatggaaatg cttttgctat tttaactgct ga                         162
```

<210> SEQ ID NO 782
<211> LENGTH: 162
<212> TYPE: DNA
<213> ORGANISM: Artificial Sequence
<220> FEATURE:
<223> OTHER INFORMATION: Defensin like

<400> SEQUENCE: 782
gatggcgtga aactgtgcga aagaccgagc aaaacctgga gcggcaactg cggcaacacc    60
aaacattgcg ataaacagtg cagaagctgg gaaggcgcca acatggtgc ttgccacgtg    120 cgcagcggca aacataaatg cttttgctat tttaactgct ga                       162

<210> SEQ ID NO 783
<211> LENGTH: 162
<212> TYPE: DNA
<213> ORGANISM: Artificial Sequence
<220> FEATURE:
<223> OTHER INFORMATION: Defensin like

<400> SEQUENCE: 783
gatggcgtga aactgtgcga aagagcgagc caaacctgga gcggccactg cggcaacacc    60
aaacattgcg ataaccagtg caaaagctgg gaaaaagcca acatggtgc ttgccacgtg    120 cgcagcggca aacataaatg cttttgctat tttaactgct ga                       162

<210> SEQ ID NO 784
<211> LENGTH: 156
<212> TYPE: DNA
<213> ORGANISM: Artificial Sequence
<220> FEATURE:
<223> OTHER INFORMATION: Defensin like

<400> SEQUENCE: 784
cagaaactgt gcgaaaaagc gagcaaaaacc tggaccggca actgcggcaa caccaaacat    60
tgcgataaac agtgcagaag ctgggaaaaa gccaaacatg gtgcttgcca cgtgcgcaac    120
ggcaaatgga aatgcttttg ctattttaac tgctga                              156

<210> SEQ ID NO 785
<211> LENGTH: 162
<212> TYPE: DNA
<213> ORGANISM: Artificial Sequence
<220> FEATURE:
<223> OTHER INFORMATION: Defensin like

<400> SEQUENCE: 785
gatggcgtga aactgtgcga aaagcgagc aaaacctgga gcggcaactg cggcaacacc     60
aaacattgcg ataaacagtg cagaagctgg gaaaaagccg cccatggtgc ttgccacgtg    120
cgcagcggca aatggaaatg cttttgctat tttaactgct ga                       162

<210> SEQ ID NO 786
<211> LENGTH: 162
<212> TYPE: DNA
<213> ORGANISM: Artificial Sequence
<220> FEATURE:
<223> OTHER INFORMATION: Defensin like

<400> SEQUENCE: 786
gatggcgtga aactgtgcga aaagcgagc aaaacctgga ccggccactg cggcaacacc     60
aaacattgcg ataaacagtg caaaaactgg gaaggcgcca acatggtgc ttgccacaaa    120

-continued

| | |
|---|---|
| cgcagcggca aatggaaatg cttttgctat tttaactgct ga | 162 |

<210> SEQ ID NO 787
<211> LENGTH: 162
<212> TYPE: DNA
<213> ORGANISM: Artificial Sequence
<220> FEATURE:
<223> OTHER INFORMATION: Defensin like

<400> SEQUENCE: 787

| | |
|---|---|
| gatggcgtga aactgtgcga aaaagcgagc aaaacctgga gcggcaactg cggcaacacc | 60 |
| aaacattgcg ataaacagtg caaaaactgg gaaggcgccg cccatggtgc ttgccacaaa | 120 |
| cgcaacggca aatggaaatg cttttgctat tttaactgct ga | 162 |

<210> SEQ ID NO 788
<211> LENGTH: 162
<212> TYPE: DNA
<213> ORGANISM: Artificial Sequence
<220> FEATURE:
<223> OTHER INFORMATION: Defensin like

<400> SEQUENCE: 788

| | |
|---|---|
| gatggcgtga aactgtgcga aaaagcgagc caaacctgga ccggccactg cggcaacacc | 60 |
| aaacattgcg ataaacagtg caaaagctgg gaaggcgcca acatggtgc ttgccacaaa | 120 |
| cgcaacggca aatggaaatg cttttgctat tttaactgct ga | 162 |

<210> SEQ ID NO 789
<211> LENGTH: 162
<212> TYPE: DNA
<213> ORGANISM: Artificial Sequence
<220> FEATURE:
<223> OTHER INFORMATION: Defensin like

<400> SEQUENCE: 789

| | |
|---|---|
| gatggcgtga aactgtgcga aaaagcgagc aaaacctgga ccggccactg cggcaacacc | 60 |
| aaacattgcg ataaacagtg cagaaactgg gaaggcgccg cccatggtgc ttgccacgtg | 120 |
| cgcagcggca aacataaatg cttttgctat tttaactgct ga | 162 |

<210> SEQ ID NO 790
<211> LENGTH: 162
<212> TYPE: DNA
<213> ORGANISM: Artificial Sequence
<220> FEATURE:
<223> OTHER INFORMATION: Defensin like

<400> SEQUENCE: 790

| | |
|---|---|
| gatggcgtga aactgtgcga aagagcgagc aaaacctgga ccggcaactg cggcaacacc | 60 |
| aaacattgcg ataaccagtg caaaagctgg gaaggcgcca acatggtgc ttgccacgtg | 120 |
| cgcaacggca aacataaatg cttttgctat tttaactgct ga | 162 |

<210> SEQ ID NO 791
<211> LENGTH: 162
<212> TYPE: DNA
<213> ORGANISM: Artificial Sequence
<220> FEATURE:
<223> OTHER INFORMATION: Defensin like

<400> SEQUENCE: 791

| | |
|---|---|
| gatggcgtga aactgtgcga aagaccgagc aaaacctgga ccggccactg cggcaacacc | 60 |
| aaacattgcg ataaacagtg cagaaactgg gaaggcgccg cccatggtgc ttgccacgtg | 120 |

```
cgcaacggca aacataaatg cttttgctat tttaactgct ga                              162

<210> SEQ ID NO 792
<211> LENGTH: 6
<212> TYPE: PRT
<213> ORGANISM: Artificial Sequence
<220> FEATURE:
<223> OTHER INFORMATION: Synthetic Construct

<400> SEQUENCE: 792

His His His His His His
  1               5
```

US 7,785,828 B1

PRODUCTION OF ANTIMICROBIAL PROTEINS IN FUSION PROTEINS

CROSS-REFERENCE TO RELATED APPLICATIONS

This application is a national stage filing under 35 U.S.C. §371 of PCT Application No. PCT/US2004/003378, and claims benefit of U.S. Provisional Patent Application No. 60/445,493, filed Feb. 6, 2003, the entire contents of which are incorporated herein for all purposes.

SEQUENCE LISTING

The appended sequence listing is hereby incorporated by reference.

FIELD OF THE INVENTION

The invention relates to antifungal agents and finds use in agriculture, medicine and veterinary sciences.

BACKGROUND

Numerous commercially valuable plants, including common agricultural crops, are susceptible to attack by fungal pathogens. In turn, many plants produce proteins with antifungal activity, such as thionins, beta-1,3-glucanases, chitinases, and plant defensins. Plant defensins are small cysteine-rich proteins of 45-54 residues and four intramolecular cysteine bonds (see, Terras et al., 1995, *Plant Cell* 7:573-88). Transgenic plants over-expressing natural defensins have enhanced resistance to fungal diseases (Gao et al., 2000, *Nat. Biotechnol.* 18:1307-10; Terras et al., 1995, *Plant Cell* 7:573-88; De Bolle et al., 1996, *Plant Mol. Biol.* 31:993-1008). However, the resistance is not robust enough to render the plants commercially valuable. There is a need for new antifungal compounds and new methods of inhibiting fungal infection of plants and other organisms.

BRIEF SUMMARY OF THE INVENTION

In one aspect, the invention provides polypeptides having antifungal or antimicrobial activity, polynucleotides encoding the polypeptides, transgenic plants and plant cells expressing such polypeptides or polynucleotides, and methods of using the polypeptides, polynucleotides and plants. In one embodiment, the invention provides a recombinant, synthetic or isolated polypeptide having antifungal activity and comprising (a) the sequence set forth in Table 1 (SEQ ID NOS: 1-6 and 10-11); (b) a sequence set forth in Table 2 (SEQ ID NOS: 20-339); (c) a biologically active fragment of (a) or (b); or (d) a biologically active variant of (a) or (b) or (c). These polypeptides can be referred to, for convenience, as "NPs" or "NP polypeptides." In various embodiments, the polypeptide can be part of a fusion protein, such as a cleavable fusion protein. In one embodiment, the polypeptide does not have a sequence as set forth in Table 3 (SEQ ID NOS: 340-388). In one embodiment, the polypeptide comprises a sequence as set forth in Table 2.

In a related aspect, the invention provides a polynucleotide (an "NP polynucleotide") encoding a NP polypeptide. In an embodiment, the polynucleotide can include a sequence as set forth in SEQ ID NOS: 389-791, or fragment thereof. The invention also provides a vector (such as an expression vector) comprising the NP polynucleotide, and cells (such as a bacterial cell or plant cell) comprising the NP polynucleotide or vector.

In a related aspect, the invention provides a transgenic plant or plant cell that is transformed with or expresses a heterologous polynucleotide encoding a polypeptide of the invention (e.g., a polypeptide comprising a sequence as set forth in SEQ ID NOS: 1-339). In an embodiment, the plant or cell is transformed with, or expresses, a heterologous polynucleotide comprising a sequence as set forth in SEQ ID NOS: 389-791. The invention also provides progeny and parts (e.g., seeds) of such transgenic plants. In a related aspect, the invention provides a transgenic plant cell expressing a detectable or biologically active quantity of a heterologous NP polypeptide of the invention. In a related aspect, the invention provides a transgenic plant that expresses a polypeptide of the invention and has greater resistance to disease (e.g., spread of infection) compared to a similar plant not expressing the polypeptide.

In another aspect, the invention provides a method for inhibiting a plant pathogenic fungus comprising introducing into the environment of the fungus an antifungal amount of an NP polypeptide. In one embodiment, the environment of the pathogenic fungus is a tissue of a living plant (such as a transgenic plant expressing a recombinant NP polypeptide). In one embodiment, the NP polypeptide is applied to the surface of the plant.

In another aspect, the invention provides a method for treating a fungal infection in an animal by administering a NP polypeptide to the animal. In an embodiment, the animal is a human.

In a different aspect, the invention provides a method of preparing a (purified) cysteine-containing polypeptide recombinantly expressed in a cell by (a) recombinantly expressing in a cell a cleavable fusion protein comprising an amino-terminal tag domain, a first domain encoding a heterologous polypeptide, a second domain encoding the cysteine-containing polypeptide, and a cleavage site interposed between the first and second domains; (b) separating the fusion protein from at least some cell components based on the binding of the tag domain and a binding agent; and (c) contacting the fusion protein and a cleaving agent that cleaves at the cleavage site, thereby cleaving the fusion protein to produce the cysteine-containing polypeptide as a cleavage product, where steps (b) and (c) are carried out in the presence of a reducing agent. In various embodiments, the cleaving agent is a protease and/or the reducing agent is beta-mercaptoethanol at a concentration of between about 5 mM and about 20 mM and/or the cell is a bacterial cell. In one embodiment, the cysteine-containing polypeptide is a plant defensin or is a NP polypeptide. In one aspect the tag domain is (His)$_6$ (SEQ ID NO: 792), the heterologous domain is maltose binding protein, glutathione-S-transferase or chitin binding domain, and the cleavage site comprises the sequence Ile-Glu-Asp-Gly-Arg (SEQ ID NO: 19) (recognized by Factor Xa) or Pro-Gly-Ala-Ala-His-Tyr (SEQ ID NO: 12) (recognized by Genenase I).

BRIEF DESCRIPTION OF THE FIGURES

FIGS. 2A-C show the relationship between expression of L3-135 (FIG. 2A), L2-12 (FIG. 2B) or DmAMP1 (FIG. 2C)

Figure 1:
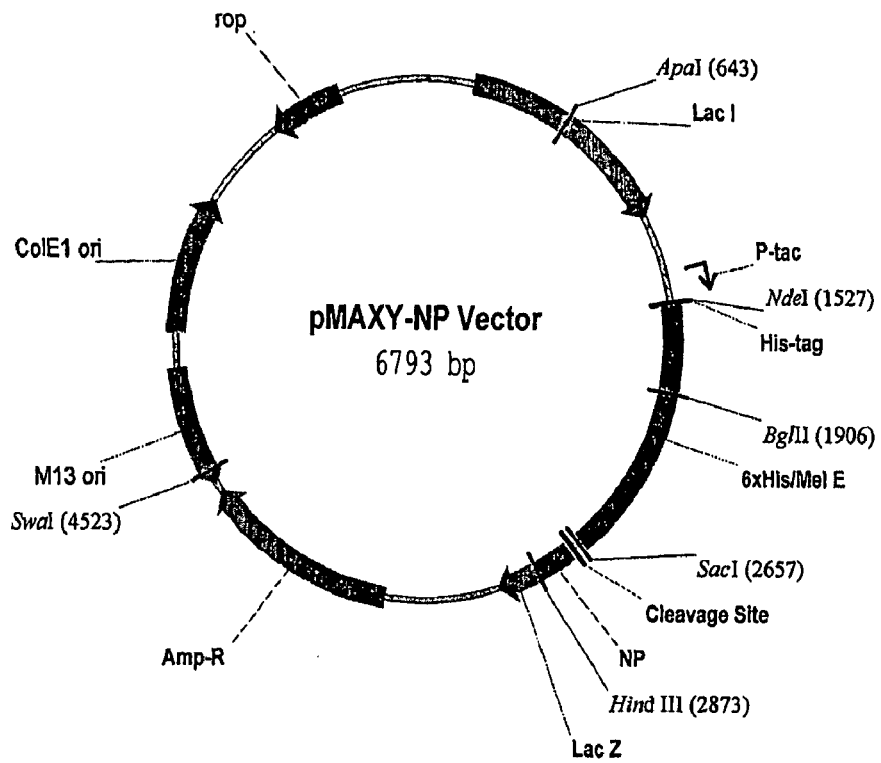
FIG. 1 shows a vector used for expression and purification of polypeptides of the invention.

in transgenic wheat plants and the extent of disease following inoculation with *Fusarium graminearum*.

DETAILED DESCRIPTION

1. Polypeptides with Antifungal Activity and Polynucleotides Encoding Such Polypeptides In one aspect, the invention provides novel polypeptides ("NPs" or "NP polypeptides") with antifungal activity. Using techniques of in vitro DNA recombination, we have discovered novel polypeptides with greater antifungal activity than naturally occurring plant defensins. The polypeptides of the invention were discovered by (1) carrying out oligonucleotide-mediated nucleic acid recombination of nucleic acids related to plant defensins to produce diversified variants of the parental nucleic acids, generally as described in PCT publication WO 00/42561, (2) identifying such variants encoding polypeptides with antifungal activity, and (3) determining the sequence of such variants and encoded polypeptides. In this context, "nucleic acids related to plant defensins" includes, without limitation, nucleic acids comprising sequences encoding at least of portion of (a) wild-type plant defensins and/or (b) defensin mutants (see, e.g., De Samblanx et al., 1997, *J. Biol. Chem.* 272:1171-79) and/or (c) diversified variants produced by recombination (a) and/or (b), and the like.

In one series of embodiments, the NPs of the invention are biologically active polypeptides that:

a) comprise an amino acid sequence set forth in Table 1;

b) comprise an amino acid sequence set forth in Table 2;

c) comprise a biologically active fragment of a polypeptide having an amino acid sequence set forth in Table 1 or Table 2;

d) comprise an amino acid sequence that is a conservative variant of (a), (b) or (c);

e) comprise an amino acid sequence that is a digestible variant of (a), (b) or (c).

In a related embodiment, the invention provides a cleavable fusion protein comprising a sequence of an aforementioned NP polypeptide.

In related aspects, the invention provides polynucleotides encoding the novel polypeptides, transgenic plants and plant cells comprising the polynucleotides, and animal and bacterial cells comprising the polynucleotides. The polypeptides and polynucleotides of the invention can be recombinant, synthetic (i.e., at least a portion is chemically synthesized), and/or purified (e.g., separated from at least one other compound with which it is associated in a cell in which it is expressed). Also provided are methods for producing and using the NP polynucleotides and polypeptides of the invention.

These, and other, aspects of the invention are discussed in greater detail below.

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, MOLECULAR CLONING: A LABORATORY MANUAL, second edition (Sambrook et al., 1989) and MOLECULAR CLONING: A LABORATORY MANUAL, third edition (Sambrook and Russel, 2001), (jointly referred to herein as "Sambrook"); CURRENT PROTOCOLS IN MOLECULAR BIOLOGY (F. M. Ausubel et al., eds., 1987, including supplements and revisions through 2001); PCR: THE POLYMERASE CHAIN REACTION, (Mullis et al., eds., 1994); Harlow and Lane, 1988, ANTIBODIES, A LABORATORY MANUAL, Cold Spring Harbor Publications, New York, and Harlow and Lane, 1999, USING ANTIBODIES: A LABORATORY MANUAL Cold Spring Harbor Laboratory Press, Cold Spring Harbor, N.Y. (jointly referred to herein as "Harlow and Lane"), Beaucage et al. eds., CURRENT PROTOCOLS IN NUCLEIC ACID CHEMISTRY, 2000, John Wiley & Sons, Inc., New York); Weissbach & Weissbach, METHODS FOR PLANT MOLECULAR BIOLOGY, 1989, Academic Press; and Gelvin et al., 1990, PLANT MOLECULAR BIOLOGY MANUAL, Kluwer Academic Publishers.

2. Structure and Characteristics of Novel Polypeptides (NPs) with Antifungal Activity and Polynucleotides Encoding Them

2.1 Novel Polypeptides

As noted supra; the NPs of the invention can comprise an amino acid sequence set forth in Tables 1 and 2. Table 1 shows the structure, using the one-letter amino acid code, of certain NP polypeptides of the invention. Table 2 shows the sequences of selected NP polypeptides of the invention.

The NP polypeptides of the invention are useful, inter alia, because they exhibit antifungal activity. As used herein, a polypeptide is "biologically active" or has "biological activity" or has "antifungal activity" when the polypeptide kills, or inhibits growth of, at least one species of fungus. The NP polypeptides of the invention are useful as antifungal agents against all fungal and/or oomycete plant pathogens including, without limitation, *Fusarium graminearum, Septoria tritici, Mycospherella fijiensis; Pyricularia oryzae; Rhizoctonia solani; A. brassicola; A. pisi; B. cinerea; C. beticola; C. lindemuthianum; F. culmorum; P. infestans; S. sclerotianum; S. nodorum; T. hamatum; V. dahliae; Z. inaequalis; F. oxysporum; N. haematococca; P. digitatum; P. betae; P. tritici-repentis; V. albo-atrum; A. Solani; F. culmorum; F. monoliforme*; and *A. alternaria*. These and other fungi are widely available and can be obtained from the American Type Culture Collection (ATCC), P.O. Box 1549, Manassas, Va. 20108 (see worldwide web at atcc. org/SearchCatalogs/Fungi_Yeasts.cfm) as well as other sources.

The antifungal activity of a polypeptide can be determined using any assay suitable for detecting the characteristic antifungal activities of plant defensins, including in vitro assays and in vivo assays. Exemplary in vitro assays for antifungal activity include (i) those described in the examples, infra (e.g., Example 2); (ii) the assay described by Terras et al., 1992, *J. Biological Chemistry* 267:15301-309; (iii) the assay of U.S. Pat. No. 5,514,779; (iv) the assay described in De Samblanx et al., 1997, *J. Biol. Chem.* 272:1171-79; (v) other assays useful for detecting antifungal activity (e.g., defensin-type antifungal activity). Exemplary in vivo assays include the "infiltration assay" described in detail in Example IV, infra, as well as the field assay described in Snijders et al., 1992, *Can. J. Bot.* 70:1570-76, and numerous other assays known in the art. Plants in which in vivo assays can be carried out include, without limitation, using conventional (wild type) plants, transgenic plants (e.g., plants expressing a NP polypeptide of the invention).

In describing antifungal activity of an NP, reference can be made to the antifungal effect of the NP on a specified "reference" fungus. An example of a reference fungus is *Fusarium graminearum*. Another example of a reference fungus is *Septoria tritici*. Similarly, in describing antifungal activity of an NP, reference can be made, for comparison, to the antifungal effect of the NP relative to a specified reference protein, such as a naturally occurring plant defensin protein. Thus, a particular NP polypeptide can be described as having antifungal activity against *S. tritici* that is 10-fold higher than that of a similar amount and concentration of the natural defensin Rs-AFP2 (i.e., having the sequence of Rs-AFP2 set forth in Table 3). As is discussed infra, a surprising property of the NPs of the invention is that they have significantly higher antifungal activity than do wild-type defensins.

Because of their antifungal properties, the NP polypeptides of the invention and polynucleotides encoding them are useful, inter alia, in protecting plants susceptible to attack by fungal pathogens, by killing the pathogenic fungus or inhibiting fungal growth. Such protection is accomplished by introducing a NP polypeptide of the invention into the environment of the pathogenic fungi. In this context, the phrase "introducing into the environment of the pathogenic fungi" is intended to encompass an environment in which a pathogenic fungus may appear (e.g., plant surface or plant tissue of a plant susceptible to fungal attack) as well as an environment in which a pathogenic fungus is present (e.g., an infected plant tissue). Thus, in one aspect, the method involves contacting a fungus and a NP polypeptide. Usually, the amount of a NP polypeptide contacted with the fungus is an antifungal amount (sufficient to kill or inhibit growth of the fungus).

In one embodiment, a NP is introduced into the environment of a pathogenic fungi by applying the polypeptide to the surface of a susceptible plant. Such application can be accomplished by, for example, dusting, spraying, or seed treatment, using methods and formulations well known in the agricultural and antimicrobial arts. In one embodiment, the NP is introduced into the environment by infiltration (e.g., as described herein below).

In another embodiment, a gene encoding a NP operably linked to a promoter is introduced into the genome of a susceptible plant to create a transgenic plant, and the NP polypeptide is expressed in at least one cell of the plant or its progeny (which progeny are also "transgenic plants"). See, e.g., Section 3, infra.

In embodiments of the invention in which an NP is expressed in or contacted with a plant part or tissue, the plant can be any plant infected with or susceptible to infection with a fungus or oomycete (including, without limitation, pathogens listed herein). In one embodiment, the plant is a commercially valuable plant. Such plants include agriculturally valuable plants such as, without limitation, wheat, banana, rice, corn, sorghum, maize, rye, barley, oats, millet, triticale, sunflower, alfalfa, rapeseed, soybean, potato, tomato, cotton, pepper, cucumber, melons, lettuce, strawberry and beans. However, this list is not to be construed as limiting, and the methods of the invention can be practiced with any plant species susceptible to attack and damage by a pathogenic fungus or oomycete including, again without limitation, species from the genera *Fragaria, Lotus, Medicago, Onobrychis, Trifolium, Trigonella, Vigna, Citrus; Linum, Geranium, Manicot, Daucus, Arabidopsis, Brassica, Raphanus, Sinapis, Atropa, Capsicum, Datura, Hyoscyamus, Lycopersiomi, Nicotiana, Solanum, Petunia, Digitalis, Majorana, Cichorium, Helianthus, Lactuca, Bromus, Asparagus, Antirrhinum, Hemerocallis, Nemesia, Pelargonium, Panicum, Pennisetum, Ranunculus, Senecio, Salpiglossis, Cucumis, Browallia, Glycine, Lolium, Triticum*, and *Datura*.

The NPs of the invention also find use as insecticidal agents. Defensins, as a class, have homology to chitin binding proteins. Some chitin-binding proteins are known to have an effect against insects that possess an exoskeleton comprising chitin. The sequence similarity between naturally occurring defensins and known chitin-binding proteins implies that the defensins may also possess insecticidal properties. Likewise, the NPs of the inventions may be used as insecticidal agents.

The NPs of the invention also find use as components of therapeutic compositions. For example, a composition containing a NP polypeptide may be administered to an animal to inhibit a fungal infection.

2.1.1 NP Families

Three families of novel polypeptides (NPs) of the invention are described below with reference to amino acid sequence: the "NP-Dm" family, the "NP-Rs" family, and the "NP-Div" family. As discussed below, Table 1 provides formulae defining NPs of each family. Table 2 provides exemplary NPs in each family. The NPs described in Table 2 exhibited up to 30-fold (or more) greater antifungal activity than the naturally occurring plant defensin proteins tested (either RsAFP1 for L1 and L2 clones or DmAMP1 for L3, L4, L5, L6, L7, L9, L10 and L11 clones), as measured in assays against *Fusarium graminearium* and/or *Septoria tritici*. Following the guidance of the present specification, additional polypeptides with antifungal activity are prepared by (i) obtaining a novel polypeptide with a sequence as described herein below and (ii) assaying the antifungal activity of the novel polypeptide.

2.1.1.1 NP-Dm Family

In an embodiment, the NP has a sequence as shown for NP-Dm (SEQ ID NO:1) or NP-Dm* (SEQ ID NO: 10) (Table 1). In one series of embodiments, the NP has the sequence of NP-Dm and deviates from the consensus sequence NLCERASKTWSGNCGNTKHCDNQCKS WEGAKHGACHVRNGKWKCFCYFNC (SEQ ID NO: 7) at no more than 17, no more than 16, no more than 15, no more than 14, no more than 13, no more than 12, no more than 11, no more than 10, no more than 9, no more than 8, no more than 7, no more than 6, no more than 5, no more than 4, no more than 3, no more than 2, no more than 1, or no more than 0 positions. In an embodiment, the sequence of the NP is other than a sequence of a polypeptide shown or listed by accession number in Table 3.

The antifungal activity of a specific polypeptide with a sequence of NP-Dm can be determined using standard assays, or the assays described herein in Examples II & III, infra. Preferably, the NP has antifungal activity against *Fusarium graminearium* that is greater than the activity of Dm-AMP1, e.g., in various embodiments at least about 2-fold greater, at least about 4-fold greater, at least about 5-fold greater, at least about 8-fold greater, at least about 10-fold greater, at least about 15-fold greater, at least about 20-fold greater, or at least about 30-fold greater. Preferably the NP also has activity against *Septoria tritici*, e.g., activity that is greater than that of DM-AMP1 by at least about 2-fold, at least about 4-fold, at least 5-fold, or at least about 8-fold.

In a related embodiment, the NP comprises a sequence as shown in Table 2. (Table 2A). Table 2A also shows the antifungal activity of specific NP polypeptides relative to Dm-AMP1 activity.

It will be appreciated that the invention also provides NP polypeptides that are fragments, variants or fusion proteins, all as described herein, that comprise a sequence of a NP-Dm polypeptide. In an embodiment, the fragments, variants or fusion proteins have antifungal activity as described herein.

2.1.1.2 NP-Rs Family

In another embodiment, the NP has a sequence as shown for NP-Rs (SEQ ID NO:2) (Table 1). In one series of embodiments, the NP has the sequence of NP-Rs and deviates from the consensus sequence QKLCQRPSRTWSGVCGNSNACKNQCIRLEKARHGSCNYRFP AHKCICYFPC (SEQ ID NO: 8) at no more than 12, no more than 11, no more than 10, no more than 9, no more than 8, no more than 7, no more than 6, no more than 5, no more than 4, no more than 3, no more than 2, no more than 1, or no more than 0 positions.

In an embodiment, the sequence of the NP is other than a sequence of a polypeptide shown in Table 3. In one embodiment, the residue at position 5 is not a hydrophobic residue (e.g., A, L, I, V, P, F, W, M). In one embodiment, the residue at position 5 is not methionine. In one embodiment, the residue at position 9 is not a basic residue (e.g., K, R, H). In one embodiment, the residue at position 16 is not a hydrophobic residue. In one embodiment, the residue at position 16 is not methionine. In one embodiment, the residue at position 39 is not a basic residue:

The antifungal activity of a specific polypeptide with a sequence of NP-Rs can be determined using standard assays, or the assays described herein in Examples II & III, infra. Preferably, the NP has antifungal activity against *Fusarium graminearium* that is greater than the activity of Rs-AFP2, e.g., in various embodiments at least about 2-fold greater, at least about 4-fold greater, at least about 5-fold greater, at least about 8-fold greater, at least about 10-fold greater, at least about 15-fold greater, at least about 20-fold greater, or at least about 30-fold greater. Preferably the NP also has activity against *Septoria tritici*, e.g., activity that is greater than that of DM-AMP1 by at least about 2-fold, at least about 4-fold, at least about 5-fold, at least about 8-fold, or at least about 10-fold.

In a related embodiment, the NP comprises a sequence as shown in Table 2 (Table 2B). Table 2B also shows the antifungal activity of specific NP polypeptides relative to Rs-AFP2 activity.

It will be appreciated that the invention also provides NP polypeptides that are fragments, variants or fusion proteins, all as described herein, that comprise a sequence of an NP-Rs polypeptide. In an embodiment, the fragments, variants or fusion proteins have antifungal activity as described herein.

2.1.13 NP-DIV Family

In an embodiment, the NP has a sequence as shown for NP-DIV 1 (SEQ ID NO:3); NP-DIV2 (SEQ ID NO:4); NP-DIV3 (SEQ ID NO:5); NP-DIV4 (SEQ ID NO:6); or NP-DIV4* (SEQ ID NO: 11); (Table 1). In one series of embodiments, the NP has the sequence of NP-DIV1, NP-DIV2, NP-DIV3, or NP-DIV4 and deviates from the consensus sequence DGVKLCERASQTWTGHCGNTKHCDKQCK-NWEGAKHGACH VRNGKWKCFCYFNC (SEQ ID NO: 9) at no more than 15, no more than 14, no more than 13, no more than 12, no more than 11, no more than 10, no more than 9, no more than 8, no more than 7, no more than 6, no more than 5, no more than 4, no more than 3, no more than 2, no more than 1, or no more than 0 positions (including up to 3 amino-terminal deletions). In an embodiment, the sequence of the NP is other than a sequence of a polypeptide shown in Table 3.

The antifungal activity of a specific polypeptide with a sequence of NP-DIV can be determined using standard assays, or the assays described herein in Examples II & infra. Preferably, the NP has antifungal activity against *Fusarium graminearium* that is greater than the activity of Dm-AMP 1, e.g., in various embodiments at least about 2-fold greater, at least about 4-fold greater; at least about 5-fold, at least about 8-fold greater, at least about 10-fold greater, at least about 15-fold greater, at least about 20-fold greater, or at least about 30-fold greater: Preferably the NP also has activity against *Septoria tritici*, e.g., activity that is greater than that of DM-AMP1 by at least about 2-fold, at least about 4-fold, at least about 5-fold, or at least about 8-fold, or at least about 10-fold.

In a related embodiment, the NP comprises a sequence as shown in Table 2, (Table 2C). Table 2C also shows the antifungal activity of specific NP polypeptides relative to Dm-AMP1 activity.

It will be appreciated that the invention also provides NP polypeptides that are fragments, variants or fusion proteins, all as described herein below, that comprise a sequence of a NP-DIV polypeptide. In an embodiment, the fragments, variants or fusion proteins have antifungal activity as described herein.

2.2 Biologically Active Fragments and Variants of NP polypeptide

The invention further provides biologically active fragments and variants of the NP polypeptides described supra (hereinafter, "reference polypeptides"). In an embodiment, the polypeptide is a fragment of a polypeptide shown in Table 2. In an embodiment, the fragment comprises at least about 30, usually at least about 35, generally at least about 40, and often at least about 45 residues of the sequence supra. The invention also provides biologically active variants of one of the following reference polypeptides: a polypeptide having an amino acid sequence set forth in Table 1 (or biologically active fragment thereof) or a polypeptide having an amino acid sequence set forth in Table 2 (or biologically active fragment thereof). In one embodiment, the invention provides an NP that is selected from L3-135 (SEQ ID NO: 59); L3-64 (SEQ ID NO: 78); L3-71 (SEQ ID NO: 80); L5-13 (SEQ ID NO: 112); L6-28 (SEQ ID NO: 159); L6-40 (SEQ ID NO: 167); L6-60 (SEQ ID NO: 180); L6-75 (SEQ ID NO: 190); L9-9 (SEQ ID NO: 203); L9-21 (SEQ ID NO: 211); L9-29 (SEQ ID NO: 216); and biologically active fragments thereof.

In one embodiment, the NP of the invention is a conservative variant of a reference polypeptide. A "conservative variant" of a polypeptide having a particular amino acid sequence refers to a variant that differs from the reference sequence by substitutions of amino acids with other amino acids having similar properties (e.g., acidic, basic, positively or negatively charged, polar or non-polar, etc.) such that the substitutions do not reduce the antifungal activity of the variant compared to the reference sequence. The following six groups each contain amino acids that are conservative substitutions for one another: 1) alanine (A), serine (S), threonine (T); 2) aspartic acid (D), glutamic acid (E); 3) asparagine (N), glutamine (Q); 4) arginine (R), lysine (K); 5) isoleucine (I), leucine (L), methionine (M), valine (V); and 6) phenylalanine (F), tyrosine (Y), tryptophan (W) (see also, Creighton, 1984, PROTEINS, W.H. Freeman and Company). One of skill in the art will appreciate that the above-identified substitutions are not the only possible conservative substitutions. For example, individual substitutions, deletions or additions which alter, add or delete a single amino acid or a small percentage of amino acids in a reference sequence (e.g., in embodiments, up to 2, 3, 4 or 5 amino acids) can also be conservative variant." The substitutions are such that they do not reduce the antifungal activity of the variant compared to the reference sequence as assayed supra. Many methods will be apparent to the practitioner of ordinary skill for making variant NPs, including de novo synthesis of an NP variant of defined sequence and in vitro mutagenesis (e.g., by in vitro recombination) of an existing polynucleotide encoding an NP described herein (e.g., as listed in Table 2).

2.3 Polynucleotides Encoding NP Polypeptides

Polynucleotides encoding NP polypeptides (sometimes referred to as "NP polynucleotides" or "NP-encoding polynucleotides") find a variety of uses. In one embodiment, the NP polynucleotide is used for recombinant expression (e.g. in bacterial or eukaryotic expression systems) of quantities of NP polypeptides. In a related embodiment, the NP polynucleotide is used to generate a recombinant plant expressing a NP polypeptide. In a related embodiment, the NP polynucleotide is used as a parental nucleic acid for recursive in vitro DNA recombination (e.g., oligonucleotide mediated nucleic acid recombination, such as described in PCT Publication WO 00/42561) to prepare polynucleotides encoding novel polypeptides with antifungal activity.

It will be appreciated that the sequence of a polynucleotide encoding any particular polypeptide (e.g., an NP listed in Table 1 or Table 2) can be determined based on the amino acid sequence of the polypeptide with reference to the genetic code. Because of the degeneracy of the genetic code, a variety of nucleic acid sequences will encode each NP amino acid sequence and the nucleotide sequence can be designed with the appropriate codons for the particular amino acid sequence desired.

GENETIC CODE
SECOND POSITION

| FIRST POSITION | T | C | A | G | THIRD POSITION |
|---|---|---|---|---|---|
| T | TTT Phe [F] | TCT Ser [SI] | TAT Tyr [Y] | TGT Cys [C] | T |
|   | TTC Phe [F] | TCC Ser [SI] | TAC Tyr [Y] | TGC Cys [C] | C |
|   | TTA Leu [L] | TCASer [S] | TAA Ter | TGA Ter [W] | A |
|   | TTG Leu [L] | TCG Ser [S] | TAG Ter | TGG Trp [W] | G |
| C | CTT Leu [L] | CCT Pro [P] | CAT His [H] | CGT Arg [R] | T |
|   | CTC Leu [L] | CCC Pro [P] | CAC His [H] | CGC Arg [R] | C |
|   | CTA Leu [L] | CCA Pro [P] | CAA Gln [Q] | CGA Arg [R] | A |
|   | CTG Leu [L] | CCG Pro [P] | CAG Gln [Q] | CGG Arg [R] | G |
| A | ATT Ile [I] | ACT Thr [T] | AAT Asn [N] | AGT Ser [S] | T |
|   | ATC Ile [I] | ACC Thr [T] | AAC Asn [N] | AGC Ser [S] | C |
|   | ATA Ile [I] | ACA Thr [T] | AAA Lys [K] | AGA Arg [R] | A |
|   | ATG Met [M] | ACG Thr [T] | AAG Lys [K] | AGG Arg [R] | G |
| G | GTT Val [V] | GCT Ala [A] | GAT Asp [D] | GGT Gly [G] | T |
|   | GTC Val [V] | GCC Ala [A] | GAG Asp [D] | GGC Gly [G] | C |
|   | GTA Val [V] | GCA Ala [A] | GAA Glu [E] | GGA Gly [G] | A |
|   | GTG Val [V] | GCG Ala [A] | GAG Glu [E] | GGG Gly [G] | G |

Exemplary polynucleotides encoding the NP polypeptides of Table 2 are provided in SEQ ID NO: 20-339. As is well known, different organisms exhibit preferences in codon use. When expression of the NP polynucleotide in a particular host cell is desired, preferred codons can be selected to optimize expression in that host. For example, for expression in a plant (i.e., a transgenic plant) preferred codons for the intended plant host in which the sequence will be expressed can be used, as is described below. Similarly, preferred codons can be selected for expression in bacteria, yeast, animal (e.g., mammalian), and other cells. Codon preferences are known in the art and codon optimization can be done using the information in the Codon Usage Database provided by GenBank (worldwide web at kazusa.or.jp/codon/).

For expression in plant cells (e.g., in transgenic plants) sequences and codon usage can be selected to maximize expression. The preferred codon usage in plants differs from the preferred codon usage in certain other organisms, e.g., microorganisms. Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome. Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription; In addition, monocotyledons may recognize AT-rich sequences as splice sites (see below).

In addition, plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be enhanced by the inclusion of a eukaryotic consensus translation initiator at the ATG. Clontech (1993/1994 catalog, page 210, incorporated herein by reference) have suggested one sequence as a consensus translation initiator for the expression of the E. coli uidA gene in plants. Further, Joshi (N.A.R. 15: 6643-6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

| Position Before the Initiating ATG in 14 Maize Genes: | | | | | | | | | |
|---|---|---|---|---|---|---|---|---|---|
| −10 | −9 | −8 | −7 | −6 | −5 | −4 | −3 | −2 | −1 |
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

A polynucleotide encoding an NP of the invention can be obtained by conventional techniques, including de novo chemical synthesis or mutagenesis of isolated (e.g., cloned) defensin polynucleotides. Nucleic acids encoding naturally occurring defensins are readily obtained (for example they can be obtained or chemical synthesis or by molecular cloning from plant nucleic acids, based on the published sequences). In one embodiment, a polynucleotide is synthetic, e.g., chemically synthesized using phosphoramidite chemistry (see, e.g., Beaucage et al. eds., *Current Protocols in Nucleic Acid Chemistry* John Wiley & Sons, Inc., New York, 2000), e.g., using an automated DNA synthesizer (e.g., Expedite 8909; Perceptive Biosystems, Framington, Mass.). In one embodiment, the DNA sequences encoding the NP amino acid sequences are assembled from chemically synthesized DNA oligonucleotides by means of PCR. In an embodiment, the complete sequence is assembled from overlapping oligonucleotides prepared by standard methods and assembled into a complete coding sequence for subsequent transfer into a host cell, e.g., a plant host cell. See, e.g., Edge, 1981, *Nature* 292:756; Nambair, et al., 1984, *Science* 223: 1299; Jay, et al., 1984, *J. Biol Chem* 259:6311.

In one aspect, the invention provides a vector comprising a NP polynucleotide of the invention. In an embodiment, the vector is an expression vector. Expression vectors typically include transcriptional and/or translational control signals (e.g., the promoter, ribosome-binding site, and ATG initiation codon) operably linked to the NP coding sequence. Expression vectors suitable for expression in plants are discussed in some detail infra in Section 3. As already noted, the choice of codons can be used to optimize expression in a particular cell type. In addition, the efficiency of expression can be enhanced by the inclusion of enhancers appropriate to the cell system in use. In one aspect, the vector encodes a fusion protein comprising a NP polypeptide sequence.

2.4 Production of NP Polypeptides by Recombinant Expression and Chemical Synthesis As noted supra, in one aspect of the invention, NP polynucleotides are expressed to produce NP polypeptides. Any of a variety of conventional expression systems can be used, including expression in bacteria, yeast, plant, insect, eukaryotic, animal, and mammalian cells, as well as cell-free expression systems. See, e.g., Ausubel, supra and Sambrook, supra for general recombinant techniques useful for NP polypeptide expression. In one embodiment of the invention, DNA encoding a NP polypeptide is inserted into DNA constructs capable of introduction into and expression in host cell, for example, bacterial (e.g., *E. coli, Bacillus subtilus*), yeast (e.g., *Saccharomyces*), insect (e.g., *Spodoptera frugiperda*), plant, or mammalian cell culture systems. In an embodiment, appropriate expression vectors which integrate into the host cell chromosome are used. In an embodiment, as discussed in detail below, the DNA construct is capable of expression in a plant cell, such as a transgenic plant cell. In one embodiment, the NP polypeptide is expressed in a plant cell comprising a transgene encoding the NP. In one aspect, the invention provides a cell (e.g., bacterial, plant, animal, yeast, mammalian, insect or fungal, cell) comprising a polynucleotide (e.g., expression vector) encoding an NP polypeptide of the invention.

Following expression, a NP polypeptide optionally can be isolated from the expression system. Isolation and purification of the NP polypeptides of the present invention can be carried out by methods that are generally well known in the art. These methods include, but are not limited to, ion exchange, hydrophobic interaction, HPLC or affinity chromatography, to achieve the desired purity. In one embodiment, NP polypeptides are purified using immunoaffinity chromatography. In one embodiment, the NP is expressed as a cleavable fusion protein and isolated as described herein below.

Although recombinant expression of NP polypeptides has certain advantages, the polypeptides can also be prepared by other methods, such as chemical synthesis. Polypeptides, such as NP polypeptides, can be chemically synthesized using methods well known in the art (see, e.g., Caruthers et al., 1980, *Nucleic Acids Res. Symp. Ser.*, 215-223; Horn et al., 1980, *Nucleic Acids Res. Symp. Ser.*, 225-232; Roberge, et al., 1995, *Science* 269:202) including automated protein synthesis methods. The newly synthesized polypeptide can be partially or substantially purified, if desired, by preparative high performance liquid chromatography (e.g., Creighton, PROTEINS, STRUCTURES AND MOLECULAR PRINCIPLES, WH Freeman and Co, New York N.Y., 1983), preparative electrophoresis, or other methods. The purified polypeptide can be allowed to fold into biologically active forms in vitro (see, e.g., Yon, J. M., 1997, *Cell Mol Life Sci.* 53:557-567; Levitt et al., 1997, *Annu. Rev. Biochem.* 66:549-79).

2.5 Fusion Proteins, Cleavable Fusion Proteins, and the Use of Cleavable Fusion Proteins for the Purification of NPs and Other Cysteine-Containing Polypeptides

2.5.1 NP Fusion Proteins Generally

The invention also provides fusion proteins comprising a sequence encoding an NP (e.g., including biologically active variants and fragments as disclosed herein). As used herein, the term "fusion protein," has its normal meaning in the art, i.e., a composite protein encoded by a single contiguous amino acid sequence, made up of two (or more) distinct, heterologous polypeptides which are not normally fused together in a single amino acid sequence. Fusion proteins can be useful in providing enhanced expression of the NP polypeptide constructs, or in producing NP polypeptides having other desirable properties, for example, comprising a label (such as an enzymatic reporter group), binding group, or antibody epitope. Fusion proteins generally are described in Ausubel et al., supra, and Sambrook, supra.

The invention further provides cleavable fusion proteins, comprising a first polypeptide domain (a "heterologous domain"), a second domain with the sequence of a biologically active NP polypeptide ("NP domain"), and a cleavage site between the first and second domains. The NP domain can be any NP polypeptide sequence of the invention. The heterologous domain can be any of a variety of polypeptides, including, for example, maltose binding protein (Guan et al., 1987, *Gene* 67:21-30; Maim et al., 1988, *Gene* 74:365-373); glutathione-S-transferase (Smith et al., 1988, *Gene* 67:31-40), His Tag (Novagen); FLAG-Tag (Stratagene); chitin binding domain (New England Biolabs); and fusion polypeptide domains, e.g., N-terminal (histidine)$_6$ fused to the maltose binding protein, as described in the Examples, infra. The NP domain can be amino-terminal or carboxy-terminal to the heterologous domain. Thus the sequence of domains in the cleavable fusion protein can be $NH_2$-(heterologous domain)-(cleavage domain)-(NP domain)-$CO_2$ or $NH_2$-(NP domain)-(cleavage domain)-(heterologous domain)-$CO_2$. The cleavage site can be a chemical cleavage site or a protease cleavage site. Exemplary chemical cleavage sites include, without limitation, sites cleaved by the protein cleaving agents cyanogen bromide, 2-(2-nitrophenylsulphenyl)-3-methyl-3'-bromoindolene, hydroxylamine, and the like. Exemplary protease cleavage sites include sequences recognized by, without limitation, Factor Xa, enterokinase, or Genenase I (produced by Genencor International and available from New England Biolabs). Preferably, the site is designed so that cleavage of the fusion protein at the site does not destroy the activity of the encoded NP protein, i.e., so that a biologically active NP protein or fragment is produced by the cleavage. The uncleaved fusion protein may or may not be biologically active.

2.5.2 Use of Cleavable Fusion Proteins for the Purification of NPs and Other Cysteine-Containing Polypeptides As is noted above, a variety of methods can be used to express and purify NP polypeptides of the invention. However, conventional purification methods generally result in low yields of recombinantly expressed small, cysteine-rich polypeptides particularly when expressed in bacterial, systems. In one aspect, the present invention provides a new method for expressing and purifying biologically active polypeptides. The method is particularly well suited to (but not limited to) use for production of small, cysteine-rich polypeptides, such as certain NP polypeptides of the invention. In this context, a "small" polypeptide refers to a polypeptide that is less than about 200 residues in length, often less than about 150 residues in length, often less than about 100 residues in length, often less than about 75 residues in length, and most often less than about 60 residues in length. Polypeptides that can be recombinantly produced and purified using this method include, without limitation, other cysteine-containing and cysteine-rich proteins. In this context, "cysteine-containing" means a polypeptide containing at least 2 cysteine residues forming a disulfide bridge. In this context, "cysteine rich" means at least about 8% of the residues in the desired protein are cysteine amino acids involved in formation of a disulfide bridge in the mature polypeptide. Often at least about 10% (e.g., 6 cysteines in a 50 residue polypeptide), sometimes at least about 12%, and sometimes at least 14% of the residues in the desired protein are cysteine amino acids involved in formation of a disulfide bridge in the mature polypeptide. It will be apparent that all cysteine-rich proteins are also cysteine-containing proteins. Cysteine-rich proteins polypeptides include, in addition to NPs of the invention, defensins, tachyplesin (see, e.g., U.S. Pat. No. 5,488, 035), thionins, lipid transfer proteins (LTPs), hevein-like and knottin-like proteins and snakins (Garcia-Olmedo et al., 1998, *Biopoly* 47:479-491).

For simplicity, the method will be described in terms of purification of a small, cysteine-containing protein, although, as noted, use of the method is not limited to these polypeptides. According to the method, the cysteine-containing protein (e.g., NP polypeptide) is expressed as a cleavable fusion protein, as is described supra for NP polypeptides. The cleavable fusion protein has the structure:

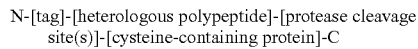
N-[tag]-[heterologous polypeptide]-[protease cleavage site(s)]-[cysteine-containing protein]-C The tag moiety of the fusion protein is used for the purification of the fusion protein and the heterologous polypeptide moiety increases the solubility of the fusion protein compared to the cysteine-containing protein alone.

The "heterologous polypeptide" can be any of a variety of polypeptide sequences. Preferably the heterologous polypeptide can be expressed as a recombinant protein in cells (e.g., prokaryotic or eukaryotic expression systems such as *E. coli*, yeast, or mammalian cells) at high levels and remain soluble when overexpressed. In one embodiment, the heterologous polypeptide has a molecular mass different from that of cysteine-containing protein to which it is fused. Examples of suitable heterologous polypeptides include maltose binding protein (Guan et al., 1987, *Gene* 67:21-30; Maina et al., 1988, *Gene* 74:365-373); glutathione-S-transferase (Smith et al., 1988, *Gene* 67:31-40), and chitin binding domain (New England Biolabs).

The "tag" is any short peptide moiety that can be specifically bound to a binding agent such that the fusion protein can be separated from unbound components (such as unrelated proteins in a cell lysate). Generally the binding agent is immobilized (e.g., bound to a solid phase) for use in chromatography. A preferred example of a tag is a peptide comprising polyhistidine tracts, e.g. $(His)_6$ or histidine-tryptophan sequences that can be bound by a binding agent that is a resin containing nickel or copper ions (i.e., metal-chelate affinity chromatography) (e.g., "His Tag", Novagen). Another example of a tag is a peptide sequence that is bound by a binding agent that is a specific antibody (e.g., the Xpress™ epitope, Invitrogen, Inc., San Diego Calif.). Other examples of tags include Protein A domains or fragments, which allow purification on immobilized immunoglobulin, the domain utilized in the FLAGS extension/affinity purification system (Immunex Corp, Seattle Wash.), polyanionic or polycationic peptides that can be bound to ion exchange matrices, and highly hydrophobic peptides, and the like. Typically the "tag" is fewer than 50 residues, often fewer than 25 residues and sometimes fewer than 10 residues in length.

The "protease cleavage" site can be any site that can be cleaved without destroying the activity (e.g., antifungal activity) of the cysteine-rich protein. In one embodiment, the cleavage site is recognized by Factor Xa (e.g., Ile-Glu/Asp-Gly-Arg) (SEQ ID NO: 13) or Genenase I (e.g., Pro-Gly-Ala-Ala-His-Tyr) (SEQ ID NO: 14). A variety of other sites (e.g., recognized by enterokinase) can also be used. Cleavage is affected, to some extent, by amino acid residues adjacent to the protease cleavage site. To facilitate efficient purification of a variety of different polypeptides, a construct (e.g., vector) can be prepared that includes multiple cleavage sites (e.g., both a Factor Xa site and a Genenase I site). Preferably, the cleavage site is designed so that, upon cleavage, the cysteine-rich polypeptide (e.g., NP polypeptide) is released without addition of any amino-terminal residue not present in the cysteine-rich protein.

In one embodiment, a polynucleotide encoding the fusion protein is incorporated into an expression vector so that the fusion protein is expressed in a cell, e.g., a bacterial cell, e.g., an *E. coli* cell. Numerous suitable vectors are know, e.g., pMAL vectors (see, e.g., CURRENT PROTOCOLS IN MOLECULAR BIOLOGY, Greene Associates/Wiley Interscience, New York, LaVallie et al., Eds., pp 16.4.1-16.4.17).

The ordinarily skilled practitioner guided by this disclosure will be able to prepare polynucleotides suitable for expression of the cleavable fusion proteins disclosed herein using routine molecular biological techniques (as described, for example, in Ausubel supra and Sambrook, supra).

In one embodiment, as described in Example 1, infra, bacterial (e.g., *E. coli*) cells are transformed with the fusion protein expression vector using standard methods (e.g., see Ausubel supra). Transformants are cultured, and the cells are concentrated and lysed. Any lysis method suitable for purification of proteins from bacteria can be used. In one embodiment the cells are lysed using B-PER reagent (Pierce Chemicals, Rockford, Ill.).

Following cell lysis, insoluble material is removed by centrifugation (e.g., 27000×g for 20 min) and fusion protein is purified (e.g., partially purified) from other cell components in the supernatant using the tag moiety. For example, when the tag is poly-histidine, commercially available nickel resins can be used to bind the fusion protein and unbound materials removed by "washing" with a suitable buffer. The fusion protein is eluted from the nickel resin using a buffered solution containing histidine. Other separation reagents that bind different "tags" well be known to the practitioner.

According to the present method, the lysis and initial washing steps are carried out using solutions containing a reducing agent (e.g., 2-mercaptoethanol or dithiothreitol) to prevent misfolding of the recombinant protein. In one embodiment, 2-mercaptoethanol is used at a concentration of between about 5 mM and 20 mM.

The purified (or partially purified) fusion protein is treated with a protease specific for the fusion protein cleavage site under conditions that cleave the cysteine-rich moiety from the heterologous moiety. The cysteine-rich protein can then be further purified, if desired. In one embodiment the cysteine-rich protein is purified until it is substantially pure. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition.

3. Transgenic Plants

In one aspect, the invention provides a plant comprising a transgene encoding an NP of the invention. "Plant" refers to either a whole plant, a plant part, a plant cell, or a group of plant cells. Methods for genetic modification of plants are well known in the art and are described in, for example, U.S. Pat. No. 5,488,035; WO 00/61731; and WO 94/16076. The following sections provide information useful in the production of transgenic plants generally, and particularly transgenic plants expressing an exogenous NP polypeptide.

3.1 Plant Transgenes And Vectors

Usually the transgene is contained in a vector useful for stable transformation of plant cells or for the establishment of transgenic plants. Suitable vectors are known in the art, see e.g., Weissbach & Weissbach, 1989, Methods for Plant Molecular Biology, Academic Press, Gelvin et al., 1990, Plant Molecular Biology Manual, Kluwer Academic Publishers, and Jones et al., 1992, *Transgenic Research* 1:285-297. Typically, plant transformation vectors include the NP encoding sequence operably linked to regulatory sequences (e.g., promoter and/or enhancer), a transcription initiation start site, a ribosome binding site, an RNA processing signal, a transcription termination site, and/or a polyadenylation signal and/or a selectable marker.

Suitable promoters for expression of NPs in transgenic plants include plant promoter regulatory regions (e.g., a regulatory region controlling inducible or constitutive, environmentally- or developmentally-regulated, or cell- or tissue-specific expression), synthetic promoters, and non-plant promoters (modified, if necessary, for function in plant cells). Examples of constitutive plant promoters useful for expression of the NP polypeptide includes cauliflower mosaic virus (CaMV) 35S promoter (Benfey and Chua, 1990, *Science* 250:959-966; nopaline synthase promoter (An et al., 1988, *Plant Physiol.* 88:547); and octopine synthase promoter (Fromm et al., 1989, *Plant Cell* 1:977). As discussed below, expression can be constitutive expression throughout the plant. Alternatively spatial or temporal regulation of expression of the provided nucleic acid molecule can be accomplished, e.g., using a variety of plant gene promoters that are regulated in response to environmental, hormonal, chemical, and/or developmental signals can be used for expression of the nucleic acid molecule in plant cells.

Typically, NP coding sequences intended for expression in transgenic plants are first assembled in expression cassettes behind a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be easily transferred to the plant transformation vectors described below. The following is a description of various components of typical expression cassettes.

3.1.1 Promoters

The selection of the promoter used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and the selection will reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in expression cassettes.

a. Constitutive Expression, the Ubiquitin Promoter

Ubiquitin is a gene product known to accumulate in many cell types and its promoter has been cloned from several species for use in transgenic plants (e.g. sunflower—Binet et al. Plant Science 79: 87-94 (1991); maize—Christensen et al. Plant Molec. Biol. 12: 619-632 (1989); and *Arabidopsis*—Collis et al., J. Biol. Chem. 265:12486-12493 (1990) and *Norris et al., Plant Mol. Biol.* 21:895-906 (1993)). The maize ubiquitin promoter has been developed in transgenic monocot systems and its sequence and vectors constructed for monocot transformation are disclosed in the patent publication EP 0 342 926 (to Lubrizol) which is herein incorporated by reference. Taylor et al. (Plant Cell Rep. 12: 491-495 (1993)) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is ideal for use with the nucleotide sequences of the present invention. The ubiquitin promoter is suitable for gene expression in transgenic plants, both monocotyledons and dicotyledons. Suitable vectors are derivatives of pAHC25 or any of the transformation vectors described in this application, modified by the introduction of the appropriate ubiquitin promoter and/or intron sequences.

b. Constitutive Expression, the CaMV 35S Promoter

Construction of the plasmid pCGN1761 is described in the published patent application EP 0 392 225 (Example 23), which is hereby incorporated by reference pCGN1761 contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative is designated pCGN1761ENX. pCGN1761ENX is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949, incorporated herein by reference.

c. Constitutive Expression, the Actin Promoter

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163-171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150-160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150-160 (1991)) can be easily modified for gene expression and are particularly suitable for use in monocotyledonous hosts. For example, promoter-containing fragments is removed from the McElroy constructions and used to replace the double 35S promoter in pCGN1761ENX, which is then available for the insertion of specific gene sequences. The fusion genes thus constructed can then be transferred to appropriate transformation vectors. In a separate report, the rice ActI promoter with its first intron has also been found to direct high expression in cultured barley cells (Chibbar et al. Plant Cell Rep. 12: 506-509 (1993)).

d. Inducible Expression, PR-1 Promoters

The double 35S promoter in pCGN1761ENX may be replaced with any other promoter of choice that will result in suitably high expression levels. By way of example, one of the chemically regulatable promoters described in U.S. Pat. No. 5,614,395, such as the tobacco PR-1a promoter, may replace the double 35S promoter. Alternately, the *Arabidopsis* PR-1 promoter described in Lebel et al., Plant J. 16:223-233 (1998) may be used. The promoter of choke is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104, which is hereby incorporated by reference) and transferred to plasmid pCGN1761ENX (Uknes et al., Plant Cell 4: 645-656 (1992)). pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

e. Inducible Expression, an Ethanol-Inducible Promoter

A promoter inducible by certain alcohols or ketones, such as ethanol, may also be used to confer inducible expression of a coding sequence of the present invention. Such a promoter is for example the alcA gene promoter from *Aspergillus nidulans* (Caddick et al. (1998) Nat. Biotechnol 16:177-180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) Nat. Biotechnol 16:177-180) are replaced by a coding sequence of the present invention to form an expression cassette having the coding sequence under the control of the alcA gene promoter. This is carried out using methods well known in the art.

f. Inducible Expression, a Glucocorticoid-Inducible Promoter

Induction of expression of a nucleic acid sequence of the present invention using systems based on steroid hormones is also contemplated. For example, a glucocorticoid-mediated induction system is used (Aoyama and Chua (1997) The Plant Journal 11: 605-612) and gene expression is induced by application of a glucocorticoid, for example a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GAL4 DNA-binding domain (Keegan et al. (1986) Science 231: 699-704) fused to the transactivating domain of the herpes viral protein VP16 (Triezenberg et al. (1988) Genes Devel. 2: 718-729) fused to the hormone-binding domain of the rat glucocorticoid receptor (Picard et al. (1988) Cell 54: 1073-1080). The expression of the fusion protein is controlled by any promoter suitable for expression in plants known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the insecticidal toxin.

g. Root Specific Expression

Another pattern of gene expression is root expression. A suitable root promoter is the promoter of the maize metallothionein-like (MU) gene described by de Framond (FEBS 290: 103-106 (1991)) and also in U.S. Pat. No. 5,466,785, incorporated herein by reference. This "MTL" promoter is transferred to a suitable vector such as pCGN1761ENX for the insertion of a selected gene and subsequent transfer of the entire promoter-gene-terminator cassette to a transformation vector of interest.

h. Wound-Inducible Promoters

Wound-inducible promoters may also be suitable for gene expression. Numerous such promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

i. Pith-Preferred Expression

Patent Application WO 93/07278, which is herein incorporated by reference, describes the isolation of the maize trpA gene, which is preferentially expressed in pith cells. The gene sequence and promoter extending up to −1726 by from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

j. Leaf-Specific Expression

A maize gene encoding phosphoenol carboxylase (PEPC) has been described by Hudspeth & Grula (Plant Molec Biol 12: 579-589 (1989)). Using standard molecular biological techniques the promoter for this gene can be used to drive the expression of any gene in a leaf-specific manner in transgenic plants.

k. Pollen-Specific Expression

WO 93/07278 describes the isolation of the maize calcium-dependent protein kinase (CDPK) gene which is expressed in pollen cells. The gene sequence and promoter extend up to 1400 by from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

3.1.2 Transcriptional Terminators

A variety of transcriptional terminators are available for use in expression cassettes. These are responsible for the termination of transcription beyond the transgene and correct mRNA polyadenylation. Appropriate transcriptional terminators are those that are known to function in plants and include the CaMV 35S terminator, the tml terminator, the nopaline synthase terminator and the pea rbcS E9 terminator. These can be used in both monocotyledons and dicotyledons. In addition, a gene's native transcription terminator may be used.

3.1.3 Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Collis et al., Genes Develop. 1: 1183-1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically; leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. '15: 65-79 (1990)). Other leader sequences known in the art ' include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154: 9-20); human immunoglobulin heavy-chain binding protein (BiP) leader, (Macejak, D. G., and Sarnow, P., Nature 353: 90-94 (1991); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie, D. R. et al., Molecular Biology of RNA, pages 237-256 (1989); and Maize Chlorotic Mottle Virus leader (MCMV) (Lommel, S. A. et al., Virology 81:382-385 (1991). See also, Della-Cioppa et al., Plant Physiology 84:965-968 (1987).

In addition to incorporating one or more of the aforementioned elements into the 5' regulatory region of a target expression cassette of the invention, other elements peculiar to the target expression cassette may also be incorporated. Such elements include but are not limited to a minimal promoter. By minimal promoter it is intended that the basal promoter elements are inactive or nearly so without upstream activation. Such a promoter has low background activity in plants when there is no transactivator present or when enhancer or response element binding sites are absent. One minimal promoter that is particularly useful for target genes in plants is the Bz1 minimal promoter, which is obtained from the bronze1 gene of maize. The Bz1 core promoter is obtained from the "myc" mutant Bz1-luciferase construct pBz1LucR98 via cleavage at the NheI site located at −53 to −58. Roth et al., Plant Cell 3:317 (1991). The derived Bz1 core promoter fragment thus extends from −53 to +227 and includes the Bz1 intron-1 in the 5' untranslated region. Also useful for the invention is a minimal promoter created by use of a synthetic TATA element. The TATA element allows recognition of the promoter by RNA polymerase factors and confers a basal level of gene expression in the absence of activation (see generally, Mukumoto (1993) Plant Mol Biol 23: 995-1003; Green (2000) Trends Biochem Sci 25: 59-63)

3.1.4 Targeting of the Gene Product Within the Cell

In some embodiments it will be desirable to target NPs expressed in transgenic plants to specific parts of the plants, for example to target pathogens (for example, expression in roots to target soil pathogens). In exemplary embodiments, the NP is expressed in the apoplast, the vacuole, leaves and/or roots. In a particular embodiment, the NP is targeted to the apoplast, e.g., as described in Example V, infra. Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized. See also, the section entitled "Expression With Chloroplast Targeting" in Example 37 of U.S. Pat. No. 5,639,949.

Other gene products are localized to other organelles such as the mitochondrion and the peroxisome (e.g. Unger et al. Plant Molec. Biol. 13: 411-418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting cellular protein bodies has been described by Rogers et al. (Proc. Natl. Acad. Sci. USA 82: 6512-6516 (1985)).

In addition, sequences have been characterized which cause the targeting of gene products to other cell compartments. Amino terminal sequences are responsible for targeting to the ER, the apoplast, and extracellular secretion from aleuron cells (Koehler & Ho, Plant Cell 2: 769-783 (1990)). Additionally, amino terminal sequences in conjunction with carboxy terminal sequences are responsible for vacuolar targeting of gene products (Shinshi et al. Plant Molec. Biol. 14: 357-368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site, and the fusion constructed should take into account any amino acids after the cleavage site which are required for cleavage. In some cases this requirement may be fulfilled by the addition of a small number of amino acids between the cleavage site and the transgene ATG or, alternatively, replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by Bartlett et al. In: Edelmann et al. (Eds.) Methods in Chloroplast Molecular Biology, Elsevier pp 1081-1091 (1982) and Wasmann et al. Mol. Gen. Genet. 205: 446-453 (1986). These construction techniques are well known in the art and are equally applicable to mitochondria and peroxisomes.

The above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

3.2 Construction Of Plant Transformation Vectors

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259-268 (1982); Bevan et al., Nature 304:184-187 (1983)), the bar gene, which confers resistance to the herbicide phosphinothricin (White et al., Nucl. Acids Res 18: 1062 (1990), Spencer et al. Theor. Appl. Genet. 79: 625-631 (1990)), the hph gene, which confers resistance to the antibiotic hygromycin (Blochinger & Diggelmann, Mol Cell Biol 4: 2929-2931), and the dhfr gene, which confers resistance to methatrexate (Bourouis et al., EMBO J. 2(7): 1099-1104 (1983)), the EPSPS gene, which confers resistance to glyphosate (U.S. Pat. Nos. 4,940,935 and 5,188,642), the mannose-6-phosphate isomerase gene, which provides the ability to metabolize mannose (U.S. Pat. Nos. 5,767,378 and 5,994,629), and the cah gene (U.S. Pat. No. 6,268,547).

3.2.1. Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

a. pCIB200 and pCIB2001

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446-455 (1985)) allowing excision of the tetracycline-resistance gene, followed by insertion of an AccI fragment from pUC4K carrying an NPTII (Messing & Vierra, Gene 19: 259-268 (1982): Bevan et al., Nature 304: 184-187 (1983): McBride et al., Plant Molecular Biology 14: 266-276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153-161 (1987)), and the XhoI-digested fragment are cloned into SalI-digested pTJS75kan to create pCIB200 (see also EP 0 332 104, example 19). pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

b. pCIB10 and Hygromycin Selection Derivatives Thereof.

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153-161 (1987)). Various derivatives of pCIB10 are constructed which incorporate the gene for hygromycin B phosphotransferase described by Gritz et al. (Gene 25: 179-188 (1983)). These derivatives enable selection of transgenic plant cells on hygromycin only (pCIB743), or hygromycin and kanamycin (pCIB715, pCIB717).

3.2.2 Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-Agrobacterium transformation is described.

a. pCIB3064 pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 by away from the unique SalI site and 101 and 42 by away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 is obtained from the John Innes Centre, Norwich and the a 400 by SmaI fragment containing the bar gene from *Streptomyces viridochromogenes* is excised and inserted into the HpaI site of pCIB3060 (Thompson et al. EMBO J. 6: 2519-2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

b. pSOG19 and pSOG35 pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 by of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

3.2.3 Vector Suitable for Chloroplast Transformation

For expression of a nucleotide sequence of the present invention in plant plastids, plastid transformation vector pPH143 (WO 97/32011, example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

3.3 Plant Transformation, Regeneration and Propagation 3.3.1 Generally

Methods for transformation and regeneration of both monocotyledonous and dicotyledonous plant cells is well known. Suitable methods for transformation include electroporation of plant protoplasts, liposome-mediated transformation, polyethylene glycol (PEG) mediated transformation, transformation using viruses, micro-injection of plant cells, micro-projectile bombardment of plant cells, vacuum infiltration, use of Ti plasmid vectors, and transformation mediated by use of bacteria from genus *Agrobacterium* (e.g., *Agrobacterium tumefaciens*). For example, have been utilized for the delivery of foreign DNA, as well as direct DNA uptake, liposomes, electroporation, microinjection, and microprojectiles. In addition, bacteria from the can be utilized to transform plant cells.

Methods for regeneration of plants are also well known in the art: Normally, regeneration will be involved in obtaining a whole plant from the transformation process. The term "transgenote" refers to the immediate product of the transformation process and to resultant whole transgenic plants. The term "regeneration" as used herein, means growing a whole plant from a plant cell, a group of plant cells, a plant part or a plant piece (e.g. from a protoplast, callus, or tissue part). Plant regeneration from cultural protoplasts is described in Evans et al., "Protoplasts Isolation and Culture," HANDBOOK OF PLANT CELL CULTURES 1: 124-176 (MacMillan Publishing Co. New York 1983); M. R. Davey, "Recent Developments in the Culture and Regeneration of Plant Protoplasts," Protoplasts, (1983)—Lecture Proceedings, pp. 12-29, (Birkhauser, Basal 1983); P. J. Dale, "Protoplast Culture and Plant Regeneration of Cereals and Other Recalcitrant Crops," Protoplasts (1983)—Lecture Proceedings, pp. 31-41, (Birkhauser, Basel 1983); and H. Binding, "Regeneration of Plants," Plant Protoplasts, pp. 21-73, (CRC Press, Boca Raton 1985).

Regeneration from protoplasts varies from species to species of plants, but generally a suspension of transformed protoplasts containing copies of the exogenous sequence is first made. In certain species embryo formation can then be induced from the protoplast suspension, to the stage of ripening and germination as natural embryos. The culture media will generally contain various amino acids and hormones, such as auxin and cytokinins. It is sometimes advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable. Regeneration also occurs from plant callus, explants, organs or parts. Transformation can be performed in the context of organ or plant part regeneration. See, Methods in Enzymology, vol. 118; and Klee et al., 1987 *Annual Review of Plant Physiology* 38:467-486.

Suitable plants for transformation of a vector expressing NP polypeptides include any plant that can be genetically modified (e.g., by protoplast transformation techniques), including both monocotyledonous and dicotyledonous plants. Exemplary plants include, without limitation, those described elsewhere herein (e.g., Section 2, supra).

33.2 Representative Techniques for Transforming Dicotyledonous Plants, Monocotyledonous Plants, and Plastids a. Transformation of Dicotyledons Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g. pCIB200 or pCIB2001) to an appropriate *Agrobacterium* strain which may depend of the complement of vir genes carried by the host *Agrobacterium* strain either on a co-resident Ti plasmid or chromosomally (e.g. strain CIB542 for pCIB200 and pCIB2001 (Uknes et al. Plant Cell 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Höfgen & Willmitzer, Nucl. Acids Res. 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050; 5,036,006; and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

b. Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093-1096 (1986)).

Patent Applications EP 0 292 435, EP 0 392 225, and WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603-618 (1990)) and Fromm et al. (Biotechnology 8: 833-839 (1990)) have published techniques for transformation of A188-derived maize line using particle bombardment. Furthermore, WO 93/07278 and Koziel et al. (Biotechnology 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379-384 (1988); Shimamoto et al. Nature 338: 274-277 (1989); Datta et al. Biotechnology 8: 736-740 (1990)). Both types are also routinely transformable using particle bombardment (Christou et al. Biotechnology 9: 957-962 (1991)). Furthermore, WO 93/21335 describes techniques for the transformation of rice via electroporation.

Patent Application 0 332 581 describes techniques for the generation, transformation and regeneration of Pooideae protoplasts. These techniques allow the transformation of *Dac-*

*tylis* and wheat. Furthermore, wheat transformation has been described by Vasil et al. (Biotechnology 10: 667-674 (1992)) using particle bombardment into cells of type C long-term regenerable callus, and also by Vasil et al. (Biotechnology 11: 1553-1558 (1993)) and Weeks et al. (Plant Physiol. 102: 1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, Physiologia Plantarum 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

c. Transformation of Plastids

Seeds of *Nicotiana tabacum* c.v. 'Xanthi nc' are germinated seven per plate in a 1" circular array on T agar medium and bombarded 12-14 days after sowing with 1 µm tungsten particles (M10, Biorad, Hercules, Calif.) coated with DNA from plasmids pPH143 and pPH145 essentially as described (Svab, Z. and Maliga, P. (1993) PNAS 90, 913-917). Bombarded seedlings are incubated on T medium for two days after which leaves are excised and placed abaxial side up in bright light (350-500 mmol photons/m2/s) on plates of RMOP medium (Svab, Z., Hajduldewicz, P. and Maliga, P. (1990) PNAS 87, 8526-8530) containing 500 µg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) Molecular Cloning: A Laboratory Manual, Cold Spring Harbor. Laboratory, Cold Spring Harbor). BamHI/EcoRI-digested total cellular DNA (Mettler, I. J. (1987) Plant Mol Biol Reporter 5, 346-349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on spectinomycin-containing MS/IBA medium (McBride, K. E. et al. (1994) PNAS 91, 7301-7305) and transferred to the greenhouse.

3.3.3 Regeneration and Propagation

In vegetatively propagated crops, the mature transgenic plants are propagated by the taking of cuttings or by tissue culture techniques to produce multiple identical plants for trialling, such as testing for production characteristics. Selection of desirable transgenotes is made and new varieties are obtained thereby, and propagated vegetatively for commercial sale.

In seed propagated crops, the mature transgenic plants are self crossed to produce a homozygous inbred plant. The inbred plant produces seed containing the gene for the newly introduced foreign gene activity level. These seeds can be grown to produce plants that would produce the selected phenotype. The inbreds according to this invention can be used to develop new hybrids. In this method a selected inbred line is crossed with another inbred line to produce the hybrid. The offspring resulting from the first experimental crossing of two parents is known in the art as the F1 hybrid, or first filial generation. Of the two parents crossed to produce F1 progeny according to the present invention, one or both parents can be transgenic plants. Parts obtained from the regenerated plant, such as flowers, seeds, leaves, branches, fruit, and the like are covered by the invention, provided that these parts comprise cells which have been so transformed. Progeny and variants, and mutants of the regenerated plants are also included within the scope of this invention, provided that these parts comprise the introduced DNA sequences. Progeny and variants, and mutants of the regenerated plants are also included within the scope of this invention.

The plants obtained via transformation with a nucleic acid sequence of the present invention can be any of a wide variety of plant species, including those of monocots and dicots; however, the plants used in the method of the invention are preferably selected from the list of agronomically important target crops set forth herein. The expression of a gene of the present invention in combination with other characteristics important for production and quality can be incorporated into plant lines through breeding. Breeding approaches and techniques are known in the art. See, for example, Welsh J. R., Fundamentals of Plant Genetics and Breeding, John Wiley & Sons, NY (1981); Crop Breeding, Wood D. R. (Ed.) American Society of Agronomy Madison, Wis. (1983); Mayo O., The Theory of Plant Breeding, Second Edition, Clarendon Press, Oxford (1987); Singh, D. P., Breeding for Resistance to Diseases and Insect Pests, Springer-Verlag, NY (1986); and Wricke and Weber, Quantitative Genetics and Selection Plant Breeding, Walter de Gruyter and Co., Berlin (1986).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damage caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding, which aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties, different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical, or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, that for example, increase the effectiveness of conventional methods such as herbicide or pesticide treatment or allow one to dispense with said methods due to their modified genetic properties. Alternatively new crops with improved stress tolerance can be obtained, which, due to their optimized genetic "equipment" yield harvested product of better quality than products that were not able to tolerate comparable adverse developmental conditions.

In seed production, germination quality and uniformity of seeds are essential product characteristics. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides, or mixtures thereof. Customarily used protectant coatings comprise compounds such as captan, carboxin, thiram (TMTD®), methalaxyl (APRON®), and pirimiphos--methyl (ACTELLIC®). If desired, these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

4. Therapeutic Use of NP Polypeptides

The antifungal polypeptides and compositions of the invention can be used to treat or prevent fungal infections in animals, e.g., mammals such as humans. Treatment and prevention, with regard to an actual or potential fungal infection, refers broadly to alleviation or amelioration of one or more symptoms of fungal infection, diminishment of extent of disease, stabilized (i.e., not worsening) state of disease, preventing spread of disease, delay or slowing of disease progression, amelioration or palliation of the disease state. The NP polypeptide composition may be administered by the systemic, local or topical route. For administration, the NP polypeptides of the invention can be combined with a pharmaceutically acceptable vehicle. The particular mode of administration and dosage may be determined according to the criteria generally taken into account in establishing a treatment appropriate for an animal or human patient, such as (in the case of a patient) their age and body weight.

In an alternative embodiment, the polypeptides are incorporated into soap, shampoo, lotions or the like, for use on an animal or by a human.

5. Examples

5.1 Example I

Expression and Purification of NPs

Novel polynucleotides were prepared by in vitro recombination of (a) nucleic acids encoding naturally occurring plant defensins and/or (b) nucleic acids encoding mutants of naturally occurring plant defensins and/or (c) polynucleotides produced in (a) and/or (b). To characterize the antifungal polynucleotides, the encoded polypeptides were expressed and purified as described in this example, and antifungal activity determined as described in Example II.

Expression of biologically functional NPs and wild-type defensins was achieved by producing a fusion protein that included a maltose-binding protein (MBP) and an NP or defensin. DNA encoding the NP/defensin was fused to the C-terminus of the MelE gene in the *E. coli* expression vector pMAL (New England Biolabs; see, Guan et al., 1987, *Gene* 67:21-30; and Maina et al., 1988, *Gene* 74:365-73). Sequences encoding the cleavage site of proteases Factor Xa or Genenase I were also incorporated between the genes of MBP and NP/defensin, so that NP/defensin could be cleaved from the fusion protein without additional extra amino acids at its N-terminus. To increase the efficiency of purification of biologically active proteins, a histidine tag was also added to the N-terminus of MBP. The vectors used for expression and purification of the defensins and NPs is shown in FIG. 1.

The constructed plasmid vector was transformed into cells of *E. coli* XL-1 Blue. Transformants were grown in 2YT medium containing 50 µg/ml carbenicillin to a cell density of $O.D._{600}$=0.6-0.9. Expression of the fusion protein was induced by addition of IPTG into the culture to a final concentration of 1 mM. Cells were grown for 4-16 hours to saturation before harvesting.

Cells were harvested by centrifugation and then lysed with B-PER reagent (Pierce Chemicals, Rockford, Ill. cat. no 78260) to obtain the fraction of soluble proteins. (Alternatively, any *E. coli* lysis buffer can be used to lyse cells). The fusion protein was purified from the cell lysate supernatant utilizing the histidine tag. Cell lysate was incubated with Ni-NTA agarose resins for 20 minutes to 1 hour. The resins were washed with 5 mM Tris buffer pH 8 to remove all unbound proteins. 10 mM of 2-mercaptoethanol was included in the lysis and washing buffers (5 mM Tris pH 8) to allow partial refolding of the NP proteins. Elution of the bound fusion protein was done with: 20 mM Tris pH 8, 2 mM CaCl$_2$, 100 mM KCl, 20-40 mM histidine. The use of histidine in the elution buffer allowed the purified fusion protein to be used for antifungal assays directly after cleavage by proteases.

To release the NP protein, the purified fusion protein was incubated with Factor Xa or Genenase I at room temperature for 8 to 24 hours (using approximately 1 μg protein per 50 μg fusion protein. The cleaved protein sample was then used in antifungal activity assays described in Example II. This method resulted in high level production of the fusion protein with yield of up to 60 mg/L of culture (corresponding to 5-6 mg NP protein/L culture).

5.2 Example II

Antifungal Activity Assay and Results

Pathogens *Fusarium graminearum* and *Septoria tritici* were cultured on potato dextrose agar or V8 agar at 25° C. The antifungal activity assay of NP polypeptides and defensins was done as described by Terras et al., 1992, *J. Biological Chemistry* 267:15301-309, with modifications. Agar plates of the fungal culture were flooded with 2×SMF medium (SMF medium: 2.5 mM K$_2$HPO$_4$, 50 μM MgSO$_4$, 5 μM FeSO$_4$, 0.1 μM CoCl$_2$, 0.1 μM CuSO$_4$, 2 μM Na$_2$MoO$_4$, 0.5 μM H$_3$BO$_3$, 0.1 μM KI, 0.5 μM ZnSO$_4$, 0.1 μM MnSO$_4$, 1 mM CaCl$_2$, 50 mM KCl, 20 g/l glucose, 2 g/l asparagine, 40 g/l methionine, 2 mg/l myo-inositol, 0.2 mg/l biotin, 1 mg/l thiamine-HCl, 0.2 mg/l pyridoxin-HCl). The suspension was filtered through 3 layers of sterile cheesecloth and then diluted to a concentration of 10$^4$ to 10$^5$ spores/ml. The fungal spores were germinated in a 96 well microtiter plate at 25° C. for 8 to 18 hours.

Wild-type defensin protein samples were mixed with an equal volume of germinated spores and incubation was continued. The wild-type defensins used were *Raphanus sativus* Antifungal protein 2 (Rs-AFP2) [see, e.g., WO 93/05153] and *Dahlia merckii* Antifungal protein 1 (Dm-AMP1) [see, e.g., WO 93/05153]. The inhibitory activity of each wild-type defensin protein sample was measured and recorded after 16 to 96 hours of incubation with the fungal cultures by microscopy or absorbance of O.D. 595 as described in Terras et al., 1992, *J. Biological Chemistry* 267:15301-309. Briefly, plates were scored every 24 hour for inhibition either visually or via a spectrophotometer. The antifungal activity of NP polypeptides was determined in the same manner. Wells with NP polypeptide were examined for growth inhibition, compared with wells containing no NP to determine if inhibition was present, and compared to wells containing Rs-AFP2 or Dm-AMP1. To determine the antifungal activity of NPs compared to wild-type defensins, the NP polypeptides were subjected to serial dilutions and the activity of the diluted NP polypeptide compared to that of the wild type defensins. The results of these assays are reported in Table 2.

5.3 Example III

Antifungal Activity Assay and Results Using HPLC-Purified NPs

Additional assays were conducted with HPLC-purified NPs. Recombinantly expressed NPs prepared as in Example I were purified by Ni-NTA agarose chromatography followed by RP-HPLC purification. The concentration of the HPLC-purified NP protein was determined by capillary electrophoresis (CE). CE was carried out on a 100 cm (91.5 cm effective length)×50 μm ID polyimide coated fused silica capillary (Composite Metal Services; Hallow, Worcestershire, UK) at 20° C. The electrolyte was aqueous di-sodium hydrogen orthophosphate (20 mM), containing CTAB (2 mM), adjusted to pH 6.5 with orthophosphoric acid. The capillary was flushed with electrolyte for 3 min between injections. Separations were performed at an applied voltage of 30 kV (negative polarity). Protein samples (2 mg mL−1) were prepared in de-ionized water. Injections were made hydrodynamically using a pressure of 50 mbar for 20 s. Detection was by UV at 280 nm with a bandwidth of 4 nm. For quantification, a tryptophan standard (0.1 mg ml−1) was used in triplicate at the start of the run and as a bracketing standard after every five samples. Samples were then quantified against the average corrected area of the tryptophan standard. Protein samples were normalized and assayed for antifungal activity as described above. (Assays were conducted using the pathogen, *Mycosphaerella fijiensis* as well as *F. graminearum* and *S. tritici*).

NP polypeptides had antifungal activity against *Fusarium graminearum* and/or *Septoria tritici* and/or *Mycosphaerella fijiensis*, as shown in Table 4. In Table 4, antifungal activity compared to DmAMP1 is shown, with + indicating 1- to 5-fold improvement compared to DmAMP1; ++ indicating >5- to 10-fold improvement; and +++ indicating >10-fold improvement.

The improvement of activity ranged from 1×-60× over DmAMP1. While some clones had increased activity against one or two of the fungal pathogens, the majority of the shuffled defensins showed improvement in activities against all pathogens tested.

5.4 Example IV

Infiltration Assays for Antifungal Activity

This example describes an in vivo assay for antifungal activity or other antimicrobial activity. This assay, referred to as an "infiltration assay' or 'in planta assay' is carried out by infiltrating NP protein (e.g., using a syringe, vacuum or via the vascular system of the plant) into a plant part. Typically, the concentration of NP introduced into the plant is similar to that the level of protein that would be expressed in a plant transgenic for the NP). The plant is then infected with a pathogen and the effect of the NP on resistance is determined. By way of illustration, the assay is described for use in wheat, although it will be apparent that the assay can be used in a variety of plants with modifications evident to the ordinarily skilled practitioner.

Wheat head in planta assay to assess antimicrobial activity

1. Harvest wheat head(s) from plants at the onset of anthesis (anthers visible in the center of the head and have a yellow color) leaving approximately 10 cm of the culm. It is essential that detached wheat heads are at the correct flowering stage.

2. Place the wheat head in a 10 ml plastic tube containing 300 micrograms of the test protein (NP) dissolved in water.

3. Following uptake of the protein solution, add water to the tube so as to maintain at least 2 ml in the tube at all times.

4. 12 hours after protein uptake, inoculate the plant with 5-10 μl of a fungal spore solution between the lemma and the palea of one spikelet in the middle of the detached wheat head. An exemplary solution contains *Fusarium graminearum* spores at a concentration of 10$^4$ spores/ml.

5. After inoculation incubate at 100% relative humidity (RH) and 16° C. for 48 hours with an 8 hour day length (following inoculation start with initial 16 hours of darkness).

6. After the initial 48 hours incubation change conditions to 70% RH and 21° C. for 16 h of light and 95% RH and 16° C. for 8 h of darkness.

7. Score plants every 2 days for progression of the disease above and below the point of inoculation.

A variety of disease symptoms can be scored. The ability of the fungus to grow within the plant, the spread of symptoms from the inoculation site, and the accumulation of mycotoxin can be measured. Disease symptoms (e.g., necrosis and/or bleaching of the spikelet) can be recorded and glumes from the rated spikelets then plated to detect the presence of the fungus and the remainder of the spikelet tested for the presence and level of mycotoxin. An exemplary assay is also described in Sanyal et al. "Measuring differences in the ability of strains of *Fusarium graminearum* to spread within wheat heads" published at http://www.cdl.umn.edu/posters/posters.html 5.5 Example V Generation of NP-Transgenic Wheat This example shows the construction of constructs suitable for generating transgenic plants expressing (1) naturally occurring plant defensins or (2) NP polypeptides, and the transformation of wheat using bombardment and the Phosphomannose Isomerase Gene, pmi, as a selectable marker for selection on mannose.

A. Construction of Transgene

The NP polypeptide DNA sequence was cloned into an expression cassette comprising the ubiquitin promoter to drive expression (UBImod), a monocot optimized PR1a signal peptide (PR1a) to allow secretion into the apoplast and a nopaline synthase (NOS) terminator to terminate transcription. The NP/defensin is one of either L2-12, L2-52, L3-135, L6-28 and the wildtype defensins RsAFP2 and DmAMP1. PR1a signal peptide is a published sequence from PR1a (tobacco). The nucleotide sequence was optimized for expression in wheat by altering the codon usage. The monocot optimized PR1a sequence was: MGFVLFSQLPSFLLVSTLLLFLVISHSCRA (amino acid) (SEQ ID NO: 15); atgggettcgtgctgttcagccagetgc-ccagettectgctggtgagcaccctgctgctgttcctggtgatcagccacaget gccgcgcc (nucleic acid) (SEQ ID NO: 16). The transgene is structured as follows: UBImod-PR1a—NP/defensin-NOS. The selectable marker, PMI (*E. coli* manA) was also cloned into an expression cassette comprising the ubiquitin promoter to drive expression (UBI), the manA gene and the 35S terminator to terminate transcription. The transgene is structured as follows: UBI-manA-35S. (An alternative terminator would be the nopaline synthase (NOS) terminator in which case, the transgene would be structured as follows: UBI-manA-NOS.)

Fragments containing these transgenes are prepared as described in Christensen et al., 1992 (Plant Mol. Biol. 18:675-689). DNA is extracted using the Qiagen® Mega preparation kit (Valencia, Calif.). Typically, 250 μg of plasmid DNA is digested in a final volume of 500 μl and then run on 0.8% agarose gel in TBE buffer. The band containing the fragment DNA is cut from the gel and electroeluted for 3 hrs at 200 volts using Elutrap® (Schleicher and Schuell, Keene, N.H.). The DNA is then precipitated and resuspended in 100 μl of TE buffer to a final concentration of 1 μg/μl.

B. Plant Material

Wheat immature embryos (IES), 0.75-1.25 mm diameter, from the spring variety Fielder are aseptically isolated from wheat spikes approximately 14 days after pollination. The IES are placed on callus induction medium with the scutellum facing up and the embryonic axes in contact with the medium. The callus induction medium, 3MS3S, contains Murashige and Skoog (MS) salts (Murashige & Skoog, 1962, *Physiol Plant* 15:473-97) and vitamins, 30 g/l sucrose, 3 mg/l 2,4-D, 300 mg/l glutamine and 150 mg/l asparagine. The IES are cultured in the dark at 25° C. for approximately one week then evaluated for embryogenic response as indicated by swelling of the scutellar tissue and the formation of glossy, smooth, pre-globular, structures. Only high quality, responding embryos are used for transformation.

C. Transformation

Approximately 30 to 60 wheat IES with embryogenic responses, are arranged in a 2.5 cm diameter circle with the scutellum facing upward. Wheat tissues are exposed to a high osmotic (plasmolysis) treatment approximately four hours prior to gene delivery, (and roughly 16 hours post bombardment).

Fragment or plasmid DNA is precipitated onto <1μ gold microcarriers generally as described in Barcelo and Lazzeri, 1995, *Transformation of cereals by microprojectile bombardment of immature inflorescence and scutellum tissue*. In: Jones H, ed. METHODS IN MOLECULAR BIOLOGY: PLANT GENE EXPRESSION PROTOCOLS, Totowa, N.J.: Human Press Inc, 113-123. For gene delivery, the ratio of GOI (gene of interest) DNA to selectable marker (SM) DNA is about 1:1 when the GOI is in the form of a fragment and about 1.5:1 when the GOI is in the form of a plasmid; the amount of DNA used is variable (e.g., 0.4-2 ug). Genes are delivered to the target tissue cells using the PDS-1000He Biolistics™ device. The settings on the device are as follows: 8 mm between the rupture disk and the macrocarrier, 10 mm between the macrocarrier and the stopping screen and 7 cm between the stopping screen and the target. The target plates are shot twice using 1100-psi rupture disks. To reduce tissue damage from the shock wave of the helium blast, a stainless steel mesh, 200 openings per linear inch horizontally and vertically (McMaster-Carr, New Brunswick, N.J.), is placed between the stopping screen and the target tissue.

After gene delivery, wheat tissues are incubated in the dark at 25° C. After approximately 24 hours of plasmolysis, bombarded wheat embryos are moved to 3MS3S medium and incubated without subculture in the dark for four weeks for continued callus initiation.

D. Selection and Regeneration

The embryogenic tissue that develops during the four-week initiation period is separated from the non-embryogenic tissue and placed on a regeneration/selection medium. The regeneration/selection medium, NG, is 3MS3S without 2,4-D but with 1 mg/l gibberellic acid (GA3) and 1 mg/l napthele-neacetic acid (NAA). For pmi selection in wheat, the carbohydrate source in the NG medium is altered to contain 10 g/l mannose and 5 g/l sucrose. Following growth in the light at 24° C. for two weeks, the tissue is transferred to MS medium with 15 g/l sucrose plus 10 g/l mannose, 300 mg/l glutamine and 150 mg/l asparagine (MS1.5M 1S). Some shoots continued to regenerate on this medium while others stopped growing. Vigorously growing shoots are transferred to larger containers on medium consisting of ½ strength MS major and minor salts (2.15 g/l powder, Sigma, St. Louis, Mo., USA), full strength MS vitamins and 15 g/l mannose.

5.6 Example VI

Generation of Transformed Lines

Wheat plants transformed with polynucleotides encoding NPs (L3-135, L6-28, L2-12 and L2-52) or wildtype defensins (Dm-AMP1 or Rs-AFP2) were made as described in Example V.

5.7 Example VII

In Planta Efficacy Assessment of a Subset of NPs

Wheat plants transformed with either NPs (L3-135, L6-28, L2-12 and L2-52) or wildtype defensins (Dm-AMP1 or Rs-AFP2) were assessed for their ability to control *Fusarium graminearum*. Plants were point inoculated with *F. graminearum* and disease severity measure by spread of the infection from the point of inoculation in a *Fusarium* head blight assay. Disease spread was then compared to NP or wildtype defensin expression level in the infected plant to determine the level of protection.

The *Fusarium* head blight assay for transgenic wheat plants was carried out as follows: The uppermost fully formed spikelet from the primary head at mid-anthesis was inoculated with 20λ of *F. graminearum* spores (100,000 spores/mL). Following inoculation, plants were maintained in the dark at 16° C. and 100% relative humidity (RH) for, 72 hours and then transferred to the glasshouse and maintained at a daily schedule of 16 hours at 24° C. and 70% RH with light and 8 hours at 16° C. and 95% RH in darkness. Disease was assessed as spread from the inoculated spikelet and monitored at 10 and 17 days post-inoculation.

Quantitative competition ELISA was used to assess NP and defensin concentration in planta. Assay plates were coated with the appropriate NP and competed with NP in a homogenised leaf from the transgenic plant for binding to a polyclonal antibody raised against the wildtype defensin. Plates were washed and antibody bound to the immobilised peptide was detected using an enzyme labelled secondary antibody and the appropriate substrate. Signal in the assay was inversely proportional to the concentration of the NP in the plant sample, as confirmed in control experiments carried out using purified and quantified wild type and variant defensins as well as spiked assays using a plant background. Low expression levels were found in the L6-28 construct, possibly due to production of mRNA that was not very stable in plants. Expression levels for L2-52 and L2-12 were comparable to the Rs-AFP2 wild type.

The extent of disease spread was compared to NP or wildtype defensin expression level in the infected plant. The NP (L3-135) displays a clear inverse correlation between expression level and disease spread where the wildtype defensin expression has no effect on disease spread (FIGS. 2A and 2C). This indicates that high levels of expression of the NP results in improved resistance to *F. graminearum*, whereas high levels of expression of the wildtype defensin had no obvious effect on resistance. A protective effect was also seen for L2-12 transformed lines (FIG. 2B). No clear correlation was seen in the L6-28 and L2-52 transformed lines.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

TABLE 1

| | |
|---|---|
| NP-Dm: | amino-(N/E/K)-LCE-(K/R)-AS-(K/L)-TW-(S/T)-GNCGNT-(G/K)-(H/N)-C-(D/N)-(N/T)-(Q/K)-C-(K/R)-(S/N)-WE-(G/S/I)-A-(A/K)-HGACH-(V/K)-R-(N/S)-GK-(H/W)-(M/K)-CFCYFNC-carboxy (SEQ ID NO: 1) |
| NP-Rs: | amino-Q-(K/Q)-LC-(E/Q)-(R/K)-PS-(G/R)-TWSGVC-(G/M)-N-(N/S)-N-ACKNQCI-(R/N)-LE-(K/G)-A-(K/R)-HGSCNY-(R/V)-FPAHKCICY-(F/V)-PC-carboxy (SEQ ID NO: 2) |
| NP-DIV1 | amino-(K/N/Q)-LCE-(R/K)-(A/P)-S-(Q/K)-TW-(T/S)-G-(H/N)-CGNTKHCD-(K/N)-QC-(K/R)-(N/S)-WE-(G/K)-A-(K/A)-HGACH-(V/K)-R-(N/S)-GK-(W/H)-KCFCYF-(N/S)-C-carboxy (SEQ ID NO: 3) |
| NP-DIV2 | amino-V-(K/N/Q)-LCE-(R/K)-(A/P)-S-(Q/K)-TW-(T/S)-G-(H/N)-CGNTKHCD-(K/N)-QC-(K/R)-(N/S)-WE-(G/K)-A-(K/A)-HGACH-(V/K)-R-(N/S)-GK-(W/H)-KCFCYF-(N/S)-C-carboxy (SEQ ID NO: 4) |
| NP-DIV3 | amino-G-V-(K/N/Q)-LCE-(R/K)-(A/P)-S-(Q/K)-TW-(T/S)-G-(H/N)-CGNTKHCD-(K/N)-QC-(K/R)-(N/S)-WE-(G/K)-A-(K/A)-HGACH-(V/K)-R-(N/S)-GK-(W/H)-KCFCYF-(N/S)-C-carboxy (SEQ ID NO: 5) |
| NP-DIV4 | amino-D-G-V-(K/N/Q)-LCE-(R/K)-(A/P)-S-(Q/K)-TW-(T/S)-G-(H/N)-CGNTKHCD-(K/N)-QC-(K/R)-(N/S)-WE-(G/K)-A-(K/A)-HGACH-(V/K)-R-(N/S)-GK-(W/H)-KCFCYF-(N/S)-C-carboxy (SEQ ID NO: 6) |
| NP-Dm* | amino-(N/E)-L-C-E-(K/R)-A-S-K-T-W-(T/S)-G-N-C-G-N-T-K-H-C-D-(T/N)-Q-C-(K/R)-(N/S)-W-E-(G/S)-A-(A/K)-H-G-A-C-H-(V/R)-R-(S/N)-G-K-(H/W)-K-C-F-C-Y-F-N-C-carboxy (SEQ ID NO: 10) |
| NP-DIV4* | amino-D-G-V-K-L-C-E-(R/K)-(A/P)-S-(K/Q)-T-W-(S/T)-G-(H/N)-C-G-N-T-K-H-C-D-(KN/T)-Q-C-(K/R)-(N/S)-W-E-(K/G)-A-(A/K)-H-G-A-C-H-(V/K)-R-(N/S)-G-K-W-K-C-F-C-Y-F-N-C-carboxy (SEQ ID NO: 11) |

TABLE 2

Table 2A: Sequences of clones from Rs-AFP2 based libraries:

| | Activity | | | |
|---|---|---|---|---|
| | (1) | (2) | | |
| L2-04 | + | + | QKLCERPSGTWSGVCGNNNACKNQCIRLEKARHGSCNYRFPAHKCICYFPC | (SEQ ID NO: 20) |
| L2-12 | ++ | + | QKLCQKPSRTWSGVCGNNNACKNQCIRLEKARHGSCNYVFPAHKCICYFPC | (SEQ ID NO: 21) |
| L2-23 | + | + | QKLCQRSSRTWSGVCGNSNACKNQCIRLEGARHGSCNYVFPAHKCICYFPC | (SEQ ID NO: 22) |
| L2-32 | + | + | QKLCQRPSRTWSGVCGNSNACKNQCINLEGAKHGSCNYRFPAHKCICYVPC | (SEQ ID NO: 23) |
| L2-20 | + | + | QKLCERPSGTWSGVCGNSNACKNQCIRLEKARHGSCNYRFPAHKCICYFPC | (SEQ ID NO: 24) |

TABLE 2-continued

Table 2A: Sequences of clones from Rs-AFP2 based libraries:

| | Activity | | | |
|---|---|---|---|---|
| | (1) | | (2) | |
| L2-52 | + | + | QKLCQRPSGTWSGVCMNNNACKNQCIRLEKAKHGSCNYVFPAHKCICYFPC | (SEQ ID NO: 25) |
| L2-05 | + | + | QKLCERPSRTWSGVCGNSNACKNQCINLEGARHGSCNYRFPAHKCICYFPC | (SEQ ID NO: 26) |
| L2-21 | + | + | QKLCERPSGTWSGVCGNSNACKNQCIRLEGARHGSCNYRFPAHKCICYFPC | (SEQ ID NO: 27) |
| L2-26 | + | + | QKLCEKPSGTWSGVCGNSNACKNQCIRLEKARHGSCNYRFPAHKCICYFPC | (SEQ ID NO: 28) |
| L2-28 | + | + | QKLCQRPSGTWSGVCGNNNACKNQCIRLEGAKHGSCNYIFPAHKCICYFPC | (SEQ ID NO: 29) |
| L2-08 | + | + | QKLCQRPSRTWSGVCGNSNACKNQCINLEKARHGSCNYRFPAHKCICYFPC | (SEQ ID NO: 30) |
| L2-49 | + | + | QKLCQRSSRTWSGVCGNNNACKNQCIRLEGARHGSCNYRFPAHKCICYFPC | (SEQ ID NO: 31) |
| L2-55 | + | + | QKLCQRPSGTWSGVCGNNNACKNQCIRLEGARHGSCNYRFPAHKCICYFPC | (SEQ ID NO: 32) |
| L2-54 | + | + | QKLCQRPSRTWSGVCMNNNACKNQCIRLEGARHGSCNYRFPAHKCICYFPC | (SEQ ID NO: 33) |
| L2-53 | 0 | + | QKLCERPSGTWSGVCMNSNACKNQCIRLEGARHGSCNYVFPAHKCICYFPC | (SEQ ID NO: 34) |
| L2-30 | + | + | QKLCQRPSRTWSGVCGNSNACKRQCIRLEKARHGSCNYRFPAHKCICYFPC | (SEQ ID NO: 35) |
| L2-35 | + | + | QKLCQKPSRTWSGVCGNSNACKNQCIRLEKARHGSCNYVFPAHKCICYVPC | (SEQ ID NO: 36) |
| L2-36 | + | + | QKLCQRPSGTWSGVCGNNNACKNQCINLEGARHGSCNYRFPAHKCICYFPC | (SEQ ID NO: 37) |
| L2-57 | + | + | QKLCQRPSGTWSGVCMNNNACKNQCIRLEKARHGSCNYRFPAHKCICYFPC | (SEQ ID NO: 38) |
| L2-58 | + | + | QKLCQRPSRTWSGVCGNNNACKNQCIRLEKARHGSCNYRFPAHKCICYVPC | (SEQ ID NO: 39) |
| L2-45 | + | + | QKLCERSSRTWSGVCGNSNACKNQCIRLEGARHGSCNYVFPAHKCICYFPC | (SEQ ID NO: 40) |
| L2-46 | + | + | QKLCQRPSGTWSGVCGNSNACKNQCIRLEGARHGSCNYRFPAHKCICYFPC | (SEQ ID NO: 41) |
| L2-61 | + | + | QKLCQRPSRTWSGVCMNSNACKNQCIRLEKARHGSCNYRFPAHKCICYFPC | (SEQ ID NO: 42) |
| L1-04 | + | + | QQLCQRPSRTWSGVCMNNNACKNQCIRLEGARHGSCNYRFPAHACICYVPC | (SEQ ID NO: 43) |
| L1-01 | + | 0 | QKLCEKPSRTWSGVCGNNNACKNQCIRLEKARHGSCNYRFPAHKCICYVPC | (SEQ ID NO: 44) |
| Consensus | | | QKLCQRPSRTWSGVCGNSNACKNQCIRLEKARHGSCNYRFPAHRCICYFPC | (SEQ ID NO: 8) |

Key: In Tables 2A-C, NP names, sequences, and antifungal activity (measured as described in Examples 1 and 2) is provided. The first antifungal activity value (1) is the antifungal activity of the NP against *Fusarium graminearium*. In Tables 2A and 2C, the second antifungal activity value (2) is the antifungal activity against *Septoria tritici*. In each case, + indicates a 1- to 5-fold improvement in activity compared to a reference defensin protein (DmAMP for Tables 2A and 2C, and Rs-AFP2 for Table 2B); ++ indicates a >5- to 10-fold improvement; and +++ indicates a >10-fold improvement. In Table 2A, "0" indicates no activity detected.

Table 2B: Sequences of clones from Dm-AMP1 based libraries:

| | Activity (1) | | |
|---|---|---|---|
| L3-02 | ++ | NLCERASLTWTGNCGNTKHCDTQCKNWEGAKHGACHVRNGKWKCFCYFNC | (SEQ ID NO: 45) |
| L3-04 | ++ | ELCEKASKTWSGNCGNTKHCDNQCRSWEGAAHGACHKRSGKWKCFCYFNC | (SEQ ID NO: 46) |
| L3-07 | +++ | NLCERASKTWSGNCGNTKHCDTQCRNWEGAKHGACHKRSGKWKCFCYFNC | (SEQ ID NO: 47) |
| L3-100 | + | NLCERASKTWSGNCGNTKHCDDQCKSWEGAAHGACHKRSGKWKCFCYFNC | (SEQ ID NO: 48) |
| L3-102 | + | NLCEKASKTWTGNCGNTKHCDNQCKSWEGAAHGACHVRSGKHMCFCYFNC | (SEQ ID NO: 49) |
| L3-103 | + | KLCERASKTWSGNCGNTKHCDDQCKNWESAAHGACHVRSGNHKCFCYFNC | (SEQ ID NO: 50) |
| L3-105 | + | NLCEKASLTWTGNCGNTKHCDTQCKNWEGAKHGACHVRSGKWKCFCYFNC | (SEQ ID NO: 51) |
| L3-107 | + | NLCEKASLTWTGNCGNTKHCDTQCKNWEGAKHGACHVRNGNHKCFCYFNC | (SEQ ID NO: 52) |

-continued

Table 2B: Sequences of clones from Dm-AMP1 based libraries:

| | Activity (1) | | |
|---|---|---|---|
| L3-110 | + | ELCERASLTWTGNCGNTKHCDTQCKNWEGAAHGACHVCSGKHKCFCYFNC | (SEQ ID NO: 53) |
| L3-111 | + | NLCEKASLTWSGNCGNTKHCDNKCKNWEGAAHGACHKRNGKWKCFCYFNC | (SEQ ID NO: 54) |
| L3-112 | + | NLCERASLTWSGNCGNTKHCDTQCKSWESAKHGACHVRSGKHMCFCYFNC | (SEQ ID NO: 55) |
| L3-115 | + | NLCEKASLTWSGNCGNTRHCDTQCRSWEGAAHGACHVRSGNHKCFCYFNC | (SEQ ID NO: 56) |
| L3-116 | + | KLCERASKTWSGNCGNTKHCDNQCRSWEGAKHGACHVRSGKWMCFCYFNC | (SEQ ID NO: 57) |
| L3-128 | + | NLCERASLTWSGNCGNTKHCDDQCRNWEGAKHGACHVRNGKWKCFCYFNC | (SEQ ID NO: 58) |
| L3-135 | +++ | ELCEKASKTWSGNCGNTKHCDTQCKNWEGAKHGACHVRSGKHKCFCYFNC | (SEQ ID NO: 59) |
| L3-138 | + | ELCEKASKTWSGNCGNTKHCDTKCKNWEGAKHGACHKRNGKWMCFCYFNC | (SEQ ID NO: 60) |
| L3-139 | +++ | ELCEKASKTWTGNCGNTKHCDTQCKNWEGAKHGACHVRNGKHKCFCYFNC | (SEQ ID NO: 61) |
| L3-14 | ++ | NLCERASKTWTGNCGNTGHCDNKCKSWEGAKHGACHVRNGKWMCFCYFNC | (SEQ ID NO: 62) |
| L3-140 | ++ | NLCEKASKTWSGNCGNTKHCDDQCRNWEGAKHGACHVRNGKWKCFCYFNC | (SEQ ID NO: 63) |
| L3-144 | +++ | NLCERASKTWSGNCGNTKHCDTQCKNWEGAKHGACHKRSGKWMCFCYFNC | (SEQ ID NO: 64) |
| L3-147 | ++ | ELCEKASKTWTGNCGNTKHCDNQCKSWEGAAHGACHKRSGKWMCFCYFNC | (SEQ ID NO: 65) |
| L3-27 | ++ | ELCERASKTWSGNCGNTKHCDNQCKSWEGAKHGACHKRSGKHKCFCYFNC | (SEQ ID NO: 66) |
| L3-28 | ++ | NLCERASKTWTGNCGNTKHCDTQCKNWESAKHGACHVRSGKHKCFCYFNC | (SEQ ID NO: 67) |
| L3-30 | ++ | NLCERASKTWSGNCGNTKHCDTQCRNWESAAHGACHKRNGKWKCFYCFNC | (SEQ ID NO: 68) |
| L3-33 | + | NLCERASKTWSGNCGNTGHCNNQCRSWEGAKHGACHVRSGKHKCFCYFNC | (SEQ ID NO: 69) |
| L3-37 | + | NLCERASKTWSGNCGNTKHCDTQCRKWEGAKHGACHKRNGKWMCFCYFNC | (SEQ ID NO: 70) |
| L3-42 | +++ | NLCERASKTWTGNCGNTKHCDTQCKNWEGAKHGACHKRNGKWKCFCYFNC | (SEQ ID NO: 71) |
| L3-45 | + | NLCERASLTWTGNCGNTGHCDTKCRNWEGAKHGACHKPNGKWKCFCYFNC | (SEQ ID NO: 72) |
| L3-46 | ++ | NLCERASKTWTGNCGNTKHCDTKCRSWESAKHGACHKRNGKWKCFCYFNC | (SEQ ID NO: 73) |
| L3-54 | + | NLCEKASKTWTGNCGNTKHCDTQCKSWEGAAHGACHKRSGKWKCFCYFNC | (SEQ ID NO: 74) |
| L3-55 | ++ | NLCEKASKTWTGNCGNTKHCDTQCKSWEGAAHGACHVRSGKHKCFCYFNC | (SEQ ID NO: 75) |
| L3-57 | + | NLCEKASKTWTGNCGNTGHCDTQCRNWEGAKHGACHKRNGKHKCFCYFNC | (SEQ ID NO: 76) |
| L3-63 | + | ELCEKASKTWTGNCGNTKHCDNQCKNWEGAKHGACHVRSGKWKCFCYFNC | (SEQ ID NO: 77) |
| L3-64 | + | NLCEKASKTWTGNCGNTKHCDTQCKSWESAKHGACHVRSGKHKCFCYFNC | (SEQ ID NO: 78) |
| L3-67 | + | ELCEKASLTWTGNCGNTKHCDTQCRNWEGAKHGACHKRSGKWKCFCYFNC | (SEQ ID NO: 79) |
| L3-71 | +++ | NLCEKASKTWTGNCGNTKHCDNQCRNWEGAAHGACHKRNGKWKCFCYFNC | (SEQ ID NO: 80) |
| L3-77 | ++ | NLCERASKTWTGNCGNTKHCDTQCKIWEGAKHGACHKRSGKWKCFCYFNC | (SEQ ID NO: 81) |
| L3-79 | ++ | NLCEKASKTWTGNCGNTKHCDNQCKNWESAAHGACHKRNGKWKCFCYFNC | (SEQ ID NO: 82) |
| L3-81 | + | NLCERASLTWSGNCGNTKHCDDQCKSWESAKHGACHKRNGKHKCFCYFNC | (SEQ ID NO: 83) |
| L3-84 | + | NLCEKASLTWSGNCGNTKHCDDKCKSWEGAKHGACHVRNGKHKCFCYFNC | (SEQ ID NO: 84) |
| L3-87 | ++ | ELCERASKTWTGNCGNTKHCDNQCRSWESAAHGACHKRSGKWKCFCYFNC | (SEQ ID NO: 85) |
| L3-88 | + | NLCEKASKTWTGNCGNTGHCDTQCKNWEGAKHGACHKRSGKWKCFCYFNC | (SEQ ID NO: 86) |
| L3-90 | + | NLCEKASKTWTGNCGNTKHCDTQCKNWEGAKHGACHVRSGKHMCFCYFNC | (SEQ ID NO: 87) |
| L3-93 | + | NLCEKASKTWTGNCGNTKHCDDQCKNWEGAKHGACHKRNGKWMCFCYFNC | (SEQ ID NO: 88) |
| L3-95 | + | NLCEKASKTWSGNCGNTKHCDTQCKNWESAKHGACHKRNGKHKCFCYFNC | (SEQ ID NO: 89) |

-continued

Table 2B: Sequences of clones from Dm-AMP1 based libraries:

| | Activity (1) | | |
|---|---|---|---|
| L3-96 | + | ELCERASLTWTGNCGNTKHCDTQCKSWEGAKHGACHKRSGKWKCFCYFNC | (SEQ ID NO: 90) |
| L3-97 | + | KLCERASLTWSGNCGNTKHCDTKCKNWEGAKHGACHKRNGKWKCFCYFNC | (SEQ ID NO: 91) |
| L3-98 | ++ | NLCERASKTWTGNCGNTKHCDNQCRNWESAAHGACHKRSGKWKCFCYFNC | (SEQ ID NO: 92) |
| L4-1 | + | NLWEKASLTWTGNCGNTKHCDNQCKNWESAAHGACHKRSGKWMCFCYFNC | (SEQ ID NO: 93) |
| L4-10 | + | NLCERASKTWTGNCGNTGHCDNKCKSWEGAKHGACHVRSGKWMCFCYFNC | (SEQ ID NO: 94) |
| L4-11 | + | ELCERASKTWSGNCGNTKHCDTQCRNWESAKHGACHVRSGKWKCFCYFNC | (SEQ ID NO: 95) |
| L4-18 | + | KLCEKASKTWTGNCGNTKHCDTQCKSWEGAKHGACHKRNGKWMCFCYFNC | (SEQ ID NO: 96) |
| L4-2 | + | NLCEKASKTWTGNCGNTGHCDNKCKSWEGAKHGACHIRSGKWKCFCYFNC | (SEQ ID NO: 97) |
| L4-20 | + | NLCEKASLTWSGNCGNTKHCDTQCKSWESAAHGACHKRSGKHKCFCYFNC | (SEQ ID NO: 98) |
| L4-22 | + | NLCERASKTWSGNCGNTKHCDTQCRSWEGAAHGACHKRSGKHMCFCYFNC | (SEQ ID NO: 99) |
| L4-22 | + | ELCEKASKTWSGNCGNTKHCDTKCKSWESAKHGACHKRSGNWKCFCYFNC | (SEQ ID NO: 100) |
| L4-23 | + | ELCEKASKTWTGNCGNTKHCDTQCKSWEGAAHGACHKRNGKWMCFCYFNC | (SEQ ID NO: 101) |
| L4-26 | + | NLCERASLTWTGNCGNTKHCDNQCKSWEGAAHGACHVRNGKHKCFCYFNC | (SEQ ID NO: 102) |
| L4-27 | + | ELCERASKTWTGNCGNTKHCDTQCKSWEGAAHGACHVRSGKHKCFCYFNC | (SEQ ID NO: 103) |
| L4-3 | + | ELCEKASLTWSGNCGNTKHCDTQCRNWEGAKHGACHKRNGKWMCFCYFNC | (SEQ ID NO: 104) |
| L4-4 | + | NLCERASLTWTGNCGNTGHCDTQCKSWEGAKHGACHKRNGKWKCFCYFNC | (SEQ ID NO: 105) |
| L4-5 | + | NLCEKASKTWSGNCGNTKHCDTQCRNWESAAHGACHKRNGKWKCFCYFNC | (SEQ ID NO: 106) |
| L4-8 | + | NLCERASKTWSGNCGNTKHCDNKCKNWESAAHGACHVRNGKHMCFCYFNC | (SEQ ID NO: 107) |
| L4-9 | + | NLCERASKTWSGNCGNTKHCDDQCRSWEGAKHGACHKRSGKWMCFCYFNC | (SEQ ID NO: 108) |
| L5-10 | ++ | NLCEKASKTWTGNCGNTKHCDTQCRSWEGAKHGACHVRNGKHKCFCYFNC | (SEQ ID NO: 109) |
| L5-11 | ++ | NLCEKASKTWSGNCGNTKHCDTQCRNWEGAAHGACHKRSGKWKCFCYFNC | (SEQ ID NO: 110) |
| L5-12 | ++ | NLCEKASKTWSGNCGNTGHCDTQCKNWEGAKHGACHVRNGKHKCFCYFNC | (SEQ ID NO: 111) |
| L5-13 | ++ | NLCEKASKTWSGNCGNTKHCDTQCKSWEGAKHGACHVRNGKHKCFCYFNC | (SEQ ID NO: 112) |
| L5-14 | + | NLCEKASKTWTGNCGNTKHCDNQCRSWEGAAHGACHKRNGKWKCFCYFNC | (SEQ ID NO: 113) |
| L5-15 | + | NLCEKASKTWTGNCGNTKHCDNQCKSWEGAKHGACHKRSGKWKCFCYFNC | (SEQ ID NO: 114) |
| L5-17 | ++ | NLCERASKTWSGNCGNTKHCDTKCRSWEGAKHGACHVRNGKWKCFCYFNC | (SEQ ID NO: 115) |
| L5-18 | ++ | NLCEKASKTWTGNCGNTKHCDTQCKSWEGAKHGACHVRNGKHKCFCYFNC | (SEQ ID NO: 116) |
| L5-2 | + | NLCERASKTWSGNCGNTKHCDTQCKSWEGAAHGACHKRNGKWKCFCYFNC | (SEQ ID NO: 117) |
| L5-20 | + | NLCERASKTWSGNCGNTKHCDNQCKSWEGAAHGACHKRSGKHKCFCYFNC | (SEQ ID NO: 118) |
| L5-21 | + | NLCEKASKTWTGNCGNTKHCDTQCKSWEGAKHGACHKRSGKWKCFCYFNC | (SEQ ID NO: 119) |
| L5-22 | +++ | NLCEKASKTWTGNCGNTKHCDTQCKSWEGAKHGACHKRNGKWKCFCYFNC | (SEQ ID NO: 120) |
| L5-23 | +++ | NLCEKASKTWTGNCGNTKHCDTQCRSWEGAAHGACHVRSGKHKCFCYFNC | (SEQ ID NO: 121) |
| L5-24 | +++ | NLCEKASKTWTGNCGNTKHCDNQCKSWEGAAHGACHVRNGKHKCFCYFNC | (SEQ ID NO: 122) |
| L5-28 | + | NLCERASKTWSGNCGNTKHCDTQCKSWEGAAHGACHVRSGKHKCFCYFNC | (SEQ ID NO: 123) |
| L5-31 | + | NLCERASKTWSGNCGNTKHCDTQCKSWEGAKHGACHVRSGKHKCFCYFNC | (SEQ ID NO: 124) |
| L5-32 | + | NLCEKASKTWTGNCGNTKHCDTQCRSWEGAKHGACHVRSGKHKCFCYFNC | (SEQ ID NO: 125) |
| L5-33 | + | NLCERASKTWTGNCGNTKHCDTQCKNWEGAAHGACHVRNGKHKCFCYFNC | (SEQ ID NO: 126) |

-continued

Table 2B: Sequences of clones from Dm-AMP1 based libraries:

| | Activity (1) | | |
|---|---|---|---|
| L5-34 | + | NLCERASKTWSGNCGNTGHCDTQCKSWEGAKHGACHVRNGKHKCFCYFNC | (SEQ ID NO: 127) |
| L5-36 | + | NLCERASKTWTGNCGNTKHCDTQCKSWEGAKHGACHVRSGKHKCFCYFNC | (SEQ ID NO: 128) |
| L5-37 | ++ | NLCERASKTWTGNCGNTKHCDNQCKSWEGAKHGACHVRSGKHKCFCYFNC | (SEQ ID NO: 129) |
| L5-38 | + | NLCEKASKTWSGNCGNTKHCDTKCRNWEGAKHGACHVRNGKWMCFCYFNC | (SEQ ID NO: 130) |
| L5-40 | ++ | NLCERASKTWSGNCGNTKHCDNQCRNWEGAKHGACHVRNGKWKCFCYFNC | (SEQ ID NO: 131) |
| L5-41 | + | NLCERASKTWSGNCGNTGHCDTQCRSWEGAKHGACHVRNGKHKCFCYFNC | (SEQ ID NO: 132) |
| L5-44 | + | NLCERASKTWSGNCGNTKHCDNQCRNWEGAKHGACHVRNGKWKCFCYFNC | (SEQ ID NO: 133) |
| L5-45 | + | NLCEKASKTWTGNCGNTKHCDTQCRSWEGAKHGACHVRSGKHKCFCYFNC | (SEQ ID NO: 134) |
| L5-46 | + | NLCERASKTWTGNCGNTKHCDTQCRNWEGAKHGACHVRNGKWKCFCYFNC | (SEQ ID NO: 135) |
| L5-48 | + | NLCERASKTWSGNCGNTKHCDNQCRSWEGAKHGACHKRNGKWKCFCYFNC | (SEQ ID NO: 136) |
| L5-50 | + | NLCEKASKTWSGNCGNTKHCDTQCKSWEGAAHGACHVRSGKHKCFCYFNC | (SEQ ID NO: 137) |
| L5-52 | + | NLCERASKTWSGNCGNTKHCDNQCKSWEGAKHGACHVRNGKHMCFCYFNC | (SEQ ID NO: 138) |
| L5-55 | + | NLCEKASKTWTGNCGNTKHCDNQCKNWEGAKHGACHKRSGKWKCFCYFNC | (SEQ ID NO: 139) |
| L5-58 | + | NLCERASKTWTGNCGNTKHCDNQCKNWEGAKHGACHVRNGKWKCFCYFNC | (SEQ ID NO: 140) |
| L5-59 | + | NLCERASKTWSGNCGNTGHCDTQCRSWEGAKHGACHVRSGKHKCFCYFNC | (SEQ ID NO: 141) |
| L5-6 | +++ | NLCEKASKTWSGNCGNTKHCDNQCRSWEGAKHGACHVRNGKWKCFCYFNC | (SEQ ID NO: 142) |
| L5-8 | + | NLCEKASKTWSGNCGNTGHCDNQCKSWEGAAHGACHVRNGKHKCFCYFNC | (SEQ ID NO: 143) |
| L5-9 | ++ | NLCERASKTWSGNCGNTKHCDNQCRSWEGAKHGACHVRNGKHKCFCYFNC | (SEQ ID NO: 144) |
| L6-03 | +++ | NLCERASKTWTGNCGNTKHCDNQCKNWEGAKHGACHVRNGKWKCFCYFNC | (SEQ ID NO: 145) |
| L6-04 | ++ | NLCEKASKTWTGNCGNTKHCDNQCKNWEGAKHGACHVRNGKHKCFCYFNC | (SEQ ID NO: 146) |
| L6-05 | +++ | NLCERASKTWSGNCGNTKHCDTQCKNWEGAKHGACHVRNGKWKCFCYFNC | (SEQ ID NO: 147) |
| L6-06 | ++ | NLCERASKTWTGNCGNTKHCDNQCRSWEGAAHGACHKRNGKWKCFCYFNC | (SEQ ID NO: 148) |
| L6-07 | +++ | NLCERASKTWTGNCGNTKHCDNQCRNWEGAKHGACHVRNGKWKCFCYFNC | (SEQ ID NO: 149) |
| L6-08 | +++ | NLCERASKTWTGNCGNTKHCDNQCKNWEGAKHGACHVRNGKHKCFCYFNC | (SEQ ID NO: 150) |
| L6-12 | +++ | NLCERASKTWSGNCGNTKHCDTQCRNWEGAAHGACHKRNGKWKCFCYFNC | (SEQ ID NO: 151) |
| L6-13 | ++ | NLCEKASKTWSGNCGNTKHCDTQCRNWEGAKHGACHVRNGKHKCFCYFNC | (SEQ ID NO: 152) |
| L6-15 | ++ | NLCERASKTWSGNCGNTKHCDTQCRSWEGAKHGACHVRSGKHKCFCYFNC | (SEQ ID NO: 153) |
| L6-17 | ++ | NLCEKASKTWTGNCGNTKHCDTQCKNWEGAKHGACHVRNGKHKCFCYFNC | (SEQ ID NO: 154) |
| L6-20 | ++ | NLCEKASKTWTGNCGNTKHCDNQCRNWEGAKHGACHVRSGKHKCFCYFNC | (SEQ ID NO: 155) |
| L6-21 | +++ | NLCERASKTWTGNCGNTKHCDNQCKNWEGAKHGACHVRNGKWKCFCYFNC | (SEQ ID NO: 156) |
| L6-23 | ++ | NLCEKASKTWTGNCGNTKHCDNQCKNWEGAKHGACHVRSGKHKCFCYFNC | (SEQ ID NO: 157) |
| L6-27 | +++ | NLCERASKTWSGNCGNTKHCDTQCKSWEGAAHGACHVRNGKHKCFCYFNC | (SEQ ID NO: 158) |
| L6-28 | +++ | NLCERASKTWSGNCGNTKHCDNQCKNWEGAKHGACHVRNGKHKCFCYFNC | (SEQ ID NO: 159) |
| L6-29 | ++ | NLCEKASKTWTGNCGNTKHCDNQCRSWEGAKHGACHVRNGKHKCFCYFNC | (SEQ ID NO: 160) |
| L6-30 | ++ | NLCEKASKTWTGNCGNTKHCDNQCRNWEGAKHGACHVRNGKWKCFCYFNC | (SEQ ID NO: 161) |
| L6-32 | +++ | NLCEKASKTWTGNCGNTKHCDTQCRNWEGAKHGACHKRNGKWKCFCYFNC | (SEQ ID NO: 162) |
| L6-33 | ++ | NLCERASKTWTGNCGNTKHCDTQCRNWEGAKHGACHKRSGKWKCFCYFNC | (SEQ ID NO: 163) |

-continued

Table 2B: Sequences of clones from Dm-AMP1 based libraries:

| | Activity (1) | | |
|---|---|---|---|
| L6-35 | ++ | NLCERASKTWTGNCGNTKHCDNQCRNWEGAKHGACHVRNGKHKCFCYFNC | (SEQ ID NO: 164) |
| L6-37 | ++ | NLCERASKTWSGNCGNTKHCDNQCRNWEGAKHGACHVRSGKHKCFCYFNC | (SEQ ID NO: 165) |
| L6-39 | +++ | NLCERASKTWTGNCGNTKHCDNQCKSWEGAAHGACHVRSGKHKCFCYFNC | (SEQ ID NO: 166) |
| L6-40 | ++ | NLCERASKTWSGNCGNTKHCDNQCRNWEGAKHGACHVRNGKWKCFCYFNC | (SEQ ID NO: 167) |
| L6-41 | +++ | NLCERASKTWTGNCGNTKHCDNQCKNWEGAKHGACHVRNGKWKCFCYFNC | (SEQ ID NO: 168) |
| L6-42 | + | NLCERASKTWTGNCGNTKHCDTQCRSWEGAKHGACHVRNGKHKCFCYFNC | (SEQ ID NO: 169) |
| L6-43 | + | NLCEKASKTWSGNCGNTKHCDTQCRNWEGAKHGACHVRNGKWKCFCYFNC | (SEQ ID NO: 170) |
| L6-45 | ++ | NLCERASKTWTGNCGNTKHCDNQCRNWEGAAHGACHKRNGKWKCFCYFNC | (SEQ ID NO: 171) |
| L6-47 | ++ | NLCERASKTWTGNCGNTKHCDNQCKNWEGAAHGACHVRNGKHKCFCYFNC | (SEQ ID NO: 172) |
| L6-48 | ++ | NLCEKASKTWSGNCGNTKHCDNQCKSWEGAKHGACHVRNGKHKCFCYFNC | (SEQ ID NO: 173) |
| L6-52 | + | NLCERASKTWTGNCGNTKHCDTQCKSWEGAKHGACHVRNGKWKCFCYFNC | (SEQ ID NO: 174) |
| L6-55 | + | NLCEKASKTWTGNCGNTKHCDNQCRNWEGAAHGACHVRNGKHKCFCYFNC | (SEQ ID NO: 175) |
| L6-56 | ++ | NLCERASKTWSGNCGNTKHCDNQCRNWEGAKHGACHKRNGKWKCFCYFNC | (SEQ ID NO: 176) |
| L6-57 | +++ | NLCERASKTWSGNCGNTKHCDTQCRNWEGAAHGACHVRNGKHKCFCYFNC | (SEQ ID NO: 177) |
| L6-58 | +++ | NLCERASKTWTGNCGNTKHCDTQCKNWEGAKHGACHVRSGKHKCFCYFNC | (SEQ ID NO: 178) |
| L6-59 | +++ | NLCERASKTWSGNCGNTKHCDNQCRNWEGAAHGACHVRNGKHKCFCYFNC | (SEQ ID NO: 179) |
| L6-60 | ++ | NLCERASKTWSGNCGNTKHCDNQCKNWEGAKHGACHVRNGKHKCFCYFNC | (SEQ ID NO: 180) |
| L6-61 | ++ | NLCERASKTWSGNCGNTKHCDNQCKSWEGAAHGACHVRNGKHKCFCYFNC | (SEQ ID NO: 181) |
| L6-62 | + | NLCERASKTWTGNCGNTKHCDTQCRSWEGAKHGACHVRNGKWKCFCYFNC | (SEQ ID NO: 182) |
| L6-63 | + | NLCERASKTWSGNCGNTKHCDTQCRNWEGAKHGACHVRNGKHKCFCYFNC | (SEQ ID NO: 183) |
| L6-64 | ++ | NLCERASKTWSGNCGNTKHCDNQCRNWEGAAHGACHVRNGKHKCFCYFNC | (SEQ ID NO: 184) |
| L6-66 | ++ | NLCERASKTWTGNCGNTKHCDNQCRNWEGAAHGACHVRNGKHKCFCYFNC | (SEQ ID NO: 185) |
| L6-69 | +++ | NLCEKASKTWTGNCGNTKHCDTQCKNWEGAKHGACHVRNGKWKCFCYFNC | (SEQ ID NO: 186) |
| L6-70 | +++ | NLCERASKTWSGNCGNTKHCDNQCKNWEGAAHGACHVRNGKHKCFCYFNC | (SEQ ID NO: 187) |
| L6-71 | +++ | NLCERASKTWTGNCGNTKHCDTQCKSWEGAKHGACHVRNGKHKCFCYFNC | (SEQ ID NO: 188) |
| L6-74 | + | NLCEKASKTWSGNCGNTKHCDTQCRSWEGAKHGACHVRSGKHKCFCYFNC | (SEQ ID NO: 189) |
| L6-75 | ++ | NLCERASKTWTGNCGNTKHCDNQCRSWEGAKHGACHVRNGKHKCFCYFNC | (SEQ ID NO: 190) |
| L6-77 | ++ | NLCERASKTWTGNCGNTKHCDTQCKNWEGAKHGACHVRNGKWKCFCYFNC | (SEQ ID NO: 191) |
| L6-78 | ++ | NLCERASKTWTGNCGNTKHCDTQCRNWEGAKHGACHVRNGKHKCFCYFNC | (SEQ ID NO: 192) |
| L6-83 | +++ | NLCERASKTWSGNCGNTKHCDTQCKNWEGAKHGACHVRNGKHKCFCYFNC | (SEQ ID NO: 193) |
| L6-84 | +++ | NLCERASKTWTGNCGNTKHCDTQCKSWEGAKHGACHVRNGKHKCECYFNC | (SEQ ID NO: 194) |
| L6-85 | +++ | NLCERASKTWTGNCGNTKHCDNQCRNWEGAAHGACHVRSGKHKCFCYFNC | (SEQ ID NO: 195) |
| L9-01 | +++ | NLCERASKTWSGNCGNTKHCDNQCKNWEGAAHGACHVRNGKHKCFCYFNC | (SEQ ID NO: 196) |
| L9-03 | +++ | NLCERASKTWSGNCGNTKHCDNQCKSWEGAKHGACHKRNGKWKCECYFNC | (SEQ ID NO: 197) |
| L9-04 | ++ | NLCERASKTWTGNCGNTKHCDNQCKSWEGAKHGACHKRSGKWKCFCYFNC | (SEQ ID NO: 198) |
| L9-05 | ++ | NLCEKASKTWSGNCGNTKHCDNQCKNWEGAKHGACHVRSGKHKCFCYFNC | (SEQ ID NO: 199) |
| L9-06 | ++ | NLCEKASKTWTGNCGNTKHCDTQCRNWEGAKHGACHKRSGKWKCFCYFNC | (SEQ ID NO: 200) |

-continued

Table 2B: Sequences of clones from Dm-AMP1 based libraries:

| | Activity (1) | | |
|---|---|---|---|
| L9-07 | +++ | NLCEKASKTWSGNCGNTKHCDNQCRSWEGAKHGACHKRNGKWKCFCYFNC | (SEQ ID NO: 201) |
| L9-08 | ++ | NLCEKASKTWSGNCGNTKHCDTQCKSWEGAKHGACHKRSGKWKCFCYFNC | (SEQ ID NO: 202) |
| L9-09 | +++ | NLCERASKTWSGNCGNTKHCDTQCRNWEGAKHGACHKRSGKWKCFCYFNC | (SEQ ID NO: 203) |
| L9-11 | ++ | NLCERASKTWSGNCGNTKHCDNQCRSWEGAKHGACHVRSGKWKCFCYFNC | (SEQ ID NO: 204) |
| L9-12 | +++ | NLCERASKTWTGNCGNTKHCDNQCRNWEGAKHGACHKRNGKWKCFCYFNC | (SEQ ID NO: 205) |
| L9-13 | +++ | NLCERASKTWSGNCGNTKHCDTQCKNWEGAAHGACHKRNGKWKCFCYFNC | (SEQ ID NO: 206) |
| L9-14 | +++ | NLCERASKTWSGNCGNTKHCDTQCRSWEGAAHGACHKRNGKWKCFCYFNC | (SEQ ID NO: 207) |
| L9-15 | +++ | NLCERASKTWTGNCGNTKHCDNQCRNWEGAKHGACHKRSGKWKCFCYFNC | (SEQ ID NO: 208) |
| L9-16 | +++ | NLCERASKTWSGNCGNTKHCDNQCRSWEGAKHGACHVRSGKHKCFCYFNC | (SEQ ID NO: 209) |
| L9-18 | +++ | NLCERASKTWSGNCGNTKHCDNQCKSWEGAAHGACHKRNGKWKCFCYFNC | (SEQ ID NO: 210) |
| L9-21 | +++ | NLCERASKTWSGNCGNTKHCDTQCKNWEGAKHGACHVRNGKHKCFCYFNC | (SEQ ID NO: 211) |
| L9-22 | +++ | NLCERASKTWTGNCGNTKHCDNQCRNWEGAKHGACHVRSGKHKCFCYFNC | (SEQ ID NO: 212) |
| L9-23 | +++ | NLCERASKTWSGNCGNTKHCDNQCRSWEGAKHGACHVRNGKHKCFCYFNC | (SEQ ID NO: 213) |
| L9-26 | +++ | NLCERASKTWSGNCGNTKHCDTQCKSWEGAKHGACHVRNGKHKCFCYFNC | (SEQ ID NO: 214) |
| L9-27 | +++ | NLCERASKTWSGNCGNTKHCDNQCRNWEGAKHGACHVRSGKHKCFCYFNC | (SEQ ID NO: 215) |
| L9-29 | +++ | NLCERASKTWTGNCGNTKHCDTQCKSWEGAKHGACHVRSGKHKCFCYFNC | (SEQ ID NO: 216) |
| L9-30 | +++ | NLCERASKTWSGNCGNTKHCDNQCRNWEGAKHGACHKRSGKWKCFCYFNC | (SEQ ID NO: 217) |
| L9-32 | +++ | NLCERASKTWSGNCGNTKHCDTQCRNWEGAKHGACHKRNGKWKCFCYFNC | (SEQ ID NO: 218) |
| L9-33 | ++ | NLCERASKTWTGNCGNTKHCDNQCKSWEGAKHGACHVRNGKHKCFCYFNC | (SEQ ID NO: 219) |
| L9-36 | +++ | NLCEKASKTWTGNCGNTKHCDNQCRNWEGAAHGACHKRSGKWKCFCYFNC | (SEQ ID NO: 220) |
| L9-37 | ++ | NLCERASKTWSGNCGNTKHCDTQCRSWEGAKHGACHKRSGKWKCFCYFNC | (SEQ ID NO: 221) |
| L9-40 | ++ | NLCERASKTWSGNCGNTKHCDNQCRSWEGAAHGACHVRSGKHKCFCYFNC | (SEQ ID NO: 222) |
| L9-41 | +++ | NLCERASKTWSGNCGNTKHCDTQCRSWEGAAHGACHKRSGKWKCFCYFNC | (SEQ ID NO: 223) |
| L9-45 | +++ | NLCERASKTWTGNCGNTKHCDTQCKNWEGAKHGACHKRNGKWKCFCYFNC | (SEQ ID NO: 224) |
| L9-46 | +++ | NLCERASKTWSGNCGNTKHCDTQCRNWEGAKHGACHKRNGKWKCFCYFNC | (SEQ ID NO: 225) |
| L9-47 | ++ | NLCERASKTWSGNCGNTKHCDTQCRSWEGAKHGACHVRNGKHKCFCYFNC | (SEQ ID NO: 226) |
| L9-48 | ++ | NLCERASKTWSGNCGNTKHCDNQCRSWEGAKHGACHVRSGKHKCFCYFNC | (SEQ ID NO: 227) |
| L10-01 | + | NLCERASKTWSGNCGNTKHCDNQCKSWEGAKHGACHVRNGKWKCFCYFNC | (SEQ ID NO: 228) |
| L10-03 | +++ | NLCERASKTWSGNCGNTKHCDTQCKNWEGAKHGACHKRNGKWKCFCYFNC | (SEQ ID NO: 229) |
| L10-09 | + | NLCERASKTWSGNCGNTKHCDNQCKSWEGAAHGACHVRNGKHKCFCYFNC | (SEQ ID NO: 230) |
| L10-10 | ++ | NLCERASKTWSGNCGNTKHCDNQCKSWEGAQHGACHVRNGKHKCFCYFNC | (SEQ ID NO: 231) |
| L10-11 | + | NLCERASKTWSGNCGNTKHCDTQCRNWEGAKHGACHVRNGKWKCFCYFNC | (SEQ ID NO: 232) |
| L10-14 | ++ | NLCERASKTWTGNCGNTKHCDTQCRSWEGAKHGACHKRNGKWKCFCYFNC | (SEQ ID NO: 233) |
| L10-17 | + | NLCERASKTWTGNCGNTKHCDNQCKSWEGAKHGACHVRNGKWKCFCYFNC | (SEQ ID NO: 234) |
| L10-19 | + | NLCERASKTWSGNCGNTKHCDTQCKSWEGAKHGACHVRSGKHKCFCYFNC | (SEQ ID NO: 235) |
| L10-20 | ++ | NLCERASKTWSGNCGNTKHCDNQCISWEGAKHGACHKRNGKWKCFCYFNC | (SEQ ID NO: 236) |
| L10-22 | +++ | NLCERASKTWTGNCGNTKHCDTQCRNWEGAKHGACHKRNGKWKCFCYFNC | (SEQ ID NO: 237) |

-continued

Table 2B: Sequences of clones from Dm-AMP1 based libraries:

| | Activity (1) | | |
|---|---|---|---|
| L10-25 | + | NLCERASKTWTGNCGNTKHCDNQCKNWEGAKHGACHKRSGKWKCFCYFNC | (SEQ ID NO: 238) |
| L10-33 | + | NLCERASKTWAGNCGNTKHCDNQCRSWEGAKHGACHVRNGKWKCFCYFNC | (SEQ ID NO: 239) |
| L10-39 | + | NLCEKASKTWSGNCGNTKHCDNQCKSWEGAAHGACHKRSGKWKCFCYFNC | (SEQ ID NO: 240) |
| L10-44 | ++ | NLCEKASKTWSGNCGNTNHCDNQCRSWEGAKHGACHVRSGKKKCFCYFNC | (SEQ ID NO: 241) |
| L10-46 | ++ | NLCERASKTWSGNCGSTKHCDNQCKNWEGAKHGACHVRSGKHKCFCYFNC | (SEQ ID NO: 242) |
| L10-49 | +++ | NLCERASKTWSGNCGNTKHCDTQCKSWEGAKHGACHVRNGKHKCFCYFNC | (SEQ ID NO: 243) |
| L10-50 | ++ | NLCERASKTWSGNCGNTKHCDNQCKNWEGAKHGACHVRNGKWKCFCYFNC | (SEQ ID NO: 244) |
| L10-51 | ++ | NLCERASKTWTGNCGNTKHCDNQCKSWEGAKHGACHKRNGKWKCFCYFNC | (SEQ ID NO: 245) |
| L10-52 | ++ | NLCERASKTWTGNCGNTKHCDTQCRSWEGAAHGACHVRGGKHKCFCYFNC | (SEQ ID NO: 246) |
| L10-53 | ++ | NLCEKASKTWTGNCGNTKHCDNQCRSWEGAKHGACHVRSGKHKCFCYFNC | (SEQ ID NO: 247) |
| L10-58 | ++ | NLCERASKTWSGNCGNTKHCDNQCRSWEGAAHGACHKRNGKWKCFCYFNC | (SEQ ID NO: 248) |
| L10-59 | ++ | NLCEKASKTWTGNCGNTKHCDNQCKSWEGAAHGACHKRSGKWKCFCYFNC | (SEQ ID NO: 249) |
| L10-60 | ++ | NLCERASKTWSSNCGNTKHCDTQCKNWEGAKHGACHVRNGKWKCFCYFNC | (SEQ ID NO: 250) |
| L10-61 | ++ | NLCERASKTWSGNCGNTKHCDTQCKNWEGAKHGACHKRSGKWKCFCYFNC | (SEQ ID NO: 251) |
| L10-62 | ++ | NLCERASKTWSGDCGNTKHCDNQCRNWEGAKHGACHKRNGKWKCFCYFNC | (SEQ ID NO: 252) |
| L10-63 | ++ | NLCEKASKTWTGNCGNTKHCDNQCKSWEGAKHGACHKRGGKWKCFCYFNC | (SEQ ID NO: 253) |
| L10-64 | ++ | NLCERASKTWTGNCGNTKHCDNQCKSWEGAKHGACHVRNGKWKCFCYFNC | (SEQ ID NO: 254) |
| L10-65 | ++ | NLCERASKTWSGNCGNTKHCDNQCKNWEGAAHGACHVRSGKHKCFCYFNC | (SEQ ID NO: 255) |
| L10-66 | ++ | NLCEKASKTWTGNCGNTKHCDNQCKSWEGAAHGACHVRNGKHKCFCYFNC | (SEQ ID NO: 256) |
| L10-67 | ++ | NLCEKASKTWSGNCGNTKHCDTQCKNWEGAKHGACHVRSGKWKCFCYFNC | (SEQ ID NO: 257) |
| L10-69 | ++ | NLCEKASKTWTGNCGNTKHCDNQCRSWEGAAHGACHVRNGKHKCFCYFNC | (SEQ ID NO: 258) |
| L10-70 | ++ | NLCERASKTWSGNCGNTKHCDNQCRNWEGAKHGACHVRSGKWKCFCYFNC | (SEQ ID NO: 259) |
| L10-71 | ++ | NLCERASKTWTGNCGNTKHCDTQCRNWEGARHGACHVRNGKWKCFCYFNC | (SEQ ID NO: 260) |
| L10-75 | ++ | NLCERASKTWSGNCGNTKHCDNQCRSWEGAAHGACHVRNGKWKCFCYFNC | (SEQ ID NO: 261) |
| L10-76 | ++ | NLCEKASKTWTGNCGNTKHCDNQCRSWEGAKHGACMKRSGKWKCFCYFNC | (SEQ ID NO: 262) |
| L10-77 | ++ | NLCERASKTWTGNCGNTKHCDNQCRSWEGAKHGACHKRSGKWKCFCYFNC | (SEQ ID NO: 263) |
| L10-78 | ++ | NLCEKASKTWSGNCGNTKHCDTQCKSWEGAAHGACHKRNGKWKCFCYFNC | (SEQ ID NO: 264) |
| L10-79 | ++ | NLCERASKTWTGNCGNTKHCDNQCRNWEGAKHGACHVRSGKWKCFCYFNC | (SEQ ID NO: 265) |
| L10-80 | ++ | NLCERASKTWTGNCGNTKHCDNQCKNWEGAAHGACHKRSGKWKCFCYFNC | (SEQ ID NO: 266) |
| L10-81 | ++ | NLCERASKTWTGNCGNTKHCDNQCRSWEGAAHGACHKRSGKWKCFCYFNC | (SEQ ID NO: 267) |
| L10-83 | ++ | NLCERASKTWTGNCGNTKHCDNQCKNWEGAAHGACHVRSGKHKCFCYFNC | (SEQ ID NO: 268) |
| L10-84 | ++ | NLCEKASKTWSGNCGNTKHCDNQCRNWEGAEHGACHVRNGKHKCFCYFNC | (SEQ ID NO: 269) |
| L10-86 | +++ | NLCERASKTWSGNCGNTKHCDNQCKSWEGAKHGACHVRNGKHKCFCYFNC | (SEQ ID NO: 270) |
| L11-01 | ++ | NLCEKASKTWSGNCGNTKHCDNQCKSWEGAAHGACHKRNGKWKCFCYFNC | (SEQ ID NO: 271) |
| L11-02 | +++ | NLCERASKTWSGNCGNTKHCDNQCKSWEGAKHGACHKRNGKWKCFCYFNC | (SEQ ID NO: 272) |
| L11-03 | ++ | NLCERASRTWSGNCGNTKHCDNQCKSWEGAKHGACHKRNGKWKCFCYFNC | (SEQ ID NO: 273) |
| L11-04 | +++ | NLCERASKTWSGNCGITKHCDNQCKSWEGAKHGACHKRNGKWKCFCYFNC | (SEQ ID NO: 274) |

-continued

Table 2B: Sequences of clones from Dm-AMP1 based libraries:

| | Activity (1) | | | |
|---|---|---|---|---|
| L11-05 | ++ | NLCERASKTWSGNCSNTKHCDNQCKSWEGAKHGACHKRNGKWKCFCYFNC | (SEQ ID NO: 275) | |
| L11-06 | +++ | NLCERASKTWSGNCGNTKHCDNQCKNWEGAKHGACHKRNGKWKCFCYFNC | (SEQ ID NO: 276) | |
| L11-07 | ++ | NLCEKASKTWSGNCGNTKHCDNQCKNWEGAKHGACHKRNGKWKCFCYFNC | (SEQ ID NO: 277) | |
| L11-08 | ++ | NLCERASKTWSGNCGNTKHCDNQCKGWEGAKHGACHKRNGKWKCFCYFNC | (SEQ ID NO: 278) | |
| L11-09 | +++ | NLCERASKTWSGNCGNTKHCDNQCKGWEGAKHGACHKRNGKWKCFCYFNC | (SEQ ID NO: 279) | |
| Consensus | | NLCERASKTWSGNCGNTKHCDNQCKSWEGAKHGACHVRNGKWKCFCYFNC | (SEQ ID NO: 7) | |

Table 2C: Sequences of clones from a mixed diversity library

| | Activity (1) | (2) | | |
|---|---|---|---|---|
| L7-99 | + | + | DGVKLCERPSQTWTGNCGNTKHCDKQCKSWEGAKHGACHKRNGKWKCFCYFNC | (SEQ ID NO: 280) |
| L7-10 | + | + | DGVKLCEKPSQTWTGHCGNTKHCDTQCRSWEGAAHGACHKRSGKWKCFCYFNC | (SEQ ID NO: 281) |
| L7-107 | + | + | DGVKLCERASKTWTGNCGNTKHCDKQCKNWEGAKHGACHKRNGKWKCFCYFNC | (SEQ ID NO: 282) |
| L7-109 | + | + | DGVKLCEKASKTWSGNCGNTKHCDKQCRSWEKAKHGACHVRNGKHKCFCYFNC | (SEQ ID NO: 283) |
| L7-11 | ++ | + | ---NLCERASKTWSGHCGNTKHCDNQCRNWEGAKHGACHKRNGKWKCFCYFNC | (SEQ ID NO: 284) |
| L7-112 | +++ | + | DGVKLCERPSKTWSGNCGNTKHCDKQCKNWEKAKHGACHVRNGKWKCFCYFNC | (SEQ ID NO: 285) |
| L7-113 | + | + | DGVKLCEKPSKTWSGHCGNTKHCDKQCKNWEKAKHGACHKRNGKWKCFCYFNC | (SEQ ID NO: 286) |
| L7-12 | ++ | + | ---NLCEKASQTWTGHCGNTKHCDKQCKSWEGAAHGACHVRSGKWKCFCYFNC | (SEQ ID NO: 287) |
| L7-123 | + | + | DGVKLCERPSQTWSGNCGNTKHCDKQCRNWEKAKHGACHKRNGKWKCFCYFNC | (SEQ ID NO: 288) |
| L7-13 | + | + | DGVKLCEKPSKTWTGHCGNTKHCDNQCKNWEKAAHGACHVRSGKWKCFCYFNC | (SEQ ID NO: 289) |
| L7-133 | + | + | DGVKLCEKPSKTWTGHCGNTKHCDKQCKNWEKAAHGACHVRNGKWKCFCYFNC | (SEQ ID NO: 290) |
| L7-14 | ++ | + | DGVKLCERASQTWSGHCGNTKHCDKQCKNWEKAAHGACHVRSGKWKCFCYFNC | (SEQ ID NO: 291) |
| L7-15 | ++ | + | DGVKLCERASQTWTGHCGNTKHCDKQCKSWEKAKHGACHVRNGKWKCFCYFNC | (SEQ ID NO: 292) |
| L7-16 | ++ | + | DGVKLCERASQTWSGHCGNTKHCDKQCRNWEGAAHGACHVRNGKWKCFCYFNC | (SEQ ID NO: 293) |
| L7-174 | +++ | + | DGVKLCEKASQTWSGNCGNTKHCDTQCRNWEGAKHGACHKRNGKWKCFCYFNC | (SEQ ID NO: 294) |
| L7-176 | +++ | + | DGVKLCERASQTWTGHCGNTKHCDNQCKNWEGAKHGACHKRSGKWKCFCYFNC | (SEQ ID NO: 295) |
| L7-178 | ++ | + | DGVKLCEKPSQTWTGHCGNTKHCDKQCKNWEGAKHGACHKRNGKWKCFCYFNC | (SEQ ID NO: 296) |
| L7-179 | +++ | + | DGVKLCERPSQTWTGHCGNTKHCDKQCRNWEGAKHGACHKRNGKWKCFCYFNC | (SEQ ID NO: 297) |
| L7-18 | + | + | ---NLCERASHTWSGHCGNTKHCDKQCRSWEGAAHGACHVRNGKRKCFCYFNC | (SEQ ID NO: 298) |
| L7-187 | ++ | + | DGVKLCEKPSKTWSGHCGNTKHCDNQCRNWEKAAHGACHVRNGKWKCFCYFNC | (SEQ ID NO: 299) |
| L7-19 | + | + | --QKLCEKASQTWTGHCGNTKHCDNQCRNWEKAAHGACHVRNGKWKCFCYFNC | (SEQ ID NO: 300) |
| L7-20 | + | + | DGVKLCERASQTWTGHCGNTKHCDTQCRSWEGAAHGACHKRNGKHKCFCYFNC | (SEQ ID NO: 301) |
| L7-213 | ++ | + | DGVKLCERASKTWSGHCGNTKHCDNQCRSWEGAKHGACHVRSGKHKCFCYFNC | (SEQ ID NO: 302) |
| L7-219 | + | + | DGVKLCERASKTWSGHCGNTKHCDKQCKNWEKAKHGACHKRSGKWKCFCYFNC | (SEQ ID NO: 303) |
| L7-231 | ++ | + | DGVKLCEKPSQTWSHCGNTKHCDNQCKNWEGAAHGACHKRSGKWKCFCYFNC | (SEQ ID NO: 304) |
| L7-337 | ++ | + | DGVKLCERASQTWTGHCGNTKHCDNQCRNWEGAKHGACHKRNGKWKCFCYFNC | (SEQ ID NO: 305) |

-continued

Table 2C: Sequences of clones from a mixed diversity library

| | Activity (1) | (2) | | |
|---|---|---|---|---|
| L7-350 | +++ | + | DGVKLCEKASQTWSGHCGNTKHCDNQCKNWEGAKHGACHKRNGKWKCFCYFNC | (SEQ ID NO: 306) |
| L7-392 | +++ | + | DGVKLCEKPSKTWSGHCGNTKHCDTQCRNWEKAKHGACHVRNGKWKCFCYFNC | (SEQ ID NO: 307) |
| L7-422 | +++ | + | DGVKLCEKASQTWSGHCGNTKHCDNQCKNWEGAKHGACHKRSGKWKCFCYFNC | (SEQ ID NO: 308) |
| L7-427 | ++ | + | DGVKLCEKPSQTWTGNCGNTKHCDTQCRNWEGAKHGACHKRNGKWKCFCYFNC | (SEQ ID NO: 309) |
| L7-432 | +++ | + | DGVKLCERASQTWTGHCGNTKHCDKQCKNWEGAKHGACHKRNGKWKCFCYFNC | (SEQ ID NO: 310) |
| L7-434 | +++ | + | DGVKLCEKASQTWSGHCGNTKHCDNQCKNWEGAKHGACHKRNGKWKCFCYFNC | (SEQ ID NO: 311) |
| L7-449 | ++ | + | DGVKLCERASKTWTGNCGNTKHCDKQCKNWEGAKHGACHVRNGKWKCFCYFNC | (SEQ ID NO: 312) |
| L7-452 | +++ | + | DGVKLCERASKTWSGHCGNTKHCDNQCRSWEGAKHGACHVRNGKWKCFCYFNC | (SEQ ID NO: 313) |
| L7-457 | +++ | + | DGVKLCERPSQTWTGNCGNTKHCDKQCKNWEKAKHGACHVRNGKWKCFCYFNC | (SEQ ID NO: 314) |
| L7-26 | ++ | + | ---NLCERPSKTWTGHCGNTKHCDKQCKSWEGAKHGACHVRSGKWKCFCYFNC | (SEQ ID NO: 315) |
| L7-27 | + | + | DGVKLCEKPSQTWSGNCGNTKHCDKQCKSWEGAKHGACHVRNGKWKCFCYFNC | (SEQ ID NO: 316) |
| L7-29 | +++ | ++ | DGVKLCEKASQTWTGHCGNTKHCDKQCKSWEGAKHGACHKRSGKWKCFCYFNC | (SEQ ID NO: 317) |
| L7-34 | + | + | --QKLCERASKTWTGHCGNTKHCDKQCKNWEKAKHGACHVRNGKWKCFCYFNC | (SEQ ID NO: 318) |
| L7-39 | ++ | + | DGVKLCERPSQTWTGNCGNTKHCDNQCRNWEGAKHGACHVRNGKWKCFCYFNC | (SEQ ID NO: 319) |
| L7-42 | + | + | DGVKLCEKASQTWTGNCGNTKHCDNQCKNWEKAKHGACHKRSGKWKCFCYFNC | (SEQ ID NO: 320) |
| L7-44 | + | + | --QKLCERPSQTWTGHCGNTKHCDTQCKSWEGAKHGACHKRNGKWKCFCYFNC | (SEQ ID NO: 321) |
| L7-46 | + | + | DGVKLCEKPSQTWTGNCGNTKHCDKQCRNWEKAKHGACHKRNGKWKCFCYFNC | (SEQ ID NO: 322) |
| L7-47 | ++ | + | DGVKLCEKPSKTWSGNCGNTKHCDNQCRSWEKAKHGACHKRSGKWKCFCYFNC | (SEQ ID NO: 323) |
| L7-53 | + | + | DGVKLCERPSKTWSGNCGNTKHCDKQCRSWEGAKHGACHVRSGKHKCFCYFNC | (SEQ ID NO: 324) |
| L7-58 | +++ | ++ | DGVKLCERASQTWSGHCGNTKHCDNQCKSWEKAKHGACHVRSGKHKCFCYFNC | (SEQ ID NO: 325) |
| L7-59 | ++ | + | --QKLCEKASKTWTGNCGNTKHCDKQCRSWEKAKHGACHVRNGKWKCFCYFNC | (SEQ ID NO: 326) |
| L7-62 | + | + | DGVKLCEKASKTWSGNCGNTKHCDKQCRSWEKAAHGACHVRSGKWKCFCYFNC | (SEQ ID NO: 327) |
| L7-68 | ++ | + | DGVKLCEKASKTWTGHCGNTKHCDKQCKNWEGAKHGACHKRSGKWKCFCYFNC | (SEQ ID NO: 328) |
| L7-70 | +++ | + | DGVKLCEKASKTWSGNCGNTKHCDKQCKNWEGAAHGACHKRNGKWKCFCYFNC | (SEQ ID NO: 329) |
| L7-71 | + | + | DGVKLCEKASQTWTGHCGNTKHCDKQCKSWEGAKHGACHKRNGKWKCFCYFNC | (SEQ ID NO: 330) |
| L7-76 | ++ | + | DGVKLCERASKTWTGNCGNTKHCDNQCKSWEGAKHGACHVRNGKHKCFCYFNC | (SEQ ID NO: 331) |
| L7-77 | + | + | DGVKLCERPSKTWTGHCGNTKHCDKQCRNWEGAAHGACHVRNGKHKCFCYFNC | (SEQ ID NO: 332) |
| L7-81 | + | + | DGVKLCERPSKTWSGNCGNTKHCDNQCRNWEGAKHGACHVRSGKWKCFCYFNC | (SEQ ID NO: 333) |
| L7-82 | ++ | + | DGVKLCERASQTWTGHCGNTKHCDNQCRSWEGAAHGACHKRSGKWKCFCYFNC | (SEQ ID NO: 334) |
| L7-83 | ++ | + | DGVKLCERPSQTWTGHCGNTKHCDKQCRNWEGAAHGACHKRSGKWKCFCYFNC | (SEQ ID NO: 335) |
| L7-87 | +++ | + | DGVKLCERPSQTWSGHCGNTKHCDKQCRNWEGAKHGACHVRNGKWKCFCYFNC | (SEQ ID NO: 336) |
| L7-89 | + | + | --QKLCERPSQTWTGHCGNTKHCDKQCKNWEGAKHGACHVRNGKWKCFCYFNC | (SEQ ID NO: 337) |
| L7-93 | +++ | + | DGVKLCERASKTWTGHCGNTKHCDKQCKNWEKAAHGACHVRNGKWKCFCYFNC | (SEQ ID NO: 338) |
| L7-94 | ++ | + | DGVKLCERPSKTWSGHCGNTKHCDKQCRSWEGAAHGACHVRNGKWKCFCYFNC | (SEQ ID NO: 339) |
| Consensus | | | DGVKLCERASQTWTGHCGNTKHCDKQCKNWEGAKHGACHVRNGKWKCFCYFNC | (SEQ ID NO: 9) |

TABLE 3

| | | | |
|---|---|---|---|
| 1) | *Arabidopasis thaliana* At-PDF1.1; | QKLCEKPSGTWSGVCGNSNACKNQCINLEGAKHGSCNYVFPAHKCICYFPC | (SEQ ID NO: 341) |
| 2) | *Arabidopasis thaliana* At-PDF1.2; | QKLCEKPSGTWSGVCGNSNACKNQCINLEGAKHGSCNYVFPAHKCICYVPC | (SEQ ID NO: 342) |
| 3) | *Raphanus sativus* Rs-AFP1; | QKLCERPSGTWSGVCGNNNACKNQCINLEKARHGSCNYVFPAHKCICYFPC | (SEQ ID NO: 343) |
| 4) | *Raphanus sativus* Rs-AFP2; | QKLCQRPSGTWSGVCGNNNACKNQCIRLEKARHGSCNYVFPAHKCICYFPC | (SEQ ID NO: 344) |
| 5) | *Raphanus sativus* Rs-AFP3; | QKLCERSSGTWSGVCGNNNACKNQCIRLEGAQHGSCNYVFPAHKCICYFPC | (SEQ ID NO: 345) |
| 6) | *Raphanus sativus* Rs-AFP4; | QKLCERSSGTWSGVCGNNNACKNQCINLEGARHGSCNYIFPYHRCICYFPC | (SEQ ID NO: 346) |
| 7) | *Dahlia merckii* Dm-AMP1; | ELCEKASKTWSGNCGNTGHCDNQCKSWEGAAHGACHVRNGKHMCFCYFNC | (SEQ ID NO: 347) |
| 8) | *Clitoria ternatea* Ct-MP1; | NLCERASLTWTGNCGNTGHCDTQCRNWESAKHGACHKRGNWKCFCYFNC | (SEQ ID NO: 348) |
| 9) | *Cnicus benedictus* Cb-AMP1; | ELCEKASKTWSGNCGNTKHCDDQCKSWEGAAHGACHVRNGKHMCFCYFNCN | (SEQ ID NO: 349) |
| 10) | *Cnicus benedictus* Cb-AMP2; | ELCEKASKTWSGNCGNTKHCDNKCKSWEGAAHGACHVRSGKHMCFCYFNC | (SEQ ID NO: 350) |
| 11) | *Raphanus sativus* Rs-AFP2; | QKLCQRPSGTWSGVCGNNNACKNQCIRLEKARHGSCNYVFPAHKCICYFPC | (SEQ ID NO: 351) |
| 12) | *Heuchera sanguinea* Hs-AFP1; | DGVKLCDVPSGTWSGHCGSSSKCSQQCKDREHFAYGGACHYQFPSVKCFCKRQC | (SEQ ID NO: 352) |
| 13) | *Raphanus sativus* Rs-AFP2; | QKLCQRPSGTWSGVCGNNNACKNQCIRLEKARHGSCNYVFPAHKCICYFPC | (SEQ ID NO: 353) |
| 14) | | QKLCERPSRTWSGVCGNNNACKNQCINLEKARHGSCNYVFPAHKCICYFPC | (SEQ ID NO: 354) |
| 15) | | QKLCERPSGTWSGVCGNNNACKNQCINLEKARHGSCNYRFPAHKCICYFPC | (SEQ ID NO: 355) |
| 16) | | QKLCERPSRTWSGVCGNNNACKNQCINLEKARHGSCNYRFPAHKCICYFPC | (SEQ ID NO: 356) |
| 17) | | QKLCMRPSGTWSGVCGNNNACKNQCINLEKARHGSCNYVFPAHKCICYFPC | (SEQ ID NO: 357) |
| 18) | | QKLCERPSGTWSGVCMNNNACKNQCINLEKARHGSCNYVFPAHKCICYFPC | (SEQ ID NO: 358) |
| 19) | | QKLCQRPSRTWSGVCGNNNACKNQCIRLEKARHGSCNYVFPAHKCICYFPC | (SEQ ID NO: 359) |
| 20) | | QKLCQRPSGTWSGVCGNNNACKNQCIRLEKARHGSCNYRFPAHKCICYFPC | (SEQ ID NO: 360) |
| 21) | | QKLCQRPSRTWSGVCGNNNACKNQCIRLEKARHGSCNYRFPAHKCICYFPC | (SEQ ID NO: 361) |
| 22) | | QKLCMRPSGTWSGVCGNNNACKNQCIRLEKARHGSCNYVFPAHKCICYFPC | (SEQ ID NO: 362) |
| 23) | | QKLCQRPSGTWSGVCMNNNACKNQCIRLEKARHGSCNYVFPAHKCICYFPC | (SEQ ID NO: 363) |
| 24) | | KLCERSSRTWSGVCGNNNACKNQCIRLEGAQHGSCNYVFPAHKCICYFPC | (SEQ ID NO: 364) |
| 25) | | KLCERSSGTWSGVCGNNNACKNQCIRLEGAQHGSCNYRFPAHKCICYFPC | (SEQ ID NO: 365) |
| 26) | | KLCERSSRTWSGVCGNNNACKNQCIRLEGAQHGSCNYRFPAHKCICYFPC | (SEQ ID NO: 366) |
| 27) | | KLCMRSSGTWSGVCGNNNACKNQCIRLEGAQHGSCNYVFPAHKCICYFPC | (SEQ ID NO: 367) |
| 28) | | KLCERSSGTWSGVCMNNNACKNQCIRLEGAQHGSCNYVFPAHKCICYFPC | (SEQ ID NO: 368) |
| 29) | | QKLCERSSRTWSGVCGNNNACKNQCINLEGARHGSCNYIFPYHRCICYFPC | (SEQ ID NO: 369) |
| 30) | | QKLCERSSGTWSGVCGNNNACKNQCINLEGARHGSCNYRFPYHRCICYFPC | (SEQ ID NO: 370) |
| 31) | | QKLCERSSRTWSGVCGNNNACKNQCINLEGARHGSCNYRFPYHRCICYFPC | (SEQ ID NO: 371) |
| 32) | | QKLCMRSSGTWSGVCGNNNACKNQCINLEGARHGSCNYIFPYHRCICYFPC | (SEQ ID NO: 372) |
| 33) | | QKLCERSSGTWSGVCMNNNACKNQCINLEGARHGSCNYIFPYHRCICYFPC | (SEQ ID NO: 373) |

TABLE 3-continued

| | | | |
|---|---|---|---|
| 34) | CAC37558 Brassica oleracea; | MAKVASIVALLFPALVIFAAFEAPTMVEAQKLCERPSGTWSGVCGNNNAC KNQCIRLEKARHGSCNYVFPAHKCICYFPC | (SEQ ID NO: 374) |
| 35) | NP_180171 Arabidopsis thaliana (Pdf 1.3); | MAKSAAIITFLFAALVLFAAFEAPIMVEAQKLCEKPSGT WSGVCGNSNACKNQCINLEGAKHGSCNYVFPAHKCICYFPC | (SEQ ID NO: 375) |
| 36) | AAN23105 Brassica rapa; | MAKFVSIITLFFAALVLFAAFEAPTMVKAQKLCERSSGTWSGVCGNNNACKNQCI NLEGARHGSCNYVFPYHRCICYFPC | (SEQ ID NO: 376) |
| 37) | BAB19054 Wasabia japonica; | MAKFASIIALLFAALVLFSAFEAPSMVEAQKLCEKSSGTWSGVCGNNNACKNQ CINLEGARHGSCNYIFPYHRCICYFPC | (SEQ ID NO: 377) |
| 38) | T07917 Brassica napus; | MAKFASIITLLFAALVVFAAFEAPTMVEAKLCERSSGTWSGVCGNNNA CKNQCIRLEGAQHGSCNYVFPAHKCICYFPC | (SEQ ID NO: 378) |
| 39) | P30232 Sinapis alba; | QKLCQRPSGTWSGVCGNNNACRNQCINLEKARHGSCNYVFPAHKCICYFPC | (SEQ ED NO: 379) |
| 40) | AY052236 Arabidopsis thaliana; | MAKSATIVTLFFAALVFFAALEAPMVEAQKLCERPSGTWSG VCGNSNACKNQCINLEKARHGSCNYVFPAHKCICYFPC | (SEQ ID NO: 380) |
| 41) | AY133787 Arabidopsis thaliana; | MAKFASIITLIFAALVLFAAFDAPAMVEAQKLCEKPSGTWSGVCGNSNAC KNQCINLEGAKHGSCNYVFPAHKCICYVPC | (SEQ ID NO: 381) |
| 42) | P30231 Sinapis alba; | QKLCERPSGTWSGVCGNNNACKNQCINLEKARHGSCNYVFPAHKCICYFPC | (SEQ ID NO: 382) |
| 43) | BG321454 (Descurainia sophia) | QKLCEKPSGTWSGVCGNSNACKNQCINLERARHGSCNYVFPAHKCICYFPC | (SEQ ID NO: 383) |
| 44) | AJ412176 Helianthus annuus HsAFP1; | ELCEKASKTWSGKCGNTRHCDDQCKSWEGAAHGACHVRGGKHMCFCYFNC | (SEQ ID NO: 384) |
| 45) | AF364865 Helianthus annuus; | MAKISVAFNAFLLLLFVLAISEIGSVKGELCEKASQTWSGTCGKTKHCDDQCK SWEGAAHGACHVRDGKHMCFCYFNCSKAQKLAQDKLRAEELAKELIEPEKATAKP | (SEQ ID NO: 385) |
| 46) | X53375 Helianthus anuus; | LVFVVAISDIATVNGKICEKPSKTWFGNCKDTDKCDKRCIDWEGAKHGACHQRE AKHMCFCYFDCDPQKNPGPPPGAPGTPGTPPAPPGKGEGDAPHPPPTPSPPGGD GGSGPAPPAGGGSPPPAGGDGGGGAPPPAGGDGGGGAPPPAGGDGGGAPPPGA | (SEQ ID NO: 386) |
| 47) | BQ989575 Lactuca sativa; | ELCEKPSKTWSGNCGNTGHCDGQCKSWEGGAHGACHVRGGKHMCFCYFNC | (SEQ ID NO: 387) |
| 48) | BQ844100 Lactuca sativa; | ELCEKXXKKWSGNCXNTGHCDGQCKSWEGGAHGACHVRGGKHMCFCYFNC | (SEQ ID NO: 388) |
| 49) | S66218 Aesculus hippocastanum; | LCNERPSQTWSGNCGNTAHCDKQCQDWEKASHGACHKRENHWKCFCYFNC | (SEQ ID NO: 340) |

TABLE 4

Antifungal Activity of Selected NPs

| Clone | Septoria tritici* | Mycosphaerella fijiensis* | Fusarium graminearum# |
|---|---|---|---|
| L3-144 | + | + | ++ |
| L3-2 | + | + | + |
| L3-42 | ++ | + | +++ |
| L3-64 | ++ | + | +++ |
| L3-71 | +++ | +++ | +++ |
| L5-12 | ++ | + | ++ |
| L5-13 | +++ | + | +++ |
| L5-22 | ++ | + | ++ |
| L5-23 | + | + | + |
| L5-24 | ++ | + | +++ |
| L6-12 | + | + | +++ |
| L6-13 | +++ | ++ | +++ |
| L6-21 | +++ | + | +++ |
| L6-27 | +++ | + | +++ |
| L6-28 | + | + | +++ |
| L6-3 | +++ | ++ | +++ |
| L6-32 | +++ | +++ | +++ |
| L6-39 | ++ | + | +++ |
| L6-40 | +++ | + | +++ |
| L6-41 | + | + | + |
| L6-5 | + | + | ++ |
| L6-57 | + | ++ | +++ |
| L6-58 | + | + | +++ |
| L6-59 | + | + | NA |
| L6-60 | +++ | + | +++ |
| L6-61 | ++ | + | +++ |
| L6-69 | +++ | + | +++ |
| L6-7 | +++ | ++ | +++ |
| L6-70 | + | + | +++ |
| L6-71 | + | + | +++ |
| L6-75 | +++ | + | +++ |
| L6-8 | ++ | + | ++ |
| L6-83 | + | + | +++ |
| L6-84 | + | +++ | +++ |
| L6-85 | + | + | +++ |
| L7-112 | + | + | + |
| L7-174 | ++ | + | +++ |
| L7-176 | + | + | + |
| L7-179 | + | + | + |
| L7-337 | + | ++ | +++ |
| L7-350 | + | + | + |
| L7-39 | + | + | + |

TABLE 4-continued

Antifungal Activity of Selected NPs

| Clone | Septoria tritici* | Mycosphaerella fijiensis* | Fusarium graminearum# |
|---|---|---|---|
| L7-392 | + | + | + |
| L7-422 | + | + | + |
| L7-427 | + | + | ++ |
| L7-432 | + | +++ | +++ |
| L7-434 | + | + | +++ |
| L7-449 | ++ | + | +++ |
| L7-452 | + | + | ++ |
| L7-457 | + | + | + |
| L7-58 | + | + | + |
| L7-82 | + | +++ | ++ |
| L7-87 | ++ | + | +++ |
| L7-94 | + | + | ++ |
| L9-1 | + | + | + |
| L9-7 | + | ++ | + |
| L9-13 | + | + | ++ |
| L9-14 | + | + | ++ |
| L9-15 | ++ | + | ++ |
| L9-16 | ++ | + | +++ |
| L9-18 | ++ | + | ++ |
| L9-21 | + | + | +++ |
| L9-22 | +++ | + | +++ |
| L9-23 | ++ | ++ | +++ |
| L9-26 | +++ | ++ | +++ |
| L9-27 | ++ | ++ | ++ |
| L9-29 | ++ | ++ | +++ |
| L9-3 | +++ | +++ | +++ |
| L9-30 | + | + | ++ |
| L9-32 | + | + | ++ |
| L9-33 | +++ | ++ | +++ |
| L9-36 | + | + | + |
| L9-41 | + | + | ++ |
| L9-45 | + | + | + |
| L9-46 | +++ | ++ | +++ |
| L9-7 | +++ | ++ | ++ |
| L9-9 | + | + | +++ |
| L10-3 | + | + | + |
| L11-2 | + | + | + |
| L11-4 | + | + | + |
| L11-6 | + | + | + |
| L11-9 | + | + | + |

*Measurement taken at 144 hours after inoculation.
Measurement taken at 72 hours after inoculation.

---

The invention claimed is:

1. A method of preparing a cysteine-containing polypeptide recombinantly expressed in a cell comprising
    a) recombinantly expressing in a cell a cleavable and soluble fusion protein comprising an amino-terminal tag domain, a first domain encoding a heterologous polypeptide, a second domain encoding the cysteine-containing polypeptide, and a cleavage site interposed between the first and second domains;
    b) separating the fusion protein from at least some cell components based on the binding of the tag domain and a binding agent; and
    c) contacting the fusion protein and a cleaving agent that cleaves at the cleavage site, thereby cleaving the fusion protein to produce the cysteine-containing polypeptide as a cleavage product, wherein the cysteine-containing polypeptide has a purity of at least 50%,
    wherein steps (b) and (c) are carried out in the presence of a reducing agent to prevent misfolding of the fusion protein.

2. The method of claim 1 wherein the cleaving agent is a protease.

3. The method of claim 2 wherein the reducing agent is beta-mercaptoethanol at a concentration of between 5 mM and 20 mM.

4. The method of claim 1 wherein the cell is a bacterial cell.

5. The method of claim 1 wherein the cysteine-containing polypeptide is a plant defensin.

6. The method of claim 1 wherein the cysteine-containing polypeptide is a NP polypeptide.

7. The method of claim 1 wherein the tag is $(His)_6$, the heterologous domain is maltose binding protein, glutathione-S-transferase or chitin binding domain, and the cleavage site comprises the sequence Ile-Glu-Asp-Gly-Arg (SEQ ID NO:19) recognized by Factor Xa or Pro-Gly-Ala-Ala-His-Tyr (SEQ ID NO: 12) recognized by Genenase I.

8. The method of claim 1 further comprising separating the cysteine-containing polypeptide from the heterologous domain polypeptide.

* * * * *